United States Patent
Zeitoun et al.

(10) Patent No.: US 11,732,294 B2
(45) Date of Patent: Aug. 22, 2023

(54) POLYNUCLEOTIDES, REAGENTS, AND METHODS FOR NUCLEIC ACID HYBRIDIZATION

(71) Applicant: Twist Bioscience Corporation, South San Francisco, CA (US)

(72) Inventors: Ramsey Ibrahim Zeitoun, San Francisco, CA (US); Siyuan Chen, San Mateo, CA (US); Richard Gantt, San Francisco, CA (US); Kristin D. Butcher, San Francisco, CA (US); E. Hutson Chilton, San Francisco, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 740 days.

(21) Appl. No.: 16/590,301

(22) Filed: Oct. 1, 2019

(65) Prior Publication Data
US 2020/0102611 A1    Apr. 2, 2020

Related U.S. Application Data

(63) Continuation of application No. 16/417,023, filed on May 20, 2019, now Pat. No. 11,492,665.

(60) Provisional application No. 62/833,440, filed on Apr. 12, 2019, provisional application No. 62/814,749, filed on Mar. 6, 2019, provisional application No. 62/814,753, filed on Mar. 6, 2019, provisional application No. 62/810,293, filed on Feb. 25, 2019, provisional application No. 62/810,343, filed on Feb. 25, 2019, provisional application No. 62/675,647, filed on May 23, 2018, provisional application No. 62/673,704, filed on May 18, 2018.

(51) Int. Cl.
| | | |
|---|---|---|
| C12Q 1/68 | (2018.01) | |
| C12Q 1/6869 | (2018.01) | |
| G16B 40/10 | (2019.01) | |
| C40B 30/10 | (2006.01) | |
| C40B 70/00 | (2006.01) | |

(52) U.S. Cl.
CPC ............ C12Q 1/6869 (2013.01); C40B 30/10 (2013.01); C40B 70/00 (2013.01); G16B 40/10 (2019.02)

(58) Field of Classification Search
CPC .. C12Q 1/6832; C12Q 1/6869; C12Q 1/6813; C40B 30/10; C40B 70/00; G16B 40/10
See application file for complete search history.

(56) References Cited

U.S. PATENT DOCUMENTS

| | | |
|---|---|---|
| 3,549,368 A | 12/1970 | Robert et al. |
| 3,920,714 A | 11/1975 | Streck |
| 4,123,661 A | 10/1978 | Wolf et al. |
| 4,415,732 A | 11/1983 | Caruthers et al. |
| 4,613,398 A | 9/1986 | Chiong et al. |
| 4,726,877 A | 2/1988 | Fryd et al. |
| 4,808,511 A | 2/1989 | Holmes |
| 4,837,401 A | 6/1989 | Hirose et al. |
| 4,863,557 A | 9/1989 | Kokaku et al. |
| 4,981,797 A | 1/1991 | Jessee et al. |
| 4,988,617 A | 1/1991 | Landegren et al. |
| 5,102,797 A | 4/1992 | Tucker et al. |
| 5,118,605 A | 6/1992 | Urdea |
| 5,137,814 A | 8/1992 | Rashtchian et al. |
| 5,143,854 A | 9/1992 | Pirrung et al. |
| 5,242,794 A | 9/1993 | Whiteley et al. |
| 5,242,974 A | 9/1993 | Holmes |
| 5,288,514 A | 2/1994 | Ellman et al. |
| 5,299,491 A | 4/1994 | Kawada |
| 5,368,823 A | 11/1994 | McGraw et al. |
| 5,384,261 A | 1/1995 | Winkler et al. |
| 5,387,541 A | 2/1995 | Hodge et al. |
| 5,395,753 A | 3/1995 | Prakash |
| 5,431,720 A | 7/1995 | Nagai et al. |
| 5,445,934 A | 8/1995 | Fodor et al. |
| 5,449,754 A | 9/1995 | Nishioka |
| 5,459,039 A | 10/1995 | Modrich et al. |
| 5,474,796 A | 12/1995 | Brennan |
| 5,476,930 A | 12/1995 | Letsinger et al. |
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |

(Continued)

FOREIGN PATENT DOCUMENTS

| | | |
|---|---|---|
| AU | 3157000 A | 9/2000 |
| CA | 2362939 A1 | 8/2000 |

(Continued)

OTHER PUBLICATIONS

Legault-Demare et al. Biochemical A N D Biophysical Research Communications vol. 28, No. 4, 1967. (Year: 1967).*
Abudayyeh et al.: C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf, 17 pages.
Acevedo-Rocha et al.: Directed evolution of stereoselective enzymes based on genetic selection as opposed to screening systems. J. Biotechnol. 191:3-10 (2014).
Adessi et al.: Solid phase DNA amplification: characterisation of primer attachment and amplification mechanisms. Nucleic Acids Res. 28(20):E87, 2000.

(Continued)

*Primary Examiner* — Jezia Riley
(74) *Attorney, Agent, or Firm* — Wilson Sonsini Goodrich & Rosati

(57) ABSTRACT

Provided herein are compositions, methods and systems relating to libraries of polynucleotides such that the libraries allow for accurate and efficient hybridization after binding to target sequences. Further provided herein are probes, blockers, additives, buffers, and methods that result in improved hybridization. Such compositions and methods are useful for improvement of Next Generation Sequencing applications, such as reducing off-target binding or reducing workflow times.

17 Claims, 91 Drawing Sheets

Specification includes a Sequence Listing.

(56) References Cited

U.S. PATENT DOCUMENTS

| | | |
|---|---|---|
| 5,510,270 A | 4/1996 | Fodor et al. |
| 5,514,789 A | 5/1996 | Kempe |
| 5,527,681 A | 6/1996 | Holmes et al. |
| 5,530,516 A | 6/1996 | Sheets |
| 5,534,507 A | 7/1996 | Cama et al. |
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |
| 5,679,522 A | 10/1997 | Modrich et al. |
| 5,683,879 A | 11/1997 | Laney et al. |
| 5,688,642 A | 11/1997 | Chrisey et al. |
| 5,700,637 A | 12/1997 | Southern et al. |
| 5,700,642 A | 12/1997 | Monforte et al. |
| 5,702,894 A | 12/1997 | Modrich et al. |
| 5,707,806 A | 1/1998 | Shuber |
| 5,712,124 A | 1/1998 | Walker |
| 5,712,126 A | 1/1998 | Weissman et al. |
| 5,739,386 A | 4/1998 | Holmes |
| 5,750,672 A | 5/1998 | Kempe |
| 5,780,613 A | 7/1998 | Letsinger et al. |
| 5,830,643 A | 11/1998 | Yamamoto et al. |
| 5,830,655 A | 11/1998 | Monforte et al. |
| 5,830,662 A | 11/1998 | Soares et al. |
| 5,834,252 A | 11/1998 | Stemmer et al. |
| 5,843,669 A | 12/1998 | Kaiser et al. |
| 5,843,767 A | 12/1998 | Beattie |
| 5,846,717 A | 12/1998 | Brow et al. |
| 5,854,033 A | 12/1998 | Lizardi |
| 5,858,754 A | 1/1999 | Modrich et al. |
| 5,861,482 A | 1/1999 | Modrich et al. |
| 5,863,801 A | 1/1999 | Southgate et al. |
| 5,869,245 A | 2/1999 | Yeung |
| 5,877,280 A | 3/1999 | Wetmur |
| 5,882,496 A | 3/1999 | Northrup et al. |
| 5,922,539 A | 7/1999 | Modrich et al. |
| 5,922,593 A | 7/1999 | Livingston |
| 5,928,907 A | 7/1999 | Woudenberg et al. |
| 5,962,272 A | 10/1999 | Chenchik et al. |
| 5,976,842 A | 11/1999 | Wurst |
| 5,976,846 A | 11/1999 | Passmore et al. |
| 5,989,872 A | 11/1999 | Luo et al. |
| 5,994,069 A | 11/1999 | Hall et al. |
| 6,001,567 A | 12/1999 | Brow et al. |
| 6,008,031 A | 12/1999 | Modrich et al. |
| 6,013,440 A | 1/2000 | Lipshutz et al. |
| 6,015,674 A | 1/2000 | Woudenberg et al. |
| 6,017,434 A | 1/2000 | Simpson et al. |
| 6,020,481 A | 2/2000 | Benson et al. |
| 6,027,898 A | 2/2000 | Gjerde et al. |
| 6,028,189 A | 2/2000 | Blanchard |
| 6,028,198 A | 2/2000 | Liu et al. |
| 6,040,138 A | 3/2000 | Lockhart et al. |
| 6,077,674 A | 6/2000 | Schleifer et al. |
| 6,087,482 A | 7/2000 | Teng et al. |
| 6,090,543 A | 7/2000 | Prudent et al. |
| 6,090,606 A | 7/2000 | Kaiser et al. |
| 6,103,474 A | 8/2000 | Dellinger et al. |
| 6,107,038 A | 8/2000 | Choudhary et al. |
| 6,110,682 A | 8/2000 | Dellinger et al. |
| 6,114,115 A | 9/2000 | Wagner, Jr. |
| 6,130,045 A | 10/2000 | Wurst et al. |
| 6,132,997 A | 10/2000 | Shannon |
| 6,136,568 A | 10/2000 | Hiatt et al. |
| 6,171,797 B1 | 1/2001 | Perbost |
| 6,180,351 B1 | 1/2001 | Cattell |
| 6,201,112 B1 | 3/2001 | Ach |
| 6,218,118 B1 | 4/2001 | Sampson et al. |
| 6,221,653 B1 | 4/2001 | Caren et al. |
| 6,222,030 B1 | 4/2001 | Dellinger et al. |
| 6,232,072 B1 | 5/2001 | Fisher |
| 6,235,483 B1 | 5/2001 | Wolber et al. |
| 6,242,266 B1 | 6/2001 | Schleifer et al. |
| 6,251,588 B1 | 6/2001 | Shannon et al. |
| 6,251,595 B1 | 6/2001 | Gordon et al. |
| 6,251,685 B1 | 6/2001 | Dorsel et al. |
| 6,258,454 B1 | 7/2001 | Lefkowitz et al. |
| 6,262,490 B1 | 7/2001 | Hsu et al. |
| 6,274,725 B1 | 8/2001 | Sanghvi et al. |
| 6,284,465 B1 | 9/2001 | Wolber |
| 6,287,776 B1 | 9/2001 | Hefti |
| 6,287,824 B1 | 9/2001 | Lizardi |
| 6,297,017 B1 | 10/2001 | Schmidt et al. |
| 6,300,137 B1 | 10/2001 | Earhart et al. |
| 6,306,599 B1 | 10/2001 | Perbost |
| 6,309,822 B1 | 10/2001 | Fodor et al. |
| 6,309,828 B1 | 10/2001 | Schleifer et al. |
| 6,312,911 B1 | 11/2001 | Bancroft et al. |
| 6,319,674 B1 | 11/2001 | Fulcrand et al. |
| 6,323,043 B1 | 11/2001 | Caren et al. |
| 6,329,210 B1 | 12/2001 | Schleifer |
| 6,346,423 B1 | 2/2002 | Schembri |
| 6,365,355 B1 | 4/2002 | McCutchen-Maloney |
| 6,372,483 B2 | 4/2002 | Schleifer et al. |
| 6,375,903 B1 | 4/2002 | Cerrina et al. |
| 6,376,285 B1 | 4/2002 | Joyner et al. |
| 6,384,210 B1 | 5/2002 | Blanchard |
| 6,387,636 B1 | 5/2002 | Perbost et al. |
| 6,399,394 B1 | 6/2002 | Dahm et al. |
| 6,399,516 B1 | 6/2002 | Ayon |
| 6,403,314 B1 | 6/2002 | Lange et al. |
| 6,406,849 B1 | 6/2002 | Dorsel et al. |
| 6,406,851 B1 | 6/2002 | Bass |
| 6,408,308 B1 | 6/2002 | Maslyn et al. |
| 6,419,883 B1 | 7/2002 | Blanchard |
| 6,428,957 B1 | 8/2002 | Delenstarr |
| 6,440,669 B1 | 8/2002 | Bass et al. |
| 6,444,268 B2 | 9/2002 | Lefkowitz et al. |
| 6,446,642 B1 | 9/2002 | Caren et al. |
| 6,446,682 B1 | 9/2002 | Viken |
| 6,451,998 B1 | 9/2002 | Perbost |
| 6,458,526 B1 | 10/2002 | Schembri et al. |
| 6,458,535 B1 | 10/2002 | Hall et al. |
| 6,458,583 B1 | 10/2002 | Bruhn et al. |
| 6,461,812 B2 | 10/2002 | Barth et al. |
| 6,461,816 B1 | 10/2002 | Wolber et al. |
| 6,469,156 B1 | 10/2002 | Schafer et al. |
| 6,472,147 B1 | 10/2002 | Janda et al. |
| 6,492,107 B1 | 12/2002 | Kauffman et al. |
| 6,518,056 B2 | 2/2003 | Schembri et al. |
| 6,521,427 B1 | 2/2003 | Evans |
| 6,521,453 B1 | 2/2003 | Crameri et al. |
| 6,555,357 B1 | 4/2003 | Kaiser et al. |
| 6,558,908 B2 | 5/2003 | Wolber et al. |
| 6,562,611 B1 | 5/2003 | Kaiser et al. |
| 6,566,495 B1 | 5/2003 | Fodor et al. |
| 6,582,908 B2 | 6/2003 | Fodor et al. |
| 6,582,938 B1 | 6/2003 | Su et al. |
| 6,586,211 B1 | 7/2003 | Staehler et al. |
| 6,587,579 B1 | 7/2003 | Bass |
| 6,589,739 B2 | 7/2003 | Fisher |
| 6,599,693 B1 | 7/2003 | Webb |
| 6,602,472 B1 | 8/2003 | Zimmermann et al. |
| 6,610,978 B2 | 8/2003 | Yin et al. |
| 6,613,513 B1 | 9/2003 | Parce et al. |
| 6,613,523 B2 | 9/2003 | Fischer |
| 6,613,560 B1 | 9/2003 | Tso et al. |
| 6,613,893 B1 | 9/2003 | Webb |
| 6,621,076 B1 | 9/2003 | Van De Goor et al. |
| 6,630,581 B2 | 10/2003 | Dellinger et al. |
| 6,632,641 B1 | 10/2003 | Brennan et al. |
| 6,635,226 B1 | 10/2003 | Tso et al. |
| 6,642,373 B2 | 11/2003 | Manoharan et al. |
| 6,649,348 B2 | 11/2003 | Bass et al. |
| 6,660,338 B1 | 12/2003 | Hargreaves |
| 6,664,112 B2 | 12/2003 | Mulligan et al. |
| 6,670,127 B2 | 12/2003 | Evans |
| 6,670,461 B1 | 12/2003 | Wengel et al. |
| 6,673,552 B2 | 1/2004 | Frey |
| 6,682,702 B2 | 1/2004 | Barth et al. |
| 6,689,319 B1 | 2/2004 | Fisher et al. |
| 6,692,917 B2 | 2/2004 | Neri et al. |
| 6,702,256 B2 | 3/2004 | Killeen et al. |
| 6,706,471 B1 | 3/2004 | Brow et al. |

(56) References Cited

U.S. PATENT DOCUMENTS

| | | |
|---|---|---|
| 6,706,875 B1 | 3/2004 | Goldberg et al. |
| 6,709,841 B2 | 3/2004 | Short |
| 6,709,852 B1 | 3/2004 | Bloom et al. |
| 6,709,854 B2 | 3/2004 | Donahue et al. |
| 6,713,262 B2 | 3/2004 | Gillibolian et al. |
| 6,716,629 B2 | 4/2004 | Hess et al. |
| 6,716,634 B1 | 4/2004 | Myerson |
| 6,723,509 B2 | 4/2004 | Ach |
| 6,728,129 B2 | 4/2004 | Lindsey et al. |
| 6,743,585 B2 | 6/2004 | Dellinger et al. |
| 6,753,145 B2 | 6/2004 | Holcomb et al. |
| 6,768,005 B2 | 7/2004 | Mellor et al. |
| 6,770,748 B2 | 8/2004 | Imanishi et al. |
| 6,770,892 B2 | 8/2004 | Corson et al. |
| 6,773,676 B2 | 8/2004 | Schembri |
| 6,773,888 B2 | 8/2004 | Li et al. |
| 6,780,982 B2 | 8/2004 | Lyamichev et al. |
| 6,787,308 B2 | 9/2004 | Balasubramanian et al. |
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | McGall et al. |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,846,922 B1 | 1/2005 | Manoharan et al. |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | Van De Goor et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,951,719 B1 | 10/2005 | Dupret et al. |
| 6,958,119 B2 | 10/2005 | Yin et al. |
| 6,960,464 B2 | 11/2005 | Jessee et al. |
| 6,969,449 B2 | 11/2005 | Maher et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 6,991,922 B2 | 1/2006 | Dupret et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,041,445 B2 | 5/2006 | Chenchik et al. |
| 7,045,289 B2 | 5/2006 | Allawi et al. |
| 7,051,574 B2 | 5/2006 | Peck |
| 7,052,841 B2 | 5/2006 | Delenstarr |
| 7,062,385 B2 | 6/2006 | White et al. |
| 7,064,197 B1 | 6/2006 | Rabbani et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 | 7/2006 | Bass et al. |
| 7,094,537 B2 | 8/2006 | Leproust et al. |
| 7,097,974 B1 | 8/2006 | Stahler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,122,364 B1 | 10/2006 | Lyamichev et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,150,982 B2 | 12/2006 | Allawi et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,183,406 B2 | 2/2007 | Belshaw et al. |
| 7,192,710 B2 | 3/2007 | Gellibolian et al. |
| 7,193,077 B2 | 3/2007 | Dellinger et al. |
| 7,195,872 B2 | 3/2007 | Agrawal et al. |
| 7,198,939 B2 | 4/2007 | Dorsel et al. |
| 7,202,264 B2 | 4/2007 | Ravikumar et al. |
| 7,202,358 B2 | 4/2007 | Hargreaves |
| 7,205,128 B2 | 4/2007 | Ilsley et al. |
| 7,205,399 B1 | 4/2007 | Vargeese et al. |
| 7,205,400 B2 | 4/2007 | Webb |
| 7,206,439 B2 | 4/2007 | Zhou et al. |
| 7,208,322 B2 | 4/2007 | Stolowitz et al. |
| 7,217,522 B2 | 5/2007 | Brenner |
| 7,220,573 B2 | 5/2007 | Shea et al. |
| 7,221,785 B2 | 5/2007 | Curry et al. |
| 7,226,862 B2 | 6/2007 | Staehler et al. |
| 7,227,017 B2 | 6/2007 | Mellor et al. |
| 7,229,497 B2 | 6/2007 | Stott et al. |
| 7,247,337 B1 | 7/2007 | Leproust et al. |
| 7,247,497 B2 | 7/2007 | Dahm et al. |
| 7,252,938 B2 | 8/2007 | Leproust et al. |
| 7,269,518 B2 | 9/2007 | Corson |
| 7,271,258 B2 | 9/2007 | Dellinger et al. |
| 7,276,336 B1 | 10/2007 | Webb et al. |
| 7,276,378 B2 | 10/2007 | Myerson |
| 7,276,599 B2 | 10/2007 | Moore et al. |
| 7,282,183 B2 | 10/2007 | Peck |
| 7,282,332 B2 | 10/2007 | Caren et al. |
| 7,282,705 B2 | 10/2007 | Brennen |
| 7,291,471 B2 | 11/2007 | Sampson et al. |
| 7,302,348 B2 | 11/2007 | Ghosh et al. |
| 7,306,917 B2 | 12/2007 | Prudent et al. |
| 7,314,599 B2 | 1/2008 | Roitman et al. |
| 7,323,320 B2 | 1/2008 | Oleinikov |
| 7,344,831 B2 | 3/2008 | Wolber et al. |
| 7,348,144 B2 | 3/2008 | Minor |
| 7,351,379 B2 | 4/2008 | Schleifer |
| 7,353,116 B2 | 4/2008 | Webb et al. |
| 7,361,906 B2 | 4/2008 | Ghosh et al. |
| 7,364,896 B2 | 4/2008 | Schembri |
| 7,368,550 B2 | 5/2008 | Dellinger et al. |
| 7,371,348 B2 | 5/2008 | Schleifer et al. |
| 7,371,519 B2 | 5/2008 | Wolber et al. |
| 7,371,580 B2 | 5/2008 | Yakhini et al. |
| 7,372,982 B2 | 5/2008 | Le Cocq |

(56) References Cited

U.S. PATENT DOCUMENTS

| | | |
|---|---|---|
| 7,384,746 B2 | 6/2008 | Lyamichev et al. |
| 7,385,050 B2 | 6/2008 | Dellinger et al. |
| 7,390,457 B2 | 6/2008 | Schembri |
| 7,393,665 B2 | 7/2008 | Brenner |
| 7,396,676 B2 | 7/2008 | Robotti et al. |
| 7,399,844 B2 | 7/2008 | Sampson et al. |
| 7,402,279 B2 | 7/2008 | Schembri |
| 7,411,061 B2 | 8/2008 | Myerson et al. |
| 7,413,709 B2 | 8/2008 | Roitman et al. |
| 7,417,139 B2 | 8/2008 | Dellinger et al. |
| 7,422,911 B2 | 9/2008 | Schembri |
| 7,427,679 B2 | 9/2008 | Dellinger et al. |
| 7,432,048 B2 | 10/2008 | Neri et al. |
| 7,435,810 B2 | 10/2008 | Myerson et al. |
| 7,439,272 B2 | 10/2008 | Xu |
| 7,476,709 B2 | 1/2009 | Moody et al. |
| 7,482,118 B2 | 1/2009 | Allawi et al. |
| 7,488,607 B2 | 2/2009 | Tom-Moy et al. |
| 7,504,213 B2 | 3/2009 | Sana et al. |
| 7,514,369 B2 | 4/2009 | Li et al. |
| 7,517,979 B2 | 4/2009 | Wolber |
| 7,524,942 B2 | 4/2009 | Wang et al. |
| 7,524,950 B2 | 4/2009 | Dellinger et al. |
| 7,527,928 B2 | 5/2009 | Neri et al. |
| 7,531,303 B2 | 5/2009 | Dorsel et al. |
| 7,534,561 B2 | 5/2009 | Sana et al. |
| 7,534,563 B2 | 5/2009 | Hargreaves |
| 7,537,936 B2 | 5/2009 | Dahm et al. |
| 7,541,145 B2 | 6/2009 | Prudent et al. |
| 7,544,473 B2 | 6/2009 | Brenner |
| 7,556,919 B2 | 7/2009 | Chenchik et al. |
| 7,563,600 B2 | 7/2009 | Oleinikov |
| 7,572,585 B2 | 8/2009 | Wang |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,588,889 B2 | 9/2009 | Wolber et al. |
| 7,595,350 B2 | 9/2009 | Xu |
| 7,604,941 B2 | 10/2009 | Jacobson |
| 7,604,996 B1 | 10/2009 | Stuelpnagel et al. |
| 7,608,396 B2 | 10/2009 | Delenstarr |
| 7,618,777 B2 | 11/2009 | Myerson et al. |
| 7,629,120 B2 | 12/2009 | Bennett et al. |
| 7,635,772 B2 | 12/2009 | McCormac |
| 7,648,832 B2 | 1/2010 | Jessee et al. |
| 7,651,762 B2 | 1/2010 | Xu et al. |
| 7,659,069 B2 | 2/2010 | Belyaev et al. |
| 7,678,542 B2 | 3/2010 | Lyamichev et al. |
| 7,682,809 B2 | 3/2010 | Sampson |
| 7,709,197 B2 | 5/2010 | Drmanac |
| 7,718,365 B2 | 5/2010 | Wang |
| 7,718,786 B2 | 5/2010 | Dupret et al. |
| 7,723,077 B2 | 5/2010 | Young et al. |
| 7,737,088 B1 | 6/2010 | Stahler et al. |
| 7,737,089 B2 | 6/2010 | Guimil et al. |
| 7,741,463 B2 | 6/2010 | Gormley et al. |
| 7,749,701 B2 | 7/2010 | Leproust et al. |
| 7,759,471 B2 | 7/2010 | Dellinger et al. |
| 7,776,021 B2 | 8/2010 | Borenstein et al. |
| 7,776,532 B2 | 8/2010 | Gibson et al. |
| 7,790,369 B2 | 9/2010 | Stahler et al. |
| 7,790,387 B2 | 9/2010 | Dellinger et al. |
| 7,807,356 B2 | 10/2010 | Sampson et al. |
| 7,807,806 B2 | 10/2010 | Allawi et al. |
| 7,811,753 B2 | 10/2010 | Eshoo |
| 7,816,079 B2 | 10/2010 | Fischer |
| 7,820,387 B2 | 10/2010 | Neri et al. |
| 7,829,314 B2 | 11/2010 | Prudent et al. |
| 7,855,281 B2 | 12/2010 | Dellinger et al. |
| 7,862,999 B2 | 1/2011 | Zheng et al. |
| 7,867,782 B2 | 1/2011 | Barth |
| 7,875,463 B2 | 1/2011 | Adaskin et al. |
| 7,879,541 B2 | 2/2011 | Kincaid |
| 7,879,580 B2 | 2/2011 | Carr et al. |
| 7,894,998 B2 | 2/2011 | Kincaid |
| 7,919,239 B2 | 4/2011 | Wang |
| 7,919,308 B2 | 4/2011 | Schleifer |
| 7,927,797 B2 | 4/2011 | Nobile et al. |
| 7,927,838 B2 | 4/2011 | Shannon |
| 7,932,025 B2 | 4/2011 | Carr et al. |
| 7,932,070 B2 | 4/2011 | Hogrefe et al. |
| 7,935,800 B2 | 5/2011 | Allawi et al. |
| 7,939,645 B2 | 5/2011 | Borns |
| 7,943,046 B2 | 5/2011 | Martosella et al. |
| 7,943,358 B2 | 5/2011 | Hogrefe et al. |
| 7,960,157 B2 | 6/2011 | Borns |
| 7,977,119 B2 | 7/2011 | Kronick et al. |
| 7,979,215 B2 | 7/2011 | Sampas |
| 7,998,437 B2 | 8/2011 | Berndt et al. |
| 7,999,087 B2 | 8/2011 | Dellinger et al. |
| 8,021,842 B2 | 9/2011 | Brenner |
| 8,021,844 B2 | 9/2011 | Wang |
| 8,034,917 B2 | 10/2011 | Yamada |
| 8,036,835 B2 | 10/2011 | Sampas et al. |
| 8,048,664 B2 | 11/2011 | Guan et al. |
| 8,053,191 B2 | 11/2011 | Blake |
| 8,058,001 B2 | 11/2011 | Crameri et al. |
| 8,058,004 B2 | 11/2011 | Oleinikov |
| 8,058,055 B2 | 11/2011 | Barrett et al. |
| 8,063,184 B2 | 11/2011 | Allawi et al. |
| 8,067,556 B2 | 11/2011 | Hogrefe et al. |
| 8,073,626 B2 | 12/2011 | Troup et al. |
| 8,076,064 B2 | 12/2011 | Wang |
| 8,076,152 B2 | 12/2011 | Robotti |
| 8,097,711 B2 | 1/2012 | Timar et al. |
| 8,137,936 B2 | 3/2012 | MacEvicz |
| 8,148,068 B2 | 4/2012 | Brenner |
| 8,154,729 B2 | 4/2012 | Baldo et al. |
| 8,168,385 B2 | 5/2012 | Brenner |
| 8,168,388 B2 | 5/2012 | Gormley et al. |
| 8,173,368 B2 | 5/2012 | Staehler et al. |
| 8,182,991 B1 | 5/2012 | Kaiser et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett et al. |
| 8,263,335 B2 | 9/2012 | Carr et al. |
| 8,268,605 B2 | 9/2012 | Sorge et al. |
| 8,283,148 B2 | 10/2012 | Sorge et al. |
| 8,288,093 B2 | 10/2012 | Hall et al. |
| 8,298,767 B2 | 10/2012 | Brenner et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,433 B2 | 11/2012 | Brenner |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,383,338 B2 | 2/2013 | Kitzman et al. |
| 8,415,138 B2 | 4/2013 | Leproust |
| 8,435,736 B2 | 5/2013 | Gibson et al. |
| 8,445,205 B2 | 5/2013 | Brenner |
| 8,445,206 B2 | 5/2013 | Bergmann et al. |
| 8,470,996 B2 | 6/2013 | Brenner et al. |
| 8,476,018 B2 | 7/2013 | Brenner |
| 8,476,598 B1 | 7/2013 | Pralle et al. |
| 8,481,292 B2 | 7/2013 | Casbon et al. |
| 8,481,309 B2 | 7/2013 | Zhang et al. |
| 8,491,561 B2 | 7/2013 | Borenstein et al. |
| 8,497,069 B2 | 7/2013 | Hutchison et al. |
| 8,500,979 B2 | 8/2013 | Elibol et al. |
| 8,501,454 B2 | 8/2013 | Liu et al. |
| 8,507,226 B2 | 8/2013 | Carr et al. |
| 8,507,239 B2 | 8/2013 | Lubys et al. |
| 8,507,272 B2 | 8/2013 | Zhang et al. |

(56) References Cited

U.S. PATENT DOCUMENTS

| | | |
|---|---|---|
| 8,530,197 B2 | 9/2013 | Li et al. |
| 8,552,174 B2 | 10/2013 | Dellinger et al. |
| 8,563,478 B2 | 10/2013 | Gormley et al. |
| 8,569,046 B2 | 10/2013 | Love et al. |
| 8,577,621 B2 | 11/2013 | Troup et al. |
| 8,586,310 B2 | 11/2013 | Mitra et al. |
| 8,614,092 B2 | 12/2013 | Zhang et al. |
| 8,642,755 B2 | 2/2014 | Sierzchala et al. |
| 8,664,164 B2 | 3/2014 | Ericsson et al. |
| 8,669,053 B2 | 3/2014 | Stuelpnagel et al. |
| 8,679,756 B1 | 3/2014 | Brenner et al. |
| 8,685,642 B2 | 4/2014 | Sampas |
| 8,685,676 B2 | 4/2014 | Hogrefe et al. |
| 8,685,678 B2 | 4/2014 | Casbon et al. |
| 8,715,933 B2 | 5/2014 | Oliver |
| 8,715,967 B2 | 5/2014 | Casbon et al. |
| 8,716,467 B2 | 5/2014 | Jacobson |
| 8,722,368 B2 | 5/2014 | Casbon et al. |
| 8,722,585 B2 | 5/2014 | Wang |
| 8,728,766 B2 | 5/2014 | Casbon et al. |
| 8,741,606 B2 | 6/2014 | Casbon et al. |
| 8,808,896 B2 | 8/2014 | Choo et al. |
| 8,808,986 B2 | 8/2014 | Jacobson et al. |
| 8,815,600 B2 | 8/2014 | Liu et al. |
| 8,889,851 B2 | 11/2014 | Leproust et al. |
| 8,932,994 B2 | 1/2015 | Gormley et al. |
| 8,962,532 B2 | 2/2015 | Shapiro et al. |
| 8,968,999 B2 | 3/2015 | Gibson et al. |
| 8,980,563 B2 | 3/2015 | Zheng et al. |
| 9,018,365 B2 | 4/2015 | Brenner et al. |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,102,731 B2 | 8/2015 | Boone et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,194,001 B2 | 11/2015 | Brenner |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,328,378 B2 | 5/2016 | Earnshaw et al. |
| 9,347,091 B2 | 5/2016 | Bergmann et al. |
| 9,375,748 B2 | 6/2016 | Harumoto et al. |
| 9,376,677 B2 | 6/2016 | Mir |
| 9,376,678 B2 | 6/2016 | Gormley et al. |
| 9,384,320 B2 | 7/2016 | Church |
| 9,384,920 B1 | 7/2016 | Bakulich |
| 9,388,407 B2 | 7/2016 | Jacobson |
| 9,394,333 B2 | 7/2016 | Wada et al. |
| 9,403,141 B2 | 8/2016 | Banyai et al. |
| 9,409,139 B2 | 8/2016 | Banyai et al. |
| 9,410,149 B2 | 8/2016 | Brenner et al. |
| 9,410,173 B2 | 8/2016 | Betts et al. |
| 9,416,411 B2 | 8/2016 | Stuelpnagel et al. |
| 9,422,600 B2 | 8/2016 | Ramu et al. |
| 9,487,824 B2 | 11/2016 | Kutyavin |
| 9,499,848 B2 | 11/2016 | Carr et al. |
| 9,523,122 B2 | 12/2016 | Zheng et al. |
| 9,528,148 B2 | 12/2016 | Zheng et al. |
| 9,534,251 B2 | 1/2017 | Young et al. |
| 9,555,388 B2 | 1/2017 | Banyai et al. |
| 9,568,839 B2 | 2/2017 | Stahler et al. |
| 9,580,746 B2 | 2/2017 | Leproust et al. |
| 9,670,529 B2 | 6/2017 | Osborne et al. |
| 9,670,536 B2 | 6/2017 | Casbon et al. |
| 9,677,067 B2 | 6/2017 | Toro et al. |
| 9,695,211 B2 | 7/2017 | Wada et al. |
| 9,718,060 B2 | 8/2017 | Venter et al. |
| 9,745,573 B2 | 8/2017 | Stuelpnagel et al. |
| 9,745,619 B2 | 8/2017 | Rabbani et al. |
| 9,765,387 B2 | 9/2017 | Rabbani et al. |
| 9,771,576 B2 | 9/2017 | Gibson et al. |
| 9,833,761 B2 | 12/2017 | Banyai et al. |
| 9,834,774 B2 | 12/2017 | Carstens |
| 9,839,894 B2 | 12/2017 | Banyai et al. |
| 9,879,283 B2 | 1/2018 | Ravinder et al. |
| 9,889,423 B2 | 2/2018 | Banyai et al. |
| 9,895,673 B2 | 2/2018 | Peck et al. |
| 9,925,510 B2 | 3/2018 | Jacobson et al. |
| 9,932,576 B2 | 4/2018 | Raymond et al. |
| 9,981,239 B2 | 5/2018 | Banyai et al. |
| 10,053,688 B2 | 8/2018 | Cox |
| 10,272,410 B2 | 4/2019 | Banyai et al. |
| 10,384,188 B2 | 8/2019 | Banyai et al. |
| 10,384,189 B2 | 8/2019 | Peck |
| 10,417,457 B2 | 9/2019 | Peck |
| 10,583,415 B2 | 3/2020 | Banyai et al. |
| 10,754,994 B2 | 8/2020 | Peck |
| 10,773,232 B2 | 9/2020 | Banyai et al. |
| 10,936,953 B2 | 3/2021 | Bramlett et al. |
| 10,963,953 B2 | 3/2021 | Sweeder et al. |
| 10,975,372 B2 | 4/2021 | Cox et al. |
| 11,185,837 B2 | 11/2021 | Banyai et al. |
| 11,214,798 B2 | 1/2022 | Brown |
| 11,236,393 B2 | 2/2022 | Dubinsky et al. |
| 11,263,354 B2 | 3/2022 | Peck |
| 11,268,149 B2 | 3/2022 | Targan et al. |
| 11,332,738 B2 | 5/2022 | Nugent et al. |
| 11,332,740 B2 | 5/2022 | Nugent et al. |
| 11,377,676 B2 | 7/2022 | Wu et al. |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0025561 A1 | 2/2002 | Hodgson |
| 2002/0058802 A1 | 5/2002 | Dellinger et al. |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |
| 2002/0119459 A1 | 8/2002 | Griffiths |
| 2002/0132308 A1 | 9/2002 | Liu et al. |
| 2002/0155439 A1 | 10/2002 | Rodriguez et al. |
| 2002/0160536 A1 | 10/2002 | Regnier et al. |
| 2002/0164824 A1 | 11/2002 | Xiao et al. |
| 2003/0008411 A1 | 1/2003 | Van Dam et al. |
| 2003/0022207 A1 | 1/2003 | Balasubramanian et al. |
| 2003/0022240 A1 | 1/2003 | Luo et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0082618 A1* | 5/2003 | Li .................. C12Q 1/6809 435/6.16 |
| 2003/0082719 A1 | 5/2003 | Schumacher et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0130827 A1 | 7/2003 | Bentzien et al. |
| 2003/0138782 A1 | 7/2003 | Evans |
| 2003/0143605 A1 | 7/2003 | Lok et al. |
| 2003/0148291 A1 | 8/2003 | Robotti |
| 2003/0148344 A1 | 8/2003 | Rothberg et al. |
| 2003/0148401 A1 | 8/2003 | Agrawal et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du Breuil Lastrucci |
| 2004/0009498 A1 | 1/2004 | Short |
| 2004/0043509 A1 | 3/2004 | Stahler et al. |
| 2004/0053362 A1 | 3/2004 | De Luca et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 | 6/2004 | McGall et al. |
| 2004/0110133 A1 | 6/2004 | Xu et al. |

(56) References Cited

U.S. PATENT DOCUMENTS

| | | |
|---|---|---|
| 2004/0175710 A1 | 9/2004 | Haushalter |
| 2004/0175734 A1 | 9/2004 | Stahler et al. |
| 2004/0191810 A1 | 9/2004 | Yamamoto |
| 2004/0213795 A1 | 10/2004 | Collins et al. |
| 2004/0219663 A1 | 11/2004 | Page et al. |
| 2004/0236027 A1 | 11/2004 | Maeji et al. |
| 2004/0248161 A1 | 12/2004 | Rothberg et al. |
| 2004/0253242 A1 | 12/2004 | Bowdish et al. |
| 2004/0259146 A1 | 12/2004 | Friend et al. |
| 2005/0022895 A1 | 2/2005 | Barth et al. |
| 2005/0049402 A1 | 3/2005 | Babcook et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0112636 A1 | 5/2005 | Hurt et al. |
| 2005/0112679 A1 | 5/2005 | Myerson et al. |
| 2005/0118706 A1 | 6/2005 | Pirrung et al. |
| 2005/0124022 A1 | 6/2005 | Srinivasan et al. |
| 2005/0137805 A1 | 6/2005 | Lewin et al. |
| 2005/0208513 A1 | 9/2005 | Agbo et al. |
| 2005/0214778 A1 | 9/2005 | Peck et al. |
| 2005/0214779 A1 | 9/2005 | Peck et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2005/0287585 A1 | 12/2005 | Oleinikov |
| 2006/0003381 A1 | 1/2006 | Gilmore et al. |
| 2006/0003958 A1 | 1/2006 | Melville et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |
| 2006/0078927 A1 | 4/2006 | Peck et al. |
| 2006/0078937 A1 | 4/2006 | Korlach et al. |
| 2006/0127920 A1 | 6/2006 | Church et al. |
| 2006/0134638 A1 | 6/2006 | Mulligan et al. |
| 2006/0160138 A1 | 7/2006 | Church |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2006/0286569 A1 | 12/2006 | Bar-Or et al. |
| 2007/0031857 A1 | 2/2007 | Makarov et al. |
| 2007/0031877 A1 | 2/2007 | Stahler et al. |
| 2007/0043516 A1 | 2/2007 | Gustafsson et al. |
| 2007/0054127 A1 | 3/2007 | Hergenrother et al. |
| 2007/0059692 A1 | 3/2007 | Gao et al. |
| 2007/0087349 A1 | 4/2007 | Staehler et al. |
| 2007/0099196 A1 | 5/2007 | Kauppinen et al. |
| 2007/0099208 A1 | 5/2007 | Drmanac et al. |
| 2007/0122817 A1 | 5/2007 | Church et al. |
| 2007/0128635 A1 | 6/2007 | MacEvicz |
| 2007/0141557 A1 | 6/2007 | Raab et al. |
| 2007/0196834 A1 | 8/2007 | Cerrina et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085511 A1 | 4/2008 | Peck et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0300842 A1 | 12/2008 | Govindarajan et al. |
| 2008/0308884 A1 | 12/2008 | Kalvesten |
| 2008/0311628 A1 | 12/2008 | Shoemaker |
| 2009/0036664 A1 | 2/2009 | Peter |
| 2009/0053704 A1 | 2/2009 | Novoradovskaya et al. |
| 2009/0062129 A1 | 3/2009 | McKernan et al. |
| 2009/0074771 A1 | 3/2009 | Koenig et al. |
| 2009/0087840 A1 | 4/2009 | Baynes et al. |
| 2009/0088679 A1 | 4/2009 | Wood et al. |
| 2009/0105094 A1 | 4/2009 | Heiner et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0246788 A1 | 10/2009 | Albert et al. |
| 2009/0263802 A1 | 10/2009 | Drmanac |
| 2009/0285825 A1 | 11/2009 | Kini et al. |
| 2009/0324546 A1 | 12/2009 | Notka et al. |
| 2010/0004143 A1 | 1/2010 | Shibahara |
| 2010/0008851 A1 | 1/2010 | Nicolaides et al. |
| 2010/0009872 A1 | 1/2010 | Eid et al. |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0099103 A1 | 4/2010 | Hsieh et al. |
| 2010/0111768 A1 | 5/2010 | Banerjee et al. |
| 2010/0160463 A1 | 6/2010 | Wang et al. |
| 2010/0167950 A1 | 7/2010 | Juang et al. |
| 2010/0173364 A1 | 7/2010 | Evans, Jr. et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0272711 A1 | 10/2010 | Feldman et al. |
| 2010/0286290 A1 | 11/2010 | Lohmann et al. |
| 2010/0292102 A1 | 11/2010 | Nouri |
| 2010/0300882 A1 | 12/2010 | Zhang et al. |
| 2010/0311960 A1 | 12/2010 | Dellinger |
| 2010/0323404 A1 | 12/2010 | Lathrop |
| 2011/0009607 A1 | 1/2011 | Komiyama et al. |
| 2011/0082055 A1 | 4/2011 | Fox et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0201528 A1 | 8/2011 | Baek et al. |
| 2011/0217738 A1 | 9/2011 | Jacobson |
| 2011/0229975 A1* | 9/2011 | Matthiesen .......... C12Q 1/6841 536/25.3 |
| 2011/0230653 A1 | 9/2011 | Novoradovskaya et al. |
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0032366 A1 | 2/2012 | Ivniski et al. |
| 2012/0046175 A1 | 2/2012 | Rodesch et al. |
| 2012/0050411 A1 | 3/2012 | Mabritto et al. |
| 2012/0094847 A1 | 4/2012 | Warthmann et al. |
| 2012/0128548 A1 | 5/2012 | West et al. |
| 2012/0129704 A1 | 5/2012 | Gunderson et al. |

(56) References Cited

U.S. PATENT DOCUMENTS

| | | |
|---|---|---|
| 2012/0149602 A1 | 6/2012 | Friend et al. |
| 2012/0164127 A1 | 6/2012 | Short et al. |
| 2012/0164633 A1 | 6/2012 | Laffler |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |
| 2012/0315670 A1 | 12/2012 | Jacobson et al. |
| 2012/0322681 A1 | 12/2012 | Kung et al. |
| 2013/0005585 A1 | 1/2013 | Anderson et al. |
| 2013/0005612 A1 | 1/2013 | Carr et al. |
| 2013/0017642 A1 | 1/2013 | Milgrew et al. |
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0040836 A1 | 2/2013 | Himmler et al. |
| 2013/0045483 A1 | 2/2013 | Treusch et al. |
| 2013/0053252 A1 | 2/2013 | Xie et al. |
| 2013/0059296 A1 | 3/2013 | Jacobson et al. |
| 2013/0059761 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |
| 2013/0137861 A1 | 5/2013 | Leproust et al. |
| 2013/0164308 A1 | 6/2013 | Foletti et al. |
| 2013/0165328 A1 | 6/2013 | Previte et al. |
| 2013/0196864 A1 | 8/2013 | Govindarajan et al. |
| 2013/0217071 A1 | 8/2013 | Montesclaros et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0261027 A1 | 10/2013 | Li et al. |
| 2013/0281308 A1 | 10/2013 | Kung et al. |
| 2013/0289246 A1 | 10/2013 | Crowe et al. |
| 2013/0296192 A1 | 11/2013 | Jacobson et al. |
| 2013/0296194 A1 | 11/2013 | Jacobson et al. |
| 2013/0298265 A1 | 11/2013 | Cunnac et al. |
| 2013/0309725 A1 | 11/2013 | Jacobson et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0031240 A1 | 1/2014 | Behlke et al. |
| 2014/0038240 A1 | 2/2014 | Temme et al. |
| 2014/0106394 A1 | 4/2014 | Ko et al. |
| 2014/0141982 A1 | 5/2014 | Jacobson et al. |
| 2014/0170665 A1 | 6/2014 | Hiddessen et al. |
| 2014/0178992 A1 | 6/2014 | Nakashima et al. |
| 2014/0221250 A1 | 8/2014 | Vasquez et al. |
| 2014/0274729 A1 | 9/2014 | Kurn et al. |
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0056609 A1 | 2/2015 | Daum et al. |
| 2015/0057625 A1 | 2/2015 | Coulthard |
| 2015/0065357 A1 | 3/2015 | Fox |
| 2015/0065393 A1 | 3/2015 | Jacobson |
| 2015/0099870 A1 | 4/2015 | Bennett et al. |
| 2015/0119293 A1 | 4/2015 | Short |
| 2015/0120265 A1 | 4/2015 | Amirav-Drory |
| 2015/0159152 A1 | 6/2015 | Allen et al. |
| 2015/0183853 A1 | 7/2015 | Sharma et al. |
| 2015/0191524 A1 | 7/2015 | Smith et al. |
| 2015/0191624 A1 | 7/2015 | Scheibel et al. |
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0240280 A1 | 8/2015 | Gibson et al. |
| 2015/0261664 A1 | 9/2015 | Goldman et al. |
| 2015/0269313 A1 | 9/2015 | Church |
| 2015/0293102 A1 | 10/2015 | Shim |
| 2015/0307875 A1 | 10/2015 | Happe et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0019341 A1 | 1/2016 | Harris et al. |
| 2016/0024138 A1 | 1/2016 | Gebeyehu et al. |
| 2016/0024576 A1 | 1/2016 | Chee et al. |
| 2016/0026753 A1 | 1/2016 | Krishnaswami et al. |
| 2016/0026758 A1 | 1/2016 | Jabara et al. |
| 2016/0032396 A1 | 2/2016 | Diehn et al. |
| 2016/0046973 A1 | 2/2016 | Efcavitch et al. |
| 2016/0046974 A1 | 2/2016 | Efcavitch et al. |
| 2016/0082472 A1 | 3/2016 | Perego et al. |
| 2016/0089651 A1 | 3/2016 | Banyai |
| 2016/0090422 A1 | 3/2016 | Reif et al. |
| 2016/0090592 A1 | 3/2016 | Banyai et al. |
| 2016/0096160 A1 | 4/2016 | Banyai et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0122800 A1 | 5/2016 | Bernick et al. |
| 2016/0152972 A1 | 6/2016 | Stapleton et al. |
| 2016/0168611 A1 | 6/2016 | Efcavitch et al. |
| 2016/0184788 A1 | 6/2016 | Hall et al. |
| 2016/0200759 A1 | 7/2016 | Srivastava et al. |
| 2016/0215283 A1 | 7/2016 | Braman et al. |
| 2016/0229884 A1 | 8/2016 | Indermuhle |
| 2016/0230175 A1 | 8/2016 | Carstens |
| 2016/0230221 A1 | 8/2016 | Bergmann et al. |
| 2016/0251651 A1 | 9/2016 | Banyai |
| 2016/0256846 A1 | 9/2016 | Smith et al. |
| 2016/0264958 A1 | 9/2016 | Toro et al. |
| 2016/0289758 A1 | 10/2016 | Akeson et al. |
| 2016/0289839 A1 | 10/2016 | Harumoto et al. |
| 2016/0297883 A1 | 10/2016 | Gallo et al. |
| 2016/0303535 A1 | 10/2016 | Banyai et al. |
| 2016/0304862 A1 | 10/2016 | Igawa et al. |
| 2016/0304946 A1 | 10/2016 | Betts et al. |
| 2016/0310426 A1 | 10/2016 | Wu |
| 2016/0310927 A1 | 10/2016 | Banyai et al. |
| 2016/0318016 A1 | 11/2016 | Hou et al. |
| 2016/0333340 A1 | 11/2016 | Wu |
| 2016/0339409 A1 | 11/2016 | Banyai |
| 2016/0340672 A1 | 11/2016 | Banyai et al. |
| 2016/0348098 A1 | 12/2016 | Stuelpnagel et al. |
| 2016/0354752 A1 | 12/2016 | Banyai et al. |
| 2016/0355880 A1 | 12/2016 | Gormley et al. |
| 2017/0017436 A1 | 1/2017 | Church |

(56) References Cited

U.S. PATENT DOCUMENTS

| | | |
|---|---|---|
| 2017/0066844 A1 | 3/2017 | Glanville |
| 2017/0067047 A1 | 3/2017 | Link et al. |
| 2017/0067099 A1 | 3/2017 | Zheng et al. |
| 2017/0073664 A1 | 3/2017 | McCafferty et al. |
| 2017/0073731 A1 | 3/2017 | Zheng et al. |
| 2017/0081660 A1 | 3/2017 | Cox |
| 2017/0081716 A1 | 3/2017 | Peck |
| 2017/0088887 A1 | 3/2017 | Makarov et al. |
| 2017/0095785 A1 | 4/2017 | Banyai et al. |
| 2017/0096706 A1 | 4/2017 | Behlke et al. |
| 2017/0114404 A1 | 4/2017 | Behlke et al. |
| 2017/0141793 A1 | 5/2017 | Strauss et al. |
| 2017/0147748 A1 | 5/2017 | Staehler et al. |
| 2017/0151546 A1 | 6/2017 | Peck et al. |
| 2017/0159044 A1 | 6/2017 | Toro et al. |
| 2017/0175110 A1 | 6/2017 | Jacobson et al. |
| 2017/0218537 A1 | 8/2017 | Olivares |
| 2017/0233764 A1 | 8/2017 | Young et al. |
| 2017/0247473 A1 | 8/2017 | Short |
| 2017/0249345 A1 | 8/2017 | Malik et al. |
| 2017/0253644 A1 | 9/2017 | Steyaert et al. |
| 2017/0298432 A1 | 10/2017 | Holt |
| 2017/0320061 A1 | 11/2017 | Venter et al. |
| 2017/0327819 A1 | 11/2017 | Banyai |
| 2017/0355984 A1 | 12/2017 | Evans et al. |
| 2017/0357752 A1 | 12/2017 | Diggans |
| 2017/0362589 A1 | 12/2017 | Banyai |
| 2018/0029001 A1 | 2/2018 | Banyai |
| 2018/0051278 A1 | 2/2018 | Cox et al. |
| 2018/0051280 A1 | 2/2018 | Gibson et al. |
| 2018/0068060 A1 | 3/2018 | Ceze et al. |
| 2018/0104664 A1 | 4/2018 | Fernandez |
| 2018/0126355 A1 | 5/2018 | Peck et al. |
| 2018/0142289 A1 | 5/2018 | Zeitoun |
| 2018/0171509 A1 | 6/2018 | Cox |
| 2018/0236425 A1 | 8/2018 | Banyai et al. |
| 2018/0253563 A1 | 9/2018 | Peck et al. |
| 2018/0264428 A1 | 9/2018 | Banyai et al. |
| 2018/0273936 A1 | 9/2018 | Cox et al. |
| 2018/0282721 A1 | 10/2018 | Cox et al. |
| 2018/0291445 A1 | 10/2018 | Betts et al. |
| 2018/0312834 A1 | 11/2018 | Cox et al. |
| 2018/0326388 A1 | 11/2018 | Banyai et al. |
| 2018/0334712 A1 | 11/2018 | Singer et al. |
| 2018/0346585 A1 | 12/2018 | Zhang et al. |
| 2018/0355351 A1 | 12/2018 | Nugent et al. |
| 2019/0060345 A1 | 2/2019 | Harrison et al. |
| 2019/0083596 A1 | 3/2019 | Orentas et al. |
| 2019/0118154 A1 | 4/2019 | Marsh et al. |
| 2019/0135926 A1 | 5/2019 | Glanville |
| 2019/0224711 A1 | 7/2019 | Demeris, Jr. |
| 2019/0240636 A1 | 8/2019 | Peck et al. |
| 2019/0314783 A1 | 10/2019 | Banyai et al. |
| 2019/0352635 A1 | 11/2019 | Toro et al. |
| 2019/0366293 A1 | 12/2019 | Banyai et al. |
| 2019/0366294 A1 | 12/2019 | Banyai et al. |
| 2020/0017907 A1 | 1/2020 | Zeitoun et al. |
| 2020/0056229 A1 | 2/2020 | Mir |
| 2020/0156037 A1 | 5/2020 | Banyai et al. |
| 2020/0181667 A1 | 6/2020 | Wu et al. |
| 2020/0222875 A1 | 7/2020 | Peck et al. |
| 2020/0283760 A1 | 9/2020 | Nugent et al. |
| 2020/0299322 A1 | 9/2020 | Indermuhle et al. |
| 2020/0299684 A1 | 9/2020 | Toro et al. |
| 2020/0308575 A1 | 10/2020 | Sato |
| 2020/0325235 A1 | 10/2020 | Tabibiazar et al. |
| 2021/0002710 A1 | 1/2021 | Gantt et al. |
| 2021/0040476 A1 | 2/2021 | Cox et al. |
| 2021/0071168 A1 | 3/2021 | Nugent et al. |
| 2021/0102192 A1 | 4/2021 | Tabibiazar et al. |
| 2021/0102195 A1 | 4/2021 | Sato et al. |
| 2021/0102198 A1 | 4/2021 | Cox et al. |
| 2021/0115594 A1 | 4/2021 | Cox et al. |
| 2021/0129108 A1 | 5/2021 | Marsh et al. |
| 2021/0142182 A1 | 5/2021 | Bramlett et al. |
| 2021/0147830 A1 | 5/2021 | Liss |
| 2021/0170356 A1 | 6/2021 | Peck et al. |
| 2021/0179724 A1 | 6/2021 | Sato et al. |
| 2021/0207197 A1 | 7/2021 | Gantt et al. |
| 2021/0332078 A1 | 10/2021 | Wu |
| 2021/0348220 A1 | 11/2021 | Zeitoun et al. |
| 2021/0355194 A1 | 11/2021 | Sato et al. |
| 2021/0395344 A1 | 12/2021 | Sato et al. |
| 2022/0032256 A1 | 2/2022 | Lackey et al. |
| 2022/0064206 A1 | 3/2022 | Fernandez et al. |
| 2022/0064313 A1 | 3/2022 | Sato et al. |
| 2022/0064628 A1 | 3/2022 | Toro et al. |
| 2022/0106586 A1 | 4/2022 | Nugent et al. |
| 2022/0106590 A1 | 4/2022 | Arbiza et al. |
| 2022/0135690 A1 | 5/2022 | Sato et al. |
| 2022/0135965 A1 | 5/2022 | Gantt et al. |
| 2022/0138354 A1 | 5/2022 | Peck |
| 2022/0145289 A1 | 5/2022 | Lackey et al. |
| 2022/0206001 A1 | 6/2022 | Sato |
| 2022/0243195 A1 | 8/2022 | Nugent et al. |
| 2022/0246236 A1 | 8/2022 | Amirav-Drory |
| 2022/0259319 A1 | 8/2022 | Sato et al. |
| 2022/0259638 A1 | 8/2022 | Brown |
| 2022/0277808 A1 | 9/2022 | Arbiza et al. |
| 2022/0281989 A1 | 9/2022 | Glanville |
| 2022/0307010 A1 | 9/2022 | Sato et al. |
| 2022/0315971 A1 | 10/2022 | Wu et al. |
| 2022/0323924 A1 | 10/2022 | Lackey et al. |
| 2022/0325276 A2 | 10/2022 | Banyai et al. |
| 2022/0325278 A1 | 10/2022 | Nugent et al. |
| 2022/0348659 A1 | 11/2022 | Sato et al. |
| 2022/0356463 A1 | 11/2022 | Shen et al. |
| 2022/0356468 A1 | 11/2022 | Sato et al. |
| 2022/0411784 A1 | 12/2022 | Sato et al. |
| 2023/0002478 A1 | 1/2023 | Sato et al. |
| 2023/0054232 A1 | 2/2023 | Peck |
| 2023/0086062 A1 | 3/2023 | Banyai et al. |
| 2023/0096464 A1 | 3/2023 | Sato |

FOREIGN PATENT DOCUMENTS

| | | |
|---|---|---|
| CA | 2720587 A1 | 10/2009 |
| CN | 1771336 A | 5/2006 |
| CN | 101277758 A | 10/2008 |
| CN | 102159726 A | 8/2011 |
| CN | 103003431 A | 3/2013 |
| CN | 103907117 A | 7/2014 |
| CN | 104520864 A | 4/2015 |
| CN | 104562213 A | 4/2015 |
| CN | 104734848 A | 6/2015 |
| CN | 104974929 A | 10/2015 |
| CN | 204714802 U | 10/2015 |
| CN | 105637097 A | 6/2016 |
| DE | 10260805 A1 | 7/2004 |
| EA | 201890763 A1 | 8/2018 |
| EP | 0090789 A1 | 10/1983 |
| EP | 0126621 B1 | 8/1990 |
| EP | 0753057 A1 | 1/1997 |
| EP | 1314783 A1 | 5/2003 |
| EP | 1363125 A2 | 11/2003 |
| EP | 1546387 A2 | 6/2005 |
| EP | 1153127 B1 | 7/2006 |
| EP | 1728860 A1 | 12/2006 |
| EP | 1072010 B1 | 4/2010 |
| EP | 2175021 A2 | 4/2010 |
| EP | 2330216 A1 | 6/2011 |
| EP | 1343802 B1 | 5/2012 |
| EP | 2504449 A1 | 10/2012 |
| EP | 2751729 A1 | 7/2014 |
| EP | 2872629 A1 | 5/2015 |
| EP | 2928500 A1 | 10/2015 |
| EP | 2971034 A1 | 1/2016 |
| EP | 3030682 A2 | 6/2016 |
| EP | 3044228 A4 | 4/2017 |
| EP | 2994509 B1 | 6/2017 |
| EP | 3204518 A1 | 8/2017 |
| JP | H07505530 A | 6/1995 |
| JP | 2001518086 A | 10/2001 |
| JP | 2002511276 A | 4/2002 |

(56) References Cited

FOREIGN PATENT DOCUMENTS

| | | |
|---|---|---|
| JP | 2002536977 A | 11/2002 |
| JP | 2002538790 A | 11/2002 |
| JP | 2003522119 A | 7/2003 |
| JP | 2004521628 A | 7/2004 |
| JP | 2004268394 A | 9/2004 |
| JP | 2006503586 A | 2/2006 |
| JP | 2006238724 A | 9/2006 |
| JP | 2007314746 A | 12/2007 |
| JP | 2008505642 A | 2/2008 |
| JP | 2008097189 A | 4/2008 |
| JP | 2008523786 A | 7/2008 |
| JP | 2008214343 A | 9/2008 |
| JP | 2009294195 A | 12/2009 |
| JP | 2010248084 A | 11/2010 |
| JP | 2012507513 A | 3/2012 |
| JP | 2015521472 A | 7/2015 |
| JP | 2016527313 A | 9/2016 |
| KR | 101339064 B1 | 1/2014 |
| WO | WO-9015070 A1 | 12/1990 |
| WO | WO-9210092 A1 | 6/1992 |
| WO | WO-9210588 A1 | 6/1992 |
| WO | WO-9309668 A1 | 5/1993 |
| WO | WO-9320242 A1 | 10/1993 |
| WO | WO-9525116 A1 | 9/1995 |
| WO | WO-9526397 A1 | 10/1995 |
| WO | WO-9615861 A1 | 5/1996 |
| WO | WO-9710365 A1 | 3/1997 |
| WO | WO-9822541 A2 | 5/1998 |
| WO | WO-9841531 A2 | 9/1998 |
| WO | WO-9942813 A1 | 8/1999 |
| WO | WO-9953101 A1 | 10/1999 |
| WO | WO-0013017 A2 | 3/2000 |
| WO | WO-0018957 A1 | 4/2000 |
| WO | WO-0042559 A1 | 7/2000 |
| WO | WO-0042560 A2 | 7/2000 |
| WO | WO-0042561 A2 | 7/2000 |
| WO | WO-0049142 A1 | 8/2000 |
| WO | WO-0053617 A1 | 9/2000 |
| WO | WO-0156216 A2 | 8/2001 |
| WO | WO-0210443 A1 | 2/2002 |
| WO | WO-0156216 A3 | 3/2002 |
| WO | WO-0220537 A2 | 3/2002 |
| WO | WO-0224597 A2 | 3/2002 |
| WO | WO-0227638 A1 | 4/2002 |
| WO | WO-0233669 A1 | 4/2002 |
| WO | WO-02072791 A2 | 9/2002 |
| WO | WO-02072864 A2 | 9/2002 |
| WO | WO-03040410 A1 | 5/2003 |
| WO | WO-03046223 A1 | 6/2003 |
| WO | WO-03054232 A2 | 7/2003 |
| WO | WO-03060084 A2 | 7/2003 |
| WO | WO-03064026 A1 | 8/2003 |
| WO | WO-03064027 A2 | 8/2003 |
| WO | WO-03064699 A2 | 8/2003 |
| WO | WO-03065038 A2 | 8/2003 |
| WO | WO-03066212 A2 | 8/2003 |
| WO | WO-03089605 A2 | 10/2003 |
| WO | WO-03093504 A1 | 11/2003 |
| WO | WO-03100012 A2 | 12/2003 |
| WO | WO-2004024886 A2 | 3/2004 |
| WO | WO-2004029220 A2 | 4/2004 |
| WO | WO-2004029586 A1 | 4/2004 |
| WO | WO-2004031351 A2 | 4/2004 |
| WO | WO-2004031399 A2 | 4/2004 |
| WO | WO-2004039953 A2 | 5/2004 |
| WO | WO-2004059556 A2 | 7/2004 |
| WO | WO-03060084 A3 | 8/2004 |
| WO | WO-2005014850 A2 | 2/2005 |
| WO | WO-2005051970 A2 | 6/2005 |
| WO | WO-2005059096 A2 | 6/2005 |
| WO | WO-2005059097 A2 | 6/2005 |
| WO | WO-2005093092 A2 | 10/2005 |
| WO | WO-2006023144 | 3/2006 |
| WO | WO-2006044956 A1 | 4/2006 |
| WO | WO-2006076679 A1 | 7/2006 |
| WO | WO-2006116476 A1 | 11/2006 |
| WO | WO-2007073171 A2 | 6/2007 |
| WO | WO-2007109221 A2 | 9/2007 |
| WO | WO-2007118214 A2 | 10/2007 |
| WO | WO-2007120627 A2 | 10/2007 |
| WO | WO-2007137242 A2 | 11/2007 |
| WO | WO-2008003116 A2 | 1/2008 |
| WO | WO-2008006078 A2 | 1/2008 |
| WO | WO-2008027558 A2 | 3/2008 |
| WO | WO-2008045380 | 4/2008 |
| WO | WO-2008054543 A2 | 5/2008 |
| WO | WO-2008063134 A1 | 5/2008 |
| WO | WO-2008063135 A1 | 5/2008 |
| WO | WO-2008068280 A1 | 6/2008 |
| WO | WO-2008103474 A1 | 8/2008 |
| WO | WO-2008109176 A2 | 9/2008 |
| WO | WO-2009132876 A1 | 11/2009 |
| WO | WO-2009126290 A3 | 12/2009 |
| WO | WO-2010001251 A2 | 1/2010 |
| WO | WO-2010025310 A2 | 3/2010 |
| WO | WO-2010025566 A1 | 3/2010 |
| WO | WO-2010027512 A2 | 3/2010 |
| WO | WO-2010053443 A1 | 5/2010 |
| WO | WO-2010089412 A1 | 8/2010 |
| WO | WO-2010141249 A2 | 12/2010 |
| WO | WO-2010141433 A2 | 12/2010 |
| WO | WO-2011020529 A2 | 2/2011 |
| WO | WO-2010141433 A3 | 4/2011 |
| WO | WO-2011053957 A2 | 5/2011 |
| WO | WO-2011056644 A2 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2011103468 A2 | 8/2011 |
| WO | WO-2011109031 A1 | 9/2011 |
| WO | WO-2011143556 A1 | 11/2011 |
| WO | WO-2011150168 A1 | 12/2011 |
| WO | WO-2011161413 A2 | 12/2011 |
| WO | WO-2012013913 A1 | 2/2012 |
| WO | WO-2012061832 A1 | 5/2012 |
| WO | WO-2012078312 A2 | 6/2012 |
| WO | WO-2012149171 A1 | 11/2012 |
| WO | WO-2012154201 A1 | 11/2012 |
| WO | WO-2013010062 A2 | 1/2013 |
| WO | WO-2013030827 A1 | 3/2013 |
| WO | WO-2013032850 A2 | 3/2013 |
| WO | WO-2013036668 A1 | 3/2013 |
| WO | WO-2013049227 A2 | 4/2013 |
| WO | WO-2013101896 A1 | 7/2013 |
| WO | WO-2013134881 A1 | 9/2013 |
| WO | WO-2013154770 A1 | 10/2013 |
| WO | WO-2013170168 A1 | 11/2013 |
| WO | WO-2013177220 A1 | 11/2013 |
| WO | WO-2014004393 A1 | 1/2014 |
| WO | WO-2014008447 A1 | 1/2014 |
| WO | WO-2014021938 A1 | 2/2014 |
| WO | WO-2014035693 A2 | 3/2014 |
| WO | WO-2014088693 A1 | 6/2014 |
| WO | WO-2014089160 A1 | 6/2014 |
| WO | WO-2014093330 A1 | 6/2014 |
| WO | WO-2014093694 A1 | 6/2014 |
| WO | WO-2014151117 A1 | 9/2014 |
| WO | WO-2014151696 A1 | 9/2014 |
| WO | WO-2014160004 A1 | 10/2014 |
| WO | WO-2014160059 A1 | 10/2014 |
| WO | WO-2014206304 A1 | 12/2014 |
| WO | WO-2015017527 A2 | 2/2015 |
| WO | WO-2015021080 A2 | 2/2015 |
| WO | WO-2015021280 A1 | 2/2015 |
| WO | WO-2015031689 A1 | 3/2015 |
| WO | WO-2015040075 A1 | 3/2015 |
| WO | WO-2015054292 A1 | 4/2015 |
| WO | WO-2015066174 A1 | 5/2015 |
| WO | WO-2015081114 A2 | 6/2015 |
| WO | WO-2015081142 A1 | 6/2015 |
| WO | WO-2015081440 A1 | 6/2015 |
| WO | WO-2015090879 A1 | 6/2015 |
| WO | WO-2015095404 A2 | 6/2015 |

(56) References Cited

FOREIGN PATENT DOCUMENTS

| | | |
|---|---|---|
| WO | WO-2015120403 A1 | 8/2015 |
| WO | WO-2015136072 A1 | 9/2015 |
| WO | WO-2015160004 A1 | 10/2015 |
| WO | WO-2015175832 A1 | 11/2015 |
| WO | WO-2016007604 A1 | 1/2016 |
| WO | WO-2016011080 A2 | 1/2016 |
| WO | WO-2016022557 A1 | 2/2016 |
| WO | WO-2016053883 A1 | 4/2016 |
| WO | WO-2016055956 A1 | 4/2016 |
| WO | WO-2016065056 A1 | 4/2016 |
| WO | WO-2016126882 A1 | 8/2016 |
| WO | WO-2016126987 A1 | 8/2016 |
| WO | WO-2016130868 A2 | 8/2016 |
| WO | WO-2016161244 A2 | 10/2016 |
| WO | WO-2016162127 A1 | 10/2016 |
| WO | WO-2016164779 A1 | 10/2016 |
| WO | WO-2016172377 A1 | 10/2016 |
| WO | WO-2016173719 A1 | 11/2016 |
| WO | WO-2016183100 A1 | 11/2016 |
| WO | WO-2017049231 A1 | 3/2017 |
| WO | WO-2017053450 A1 | 3/2017 |
| WO | WO-2017059399 A1 | 4/2017 |
| WO | WO-2017095958 A1 | 6/2017 |
| WO | WO-2017100441 A1 | 6/2017 |
| WO | WO-2017118761 A1 | 7/2017 |
| WO | WO-2017158103 A1 | 9/2017 |
| WO | WO-2017214574 A1 | 12/2017 |
| WO | WO-2018026920 A1 | 2/2018 |
| WO | WO-2018038772 A1 | 3/2018 |
| WO | WO-2018057526 A2 | 3/2018 |
| WO | WO-2018094263 A1 | 5/2018 |
| WO | WO-2018112426 A1 | 6/2018 |
| WO | WO-2018119246 A1 | 6/2018 |
| WO | WO-2018156792 A1 | 8/2018 |
| WO | WO-2018170164 A1 | 9/2018 |
| WO | WO-2018170169 A1 | 9/2018 |
| WO | WO-2018170559 A1 | 9/2018 |
| WO | WO-2018200380 A1 | 11/2018 |
| WO | WO-2018231872 A1 | 12/2018 |
| WO | WO-2019014781 A1 | 1/2019 |
| WO | WO-2019051501 A1 | 3/2019 |
| WO | WO-2019079769 A1 | 4/2019 |
| WO | WO-2019084500 A1 | 5/2019 |
| WO | WO-2019136175 A1 | 7/2019 |
| WO | WO-2019222706 A1 | 11/2019 |
| WO | WO-2020139871 A1 | 7/2020 |
| WO | WO-2020176362 A1 | 9/2020 |
| WO | WO-2020176678 A1 | 9/2020 |
| WO | WO-2020176680 A1 | 9/2020 |
| WO | WO-2020257612 A1 | 12/2020 |
| WO | WO-2021046655 A1 | 3/2021 |
| WO | WO-2021119193 A2 | 6/2021 |
| WO | WO-2022010934 A2 | 1/2022 |
| WO | WO-2022046797 A1 | 3/2022 |
| WO | WO-2022046944 A2 | 3/2022 |
| WO | WO-2022047076 A1 | 3/2022 |
| WO | WO-2022076326 A1 | 4/2022 |
| WO | WO-2022086866 A1 | 4/2022 |
| WO | WO-2022087293 A1 | 4/2022 |
| WO | WO-2022098662 A2 | 5/2022 |
| WO | WO-2022159620 A1 | 7/2022 |
| WO | WO-2022178137 A1 | 8/2022 |
| WO | WO-2022204309 A1 | 9/2022 |
| WO | WO-2022204316 A2 | 9/2022 |
| WO | WO-2022217004 A1 | 10/2022 |
| WO | WO-2022235579 A1 | 11/2022 |
| WO | WO-2022235584 A1 | 11/2022 |
| WO | WO-2022271884 A2 | 12/2022 |
| WO | WO-2023023183 A2 | 2/2023 |
| WO | WO-2023023190 A2 | 2/2023 |
| WO | WO-2023023285 A2 | 2/2023 |

OTHER PUBLICATIONS

Alexeyev et al.: "Gene synthesis, bacterial expression and purification of the Rickettsia prowazekii ATP/ADP translocase", Biochimica et Biophysics Acta, 1419:299-306, 1999.

Al-Housseiny et al.: Control of interfacial instabilities using flow geometry Nature Physics, 8:747-750, 2012.

Amblard et al.: "A magnetic manipulator for studying local rheology and micromechanical properties of biological systems", Rev. Sci. Instrum., 67(3):18-827, 1996.

Andoni and Indyk, Near-Optimal Hashing Algorithms for Approximate Nearest Neighbor in High Dimensions, Communications of the ACM, 51(1):117-122, 2008.

Arand et al.: Structure of Rhodococcus erythropolis limonene-1,2-epoxide hydrolase reveals a novel active site. EMBO J. 22:2583-2592 (2003).

Arkles et al.: The Role of Polarity in the Structure of Silanes Employed in Surface Modification. Silanes and Other Coupling Agents. 5:51-64, 2009.

Arkles. Hydrophobicity, Hydrophilicity Reprinted with permission from the Oct. 2006 issue of Paint & Coatings Industry magazine, Retrieved on Mar. 19, 2016, 10 pages.

Assembly manual for the POSaM: The ISB Piezoelelctric Oligonucleotide Synthesizer and Microarrayer, The Institute for Systems Biology, May 28, 2004 (50 pages).

Assi et al.: Massive-parallel adhesion and reactivity-measurements using simple and inexpensive magnetic tweezers. J. Appl. Phys. 92(9):5584-5586 (2002).

ATDBio, "Nucleic Acid Structure," Nucleic Acids Book, 9 pages, published on Jan. 22, 2005. from: http://www.atdbio.com/content/5/Nucleic-acid-structure.

ATDBio, "Solid-Phase Oligonucleotide Synthesis," Nucleic Acids Book, 20 pages, Published on Jul. 31, 2011. from: http://www.atdbio.com/content/17/Solid-phase-oligonucleotide-synthesis.

Au et al.: Gene synthesis by a LCR-based approach: high level production of Leptin-L54 using synthetic gene in *Escherichia coli*. Biochemical and Biophysical Research Communications 248:200-203 (1998).

Baedeker et al.: Overexpression of a designed 2.2kb gene of eukaryotic phenylalanine ammonialyase in *Escherichia coli•*. FEBS Letters, 457:57-60, 1999.

Barbee et al.: Magnetic Assembly of High-Density DNA Arrays for Genomic Analyses. Anal Chem. 80(6):2149-2154, 2008.

Barton et al.: A desk electrohydrodynamic jet printing system. Mechatronics, 20:611-616, 2010.

Beaucage et al.: Advances in the synthesis of oligonucleotides by the phosphoramidite approach. Tetrahedron. 48:2223-2311, 1992.

Beaucage et al.: Deoxynucleoside phosphoramidites—A new class of key intermediates for deoxypolynucleotide synthesis. Tetrahedron Lett. 22(20):1859-1862, 1981.

Beaucage et al.: "The Chemical synthesis of DNA/RNA" Chapter 2 in: Encyclopedia of Cell Biology, 1:36-53, 2016.

Beaulieu et al.: "PCR candidate region mismatch scanning adaptation to quantitative, high-throughput genotyping", Nucleic Acids Research, 29(5):1114-1124, 2001.

Beigelman et al.: Base-modified phosphoramidite analogs of pyrimidine ribonucleosides for RNA structure-activity studies. Methods Enzymol. 317:39-65, 2000.

Bethge et al.: "Reverse synthesis and 3'-modification of RNA." Jan. 1, 2011, pp. 64-64, XP055353420. Retrieved from the Internet: URL:http://www.is3na.org/assets/events/Category%202-Medicinal%20Chemistry%20of%20Oligonucleotides%20%2864-108%29.pdf.

Binkowski et al.: Correcting errors in synthetic DNA through consensus shuffling. Nucleic Acids Research, 33(6):e55, 8 pages, 2005.

Biswas et al.: "Identification and characterization of a thermostable MutS homolog from Thennus aquaticus", The Journal of Biological Chemistry, 271(9):5040-5048, 1996.

Biswas et al.: "Interaction of MutS protein with the major and minor grooves of a heteroduplex DNA", The Journal of Biological Chemistry, 272(20):13355-13364, 1997.

Bjornson et al.: "Differential and simultaneous adenosine Di- and Triphosphate binding by MutS", The Journal of Biological Chemistry, 278(20):18557-18562, 2003.

(56) References Cited

OTHER PUBLICATIONS

Blanchard et al.: "High-Density Oligonucleotide Arrays," Biosensors & Bioelectronics, 11(6/7):687-690, 1996.
Blanchard et al.: Genetic Engineering, Principles and Methods, vol. 20, Ed. J. Sedlow, New York: Plenum Press, p. 111-124, 1979.
Blawat et al.: Forward error correction for DNA data storage. Procedia Computer Science, 80:1011-1022, 2016.
Bonini and Mondino. Adoptive T-cell therapy for cancer: The era of engineered T cells. European Journal of Immunology, 45:2457-2469, 2015.
Bornholt et al.: A DNA-Based Archival Storage System, in International Conference on Architectural Support for Programming Languages and Operating Systems (ASPLOS), Apr. 2-6, 2016, Atlanta, GA, 2016, 637-649.
Borovkov et al.: High-quality gene assembly directly from unpurified mixtures of microassay-synthesized oligonucleotides. Nucleic Acid Research, 38(19):e180, 10 pages, 2010.
Brunet. Aims and methods of biosteganography. Journal of Biotechnology, 226:56-64, 2016.
Buermans et al.: "Next Generation sequencing technology: Advances and applications," Biochimica et Biophysica Acta (BBA)—Molecular Basis of Disease, 1842:1931-1941, 2014.
Butler et al.: In situ synthesis of oligonucleotide arrays by using surface tension. J Am Chem Soc. 123(37):8887-94, 2001.
Calvert. Lithographically patterned self-assembled films. In: Organic Thin Films and Surfaces: Directions for the Nineties, vol. 20, p. 109, ed. by Abraham Ulman, San Diego: Academic Press, 1995.
Cardelli, Two-Domain DNA Strand Displacement, Electron. Proc. Theor. Comput. Sci., 26:47-61, 2010.
Carlson. Time for New DNA Synthesis and Sequencing Cost Curves. 2014. [Online]. Available: http://www.synthesis.cc/synthesis/2014/02/time_for_new_cost_curves_2014. 10 pages.
Carr et al.: Protein-mediated error correction for de novo DNA synthesis. Nucleic Acids Res. 32(20):e162, 9 pages, 2004.
Carter and Friedman, DNA synthesis and Biosecurity: Lessons learned and options for the future. J. Craig Venter Institute, La Jolla, CA, 28 pages, Oct. 2015.
Caruthers. Chemical synthesis of deoxyoligonucleotides by the phosphoramidite method. In Methods in Enzymology, Chapter 15, 154:287-313, 1987.
Caruthers. The Chemical Synthesis of DNA/RNA: Our Gift to Science. J. Biol. Chem., 288(2):1420-1427, 2013.
Caruthers. Gene synthesis machines: DNA chemistry and its uses. Science 230(4723):281-285 (1985).
Casmiro et al.: "PCR-based gene synthesis and protein NMR spectroscopy", Structure, 5(11):1407-1412, 1997.
CeGaT. Tech Note available at https://www.cegat.de/web/wp-content/uploads/2018/06/Twist-Exome-Tech-Note.pdf (4 pgs.) (2018).
Cello et al.: Chemical synthesis of poliovirus cDNA: generation of infectious virus in the absence of natural template. Science. 297(5583):1016-8, 2000.
Chalmers et al.: Scaling up the ligase chain reaction-based approach to gene synthesis. Biotechniques. 30(2):249-52, 2001.
Chan et al.: Natural and engineered nicking endonucleases—from cleavage mechanism to engineering of strand-specificity. Nucleic Acids Res. 39(1):1-18, 2011.
Chen et al.: Programmable chemical controllers made from DNA, Nat. Nanotechnol., 8(10):755-762, 2013.
Chen et al.: Chemical modification of gene silencing oligonucleotides for drug discovery and development. Drug Discov Today. 10(8):587-93 2005.
Cheng et al.: High throughput parallel synthesis of oligonucleotides with 1536 channel synthesizer. Nucleic Acids Res. 30(18):e93, 2002.
Chilamakuri et al.: Performance comparison of four exome capture systems for deep sequencing. BMC Genomics 15(1):449 (2014).
Cho et al.: Capillary passive valve in microfluidic systems. NSTI-Nanotech. 2004; 1:263-266.
Chrisey et al.: Fabrication of patterned DNA surfaces Nucleic Acids Research, 24(15):3040-3047 (1996).
Chung et al.: One-step preparation of competent *Escherichia coli*: Transformation and storage of bacterial cells in the same solution. Proc Natl Acad Sci U S A. Apr. 1989;86(7):2172-2175.
Church et al.: Next-generation digital information storage in DNA. Science, 337:6102, 1628-1629, 2012.
Cleary et al.: Production of complex nucleic acid libraries using highly parallel in situ oligonucleotide synthesis. Nat Methods 1(3):241-248 (2004).
Cohen et al.: Human population: The next half century. Science, 302:1172-1175, 2003.
Crick. On protein synthesis. Symp Soc Exp Biol12:138-163,1958.
Cruse et al.: Atlas of Immunology, Third Edition. Boca Raton:CRC Press (pp. 282-283) (2010).
Cutler et al.: High-throughput variation detection and genotyping using microarrays. Genome Research, vol. 11, 1913-19 (2001).
Dahl et al.: Circle-to-circle amplification for precise and sensitive DNA analysis. Proc Natl Acad Sci U S A. Mar. 30, 2004;101(13):4548-53. Epub Mar. 15, 2004.
De Mesmaeker et al.: Backbone modifications in oligonucleotides and peptide nucleic acid systems. CurrOpin Struct Biol. Jun. 1995;5(3):343-55.
De Silva et al.: New Trends of Digital Data Storage in DNA. BioMed Res Int. 2016:8072463 (2016).
Deamer et al.: "Characterization of nucleic acids by nanopore analysis", Ace. Cham. Res., vol. 35, No. 10, 817-825 (2002).
Deaven. The Human Genome Project: Recombinant clones for mapping and sequencing DNA. Los Alamos Science, 20:218-249, 1992.
Deng et al.: Targeted bisulfite sequencing reveals changes in DNA methylation associated with nuclear reprogramming Nature Biotechnology, 27:352-360 (2009).
Dietrich et al.: "Gene assembly based on blunt-ended double-stranded DNA-modules", Biotechnology Techniques, vol. 12, No. 1, 49-54 (Jan. 1998).
Dillon et al.: Exome sequencing has higher diagnostic yield compared to simulated disease-specific panels in children with suspected monogenic disorders. Eur J Hum Genet 26(5):644-651 (2018).
Dormitzer et al.: Synthetic generation of influenza vaccine viruses for rapid response to pandemics. Sci Translational Medicine, 5(185):185ra68, 14 pages, 2013.
Doudna et al.: Genome editing. The new frontier of genome engineering with CRISPR-Cas9. Science 346(6213):1258096-1-1258096-9, 2014.
Douthwaite et al.: Affinity maturation of a novel antagonistic human monoclonal antibody with a long VH CDR3 targeting the Class A GPCR formyl-peptide receptor 1; mAbs, vol. 7, Iss. 1, pp. 152-166 (Jan. 1, 2015).
Dower et al.: High efficiency transformation of *E. coli* by high voltage electroporation. Nucleic Acids Res. 16(13):6127-45 (1988).
Dressman et al.: Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac et al.: Human genome sequencing using unchained base reads on self-assembling DNA nanoarrays. Science. Jan. 1, 2010;327(5961):78-81. doi: 10.1126/science.1181498. Epub Nov. 5, 2009.
Droege and Hill, The Genome Sequencer FLXTM System—Longer reads, more applications, straight forward bioinformatics and more complete data sets Journal of Biotechnology, 136:3-10, 2008.
Duffy et al.: Rapid Prototyping of Microfluidic Systems in Poly(dimethylsiloxane). Anal Chem. Dec. 1, 1998;70(23):4974-84. doi: 10.1021/ac980656z.
Duggan et al.: Expression profiling using cDNA microarrays. Nat Genet. Jan. 1999;21(1 Suppl):10-4.
Dvorsky. Living Bacteria Can Now Store Data. GIZMODO internet publication. Retrieved from https://gizmodo.com/living-bacteria-can-now-store-data-1781773517 (4 pgs) (Jun. 10, 2016).
Eadie et al.: Guanine modification during chemical DNA synthesis. Nucleic Acids Res. Oct. 26, 1987;15(20):8333-49.
Eisen. A phylogenomic study of the MutS family of proteins. Nucleic Acids Research, vol. 26, No. 18, 4291-4300 (1998).

(56) References Cited

OTHER PUBLICATIONS

Ellis et al.: DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer et al.: Biocompatible artificial DNA linker that is read through by DNA polymerases and is functional in *Escherichia coli*. Proc Natl Acad Sci U S A. Jul. 12, 2011;108(28):11338-43. doi: 10.1073/pnas.1101519108. Epub Jun. 27, 2011.
Elsik et al.: The Genome sequence of taurine cattle: A window of ruminant biology and evolution. Science, 324:522-528, 2009.
Elsner et al.: 172 nm excimer VUV-triggered photodegradation and micropatterning of aminosilane films, Thin Solid Films, 517:6772-6776 (2009).
Engler et al.: A one pot, one step, precision cloning method with high throughput capability. PLoS One. 2008;3(11):e3647. doi: 10.1371/journal.pone.0003647. Epub Nov. 5, 2008.
Engler et al.: Golden gate shuffling: a one-pot DNA shuffling method based on type IIs restriction enzymes. PLoS One. 2009;4(5):e5553. doi: 10.1371/journal.pone.0005553. Epub May 14, 2009.
Erlich and Zielinski. DNA fountain enables a robust and efficient storage architecture. Science, 355(6328):950-054, 2017.
Eroshenko et al.: Gene Assembly from Chip-Synthesized Oligonucleotides; Current Protocols in Chemical biology 4: 1-17 (2012).
European Patent Application No. 12827479.2 Extended European Search Report dated May 18, 2015.
European Patent Application No. 12827479.2 Partial European Search Report dated Jan. 29, 2015.
European Patent Application No. 14834665.3 Communication dated Jan. 16, 2018.
European Patent Application No. 14834665.3 extended European Search Report dated Apr. 28, 2017.
European Patent Application No. 14834665.3 Further Examination Report dated Nov. 28, 2018.
European Patent Application No. 14834665.3 Office Action dated May 2, 2018.
European Patent Application No. 16847497.1 Extended European Search Report dated Jan. 9, 2019.
European Patent Application No. 16871446.7 European Search Report dated Apr. 10, 2019.
Evans et al.: DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided).
Fahy et al.: Self-sustained sequence replication (3SR): an isothermal transcription-based amplification system alternative to PCR. PCR Methods Appl. Aug. 1991;1(1):25-33.
Fedoryak et al.: Brominated hydroxyquinoline as a photolabile protecting group with sensitivity to multiphoton excitation. Org. Lett., vol. 4, No. 2 , 3419-3422 (2002).
Ferretti et al.: Total synthesis of a gene for bovine rhodopsin. PNAS, 83:599-603 (1986).
Finger et al.: The wonders of Flap Endonucleases: Structure, function, mechanism and regulation. Subcell Biochem., 62:301-326, 2012.
Fodor et al.: Light-directed, spatially addressable parallel chemical synthesis. Science. 251(4995):767-773 (1991).
Fogg et al.: Structural basis for uracil recognition by archaeal family B DNA polymerases. Nature Structural Biology, 9(12):922-927, 2002.
Foldesi et al.: The synthesis of deuterionucleosides. Nucleosides Nucleotides Nucleic Acids. Oct.-Dec. 2000;19(10-12):1615-56.
Frandsen et al.: Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.
Frandsen. The USER Friendly technology. USER cloning. Oct. 7, 2010, 2 pages. http://www.rasmusfrandsen.dk/user_cloning.htm.
Fullwood et al.: Next-generation DNA sequencing of paired-end tags [PET] for transcriptome and genome analysis Genome Research, 19:521-532, 2009.
Galka et al.: QuickLib, a method for building fully synthetic plasmid libraries by seamless cloning of degenerate oligonucleotides. PLOS One, 12, e0175146:1-9 (2017).
Galka et al.: QuickLib, a method for building fully synthetic plasmid libraries by seamless cloning of degenerate oligonucleotides. PLOS One, 12, e0175146:S1 figure (2017).
Galka et al.: QuickLib, a method for building fully synthetic plasmid libraries by seamless cloning of degenerate oligonucleotides. PLOS One, 12, e0175146:S1 Table (2017).
Galka et al.: QuickLib, a method for building fully synthetic plasmid libraries by seamless cloning of degenerate oligonucleotides. PLOS One, 12, e0175146:S2 figure (2017).
Galneder et al.: Microelectrophoresis of a bilayer-coated silica bead in an optical trap: application to enzymology. Biophysical Journal, vol. 80, No. 5, 2298-2309 (May 2001).
Gao et al.: A method for the generation of combinatorial antibody libraries using pIX phage display. PNAS 99(20):12612-12616 (2002).
Gao et al.: A flexible light-directed DNA chip synthesis gated by deprotection using solution photogenerated acids. Nucleic Acids Res. Nov. 15, 2001;29(22):4744-50.
Gao et al.: Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj et al.: Graphene as a subnanometre trans-electrode membrane. Nature. Sep. 9, 2010;467(7312):190-3. doi: 10.1038/nature09379.
Garbow et al.: Optical tweezing electrophoresisof isolated, highly charged colloidal spheres. Colloids and Surfaces A: Physiochem. Eng. Aspects, vol. 195, 227-241 (2001).
GeneArt Seamless Cloning and Assembly Kits. Life Technologies Synthetic Biology. 8 pages, available online Jun. 15, 2012.
Genomics 101. An Introduction to the Genomic Workflow. 2016 edition, 64 pages. Available at: http://www.frontlinegenomics.com/magazine/6757/genomics-101/.
Geu-Flores et al.: USER fusion: a rapid and efficient method for simultaneous fusion and cloning of multiple PCR products. Nucleic Acids Res. 2007;35(7):e55. Epub Mar. 27, 2007.
Gibson Assembly. Product Listing. Application Overview. 2 pages, available online Dec. 16, 2014.
Gibson et al.: Creation of a Bacterial Cell Controlled by a Chemically Synthesized Genome. Science 329(5989):52-56 (2010).
Gibson et al.: Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Goldfeder et al.: Medical implications of technical accuracy in genome sequencing. Genome Med 8(1):24 (2016).
Goldman et al.: Towards practical, high-capacity, low-maintenance information storage in synthesized DNA, Nature, 494(7435):77-80, 2013.
Gosse et al.: Magnetic tweezers: micromanipulation and force measurement at the molecular level. Biophysical Journal, vol. 8, 3314-3329 (Jun. 2002).
Grass et al.: Robust chemical preservation of digital information on DNA in silica with error-correcting codes, Angew. Chemie—Int. Ed., 54(8):2552-2555, 2015.
Greagg et al.: A read-ahead function in archaeal DNA polymerases detects promutagenic template-strand uracil. Proc. Nat. Acad. Sci. USA, 96:9045-9050, 1999.
Grovenor. Microelectronic materials. Graduate Student Series in Materials Science and Engineering. Bristol, England: Adam Hilger, 1989; p. 113-123.
Gu et al.: Depletion of abundant sequences by hybridization (DASH): using Cas9 to remove unwanted high-abundance species in sequencing libraries and molecular counting applications. Genome Biology, 17:41, 13 pages, 2016.
Haber et al.: Magnetic tweezers for DNA micromanipulation, Rev. Sci. Instrum., vol. 71, No. 12, 4561-4570 (Dec. 2000).
Han et al.: Linking T-cell receptor sequence to functional phenotype at the single-cell level. Nat Biotechnol 32(7):684-692 (2014).

(56) References Cited

OTHER PUBLICATIONS

Hanahan and Cold Spring Harbor Laboratory, Studies on transformation of *Escherichia coli* with plasmids J. Mol. Biol. 166:557-580 (1983).
Hanahan et al.: Plasmid transformation of *Escherichia coli* and other bacteria. Methods Enzymol, vol. 204, p. 63-113 (1991).
Harada et al.: Unexpected substrate specificity of T4 DNA ligase revealed by in vitro selection. Nucleic Acids Res. May 25, 1993;21(10):2287-91.
Heckers et al.: Error analysis of chemically synthesized polynucleotides. BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al.: DNAWorks: an automated method for designing oligonucleotides for PCR-based gene synthesis. Nucleic Acids Research, vol. 30, No. 10, e43, 7 pages (2002).
Hosu et al.: Magnetic tweezers for intracellular applications. Rev. Sci. Instrum., vol. 74, No. 9, 4158-4163 (Sep. 2003).
Huang et al.: Three-dimensional cellular deformation analysis with a two-photon magnetic manipulator workstation. Biophysical Journal, vol. 82, No. 4, 2211•2223 (Apr. 2002).
Hughes et al.: Expression profiling using microarrays fabricated by an ink-jet oligonucleotide synthesizer Nat Biotech 4:342-347 (2001).
Hughes et al.: Principles of early drug discovery. Br J Pharmacol 162(2):1239-1249, 2011.
Hutchison et al.: Cell-free cloning using phi29 DNA polymerase. Proc Natl Acad Sci U S A. Nov. 29, 2005;102(48):17332-6. Epub Nov. 14, 2005.
Imgur: The magic of the internet. Uploaded May 10, 2012, 2 pages, retrieved from: https://imgur.com/mEWuW.
In-Fusion Cloning: Accuracy, Not Background. Cloning & Competent Cells, ClonTech Laboratories, 3 pages, available online Jul. 6, 2014.
International Application No. PCT/US2017/026232 International Preliminary Report on Patentability dated Feb. 26, 2019.
International Application No. PCT/US2017/045105 International Preliminary Report on Patentability dated Feb. 5, 2019.
International Application No. PCT/US2017/052305 International Preliminary Report on Patentability dated Apr. 30, 2019.
International Application No. PCT/US2017/062391 International Preliminary Report on Patentability dated May 21, 2019.
International Application No. PCT/US2018/019268 International Preliminary Report on Patentability dated Sep. 6, 2019.
International Application No. PCT/US2018/050511 International Search Report and Written Opinion dated Jan. 11, 2019.
International Application No. PCT/US2018/057857 International Search Report and Written Opinion dated Mar. 18, 2019.
International Application No. PCT/US2019/012218 International Search Report and Written Opinion dated Mar. 21, 2019.
International Application No. PCT/US2019/032992 International Search Report and Written Opinion dated Oct. 28, 2019.
International Application No. PCT/US2019/032992 Invitation to Pay Additional Fees dated Sep. 6, 2019.
Jackson et al.: Recognition of DNA base mismatches by a rhodium intercalator. J. Am. Chem. Soc., vol. 19, 12986•12987 (1997).
Jacobs et al.: DNA glycosylases: In DNA repair and beyond. Chromosoma 121:1-20 (2012)—http://www.ncbi.nlm.nih.gov/pmc/articles/PMC3260424/.
Jacobus et al.: Optimal cloning of PCR fragments by homologous recombination in *Escherichia soli*. PLoS One 10(3):e0119221 (2015).
Jager et al.: Simultaneous Humoral and Cellular: Immune Response against Cancer—Testis Antigen NY-ES0-1: Definition of Human Histocompatibility Leukocyte Antigen (HLA)-A2—binding Peptide Epitopes. J. Exp. Med. 187(2):265-270 (1998).
Jinek et al.: A Programmable dual-RNA-guided DNA endonuclease in adaptive bacterial immunity. Science, 337:816-821, 2012.
Jo et al.: Engineering therapeutic antibodies targeting G-protein-coupled receptors; Experimental & Molecular Medicine; 48; 9 pages (2016).

Karagiannis and Ei-Osta, RNA interference and potential therapeutic applications of short interfering RNAs Cancer Gene Therapy, 12:787-795, 2005.
Ke et al.: Influence of neighboring base pairs on the stability of single base bulges and base pairs in a DNA fragment. Biochemistry, Vo. 34, 4593-4600 (1995).
Kelley, Shana et al.: Single-base mismatch detection based on charge transduction through DNA, Nucleic Acids Research, vol. 27, No. 24, 4830-4837 (1999).
Kim et al.: High-resolution patterns of quantum dots formed by electrohydrodynamic jet printing for light-emitting diodes. Nano Letters, 15:969-973, 2015.
Kim et al.: Site•specific cleavage of DNA-RNA hybrids by zinc finger/Fok I cleavage domain fusions. Gene, vol. 203, 43-49 (1997).
Kim et al.: Chimeric restriction endonuclease. Proc. Natl. Acad. Sci. USA, vol. 91, 883-887 (Feb. 1994).
Kim. The interaction between Z-ONA and the Zab domain of double-stranded RNA adenosine deaminase characterized using fusion nucleases. The Journal of Biological Chemistry, vol. 274, No. 27, 19081-19086 (1999).
Kinde et al.: Detection and quantification of rare mutations with massively parallel sequencing. Proc Natl Acad Sci U S A. Jun. 7, 2011;108(23):9530-5. Epub May 17, 2011.
Kodumal et al.: Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.
Koike-Yusa et al.: Genome-wide recessive genetic screening in mammalian cells with a lentiviral CRISPR-guide RNA library. Nature Biotechnology, 32:267-273, 2014 (with three pages of supplemental "Online Methods").
Kong et al.: Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp et al.: Chemical amplification: continuous-flow PCR on a chip. Science, vol. 280, 1046-1048 (May 15, 1998).
Kosuri and Church. Large-scale de novo DNA synthesis: technologies and applications. Nature Methods, 11:499-507, 2014. Available at: http://www.nature.com/nmeth/journal/v11/n5/full/nmeth.2918.html.
Kosuri et al.: A scalable gene synthesis by selective amplification of DNA pools from high-fidelity microchips. Nature Biotechnology. 2010; 28:1295-1299.
Krayden, Inc.: A Guide to Silane Solutions. Silane coupling agents. 7 pages. Published on May 31, 2005 at: http://krayden.com/pdf/xia_silane_chemistry.pdf.
Lagally et al.: Single-Molecule DNA Amplification and Analysis in an Integrated Microfluidic Device. Analytical Chemistry. 2001;73(3): 565-570.
Lahue et al., DNA mismatch correction in a defined system. Science, vol. 425; No. 4914, 160-164 (Jul. 14, 1989).
Lambrinakos et al.: Reactivity of potassium permanganate and tetraethylammonium chloride with mismatched bases and a simple mutation detection protocol. Nucleic Acids Research, vol. 27, No. 8, 1866-1874 (1999).
Landegren et al.: A ligase-mediated gene detection technique. Science. Aug. 26, 1988;241(4869):1077-80.
Lang et al.: An automated two-dimensional optical force clamp for single molecule studies. Biophysical Journal, vol. 83, 491•501 (Jul. 2002).
Lashkari et al.: An automated multiplex oligonucleotide synthesizer: development of high-throughput, low-cost DNA synthesis. Proc Natl Acad Sci U S A. Aug. 15, 1995;92(17):7912-5.
Lausted et al.: POSaM: a fast, flexible, open-source, inkjet oligonucleotide synthesizer and microarrayer. Genome Biology, 5:R58, 17 pages, 2004. available at https://www.ncbi.nlm.nih.gov/pmc/articles/PMC507883/.

(56) References Cited

OTHER PUBLICATIONS

Leamon et al.: A massively parallel PicoTiterPlate based platform for discrete picoliter-scale polymerase chain reactions. Electrophoresis. Nov. 2003;24(21):3769-77.
Lee et al.: Microelectromagnets for the control of magnetic nanoparticles. Appl. Phys. Lett., vol. 79, No. 20, 3308-3310 (Nov. 12, 2001).
Lee et al.: A microfluidic oligonucleotide synthesizer. Nucleic Acids Research 2010 vol. 38(8):2514-2521. DOI: 10.1093/nar/gkq092.
Lee: Covalent End-Immobilization of Oligonucleotides onto Solid Surfaces; Thesis, Massachusetts Institute of Technology, Aug. 2001 (315 pages).
Leproust et al.: Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomic%20Services/Agilent_DNA_Microarray_Platform.ashx.
Leproust et al.: Synthesis of high-quality libraries of long (150mer) oligonucleotides by a novel depurination controlled process. Nucleic Acids Research. 2010; 38(8):2522-2540.
Lesnikowski et al.: Nucleic acids and nucleosides containing carboranes. J. Organometallic Chem. 1999; 581:156-169.
Leumann. DNA analogues: from supramolecular principles to biological properties. Bioorg Med Chem. Apr. 2002;10(4):841-54.
Levene et al.: Zero-mode waveguides for single-molecule analysis at high concentrations. Science. Jan. 31, 2003;299(5607):682-6.
Lewontin and Harti. Population genetics in forensic DNA typing. Science, 254:1745-1750, 1991.
Li et al.: Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).
Li et al.: Beating bias in the directed evolution of proteins: Combining high-fidelity on-chip solid-phase gene synthesis with efficient gene assembly for combinatorial library construction. First published Nov. 24, 2017, 2 pages. retrieved from: https://doi.org/10.1002/cbic.201700540.
Light source unit for printable patterning VUV-Aligner / USHIO Inc., Link here: https://www.ushio.co.jp/en/products/1005.html, published Apr. 25, 2016, printed from the internet on Aug. 2, 2016, 3 pages.
Limbachiya et al.: Natural data storage: A review on sending information from now to then via Nature. ACM Journal on Emerging Technologies in Computing Systems, V(N):Article A, May 19, 2015, 17 pages.
Link Technologies. "Product Guide 2010." Nov. 27, 2009, 136 pages. XP055353191. Retrieved from the Internet: URL:http://www.linktech.co.uk/documents/517/517.pdf.
Lipshutz et al.: High density synthetic oligonucleotide arrays. Nature Genetics Supplement, vol. 21, 20-24 (Jan. 1999).
Lishanski et al.: Mutation detection by mismatch binding protein, MutS, in amplified DNA: application to the cystic fibrosis gene. Proc. Natl. Acad. Sci. USA, vol. 91, 2674-2678 (Mar. 1994).
Liu et al.: Comparison of Next-Generation Sequencing Systems. Journal of Biomedicine and Biotechnology, 11 pages, 2012.
Liu et al.: Rational design of CXCR4 specific antibodies with elongated CDRs. JACS, 136:10557-10560, 2014.
Liu et al.: Enhanced Signals and Fast Nucleic Acid Hybridization by Microfluidic Chaotic Mixing. Angew. Chem. Int. Ed. 2006; 45:3618-3623.
Lizardi et al.: Mutation detection and single-molecule counting using isothermal rolling-circle amplification. Nat Genet. Jul. 1998;19(3):225-32.
Li et al.: Functional domains in Fok I restriction endonuclease. Proc. Natl. Acad. Sci. USA, 89:4275-4279, 1992.
Lu et al.: Methyl-directed repair of DNA base-pair mismatches in vitro. Proc. Natl. Acad. Sci. USA, 80:4639-4643, 1983.
Lund et al.: A validated system for ligation-free uracilexcision based assembly of expression vectors for mammalian cell engineering.
DTU Systems of Biology. 2011. 1 page. http://www.lepublicsystemepco.com/files/modules/gestion_rubriques/REF-B036-Lund_Anne%20Mathilde.pdf.
Ma et al.: Versatile surface functionalization of cyclic olefin copolymer (COC) with sputtered SiO2 thin film for potential BioMEMS applications. Journal of Materials Chemistry, 11 pages, 2009.
Ma et al.: DNA synthesis, assembly and application in synthetic biology. Current Opinion in Chemical Biology. 16:260-267, 2012.
Mahato et al.: Modulation of gene expression by antisense and antigene oligodeoxynucleotides and small interfering RNA Expert Opin. Drug Delivery, 2(1):3-28, 2005.
Margulies et al.: Genome sequencing in open microfabricated high-density picolitre reactors. Nature. 437(7057):376-80, 2005.
Martinez-Torrecuadrada et al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).
Matteucci et al.: Synthesis of deoxyoligonucleotides on a polymer support. J. Am. Chem. Soc. 103(11):3185-3191, 1981.
Matzas et al.: Next generation gene synthesis by targeted retrieval of bead-immobilized, sequence verified DNA clones from a high throughput pyrosequencing device. Nat. Biotechnol., 28(12):1291-1294, 2010.
Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).
McBride & Caruthers. An investigation of several deoxynucleoside phosphoramidites useful for synthesizing deoxyoligonucleotides. Tetrahedron Lett. 24: 245-248, 1983.
Mcgall et al.: Light-directed synthesis of high-density oligonucleotide arrays using semiconductor photoresists. Proc Natl Acad Sci U S A. 93(24):13555-60, 1996.
Mcgall et al.: The Efficiency of Light-Directed Synthesis of DNA Arrays on Glass Substrates. J. Am. Chem. Soc. 119(22):5081-5090, 1997.
Mei et al.: Cell-free protein synthesis in microfluidic array devices Biotechnol. Prog., 23(6):1305-1311, 2007.
Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages, http://www.diva-portal.org/smash/get/diva2:161926/FULLTEXT01.pdf.
Meyers and Friedland. Knowledge-based simulation of genetic regulation in bacteriophage lambda. Nucl. Acids Research, 12(1):1-16, 1984.
Meynert et al.: Quantifying single nucleotide variant detection sensitivity in exome sequencing. BMC Bioinformatics 14:195 (2013).
Meynert et al.: Variant detection sensitivity and biases in whole genome and exome sequencing. BMC Bioinformatics 15:247 (2014).
Milo and Phillips. Numbers here reflect the number of protein coding genes and excludes tRNA and non-coding RNA. Cell Biology by the Numbers, p. 286, 2015.
Mitra et al.: In situ localized amplification and contact replication of many individual DNA molecules. Nucleic Acids Res. 27(24):e34, 1999.
Morin et al.: Profiling the HeLa S3 transcriptome using randomly primed cDNA and massively parallel short-read sequencing. Biotechniques, 45:81-94, 2008.
Morris and Stauss. Optimizing T-cell receptor gene therapy for hematologic malignancies. Blood, 127(26):3305-3311, 2016.
Muller et al.: Protection and labelling of thymidine by a fluorescent photolabile group. Helvetica Chimica Acta, vol. 84, 3735-3741 (2001).
Mulligan. Commercial Gene Synthesis Technology PowerPoint presentation. BlueHeron® Biotechnology. Apr. 5, 2006 (48 pgs).
Nakatani et al.: Recognition of a single guanine bulge by 2-Acylamino-1,8-naphthyridine. J. Am. Chem. Soc., vol. 122, 2172-2177 (2000).
Neiman M.S.: Negentropy principle in information processing systems. Radiotekhnika, 1966, No. 11, p. 2-9.
Neiman M.S.: On the bases of the theory of information retrieval. Radiotekhnika, 1967, No. 5, p. 2-10.

(56) References Cited

OTHER PUBLICATIONS

Neiman M.S.: On the molecular memory systems and the directed mutations. Radiotekhnika, 1965, No. 6, pp. 1-8.
Neiman M.S.: On the relationships between the reliability, performance and degree of microminiaturization at the molecular-atomic level. Radiotekhnika, 1965, No. 1, pp. 1-9.
Neiman M.S.: Some fundamental issues of microminiaturization. Radiotekhnika, 1964, No. 1, pp. 3-12.
Nishikura. A short primer on RNAi: RNA-directed RNA polymerase acts as a key catalyst Cell, 107:415-418, 2001.
Nour-Eldin et al.: USER Cloning and USER Fusion: The Ideal Cloning Techniques for Small and Big Laboratories. Plant Secondary Metabolism Engineering. Methods in Molecular Biology vol. 643, 2010, pp. 185-200.
Ochman et al.: Genetic applications of an inverse polymerase chain reaction. Genetics. Nov. 1988;120(3):621-3.
Organick et al.: Random access in large-scale DNA data storage. Nature Biotechnology, Advance Online Publication, 8 pages, 2018.
Organick et al.: Scaling up DNA data storage and random access retrieval, bioRxiv, preprint first posted online Mar. 7, 2017, 14 pages.
Pan et al.: An approach for global scanning of single nucleotide variations. Proc Natl Acad Sci U S A. Jul. 9, 2002;99(14):9346-51.
Pankiewicz. Fluorinated nucleosides. Carbohydr Res. Jul. 10, 2000;327(1-2):87-105.
PCT/IL2012/000326 International Preliminary Report on Patentability dated Dec. 5, 2013.
PCT/IL2012/000326 International Search Report dated Jan. 29, 2013.
PCT/US14/049834 International Preliminary Report on Patentability dated Feb. 18, 2016.
PCT/US2014/049834 International Search Report and Written Opinion dated Mar. 19, 2015.
PCT/US2014/049834 Invitation to Pay Additional Fees and, where applicable, protest fee dated Jan. 5, 2015.
PCT/US2015/043605 International Preliminary Report on Patentability dated Feb. 16, 2017.
PCT/US2015/043605 International Search Report and Written Opinion dated Jan. 6, 2016.
PCT/US2015/043605 Invitation to Pay Additional Fees dated Oct. 28, 2015.
PCT/US2016/016459 International Preliminary Report on Patentability dated Aug. 17, 2017.
PCT/US2016/016459 International Search Report and Written Opinion dated Apr. 13, 2016.
PCT/US2016/016636 International Preliminary Report on Patentability dated Aug. 17, 2017.
PCT/US2016/016636 International Search Report and Written Opinion dated May 2, 2016.
PCT/US2016/028699 International Preliminary Report on Patentability dated Nov. 2, 2017.
PCT/US2016/028699 International Search Report and Written Opinion dated Jul. 29, 2016.
PCT/US2016/031674 International Preliminary Report on Patentability dated Nov. 23, 2017.
PCT/US2016/031674 International Search Report and Written Opinion dated Aug. 11, 2016.
PCT/US2016/052336 International Preliminary Report on Patentability dated Mar. 29, 2018.
PCT/US2016/052336 International Search Report and Written Opinion dated Dec. 7, 2016.
PCT/US2016/052916 International Preliminary Report on Patentability dated Apr. 5, 2018.
PCT/US2016/052916 International Search Report and Written Opinion dated Dec. 30, 2016.
PCT/US2016/064270 International Preliminary Report on Patentability dated Jun. 14, 2018.
PCT/US2016/064270 International Search Report and Written Opinion dated Apr. 28, 2017.
PCT/US2017/026232 International Search Report and Written Opinion dated Aug. 28, 2017.
PCT/US2017/036868 International Search Report and Written Opinion dated Aug. 11, 2017.
PCT/US2017/045105 International Search Report and Written Opinion dated Oct. 20, 2017.
PCT/US2017/052305 International Search Report and Written Opinion dated Feb. 2, 2018.
PCT/US2017/062391 International Search Report and Written Opinion dated Mar. 28, 2018.
PCT/US2017/066847 International Search Report and Written Opinion dated May 4, 2018.
PCT/US2018/022487 International Search Report and Written Opinion dated Aug. 1, 2018.
PCT/US2018/022493 International Search Report and Written Opinion dated Aug. 1, 2018.
PCT/US2018/037152 International Search Report and Written Opinion dated Aug. 28, 2018.
PCT/US2018/037161 International Search Report and Written Opinion dated Oct. 22, 2018.
PCT/US2018/037161 Invitation to Pay Additional Fees dated Aug. 27, 2018.
PCT/US2018/056783 International Search Report and Written Opinion dated Dec. 20, 2018.
PCT/US2018/19268 International Search Report and Written Opinion dated Jun. 26, 2018.
PCT/US2018/19268 Invitation to Pay Additional Fees and, where applicable, protest fee dated May 2, 2018.
PCT/US2018/22487 Invitation to Pay Additional Fees and, where applicable, protest fee dated May 31, 2018.
PCT/US2018/22493 Invitation to Pay Additional Fees and, where applicable, protest fee dated May 31, 2018.
Pease et al.: Light-generated oligonucleotide arrays for rapid DNA sequence analysis. Proc Natl Acad Sci U S A. May 24, 1994;91(11):5022-6.
Peisajovich et al.: BBF RFC 28: A method for combinatorial multi-part assembly based on the type-lis restriction enzyme aarI. Sep. 16, 2009, 7 pages.
Pellois et al.: Individually addressable parallel peptide synthesis on microchips. Nature Biotechnology, vol. 20 , 922-926 (Sep. 2002).
Petersen et al.: LNA: a versatile tool for therapeutics and genomics. Trends Biotechnol. Feb. 2003;21(2):74-81.
Pierce and Wangh. Linear-after-the-exponential polymerase chain reaction and allied technologies Real-time detection strategies for rapid, reliable diagnosis from single cells Methods Mol. Med. 132:65-85 (2007) (Abstract only).
Pierce et al.: Linear-after-the-exponential polymerase chain reaction and allied technologies. Real-time detection strategies for rapid, reliable diagnosis from single cells. Methods Mol Med. 2007;132:65-85.
Pirrung. How to make a DNA chip. Angew. Chem. Int. Ed., 41:1276-1289, 2002.
Plesa et al.: Multiplexed gene synthesis in emulsions for exploring protein functional landscapes. Science, 10.1126/science.aao5167, 10 pages, 2018.
Pon. Solid-phase supports for oligonucleotide synthesis. Methods Mol Biol. 1993;20:465-96.
Poster. Reimagine Genome Scale Research. 2016, 1 page. Available at http://www2.twistbioscience.com/Oligo_Pools_CRISPR_poster.
Powers et al.: Optimal strategies for the chemical and enzymatic synthesis of bihelical deoxyribonucleic acids. J Am Chem Soc., 97(4):875-884, 1975.
Pray. Discovery of DNA Structure and Function: Watson and Crick. Nature Education, 2008, 6 pages. available at: http://www.nature.com/scitable/topicpage/discovery-of-dna-structure-and-function-watson-397.
Prodromou et al.: Recursive PCR: a novel technique for total gene synthesis. Protein Eng. Dec. 1992;5(8):827-9.
Puigbo. Optimizer: a web server for optimizing the codon usage of DNA sequences. Nucleic Acid Research, 35(14):126-131, 2007.
Qian and Winfree. Scaling up digital circuit computation with DNA strand displacement cascades. Science, 332(6034):196-1201, 2011.

(56) References Cited

OTHER PUBLICATIONS

Qian et al.: Neural network computation with DNA strand displacement cascades, Nature, 475(7356):368-372, 2011.

Quan et al.: Parallel on-chip gene synthesis and application to optimization of protein expression. Nature Biotechnology. 2011; 29:449-452.

Rafalski and Morgante. Corn and humans: recombination and linkage disequilibrium in two genomes of similar size. Trends in Genetics, 20(2):103-111, 2004.

Raje and Murma. A Review of electrohydrodynamic-inkjet printing technology. International Journal of Emerging Technology and Advanced Engineering, 4(5):174-183, 2014.

Rastegari et al.: XNOR-Net: ImageNet Classification Using Binary Convolutional Neural Networks, in ECCV 2016, Part IV, LNCS 9908, p. 525-542, 2016.

Reimagine SequenceSpace, Reimagine Research, Twist Bioscience, Product Brochure, Published Apr. 6, 2016 online at: www2.twistbioscience.com/TB_Product_Brochure_04.2016, 8 pages.

RF Electric discharge type excimer lamp. Products Catalog. Excimer lamp light source "flat excimer," 16 pages dated Jan. 2016. From: http://www.hamamatsu.com/jp/en/product/category/1001/3026/index.html.

Richmond et al.: Amplification and assembly of chip-eluted DNA (AACED): a method for high-throughput gene synthesis. Nucleic Acids Res. Sep. 24, 2004;32(17):5011-8. Print 2004.

Roche. Restriction Enzymes from Roche Applied Science—A Tradition of Premium Quality and Scientific Support. FAQS and Ordering Guide. Roche Applied Science. Accessed Jan. 12, 2015, 37 pages.

Rogozin et al.: Origin and evolution of spliceosomal introns. Biology Direct, 7:11, 2012.

Ruminy et al.: Long-range identification of hepatocyte nuclear factor-3 (FoxA) high and low-affinity binding Sites with a chimeric nuclease. J. Mol. Bioi., vol. 310, 523-535 (2001).

Saaem et al.: In situ synthesis of DNA microarray on functionalized cyclic olefin copolymer substrate ACS Applied Materials & Interfaces, 2(2):491-497, 2010.

Saboulard et al.: High-throughput site-directed mutagenesis using oligonucleotides synthesized on DNA chips. Biotechniques. Sep. 2005;39(3):363-8.

Sacconi et al.: Three-dimensional magneto-optic trap for micro-object manipulation. Optics Letters, vol. 26, No. 17, 1359-1361 (Sep. 1, 2001).

Saiki et al.: Analysis of enzymatically amplified beta-globin and HLA-DQ alpha DNA with allele-specific oligonucleotide probes. Nature 324:163-166 (1986).

Sandhu et al.: Dual asymmetric PCR: one-step construction of synthetic genes. Biotechniques. Jan. 1992;12(1):14-6.

Sargolzaei et al.: Extent of linkage disequilibrium in Holstein cattle in North America. J. Dairy Science, 91:2106-2117, 2007.

Schaller et al.: Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.

Schmalzing et al.: Microchip electrophoresis: a method for high-speed SNP detection. Nucleic Acids Res 28(9):E43 (2000).

Schmitt et al.: New strategies in engineering T-cell receptor gene-modified T cells to more effectively target malignancies. Clinical Cancer Research, 21(23):5191-5197, 2015.

Seelig et al.: Enzyme-Free Nucleic Acid Logic Circuits, Science 314(5805):1585-1588, 2006.

Sharan et al.: Recombineering: a homologous recombination-based method of genetic engineering. Nat Profile 4(2):1-37 (originally pp. 206-223) (2009).

Sharpe and Mount. Genetically modified T cells in cancer therapy: opportunities and challenges. Disease Models and Mechanisms, 8:337-350, 2015.

Sierzchala et al.: Solid-phase oligodeoxynucleotide synthesis : a two-step cycle using peroxy anion deprotection. J. Am. Chem. Soc., vol. 125, No. 44, 13427-13441 (2003).

Simonyan and Zisserman,.Very Deep Convolutional Networks for Large-Scale Image Recognition, Published as a conference paper at Int. Conf. Learn. Represent., pp. 1-14, 2015.

Singh-Gasson et al.: Maskless fabrication of light-directed oligonucleotide microarrays using a digital micromirror array, Nature Biotechnology, vol. 17, 974-978 (Oct. 1999).

Skerra. Phosphorothioate primers improve the amplification of DNA sequences by DNA polymerases with proofreading activity. Nucleic Acids Res. Jul. 25, 1992; 20(14):3551-4.

Smith Jane et al.: Removal of Polymerase-Produced mutant sequences from PCR products. Proc. Natl. Acad. Sci. USA, vol. 94, 6847-6850 (Jun. 1997).

Smith et al.: Generating a synthetic genome by whole genome assembly: phiX174 bacteriophage from synthetic oligonucleotides. Proc Natl Acad Sci U S A. Dec. 23, 2003;100(26):15440-5. Epub Dec. 2, 2003.

Smith et al.: Generation of cohesive ends on PCR products by UDG-mediated excision of dU, and application for cloning into restriction digest-linearized vectors. PCR Methods Appl. May 1993;2(4):328-32.

Smith et al.: Mutation detection with MutH, MutL, and MutS mismatch repair proteins. Proc. Natl. Acad. Sci. USA, vol. 93, 4374-4379 (Apr. 1996).

Smith et al.: Direct mechanical measurements of the elasticity of single DNA molecules using magnetic beads. Science, vol. 258, 1122-1126 (Nov. 13, 1992).

Soni et al.: Progress toward ultrafast DNA sequencing using solid-state nanopores. Clin Chem. Nov. 2007;53(11):1996-2001. Epub Sep. 21, 2007.

Southern et al.: Analyzing and comparing nucleic acid sequences by hybridization to arrays of oligonucleotides: evaluation using experimental models. Genomics. Aug. 1992;13(4):1008-17.

Sproat et al.: An efficient method for the isolation and purification of oligoribonucleotides. Nucleosides & Nucleotides. 1995; 14(1 &2):255-273.

Srivannavit et al.: Design and fabrication of microwell array chips for a solution-based, photogenerated acid-catalyzed parallel oligonuclotide DNA synthesis. Sensors and Actuators A, 116:150-160, 2004.

Srivastava et al.: RNA synthesis: phosphoramidites for RNA synthesis in the reverse direction. Highly efficient synthesis and application to convenient introduction of ligands, chromophores and modifications of synthetic RNA at the 3'-end. Nucleic Acids Symposium Series, 52(1):103-104, 2008.

Steel, The Flow-Thru Chip a Three-dimensional biochip platform. In: Schena, Microarray Biochip Technology, Chapter 5, Natick, MA: Eaton Publishing, 2000, 33 pages.

Stemmer et al.: Single-step assembly of a gene and entire plasmid from large numbers of oligodeoxyribonucleotides. Gene. Oct. 16, 1995;164(1):49-53.

Stryer. DNA Probes and genes can be synthesized by automated solid-phase methods. Biochemistry, 3rd edition, New York: W.H. Freeman and Company, 1988; 123-125.

Stutz et al.: Novel fluoride-labile nucleobase-protecting groups for the synthesis of 3'(2')-O-amino-acylated RNA sequences. Helv. Chim. Acta. 2000; 83(9):2477-2503.

Sullivan et al.: Library construction and evaluation for site saturation mutagenesis. Enzyme Microb. Technol. 53:70-77 (2013).

Sun et al.: Structure-Guided Triple-Code Saturation Mutagenesis: Efficient Tuning of the Stereoselectivity of an Epoxide Hydrolase. ACS Catal. 6:1590-1597 (2016).

Takahashi. Cell-free cloning using multiply-primed rolling circle amplification with modified RNA primers. Biotechniques. Jul. 2009;47(1):609-15. doi: 10.2144/000113155.

Tanase et al.: Magnetic trapping of multicomponent nanowires. The Johns Hopkins University, Baltimore, Maryland, p. 1-3 (Jun. 25, 2001).

Taylor et al.: Impact of surface chemistry and blocking strategies on DNA microarrays. Nucleic Acids Research, 31(16):e87, 19 pages, 2003.

(56) References Cited

OTHER PUBLICATIONS

The Hood Laboratory, "Beta Group." Assembly Manual for the POSaM: The ISB Piezoelelctric Oligonucleotide Synthesizer and Microarrayer, Inkjet Microarrayer Manual Version 1.2, 50 pages, May 28, 2004.
The SLIC, Gibson, CPEC and SLiCE assembly methods (and GeneArt Seamless, In-Fusion Cloning). 5 pages, available online Sep. 2, 2010.
Tian et al.: Accurate multiplex gene synthesis from programmable DNA microchips. Nature. Dec. 23, 2004;432(7020):1050-4.
Tsai et al.: Dimeric CRISPR RNA-guided FokI nucleases for highly specific genome editing Nat. Biotechnol., 32(6):569-576, 2014.
Twist Bioscience | White Paper. DNA-Based Digital Storage. Retrieved from the internet, Twistbioscience.com, Mar. 27, 2018, 5 pages.
U.S. Appl. No. 14/241,874 Office Action dated Feb. 27, 2017.
U.S. Appl. No. 14/241,874 Office Action dated Jul. 14, 2016.
U.S. Appl. No. 14/241,874 Office Action dated May 4, 2018.
U.S. Appl. No. 14/452,429 Notice of Allowance dated Jun. 7, 2016.
U.S. Appl. No. 14/452,429 Office Action dated Oct. 21, 2015.
U.S. Appl. No. 14/452,429 Restriction Requirement dated Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/015,059 Final Office Action dated Jul. 17, 2019.
U.S. Appl. No. 15/015,059 Office Action dated Aug. 19, 2019.
U.S. Appl. No. 15/015,059 Office Action dated Feb. 7, 2019.
U.S. Appl. No. 15/135,434 Notice of Allowance dated Feb. 9, 2018.
U.S. Appl. No. 15/135,434 Office Action dated Nov. 30, 2017.
U.S. Appl. No. 15/135,434 Restriction Requirement dated Jul. 12, 2017.
U.S. Appl. No. 15/151,316 Office Action dated Jun. 7, 2018.
U.S. Appl. No. 15/151,316 Office Action dated Oct. 4, 2019.
U.S. Appl. No. 15/151,316 Final Office Action dated Feb. 21, 2019.
U.S. Appl. No. 15/154,879 Notice of Allowance dated Feb. 1, 2017.
U.S. Appl. No. 15/156,134 Office Action dated Apr. 4, 2019.
U.S. Appl. No. 15/187,714 Final Office Action dated Sep. 17, 2019.
U.S. Appl. No. 15/187,714 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Office Action dated Mar. 21, 2017.
U.S. Appl. No. 15/245,054 Office Action dated Oct. 19, 2016.
U.S. Appl. No. 15/268,422 Final Office Action dated Oct. 3, 2019.
U.S. Appl. No. 15/268,422 Office Action dated Mar. 1, 2019.
U.S. Appl. No. 15/268,422 Restriction Requirement dated Oct. 4, 2018.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Oct. 20, 2017.
U.S. Appl. No. 15/603,013 Final Office Action dated Nov. 6, 2019.
U.S. Appl. No. 15/619,322 Office Action dated Aug. 14, 2019.
U.S. Appl. No. 15/682,100 Office Action dated Jan. 2, 2018.
U.S. Appl. No. 15/682,100 Restriction Requirement dated Nov. 8, 2017.
U.S. Appl. No. 15/709,274 Notice of Allowance dated Apr. 3, 2019.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/816,995 Office Action dated Sep. 20, 2019.
U.S. Appl. No. 15/816,995 Restriction Requirement dated Apr. 4, 2019.
U.S. Appl. No. 15/835,243 Restriction Requirement dated Sep. 10, 2019.
U.S. Appl. No. 15/844,395 Restriction Requirement dated May 17, 2019.
U.S. Appl. No. 15/860,445 Final Office Action dated Dec. 13, 2018.
U.S. Appl. No. 15/860,445 Office Action dated May 30, 2018.
U.S. Appl. No. 15/921,479 Restriction Requirement dated May 24, 2019.
U.S. Appl. No. 15/960,319 Office Action dated Aug. 16, 2019.
U.S. Appl. No. 16/006,581 Office Action dated Sep. 25, 2019.
U.S. Appl. No. 16/409,608 Office Action dated Sep. 9, 2019.
U.S. Appl. No. 16/530,717 Office Action dated Sep. 6, 2019.
U.S. Appl. No. 14/452,429 Office Action dated Apr. 9, 2015.
U.S. Appl. No. 15/603,013 Office Action dated Jun. 26, 2019.
U.S. Appl. No. 16/239,453 Office Action dated Nov. 7, 2019.
Unger et al.: Monolithic microfabricated valves and pumps by multilayer soft lithography. Science. Apr. 7, 2000;288(5463):113-6.
Vaijayanthi et al.: Recent advances in oligonucleotide synthesis and their applications. Indian J Biochem Biophys. Dec. 2003;40(6):377-91.
Van Den Brulle et al.: A novel solid phase technology for high-throughput gene synthesis. Biotechniques. 2008; 45(3):340-343.
Van Der Werf et al.: Limonene-1,2-epoxide hydrolase from Rhodococcus erythropolis DCL14 belongs to a novel class of epoxide hydrolases. J. Bacteriol. 180:5052-5057 (1998).
Van Tassell et al.: SNP discovery and allele frequency estimation by deep sequencing of reduced representation libraries. Nature Methods, 5:247-252, 2008.
Vargeese et al.: Efficient activation of nucleoside phosphoramidites with 4,5-dicyanoimidazole during oligonucleotide synthesis. Nucleic Acids Res. Feb. 15, 1998;26(4):1046-50.
Verma et al.: Modified oligonucleotides: synthesis and strategy for users. Annu Rev Biochem 67:99-134 (1998).
Vincent et al.: Helicase-dependent isothermal DNA amplification. EMBO Rep. Aug. 2004;5(8):795-800.
Visscher et al.: Construction of multiple-beam optical traps with nanometer-resolution position sensing. IEEE Journal of Selected Topics in Quantum Electronics, vol. 2, No. 4, 1066-1076 (Dec. 1996).
Voldmans Joel et al.: Holding forces of single-particle dielectrophoretic traps. Biophysical Journal, vol. 80, No. 1, 531-541 (Jan. 2001).
Vos et al.: AFLP: A new technique for DNA fingerprinting. Nucleic Acids Res. Nov. 11, 1995;23(21):4407-14.
Wagner et al.: Nucleotides, Part LXV, Synthesis of 2'-Deoxyribonucleoside 5'-Phosphoramidites: New Building Blocks for the Inverse (5'-3')-Oligonucleotide Approach. Helvetica Chimica Acta, 83(8):2023-2035, 2000.

(56) References Cited

OTHER PUBLICATIONS

Wah et al.: Structure of Fok I has implications for DNA cleavage. Proc. Natl. Acad. Sci. USA, vol. 95, 10564-10569 (Sep. 1998).
Wah et al.: Structure of the multimodular endonuclease Fok I bound to DNA. Nature, vol. 388, 97-100 ( Jul. 1997).
Walker et al.: Strand displacement amplification—an isothermal, in vitro DNA amplification technique. Nucleic Acids Res. Apr. 11, 1992;20(7):1691-6.
Wan et al.: Deep Learning for Content-Based Image Retrieval: A comprehensive study. in Proceedings of the 22nd ACM International Conference on Multimedia—Nov. 3-7, 2014, Orlando, FL, p. 157-166, 2014.
Warr et al.: Exome Sequencing: current and future perspectives. G3: (Bethesda) 5(8):1543-1550 (2015).
Weber et al.: A modular cloning system for standardized assembly of multigene constructs. PLoS One. Feb. 18, 2011;6(2):e16765. doi: 10.1371/journal.pone.0016765.
Welz et al.: 5-(Benzylmercapto)-1H-tetrazole as activator for 2'-O-TBDMS phosphoramidite building blocks in RNA synthesis. Tetrahedron Lett. 2002; 43(5):795-797.
Westin et al.: Anchored multiplex amplification on a microelectronic chip array Nature Biotechnology, 18:199-202 (2000) (abstract only).
Whitehouse, Adrian et al.: "Analysis of the mismatch and insertion/deletion binding properties of Thermus thermophilus, HB8, MutS", Biochemical and Biophysical Research Communications, vol. 233, 834-837 (1997).
Wiedenheft et al.: RNA-guided genetic silencing systems in bacteria and archaea. Nature, 482:331-338, 2012.
Wijshoff. Structure and fluid-dynamics in Piezo inkjet printheads. Thesis. Venio, The Netherlands, published 2008, p. 1-185.
Wirtz. Direct measurement of the transport properties of a single DNA molecule. Physical Review Letters, vol. 75, No. 12, 2436-2439 (Sep. 18, 1995).
Withers-Martinez et al.: PCR-based gene synthesis as an efficient approach for expression of the A+ T-rich malaria genome. Protein Engineering, vol. 12, No. 12, 1113-1120 (1999).
Wood et al.: Human DNA repair genes. Science, vol. 291, 1284-1289 (Feb. 16, 2001).
Wosnick et al.: Rapid construction of large synthetic genes: total chemical synthesis of two different versions of the bovine prochymosin gene. Gene. 1987;60(1):115-27.
Wright and Church. An open-source oligomicroarray standard for human and mouse. Nature Biotechnology, 20:1082-1083, 2002.
Wu et al.: Sequence-Specific Capture of Protein-DNA Complexes for Mass Spectrometric Protein Identification. PLoS One. Oct. 20, 2011, vol. 6, No. 10.
Wu et al.: RNA-mediated gene assembly from DNA arrays. Angew Chem Int Ed Engl. May 7, 2012;51(19):4628-32. doi: 10.1002/anie. 201109058.
Wu et al.: Specificity of the nick-closing activity of bacteriophage T4 DNA ligase. Gene. 1989;76(2):245-54.
Wu et al.: An improvement of the on-line electrophoretic concentration method for capillary electrophoresis of proteins an experimental factors affecting he concentration effect. Analytical Sciences, vol. 16, 329-331 (Mar. 2000).
Xiong et al.: Chemical gene synthesis: Strategies, softwares, error corrections, and applications. FEMS Microbiol. Rev., 32:522-540, 2008.
Xiong et al.: A simple, rapid, high-fidelity and cost-effective PCR-based two-step DNA synthesis method for long gene sequences. Nucleic Acids Res. 2004, 32(12):e98.
Xiong et al.: Non-polymerase-cycling-assembly-based chemical gene synthesis: Strategies, methods, and progress. Biotechnology Advances. 26(2):121-134, 2008.
Xu et al.: Design of 240,000 orthogonal 25mer DNA barcode probes. PNAS, 106(7):2289-2294, 2009.
Yang et al.: Purification, cloning, and characterization of the CEL I nuclease. Biochemistry, 39(13):3533-35, 2000.

Yazdi et al.: A Rewritable, Random-Access DNA-Based Storage System, Scientific Reports, 5, Article No. 14138, 27 pages, 2015.
Yehezkel et al.: De novo DNA synthesis using single molecule PCR Nucleic Acids Research, 36(17):e107, 2008.
Yes HMDS vapor prime process application note Prepared by UC Berkeley and University of Texas at Dallas and re-printed by Yield Engineering Systems, Inc., 6 pages (http://www.yieldengineering.com/Portals/0/HMDS%20Application%20Note.pdf (Published online Aug. 23, 2013).
Youil, Rima et al.: Detection of 81 of 81 known mouse Beta-Globin promoter mutations with T4 Endonuclease VII• The EMC Method. Genomics, 32:431-435, 1996.
Young et al.: Two-step total gene synthesis method. Nucleic Acids Res. 32(7):e59, 2004.
Zhang and Seelig. Dynamic DNA nanotechnology using strand-displacement reactions, Nat. Chem., 3(2):103-113, 2011.
Zheleznaya et al.: Nicking endonucleases. Biochemistry (Mosc). 74(13):1457-66, 2009.
Zheng et al.: Manipulating the Stereoselectivity of Limonene Epoxide Hydrolase by Directed Evolution Based on Iterative Saturation Mutagenesis. J. Am. Chem. Soc. 132:15744-15751 (2010).
Zhirnov et al.: Nucleic acid memory. Nature Materials, 15:366, 2016.
Zhou et al.: Microfluidic PicoArray synthesis of oligodeoxynucleotides and simultaneous assembling of multiple DNA sequences Nucleic Acids Research, 32(18):5409-5417, 2004.
Zhou et al.: Establishment and application of a loop-mediated isothermal amplification (LAMP) system for detection of cry1Ac transgenic sugarcane. Scientific Reports May 9, 2014, vol. 4, No. 4912.
Agbavwe et al.: Efficiency, Error and Yield in Light-Directed Maskless Synthesis of DNA Microarrays. Journal of Nanobiotechnology. 9(57):1-17 (2011).
Alberts et al.: Molecular Biology of the Cell. 4th edition. New York: Garland Science; 2002. The Generation of Antibody Diversity. https://www.ncbi.nlm.nih.gov/books/NBK26860/.
Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.
Altshuler et al.: Generation of Recombinant Antibodies and Means for Increasing Their Affinity. Biochemistry (Moscow). 75(13:1584-1605 (2010).
Bai. A Novel Human scFv Library with Non-Combinatorial Synthetic CDR Diversity. PLoS One. 10(10):1-18(2015).
Berg: Biochemistry. 5th Ed. New York (2002) 148-149.
Borda et al.: Secret writing by DNA hybridization. Acta Technica Napocensis Electronics and Telecommunications. 50(2):21-24 (2009).
Chervin et al.: Design of T-cell receptor libraries with diverse binding properties to examine adoptive T-cell responses. Gene Therapy. 20(6):634-644 (2012).
Cui et al.: Information Security Technology Based on DNA Computing. International Workshop on Anti-Counterfeiting, Security and Identification (ASID); IEEE Xplore 4 pages (2007).
De Graff et al.: Glucagon-Like Peptide-1 and its Class B G Protein-Coupled Receptors: A Long March to Therapeutic Successes. Pharmacol Rev. 68(4):954-1013 (2016).
Diehl et al.: Beaming: single-molecule PCR on microparticles in water-in-oil emulsions. Nature Methods. 3(7):551-559 (2006).
European Patent Application No. 17872347.4 Extended European Search Report dated Jun. 30, 2020.
European Patent Application No. 17881617.9 European Search Report and Written Opinion dated Jul. 2, 2020.
Fernández-Quintero et al.: Characterizing the Diversity of the CDR-H3 Loop Conformational Ensembles in Relationship to Antibody Binding Properties. Front. Immunol. 9:1-11 (2019).
GE Healthcare. AKTA oligopilot plus. Data File 18-114-66 ADC. 8 pages (2006).
GE Healthcare. Robust and cost-efficient oligonucleotide synthesis. Application Note 28-4058-08 AA. 4 pages (2005).
Geetha et al.: Survey on Security Mechanisms for Public Cloud Data. 2016 International Conference on Emerging Trends in Engineering, Technology and Science (ICETETS). 8 pages (2016).

(56) References Cited

OTHER PUBLICATIONS

Goodwin et al.: immunoglobulin heavy chain variable region, partial [*Homo sapiens*]. Genbank entry (online). National Institute of Biotechnology Information. (2018) https://www.ncbi.nlm.nih.gov/protein/AXA12486.1.
Hauser et al.: Trends in GPCR drug discovery: new agents, targets and indications. Nature Reviews Drug Discovery, 16, 829-842 (2017). doi:10.1038/nrd.2017.178 https://www.nature.com/articles/nrd.2017.178.
Hood et al.: The digital code of DNA. Nature 421.6921:444-448 (2003).
Hopcroft et al.: What is the Young's Modulus of Silicon?. Journal of Microelectromechanical Systems. 19(2):229-238 (2010).
Hötzel et al.: A strategy for risk mitigation of antibodies with fast clearance. mAbs, 4(6), 753-760 (2012). doi:10.4161/mabs.22189 https://www.ncbi.nlm.nih.gov/pubmed/23778268.
Hudson: Matrix Assisted Synthetic Transformations: A Mosaic of Diverse Contributions. Journal of Combinatorial Chemistry. 1(6):403-457 (1999).
Jaiswal et al.: An architecture for creating collaborative semantically capable scientific data sharing infrastructures. Proceeding WIDM '06 Proceedings of the 8th annual ACM international workshop on Web information and data management. ACM Digital Library pp. 75-82 (2006).
Jang et al.: Characterization of T cell repertoire of blood, tumor, and ascites in ovarian cancer patients using next generation sequencing. Oncoimmunology, 4(11):e1030561:1-10 (2015).
Kalva et al.: Gibson Deletion: a novel application of isothermal in vitro recombination. Biological Procedures Online. 20(1):1-10 (2018).
Kosuri et al.: A scalable gene synthesis platform using high-fidelity DNA microchips Nat.Biotechnol. 28(12):1295-1299 (2010).
Lebl et al.: Economical Parallel Oligonucleotide and Peptide Synthesizer—Pet Oligator. Int. J. Peptide Res. Ther. 13(1-2):367-376 (2007).
Malecek et al.: Engineering improved T cell receptors using an alanine-scan guided T cell display selection system. Journal of Immunological Methods. Elsevier Science Publishers. 392(1):1-11 (2013).
MLAB 2321 Molecular Diagnostics for Clinical Laboratory Science. Mar. 6, 2015.
Momentiv. Technical Data Sheet. Silquest A-1100. Momentiv. 1-6 (2020).
(Novartis Institutes for Biomedical Research) Immunoglobulin Heavy Chain [*Homo sapiens*]. National Center for Biotechnology Information. Genbank Entry. pp. 1-2 (2018) https://h.
(Novartis Institutes for Biomedical Research) Immunoglobulin Lambda Chain [*Homo sapiens*]. National Center for Biotechnology Information. Genbank Entry, pp. 1-2 (2018) https://www.ncbi.nlm.nih.gov/nuccore/MH975524.1.
Nucleic acid thermodynamics. Wikipedia. Feb. 4, 2021.
O'driscoll et al.: Synthetic DNA: The next generation of big data storage. Bioengineered. 4(3):123-125 (2013).
Opposition to European Patent No. 3030682 filed Mar. 3, 2021.
Paul et al.: Acid binding and detritylation during oligonucleotide synthesis. Nucleic Acids Research. 15. pp. 3048-3052 (1996).
PCT/US2018/037152 International Preliminary Report on Patentability dated Dec. 17, 2019.
PCT/US2018/037161 International Preliminary Report on Patentability dated Dec. 17, 2019.
PCT/US2018/050511 International Preliminary Report on Patentability dated Mar. 17, 2020.
PCT/US2018/056783 International Preliminary Report on Patentability dated Apr. 30, 2020.
PCT/US2018/057857 International Preliminary Report on Patentability dated Apr. 28, 2020.
PCT/US2019/012218 International Preliminary Report on Patentability dated Jul. 16, 2020.
PCT/US2019/032992 International Preliminary Report on Patentability dated Nov. 24, 2020.
PCT/US2019/068435 International Preliminary Report on Patentability dated Jul. 8, 2021.
PCT/US2019/068435 International Search Report and Written Opinion dated Apr. 23, 2020.
PCT/US2020/019371 International Preliminary Report on Patentability dated Sep. 2, 2021.
PCT/US2020/019371 International Search Report and Written Opinion dated Jun. 25, 2020.
PCT/US2020/019986 International Preliminary Report on Patentability dated Sep. 10, 2021.
PCT/US2020/019986 International Search Report and Written Opinion dated Jul. 29, 2020.
PCT/US2020/019986 Invitation to Pay Additional Fees dated Jun. 5, 2020.
PCT/US2020/019988 International Preliminary Report on Patentability dated Sep. 10, 2021.
PCT/US2020/019988 International Search Report and Written Opinion dated Jul. 29, 2020.
PCT/US2020/019988 Invitation to Pay Additional Fees dated Jun. 8, 2020.
PCT/US2020/038679 International Search Report and Written Opinion dated Oct. 28, 2020.
PCT/US2020/052291 International Preliminary Report on Patentability dated Apr. 7, 2022.
PCT/US2020/052291 International Search Report and Written Opinion dated Mar. 10, 2021.
PCT/US2020/052291 Invitation to Pay Additional Fees dated Dec. 31, 2020.
PCT/US2020/052306 International Preliminary Report on Patentability dated Mar. 15, 2022.
PCT/US2020/052306 International Search Report and Written Opinion dated Mar. 2, 2021.
PCT/US2020/052306 Invitation to Pay Additional Fees dated Dec. 18, 2020.
PCT/US2020/064106 International Search Report and Written Opinion dated Jun. 3, 2021.
PCT/US2020/064106 Invitation to Pay Additional Fees dated Apr. 9, 2021.
Pigott et al.: The Use of a Novel Discovery Platform to Identify Peptide-Grafted Antibodies that Activate GLP-1 Receptor Signaling. Innovative Targeting Solutions Inc. (2013) XP055327428 retrieved from the internet: http://www.innovativetargeting.com/wo-content/uploads/2013/12/Pigott-et-al-Antibody-Engineering-2013.pdf.
Ponsel. High Affinity, Developability and Functional Size: The Holy Grail of Combinatorial Antibody Library Generation. Molecules. 16:3675-3700 (2011).
PubChem Data Sheet Acetonitrile. Printed from website https://pubchem.ncbi.nlm.nih.gov/ pp. 1-124 (2020).
PubChem Data Sheet Dichloromethane. Printed from website https://pubchem.ncbi.nlm.nih.gov/compound/Dichloromethane (2020).
PubChem Data Sheet Methylene Chloride. Printed from website https://pubchem.ncbi.nlm.nih.gov/ pp. 1-140 (2020).
Rajpal et al.: A general method for greatly improving the affinity of antibodies by using combinatorial libraries. Proc. Natl. Acad. Sci. 102(24):8466-8471 (2005).
Regep et al.: The H3 loop of antibodies shows unique structural characteristics. Proteins. 85(7):1311-1318 (2017).
Shen et al.: Multiple target capture with double-stranded DNA probes. Genome Medicine. 5:50 8 pages (2013).
Shipman et al.: Molecular recordings by directed CRISPR spacer acquisition. Science. 353(6298):1-16 (2016).
Solomon et al.: Genomics at Agilent: Driving Value in DNA Sequencing. https://www.agilent.com/labs/features/2010_genomics.html, 8 pages (Aug. 5, 2010).
U.S. Appl. No. 16/737,401 Final Office Action dated Jun. 13, 2022.
U.S. Appl. No. 14/241,874 Final Office Action dated Jan. 28, 2019.
U.S. Appl. No. 15/151,316 Final Office Action dated Jul. 9, 2020.
U.S. Appl. No. 15/156,134 Final Office Action dated Aug. 18, 2021.
U.S. Appl. No. 15/156,134 Final Office Action dated Jan. 3, 2020.
U.S. Appl. No. 15/156,134 Office Action dated Nov. 25, 2020.
U.S. Appl. No. 15/245,054 Notice of Allowance dated Dec. 14, 2017.
U.S. Appl. No. 15/272,004 Final Office Action dated Mar. 18, 2021.

(56) References Cited

OTHER PUBLICATIONS

U.S. Appl. No. 15/272,004 Office Action dated Apr. 13, 2022.
U.S. Appl. No. 15/272,004 Office Action dated Jun. 12, 2020.
U.S. Appl. No. 15/619,322 Final Office Action dated Jul. 9, 2021.
U.S. Appl. No. 15/619,322 Final Office Action dated Mar. 30, 2020.
U.S. Appl. No. 15/619,322 Office Action dated Nov. 4, 2020.
U.S. Appl. No. 15/816,995 Office Action dated May 19, 2020.
U.S. Appl. No. 15/835,342 Final Office Action dated Sep. 8, 2020.
U.S. Appl. No. 15/835,342 Office Action dated Apr. 16, 2021.
U.S. Appl. No. 15/835,342 Office Action dated Dec. 2, 2019.
U.S. Appl. No. 15/844,395 Office Action dated Jan. 24, 2020.
U.S. Appl. No. 15/902,855 Office Action dated Dec. 9, 2021.
U.S. Appl. No. 15/902,855 Restriction Requirement dated Apr. 6, 2021.
U.S. Appl. No. 15/921,479 Final Office Action dated Dec. 20, 2021.
U.S. Appl. No. 15/921,479 Final Office Action dated Jun. 15, 2020.
U.S. Appl. No. 15/921,479 Office Action dated Apr. 27, 2021.
U.S. Appl. No. 15/921,479 Office Action dated Apr. 28, 2022.
U.S. Appl. No. 15/921,479 Office Action dated Nov. 12, 2019.
U.S. Appl. No. 15/991,992 Office Action dated May 21, 2020.
U.S. Appl. No. 15/991,992 Restriction Requirement dated Mar. 10, 2020.
U.S. Appl. No. 16/031,784 Office Action dated May 12, 2020.
U.S. Appl. No. 16/039,256 Final Office Action dated Mar. 30, 2021.
U.S. Appl. No. 16/039,256 Office Action dated Aug. 20, 2020.
U.S. Appl. No. 16/039,256 Office Action dated May 10, 2022.
U.S. Appl. No. 16/039,256 Restriction Requirement dated May 18, 2020.
U.S. Appl. No. 16/128,372 Final Office Action dated Mar. 18, 2021.
U.S. Appl. No. 16/128,372 Office Action dated Dec. 13, 2021.
U.S. Appl. No. 16/128,372 Office Action dated Oct. 8, 2020.
U.S. Appl. No. 16/128,372 Restriction Requirement dated May 18, 2020.
U.S. Appl. No. 16/165,952 Office Action dated Mar. 12, 2020.
U.S. Appl. No. 16/239,453 Office Action dated May 11, 2020.
U.S. Appl. No. 16/384,678 Final Office Action dated Oct. 15, 2020.
U.S. Appl. No. 16/384,678 Office Action dated Jan. 21, 2020.
U.S. Appl. No. 16/530,717 Final Office Action dated Apr. 15, 2020.
U.S. Appl. No. 16/535,777 Final Office Action dated Oct. 20, 2020.
U.S. Appl. No. 16/535,777 Office Action dated Feb. 8, 2021.
U.S. Appl. No. 16/535,777 Office Action dated Jan. 23, 2020.
U.S. Appl. No. 16/535,779 First Action Interview dated Feb. 10, 2020.
U.S. Appl. No. 16/712,678 Office Action dated Nov. 26, 2021.
U.S. Appl. No. 16/712,678 Restriction Requirement dated Aug. 25, 2021.
U.S. Appl. No. 16/737,401 Office Action dated Jan. 5, 2022.
U.S. Appl. No. 16/737,401 Restriction Requirement dated Nov. 15, 2021.
U.S. Appl. No. 16/798,275 Final Office Action dated Aug. 30, 2021.
U.S. Appl. No. 16/798,275 Office Action dated Feb. 10, 2021.
U.S. Appl. No. 16/802,423 Restriction Requirement dated Dec. 29, 2021.
U.S. Appl. No. 16/802,439 Office Action dated Mar. 17, 2022.
U.S. Appl. No. 16/802,439 Restriction Requirement dated Oct. 1, 2021.
U.S. Appl. No. 16/854,719 Office Action dated Jun. 2, 2022.
U.S. Appl. No. 16/854,719 Office Action dated Nov. 24, 2021.
U.S. Appl. No. 16/854,719 Restriction Requirement dated Jul. 28, 2021.
U.S. Appl. No. 16/879,705 Office Action dated Sep. 9, 2021.
U.S. Appl. No. 16/906,555 Office Action dated Aug. 17, 2021.
U.S. Appl. No. 17/154,906 Office Action dated May 17, 2022.
U.S. Appl. No. 17/154,906 Office Action dated Nov. 10, 2021.
U.S. Appl. No. 17/154,906 Restriction Requirement dated Jul. 26, 2021.
U.S. Appl. No. 15/921,537 Office Action dated Apr. 1, 2020.
Van der Velde: Thesis. Finding the Strength of Glass. Delft University of Technology. 1-16 (2015).
Wikipedia. Central dogma of molecular biology. URL: https://en.wikipedia.org/wiki/Central_dogma_of_molecular_biology. 9 pages (2021).
Williams et al.: Amplification of complex gene libraries by emulsion PCR. Nature Methods. 3(7):545-550(2006).
Xu et al.: Coordination between the Polymerase and 5'-Nuclease Components of DNA Polymerase I of *Escherichia coli*. The Journal of Biological Chemistry. 275(27):20949-20955 (2000).
Yazdi et al.: DNA-Based Storage: Trends and Methods. IEEE Transactions on Molecular, Biological and Multi-Scale Communications. IEEE. 1(3):230-248 (2016).
Damha et al.: An improved procedure for derivatization of controlled-pore glass beads for solid-phase oligonucleotide synthesis. Nucleic Acids Research. 18(13):3813-3821 (1990).
PCT/US2022/023936 International Search Report and Written Opinion dated Jul. 14, 2022.
Smith et al.: Changing the peptide specificity of a human T-cell receptor by directed evolution. Nature Communications. 5:1-13 (2014).
Sommermeyer et al.: Minimal Amino Acid Exchange in Human TCR Constant Regions Fosters Improved Function of TCR Gene-Modified T Cells. Journal of Immunology. 184:6223-6231 (2010).
U.S. Appl. No. 15/902,855 Final Office Action dated Aug. 11, 2022.
U.S. Appl. No. 16/417,023 Final Office Action dated Aug. 2, 2022.
U.S. Appl. No. 16/417,023 Office Action dated Feb. 22, 2022.
U.S. Appl. No. 16/726,073 Office Action dated Jun. 30, 2022.
U.S. Appl. No. 16/802,423 Notice of Allowance dated Jul. 25, 2022.
U.S. Appl. No. 15/902,855 Office Action dated Oct. 5, 2022.
U.S. Appl. No. 17/180,614 Office Action dated Oct. 5, 2022.
Frederickson et al.: A rationally designed agonist antibody fragment that funxtionally mimics thrombopoietin. Proceedings of the National Academy of Sciences. National Academy of Sciences. 103(39):14307-14312 (2006).
Liu et al.: Functional GLP-1R antibodies identified from a synthetic GPCR-focused library demonstrate potent blood glucose control. MABS. 13(1):15 pages (2021).
U.S. Appl. No. 15/156,134 Office Action dated Dec. 8, 2022.
U.S. Appl. No. 15/619,322 Office Action dated Nov. 10, 2022.
U.S. Appl. No. 15/921,479 Final Office Action dated Jan. 9, 2023.
U.S. Appl. No. 16/726,073 Final Office Action dated Dec. 16, 2022.
U.S. Appl. No. 16/798,275 Office Action dated Feb. 3, 2023.
U.S. Appl. No. 16/921,712 Non-Final Office Action dated Nov. 25, 2022.
U.S. Appl. No. 17/030,216 Restriction Requirement dated Dec. 23, 2022.
U.S. Appl. No. 17/030,232 Restriction Requirement dated Jan. 26, 2023.
U.S. Appl. No. 17/068,551 Restriction Requirement dated Dec. 23, 2022.
U.S. Appl. No. 17/116,939 Restriction Requirement dated Dec. 27, 2022.
U.S. Appl. No. 17/120,037 Office Action dated Feb. 2, 2023.
U.S. Appl. No. 17/154,906 Office Action dated Jan. 20, 2023.
U.S. Appl. No. 17/180,614 Final Office Action dated Apr. 5, 2023.
U.S. Appl. No. 17/578,356 Notice of Allowance dated Dec. 5, 2022.

\* cited by examiner

Repeat with additional panel added

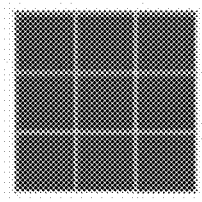 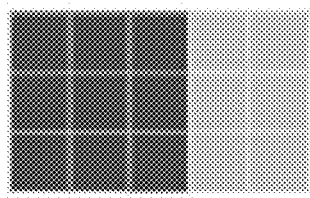
Additional Content
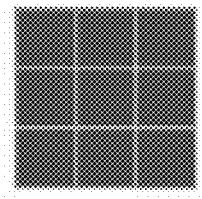 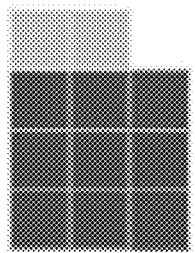
Enhanced Content
FIG. 29A

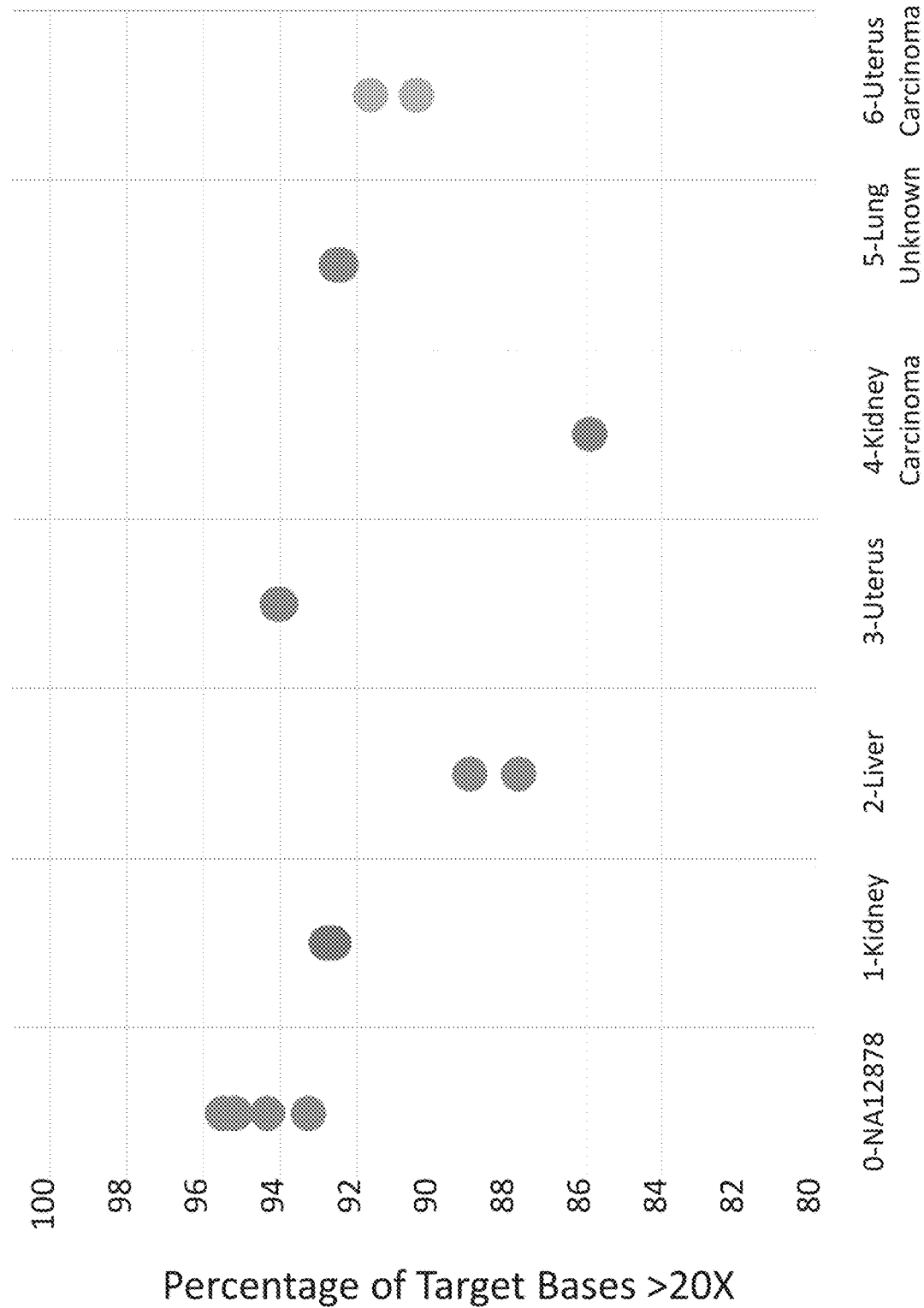

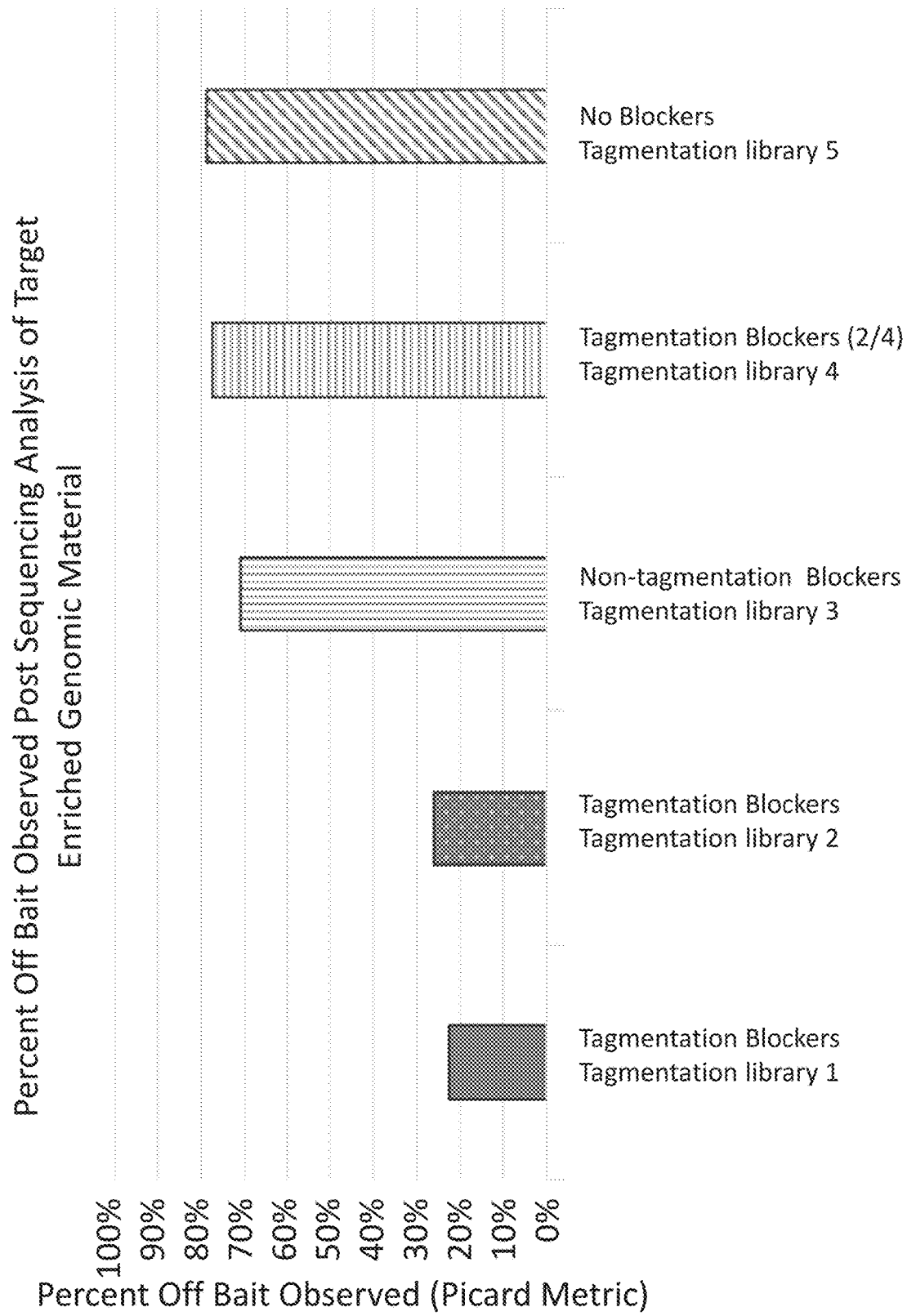

POLYNUCLEOTIDES, REAGENTS, AND METHODS FOR NUCLEIC ACID HYBRIDIZATION

CROSS-REFERENCE

This application is a continuation of U.S. patent application Ser. No. 16/417,023, filed on May 20, 2019, which claims the benefit of U.S. provisional patent application No. 62/673,704 filed on May 18, 2018, U.S. provisional patent application No. 62/810,343 filed on Feb. 25, 2019, U.S. provisional patent application no. 62/814,749 filed on Mar. 6, 2019, U.S. provisional patent application No. 62/675,647 filed May 23, 2018, U.S. provisional patent application No. 62/810,293 filed Feb. 25, 2019, U.S. provisional patent application No. 62/814,753 filed Mar. 6, 2019, U.S. provisional patent application No. 62/833,440 filed Apr. 12, 2019, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 2, 2019, is named 44854-776_301_SL.txt and is 2,072 bytes in size.

BACKGROUND

Highly efficient chemical gene synthesis with high fidelity and low cost has a central role in biotechnology and medicine, and in basic biomedical research. De novo gene synthesis is a powerful tool for basic biological research and biotechnology applications. While various methods are known for the synthesis of relatively short fragments in a small scale, these techniques often suffer from scalability, automation, speed, accuracy, and cost.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

Provided herein are methods for sequencing genomic DNA, comprising: contacting a composition comprising a first polynucleotide library comprising at least 30,000 polynucleotides, wherein each of the at least 30,000 polynucleotides is present in an amount such that, following hybridization with genomic fragments and sequencing of the hybridized genomic fragments, the polynucleotide library provides a read depth of at least 80 percent of the bases of the genomic fragments corresponding to the polynucleotides; and a total number of sequencing reads, wherein the total number of sequencing reads are capable of covering 100 percent of each of the bases of the genomic fragments corresponding to the polynucleotides at a theoretical read depth, wherein the ratio of the read depth of at least 80 percent of the bases of the genomic fragments corresponding to the polynucleotides to the theoretical read depth is at least 0.5 with a plurality of genomic fragments; enriching at least one genomic fragment that binds to the first polynucleotide library to generate at least one enriched target polynucleotide; sequencing the at least one enriched target polynucleotide; identifying one or more positions of the at least one enriched polynucleotide having less than average read depth; repeating steps a-c, wherein a second polynucleotide library comprising at least 1500 polynucleotides is added to the composition, wherein the second polynucleotide library comprises at least one polynucleotide that binds to genomic fragments comprising the one or more positions having less than average read depth, wherein the presence of the second polynucleotide library increases the read depth at the one or more positions having less than average read depth. Provided herein are methods for sequencing genomic DNA, comprising: contacting a composition comprising a first polynucleotide library comprising at least 30,000 polynucleotides, wherein each of the at least 30,000 polynucleotides is present in an amount such that, following hybridization with genomic fragments and sequencing of the hybridized genomic fragments, the polynucleotide library provides a read depth of at least 80 percent of the bases of the genomic fragments corresponding to the polynucleotides; and a total number of sequencing reads, wherein the total number of sequencing reads are capable of covering 100 percent of each of the bases of the genomic fragments corresponding to the polynucleotides at a theoretical read depth, wherein the ratio of the read depth of at least 80 percent of the bases of the genomic fragments corresponding to the polynucleotides to the theoretical read depth is at least 0.5 with a plurality of genomic fragments; enriching at least one genomic fragment that binds to the first polynucleotide library to generate at least one enriched target polynucleotide; sequencing the at least one enriched target polynucleotide; identifying one or more positions of the at least one enriched polynucleotide having less than average read depth; repeating steps a-c, wherein a second polynucleotide library is added to the composition, wherein the second polynucleotide library comprises at least one polynucleotide that binds to genomic fragments comprising the one or more positions having less than average read depth, wherein the presence of the second polynucleotide library increases the read depth at the one or more positions having less than average read depth. Further provided herein are methods wherein the first polynucleotide library and the second polynucleotide library do not comprise any common sequences. Further provided herein are methods wherein the first polynucleotide library and the second polynucleotide library comprise at least one common sequence. Further provided herein are methods wherein the presence of the second polynucleotide library increases the read depth at the one or more positions of the least one enriched target polynucleotide having less than average read depth by at least 10 fold. Further provided herein are methods wherein the presence of the second polynucleotide library increases the read depth at the one or more positions of the at least one enriched target polynucleotide having less than average read depth by at least 100 fold.

Provided herein are polynucleotide libraries, the polynucleotide library comprising at least 1500 polynucleotides, wherein less than all polynucleotides comprises a molecular tag, wherein each of the at least 5000 polynucleotides are present in an amount such that, following hybridization with genomic fragments and sequencing of the hybridized genomic fragments, the polynucleotide library provides a read depth of at least 90 percent of the bases of the genomic fragments corresponding to the polynucleotides; and a total number of sequencing reads, wherein the total number of sequencing reads are capable of covering 100 percent of each of the bases of the genomic fragments corresponding to the polynucleotides at a theoretical read depth, wherein the ratio of the read depth of at least 90 percent of the bases of the genomic fragments corresponding to the polynucleotides to the theoretical read depth is at least 0.5. Further provided herein are polynucleotide libraries wherein no more than 90% of the polynucleotides comprise a molecular tag. Further provided herein are polynucleotide libraries wherein no more than 80% of the polynucleotides comprise a molecular tag. Further provided herein are polynucleotide libraries wherein no more than 50% of the polynucleotides comprise a molecular tag. Further provided herein are polynucleotide libraries wherein no more than 25% of the polynucleotides comprise a molecular tag. Further provided herein are polynucleotide libraries wherein the molecular tag is biotin. Further provided herein are polynucleotide libraries wherein the at least 5000 polynucleotides encode for at least 5000 genes. Further provided herein are polynucleotide libraries wherein the polynucleotide library comprises at least 30,000 polynucleotides. Further provided herein are polynucleotide libraries wherein the polynucleotide library comprises at least 100,000 polynucleotides.

Provided herein are methods for enriching nucleic acids comprising: contacting the polynucleotide library described herein with a plurality of genomic fragments; enriching at least one genomic fragment that binds to the polynucleotide library to generate at least one enriched target polynucleotide; and sequencing the at least one enriched target polynucleotide. Further provided herein are methods wherein the polynucleotide library provides for at least 90 percent unique reads for the bases of the enriched target polynucleotide after sequencing. Further provided herein are methods wherein the polynucleotide library provides for at least 95 percent unique reads for the bases of the enriched target polynucleotide after sequencing. Further provided herein are methods wherein the polynucleotide library provides for at least 80 percent of the bases of the enriched target polynucleotide having a read depth within about 1.5 times the mean read depth. Further provided herein are methods wherein the polynucleotide library provides for at least 90 percent of the bases of the enriched target polynucleotide having a read depth within about 1.5 times the mean read depth.

Provided herein are polynucleotide libraries, the polynucleotide library comprising at least 5000 polynucleotides, wherein each of the at least 5000 polynucleotides is present in an amount such that, following hybridization with a composition comprising i) a genomic library, wherein the genomic library comprises polynucleotides each comprising genomic fragments, at least one index sequence, and at least one adapter; and ii) at least one polynucleotide blocker, wherein the polynucleotide blocker is complementary to at least a portion of the adapter sequence, but not complementary to the at least one index sequence; and sequencing of the hybridized genomic fragments, the polynucleotide library provides for at least 30 fold read depth of at least 90 percent of the bases of the genomic fragments under conditions wherein the total number of reads is no more than 55 fold higher than the total number of bases of the hybridized genomic fragments. Further provided herein are polynucleotide libraries wherein the composition comprises no more than four polynucleotide blockers. Further provided herein are polynucleotide libraries wherein the polynucleotide blocker comprises one or more nucleotide analogues. Further provided herein are polynucleotide libraries wherein the polynucleotide blocker comprises one or more locked nucleic acids (LNAs). Further provided herein are polynucleotide libraries wherein the polynucleotide blocker comprises one or more bridged nucleic acids (BNAs). Further provided herein are polynucleotide libraries wherein the polynucleotide blocker comprises at least 2 nucleotide analogues. Further provided herein are polynucleotide libraries wherein the polynucleotide blocker comprises at least 5 nucleotide analogues. Further provided herein are polynucleotide libraries wherein the polynucleotide blocker comprises at least 10 nucleotide analogues. Further provided herein are polynucleotide libraries wherein the polynucleotide blocker has a $T_m$ of at least 70 degrees C. Further provided herein are polynucleotide libraries wherein the polynucleotide blocker has a $T_m$ of at least 75 degrees C. Further provided herein are polynucleotide libraries wherein the polynucleotide blocker has a $T_m$ of at least 78 degrees C. Further provided herein are polynucleotide libraries wherein the polynucleotide blocker has a $T_m$ of at least 82 degrees C. Further provided herein are polynucleotide libraries wherein the polynucleotide blocker has a Tm of 80-90 degrees C. Further provided herein are polynucleotide libraries wherein the polynucleotide blocker has a $T_m$ of at least 80 degrees C. Further provided herein are polynucleotide libraries wherein the genomic library comprises genomic fragments from at least 2 different samples. Further provided herein are polynucleotide libraries wherein the genomic library comprises genomic fragments from at least 10 different samples. Further provided herein are polynucleotide libraries wherein the genomic library comprises genomic fragments from at least 2 non-identical index sequences. Further provided herein are polynucleotide libraries wherein the genomic library comprises genomic fragments from at least 16 non-identical index sequences. Further provided herein are polynucleotide libraries wherein the genomic library comprises genomic fragments further comprising at least one unique molecular identifier (UMI).

Provided herein are methods for enriching nucleic acids comprising: contacting the polynucleotide libraries described herein with a plurality of genomic fragments; enriching at least one genomic fragment that binds to the polynucleotide library to generate at least one enriched target polynucleotide; and sequencing the at least one enriched target polynucleotide. Further provided herein are methods wherein the off-target rate is less than 25%. Further provided herein are methods wherein the off-target rate is less than 20%. Further provided herein are methods wherein the molar ratio between at least one polynucleotide blocker and the complementary adapter is no more than 5:1. Further provided herein are methods wherein the molar ratio between at least one polynucleotide blocker and the complementary adapter is no more than 2:1. Further provided herein are methods wherein the molar ratio between at least one polynucleotide blocker and the complementary adapter is no more than 1.5:1.

Provided herein are compositions for nucleic acid hybridization comprising: a first polynucleotide library; a second polynucleotide library, wherein at least one polynucleotide in the first library is at least partially complimentary to at least one polynucleotide of the second library; and an additive, wherein the additive reduces off-target hybridization of the at least one polynucleotide of the first library with the at least one polynucleotide of the second library by decreasing a local concentration of the first polynucleotide library or the second polynucleotide library at an air-liquid interface. Further provided herein are compositions wherein the additive is mineral oil, a nucleotide triphosphate, polyether, or urea. Further provided herein are compositions wherein the additive is a hydrocarbon comprising at least six carbon atoms. Further provided herein are compositions wherein the additive is silicon oil. Further provided herein are compositions wherein the oil is derived from plant sources. Further provided herein are compositions wherein the composition further comprises dimethyl sulfoxide. Further provided herein are compositions wherein the composition does not comprise a formamide. Further provided herein are compositions wherein the size of the first polynucleotide library is less than 10 million bases. Further provided herein are compositions wherein the size of the first polynucleotide library is less than 1 million bases. Further provided herein are compositions wherein the size of the first polynucleotide library is less than 0.5 million bases. Further provided herein are compositions wherein the first polynucleotide library comprises as least one exon sequence. Further provided herein are compositions wherein first polynucleotide library comprises polynucleotides encoding for at least 10 genes. Further provided herein are compositions wherein the first polynucleotide library comprises polynucleotides encoding for at least 100 genes. Further provided herein are compositions wherein the first polynucleotide library comprises at least one genomic fragment. Further provided herein are compositions wherein the first polynucleotide library comprises RNA, DNA, cDNA, or genomic DNA. Further provided herein are compositions wherein the first polynucleotide library comprises genomic DNA.

Provided herein are compositions for nucleic acid hybridization comprising: a first polynucleotide library and a second polynucleotide library each comprising a plurality of polynucleotides, wherein at least one polynucleotide in the first library is at least partially complimentary to at least one polynucleotide of the second library; and an oil, wherein the oil reduces off-target hybridization of the at least one polynucleotide of the first library with the at least one polynucleotide of the second library by decreasing a local concentration of the first polynucleotide library or the second polynucleotide library at an air-liquid interface. Further provided herein are compositions wherein the additive is mineral oil, a nucleotide triphosphate, polyether, or urea. Further provided herein are compositions wherein the additive is a hydrocarbon comprising at least six carbon atoms. Further provided herein are compositions wherein the additive is silicon oil. Further provided herein are compositions wherein the oil is derived from plant sources. Further provided herein are compositions wherein the composition further comprises dimethyl sulfoxide. Further provided herein are compositions wherein the composition does not comprise a formamide. Further provided herein are compositions wherein the size of the first polynucleotide library is less than 10 million bases. Further provided herein are compositions wherein the size of the first polynucleotide library is less than 1 million bases. Further provided herein are compositions wherein the size of the first polynucleotide library is less than 0.5 million bases. Further provided herein are compositions wherein first polynucleotide library comprises as least one exon sequence. Further provided herein are compositions wherein first polynucleotide library comprises polynucleotides encoding for at least 10 genes. Further provided herein are compositions wherein first polynucleotide library comprises polynucleotides encoding for at least 100 genes. Further provided herein are compositions wherein the first polynucleotide library comprises at least one genomic fragment. Further provided herein are compositions wherein the first polynucleotide library comprises RNA, DNA, cDNA, or genomic DNA. Further provided herein are compositions wherein the first polynucleotide library comprises genomic DNA.

Provided herein are methods for reducing off-target nucleic acid hybridization, comprising: contacting a first polynucleotide library with a second polynucleotide library, wherein the first polynucleotide library and the second polynucleotide library each comprise a plurality of polynucleotides, and wherein at least one polynucleotide in the first library is at least partially complimentary to at least one polynucleotide in the second library; enriching at least one genomic fragment that binds to the second polynucleotide library to generate at least one enriched target polynucleotide, wherein enriching comprises at least one aspiration step, and wherein the at least one aspiration step comprises aspirating only liquid from the area near the air/liquid interface; and sequencing the at least one enriched target polynucleotide. Further provided herein are methods wherein the additive is oil, a nucleotide triphosphate, polyether, or urea. Further provided herein are methods wherein the additive is mineral oil. Further provided herein are methods wherein the presence of the additive decreases off-target binding. Further provided herein are methods wherein the presence of the additive decreases off-target binding by at least 10%. Further provided herein are methods wherein the presence of the additive decreases off-target binding by at least 20%. Further provided herein are methods wherein the presence of the additive decreases off-target binding by at least 30%. Further provided herein are methods wherein the off-target binding is random off-target binding. Further provided herein are methods wherein the size of the first polynucleotide library is less than 10 million bases. Further provided herein are methods wherein the size of the first polynucleotide library is less than 1 million bases. Further provided herein are methods wherein the size of the first polynucleotide library is less than 0.5 million bases. Further provided herein are methods wherein first polynucleotide library comprises as least one exon sequence. Further provided herein are methods wherein first polynucleotide library comprises polynucleotides encoding for at least 10 genes. Further provided herein are methods wherein first polynucleotide library comprises polynucleotides encoding for at least 100 genes. Further provided herein are methods wherein the first polynucleotide library comprises at least one genomic fragment. Further provided herein are methods wherein the first polynucleotide library comprises RNA, DNA, cDNA, or genomic DNA. Further provided herein are methods wherein the first polynucleotide library comprises genomic DNA.

Provided herein are methods for sequencing genomic DNA, comprising: contacting a polynucleotide library with a plurality of genomic fragments and an additive to form a mixture, wherein the additive decreases a local concentration of the polynucleotide library or the genomic fragments in the mixture at an air-liquid interface; enriching at least one genomic fragment that binds to the polynucleotide library to generate at least one enriched target polynucleotide; and sequencing the at least one enriched target polynucleotide. Further provided herein are methods wherein the additive is oil, a nucleotide triphosphate, polyether, or urea. Further provided herein are methods wherein the additive is mineral oil. Further provided herein are methods wherein the presence of the additive decreases off-target binding. Further provided herein are methods wherein the presence of the additive decreases off-target binding by at least 10%. Further provided herein are methods wherein the presence of the additive decreases off-target binding by at least 20%. Further provided herein are methods wherein the presence of the additive decreases off-target binding by at least 30%. Further provided herein are methods wherein the off-target binding is random off-target binding. Further provided herein are methods wherein the size of the first polynucleotide library is less than 10 million bases. Further provided herein are methods wherein the size of the first polynucleotide library is less than 1 million bases. Further provided herein are methods wherein the size of the first polynucleotide library is less than 0.5 million bases. Further provided herein are methods wherein the first polynucleotide library comprises as least one exon sequence. Further provided herein are methods wherein the first polynucleotide library comprises polynucleotides encoding for at least 10 genes. Further provided herein are methods wherein the first polynucleotide library comprises polynucleotides encoding for at least 100 genes. Further provided herein are methods wherein the first polynucleotide library comprises at least one genomic fragment. Further provided herein are methods wherein the first polynucleotide library comprises RNA, DNA, cDNA, or genomic DNA. Further provided herein are methods wherein the first polynucleotide library comprises genomic DNA.

BRIEF DESCRIPTION OF THE DRAWINGS

FIG. 28A shows quality of 800 kb panels. FIG. 28B shows enrichment performance of 800 kb panels. FIG. 28C shows reproducibility of probe representation within same synthesis and different amplifications. FIG. 28D shows reproducibility of probe representation between syntheses. FIG. 28E shows lot to lot reproducibility capture per probe. FIGS. 28F-28I show reproducibility of probe target enrichment performance between syntheses. FIG. 28F shows lot to lot reproducibility for percent off-target capture. FIG. 28G shows lot to lot reproducibility for percent duplicates. FIG. 28H shows lot to lot reproducibility for the fraction of target bases with greater than 30× coverage. FIG. 28I shows lot to lot reproducibility for fold-80 base penalty.

FIG. 29A is a schematic of adding or enhancing content to custom panels.

FIG. 30B shows a graph of probes with 3, 5, 10 or 15 mismatches (left to right). FIG. 30C shows a graph of probes with 20, 30, or 50 mismatches (left to right).

FIG. 31A shows a comparison of standard and adaptive probe designs for percent off target rates. FIG. 31B shows a plot of the percent off-target reads which correlates predicted effects of selective probe removal with experimental results of selective probe removal. Various amounts of the worst performing probes were removed from an exome capture library. FIG. 31C shows a graph of the percent off target as a function of selective removal of no probes (base/control), 0.4% of probes (increased), 1.7% of probes (moderate), or 3.3% of probes (strong) from an exome capture library.

FIG. 32B shows a graph of specificity as percent off target for the exome panel alone or with the RefSeq panel added. FIG. 32C shows a graph of uniformity for the exome panel alone or with the RefSeq panel added. FIG. 32D shows a graph of library size for the exome panel alone or with the RefSeq panel added. FIG. 32E shows a graph of duplicate rate for the exome panel alone or with the RefSeq panel added. FIG. 32F shows a graph of coverage rate for the exome panel alone or with the RefSeq panel added.

FIG. 39E is a plot of the percentage of target bases with greater than 20× coverage vs. various FFPE samples.

FIG. 43 is a plot of percent off bait for a library generated using a tagmentation method and various configurations of universal blockers.

DETAILED DESCRIPTION

Figure 1A:
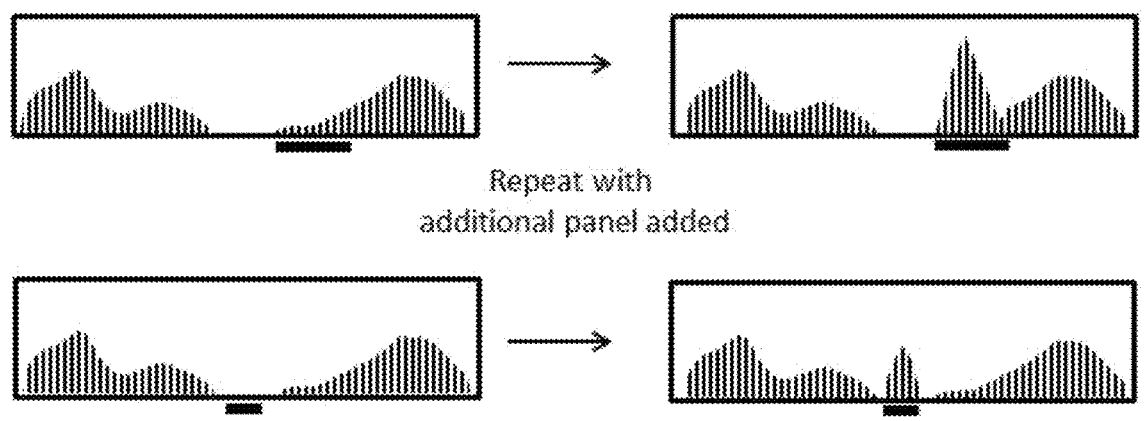
FIG. 1A depicts a schematic workflow, including analyzing nucleic acid sequencing data, spiking in additional capture probe polynucleotide libraries that target specific areas of the analyzed nucleic acids, and obtaining new sequencing data with increased read depth at targeted regions.

Provided herein are methods and compositions for designing, synthesizing and controlling hybridization events within large polynucleotide libraries. Capture probe libraries are designed and synthesized to bind to specific target sequences in a sample population of polynucleotides, which enables any number of downstream applications such as diagnostic assays, sequencing, selection assays, or other method that requires a hybridization step. Factors contributing to the overall efficiency of hybridization include capture probe stoichiometry/uniformity, capture probe labeling, dilution effects, adapter dimerization, and hybridization conditions. Another factor contributing to the overall efficiency of hybridization is the local concentration of non-target nucleic acids at an air-water interface. Such concentrations herein are controlled through the presence of additives and washing methods, leading to improved hybridization. Further provided are buffer compositions which allow reductions in hybridization times while achieving comparable sequencing depth. Further provided are blocker polynucleotides that decrease the percentage of off-target (or off-bait) reads.

Definitions

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

As used herein, the terms "preselected sequence", "predefined sequence" or "predetermined sequence" are used interchangeably. The terms mean that the sequence of the polymer is known and chosen before synthesis or assembly of the polymer. In particular, various aspects of the invention are described herein primarily with regard to the preparation of nucleic acids molecules, the sequence of the oligonucleotide or polynucleotide being known and chosen before the synthesis or assembly of the nucleic acid molecules.

The term nucleic acid encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands). Nucleic acid sequences, when provided, are listed in the 5' to 3' direction, unless stated otherwise. Methods described herein provide for the generation of isolated nucleic acids. Methods described herein additionally provide for the generation of isolated and purified nucleic acids. The length of polynucleotides, when provided, are described as the number of bases and abbreviated, such as nt (nucleotides), bp (bases), kb (kilobases), or Gb (gigabases).

Provided herein are methods and compositions for production of synthetic (i.e. de novo synthesized or chemically synthesizes) polynucleotides. The term oligonucleic acid, oligonucleotide, oligo, and polynucleotide are defined to be synonymous throughout. Libraries of synthesized polynucleotides described herein may comprise a plurality of polynucleotides collectively encoding for one or more genes or gene fragments. In some instances, the polynucleotide library comprises coding or non-coding sequences. In some instances, the polynucleotide library encodes for a plurality of cDNA sequences. Reference gene sequences from which the cDNA sequences are based may contain introns, whereas cDNA sequences exclude introns. Polynucleotides described herein may encode for genes or gene fragments from an organism. Exemplary organisms include, without limitation, prokaryotes (e.g., bacteria) and eukaryotes (e.g., mice, rabbits, humans, and non-human primates). In some instances, the polynucleotide library comprises one or more polynucleotides, each of the one or more polynucleotides encoding sequences for multiple exons. Each polynucleotide within a library described herein may encode a different sequence, i.e., non-identical sequence. In some instances, each polynucleotide within a library described herein comprises at least one portion that is complementary to sequence of another polynucleotide within the library. Polynucleotide sequences described herein may be, unless stated otherwise, comprise DNA or RNA. A polynucleotide library described herein may comprise at least 10, 20, 50, 100, 200, 500, 1,000, 2,000, 5,000, 10,000, 20,000, 30,000, 50,000, 100,000, 200,000, 500,000, 1,000,000, or more than 1,000,000 polynucleotides. A polynucleotide library described herein may have no more than 10, 20, 50, 100, 200, 500, 1,000, 2,000, 5,000, 10,000, 20,000, 30,000, 50,000, 100,000, 200,000, 500,000, or no more than 1,000,000 polynucleotides. A polynucleotide library described herein may comprise 10 to 500, 20 to 1000, 50 to 2000, 100 to 5000, 500 to 10,000, 1,000 to 5,000, 10,000 to 50,000, 100,000 to 500,000, or to 50,000 to 1,000,000 polynucleotides. A polynucleotide library described herein may comprise about 370,000; 400,000; 500,000 or more different polynucleotides.

Methods for Hybridization

Figure 33A:
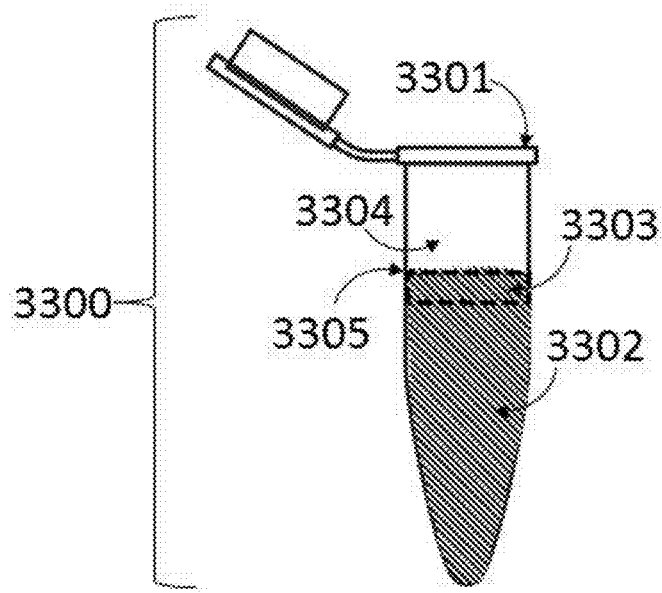
FIG. 33A depicts an exemplary hybridization reaction, wherein nucleic acids concentrate near a gas-liquid interface.
Figure 33B:
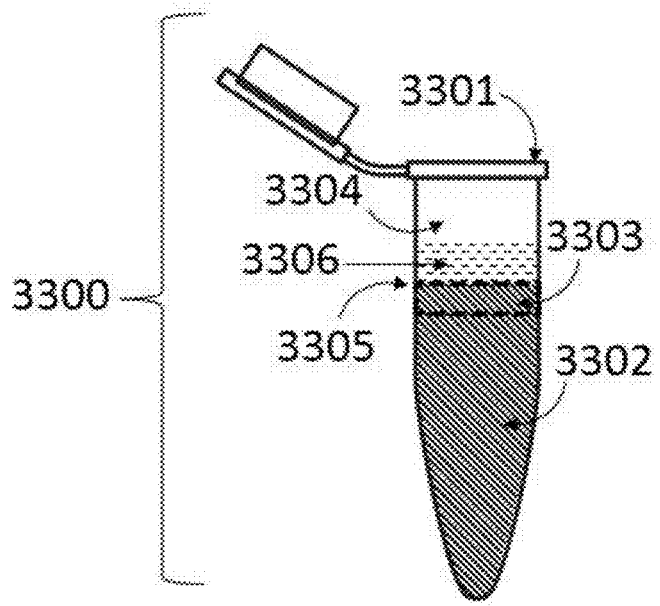
FIG. 33B depicts an exemplary hybridization reaction, wherein nucleic acids are prevented from concentrating near a gas-liquid interface by an additive.
Figure 33C:
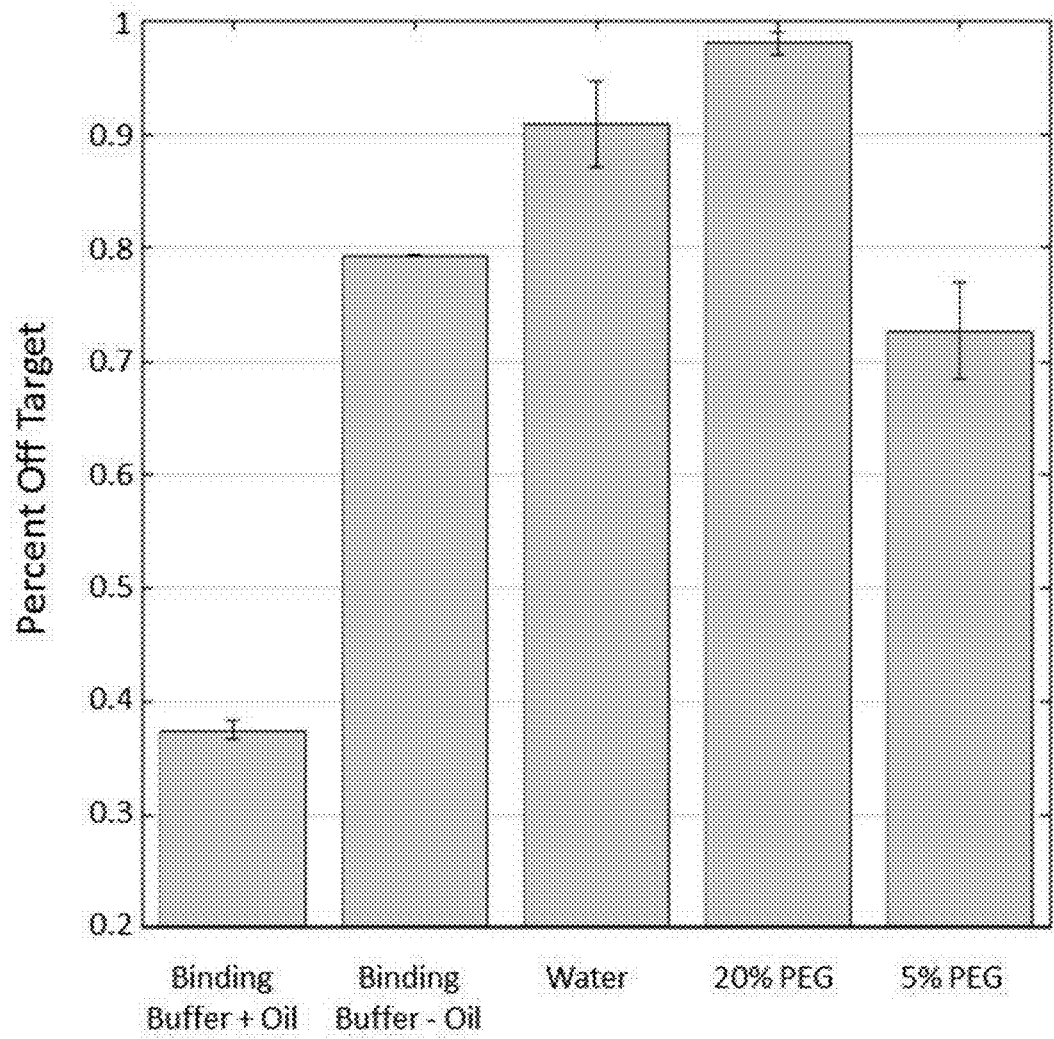
FIG. 33C depicts a plot of the percent off target vs. binding buffer comprising various additives for an enrichment and sequencing analysis.
Figure 38:
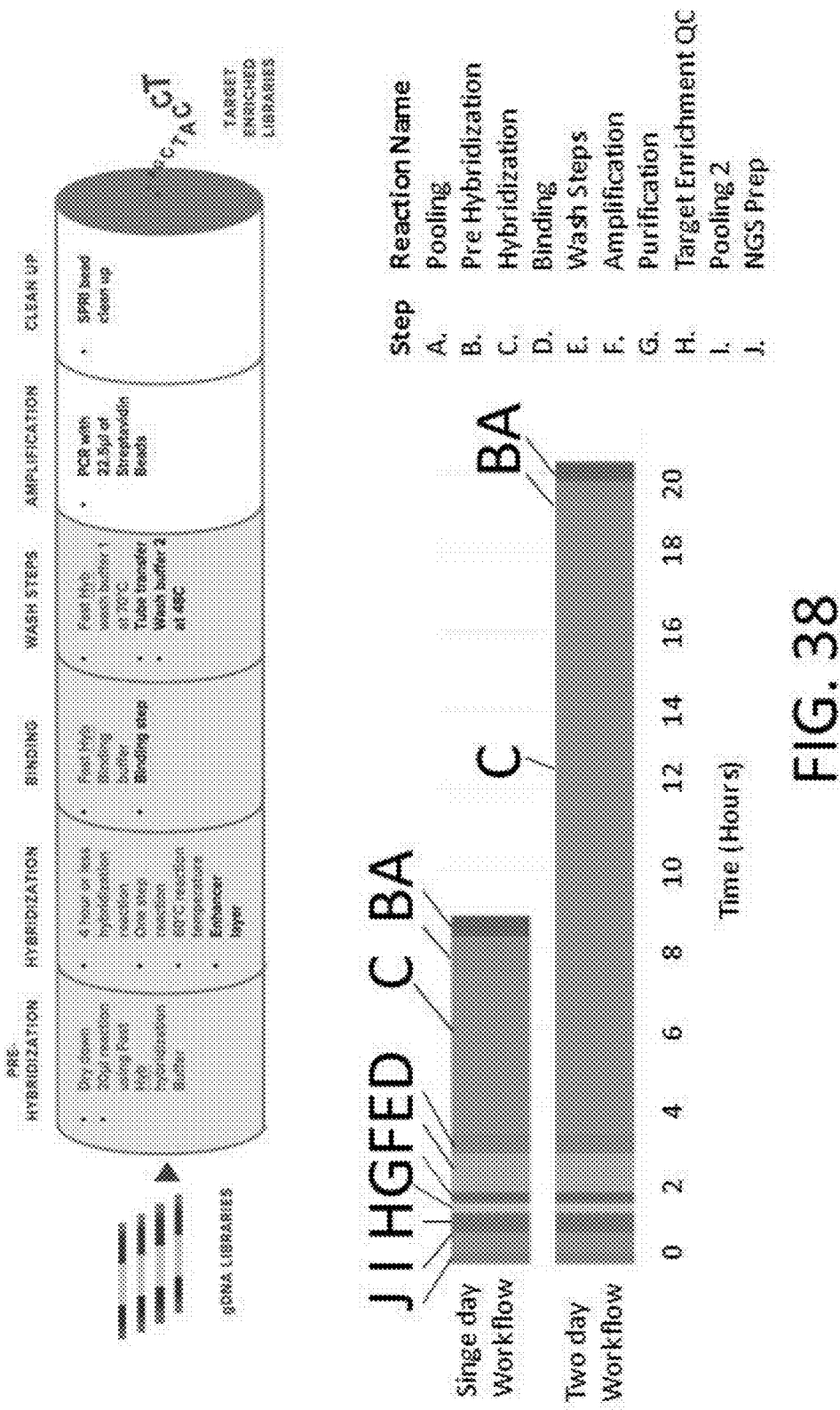
FIG. 38 depicts comparison of workflows using traditional hybridization buffers vs. a streamlined target enrichment (top) workflow that can be completed in as little as 5-9 hours. Figure discloses SEQ ID NO: 5.

Described herein are methods of hybridization designed to improve the efficiency and accuracy of capture probes binding to target nucleic acids (FIGS. 33A-33C). Such methods comprise changing the stoichiometry of individual or groups of capture probes in a capture probe library, supplementing a capture probe library with capture probes targeting alternative sequences, preventing off-target binding interactions by use of blocking polynucleotides comprising nucleobase analogues, and partial labeling of capture probe libraries. Also provided are methods to reduce off-target (or off-bait) sequencing metrics (FIGS. 33A-33B). Without being bound by theory, factors which contribute to off-target rates include the ability of probes to freely interact/hybridize with the target nucleic acids, as well as the efficiency of washing away non-hybridized, non-target nucleic acids. These factors may be influenced by a non-uniform concentration of nucleic acids in a solution, such as at a gas-liquid interface. Such hybridization reactions may be improved by addition of additives that prevent such non-uniform concentrations, and/or by controlled manipulation of such solutions. Additives or buffers in some instances also result in decreased hybridization times (FIG. 38). Such improvements often lead to significant decreases for off-target rates with smaller polynucleotide libraries (e.g., less than 1 Mb), but are also used with larger libraries, such as exome libraries. Also provided herein are de novo synthesized polynucleotides for use in hybridization to genomic DNA, for example in the context of a sequencing process. In a first step of an exemplary sequencing workflow (FIG. 2), a nucleic acid sample 208 comprising target polynucleotides is fragmented by mechanical or enzymatic shearing to form a library of fragments 209. Adapters 215 optionally comprising primer sequences and/or barcodes are ligated to form an adapter-tagged library 210. This library is then optionally amplified, and hybridized with target binding polynucleotides 217 which hybridize to target polynucleotides, along with blocking polynucleotides 216 that prevent hybridization between target binding polynucleotides 217 and adapters 215. Capture of target polynucleotide-target binding polynucleotide hybridization pairs 212, and removal of target binding polynucleotides 217 allows isolation/enrichment of target polynucleotides 213, which are then optionally amplified and sequenced 214. In some instances the addition of blockers to the hybridization reaction reduces off-target rates by preventing adapter-adapter interactions (FIG. 1B).

A first method described herein comprises changing the stoichiometry of individual or groups of capture probes in a capture probe library. For example, an enrichment and sequencing analysis is run on a nucleic acid sample, and one or more regions of the targeted sequences comprise less than desired read depth (FIG. 1A, black bar, left). Addition of a second "spike in," targeted, or (targeted) panel library increases the read depth at these less than average read depth regions (FIG. 1A, black bars, right). Such regions are in some instances regions that are already targeted by a larger capture probe library, for example an exome probe or other library. Alternatively or in combination, such regions are not already targeted by the larger probe library, and the targeted panel library adds additional sequencing information to new regions of the nucleic acid sample. Exemplary panels in some instances target genes with specific function (development, disease state, pain, physical trait, or other function), or non-coding regions such as introns. In some embodiments, the panels comprise target genes involved in disease including but not limited to cancer, neurodegenerative disease, and mitochondrial disorders.

Figure 1B:
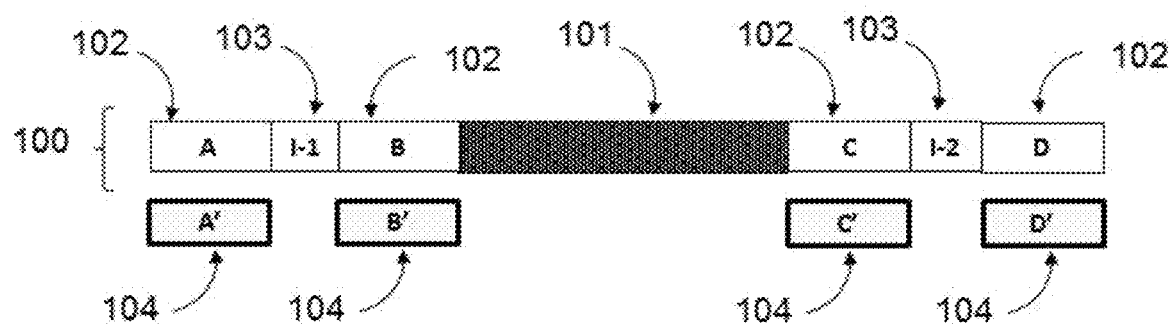
FIG. 1B depicts an exemplary a dual adapter-ligated nucleic acid with index sequences and four universal blocker polynucleotides.
Figure 2:
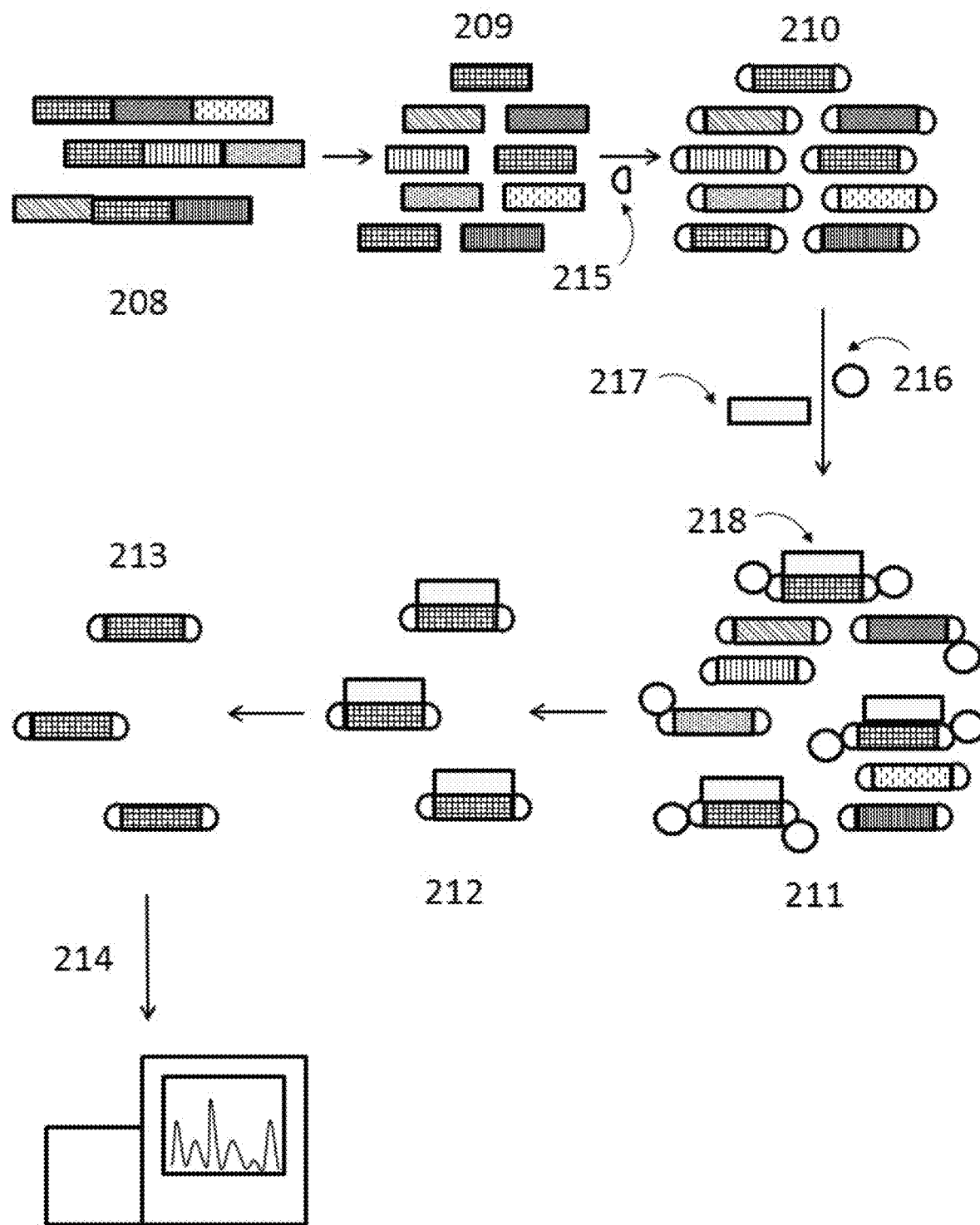
FIG. 2 depicts an exemplary workflow for enrichment and sequencing of a nucleic acid sample.

A second method described herein comprises the use of universal blockers to prevent off-target binding of capture probes to adapters ligated to genomic fragments 101, or adapter-adapter hybridization (FIG. 1B). Adapter blockers used for preventing off-target hybridization may target a portion or the entire adapter 102. In some instances, specific blockers are used that are complementary to a portion of the adapter 102 that includes the unique index sequence 103. In cases where the adapter-tagged genomic library 100 comprises a large number of different indices 103, it can be beneficial to design blockers which either do not target the index sequence 103, or do not hybridize strongly to it. For example, a "universal" blocker 104 targets a portion of the adapter 102 that does not comprise an index sequence (index independent), which allows a minimum number of blockers to be used regardless of the number of different index sequences employed (FIG. 1B). In some instances, no more than 8 universal blockers are used. In some instances, 4 universal blockers are used. In some instances, 3 universal blockers are used. In some instances, 2 universal blockers are used. In some instances, 1 universal blocker is used. In an exemplary arrangement, 4 universal blockers are used with adapters comprising at least 4, 8, 16, 32, 64, 96, or at least 128 different index sequences. In some instances, the different index sequences comprises at least or about 4, 6, 8, 10, 12, 14, 16, 18, 20, or more than 20 base pairs (bp). In some instances, a universal blocker is not configured to bind to a barcode sequence. In some instances, a universal blocker partially binds to a barcode sequence. In some instances, a universal blocker which partially binds to a barcode sequence further comprises nucleotide analogs, such as those that increase the $T_m$ of binding to the adapter (e.g., LNAs or BNAs).

The universal blockers may be used with panel libraries of varying size. In some embodiments, the panel libraries comprises at least or about 0.01, 0.02, 0.03, 0.04, 0.05, 0.06, 0.07, 0.08, 0.09, 1.0, 2.0, 4.0, 8.0, 10.0, 12.0, 14.0, 16.0, 18.0, 20.0, 22.0, 24.0, 26.0, 28.0, 30.0, 40.0, 50.0, 60.0, or more than 60.0 megabases (Mb).

Blockers as described herein may improve on-target performance. In some embodiments, on-target performance is improved by at least or about 5%, 10%, 15%, 20%, 25%, 30%, 35%, 40%, 45%, 50%, 55%, 60%, 65%, 70%, 75%, 80%, 85%, 90%, 95%, or more than 95%. In some embodiments, the on-target performance is improved by at least or about 5%, 10%, 15%, 20%, 25%, 30%, 35%, 40%, 45%, 50%, 55%, 60%, 65%, 70%, 75%, 80%, 85%, 90%, 95%, or more than 95% for various index designs. In some embodiments, the on-target performance is improved by at least or about 5%, 10%, 15%, 20%, 25%, 30%, 35%, 40%, 45%, 50%, 55%, 60%, 65%, 70%, 75%, 80%, 85%, 90%, 95%, or more than 95% is improved for various panel sizes.

Blockers may contain any number of different nucleobases (DNA, RNA, etc.), nucleobase analogues (non-canonical), or non-nucleobase linkers or spacers. For example, a blocker comprises one or more nucleobase analogues or other groups that enhance hybridization ($T_m$) between the blocker and the adapter. Nucleobase analogues and other groups include but are not limited to locked nucleic acids (LNAs), bicyclic nucleic acids (BNAs), CS-modified pyrimidine bases, 2'-O-methyl substituted RNA, peptide nucleic acids (PNAs), glycol nucleic acid (GNAs), threose nucleic acid (TNAs), xenonucleic acids (XNAs) morpholino backbone-modified bases, minor grove binders (MGBs), spermine, G-clamps, or a anthraquinone (Uaq) caps. In instances, blockers comprise spacer elements that connect two polynucleotide chains. In some instances, blockers comprise one or more nucleobase analogues selected from Table 1. In some instances, such nucleobase analogues are added to control the $T_m$ of a blocker.

TABLE 1

| Base | A | T | G |
|---|---|---|---|
| Locked Nucleic Acid (LNA) | [structure] | [structure] | [structure] |

TABLE 1-continued

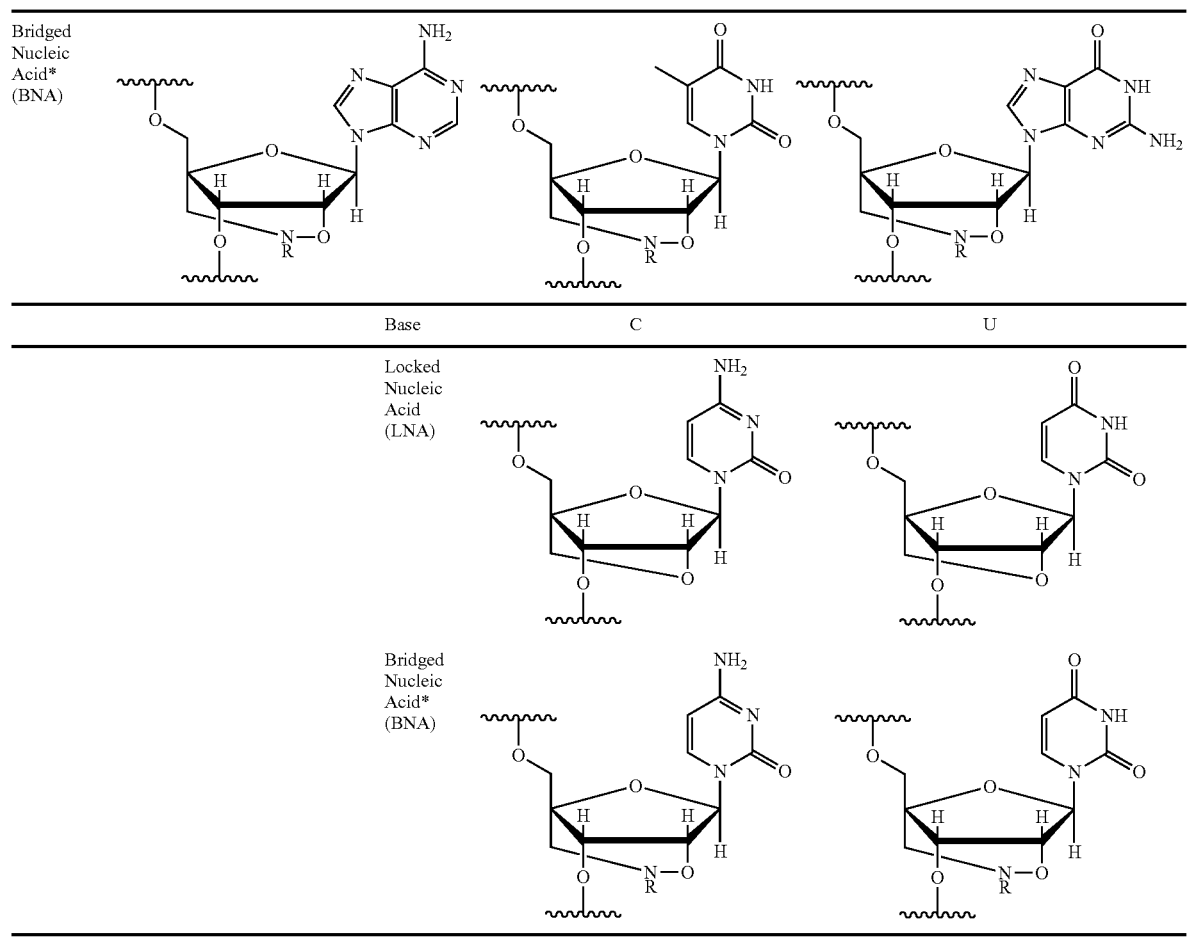

*R is H or Me.

A third method described herein comprises addition of one or more additives to a hybridization reaction to decrease off-target rates. Additives are added at any step in the hybridization workflow, such as during hybridization, or during washing steps. In an exemplary arrangement, additives are added to buffers such as hybridization buffers, binding buffers, wash buffers, or any combination thereof. In some instances, additives are added to two or more buffers, such as a hybridization buffer and a binding buffer. An exemplary hybridization reaction 3000 in a container 3001 is shown in FIG. 33A, wherein a solution 3002 comprising nucleic acid targets and polynucleotide probes is in contact with a gas 3004, forming a gas-liquid interface 3005 (such as an air-water interface). Such hybridization reactions are often hindered by a higher concentration of nucleic acids at the area 3003 adjacent to the gas-liquid interface 3005, which in some instances limits the uniform hybridization of probes to target nucleic acids, or prevents non-target nucleic acids from being removed in a wash step. Addition of additives, such as additive 3006, in some instances reduces the concentration of non-target nucleic acids at the area 3003 adjacent to the gas-liquid interface 3005, which results in decreased off-target binding. In some instances, addition of at least one additive results in a decrease in random off-target binding.

Methods described herein may comprise one or more washing steps or tube transfer steps. In some instances, washing or tube transfers are combined with the use of additives. In some instances, 1, 2, 3, 4, or more than 4 washes are performed after capture of target sequences on a solid support. In some instances, one or more wash steps is substituted with a tube transfer, wherein the captured target sequences are transferred to an unused tube or other container. In some instances, tube transfers are used in combination with wash steps. In some instances, 1, 2, 3, 4, or more than 4 tube transfers are performed during the methods described herein.

Additives for hybridization may include any number of chemical agents, or mixtures thereof that influence the structure or solubility of polynucleotides. Additives for hybridization include salts, oils, waxes, nucleotides (or nucleotide analogues), polymers, kosmotropes, chaotropes, or other additive that influences local concentrations of polynucleotides. Oils include but are not limited to petroleum-based agents (e.g., light oil, jet fuel, gasoline, kerosene, naphtha, petroleum ether, petroleum spirits, mineral oil, light mineral oil, white mineral oil), plant-based oils (olive oil, vegetable oil, soybean oil, or other plant-based oil). Polymers in some instances are hydrophobic (e.g., polysilanes) or hydrophilic (polyethers such as polyethylene glycol). In some instances, oils comprise alkanes, cycloalkanes, or silanes (silicon oils). In some instances, additives comprise liquid polymers, such as high-molecular weight, low vapor pressure, and/or low water solubility polymers. In some instances, chaotropes include alcohols (e.g., n-butanol, ethanol), guanidinium chloride, lithium perchlorate, lithium acetate, magnesium chloride, phenol, 2-propanol, sodium dodecyl sulfate, thiourea, urea, thiocyanate, or other agent that disrupts hydrogen bonding networks. In some instances kosmotropes include carbonate, sulfate, hydrogen phosphate, magnesium, lithium, zinc, aluminum, or other agent that stabilizes hydrogen bonding networks.

Additives described herein may be present at any concentration suitable for reducing off-target binding. Such concentrations are often represented as a percent by weight, percent by volume, or percent weight per volume. For example, an additive is present at about 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or about 30%. In some instances, an additive is present at no more than 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or no more than 30%. In some instances, an additive is present in at least 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or at least 30%. In some instances, an additive is present at 0.0001%-10%, 0.0002%-5%, 0.0005%-1.5%, 0.0008%-1%, 0.001%-0.2%, 0.002%-0.08%, 0.005%-0.02%, or 0.008%-0.05%. In some instances, an additive is present at 0.005%-0.1%. In some instances, an additive is present at 0.05%-0.1%. In some instances, an additive is present at 0.005%-0.6%. In some instances, an additive is present at 1%-30%, 5%-25%, 10%-30%, 15%-30%, or 1%-15%. Liquid additives may be present as a percentage of the total reaction volume. In some instances, an additive is about 10%, 20%, 30%, 40%, 50%, 60%, 75%, or about 90% of the total volume. In some instances, an additive is at least 10%, 20%, 30%, 40%, 50%, 60%, 75%, or at least 90% of the total volume. In some instances, an additive is no more than 10%, 20%, 30%, 40%, 50%, 60%, 75%, or no more than 90% of the total volume. In some instances, an additive is 5%-75%, 5%-65%, 5%-55%, 10%-50%, 15%-40%, 20%-50%, 20%-30%, 25%-35%, 5%-35%, 10%-35%, or 20%-40% of the total volume. In some instances, an additive is 25%-45% of the total volume.

A fourth method provided herein comprises controlled fluid transfer that results in a decrease of off-target rates. Without being bound by theory, such controlled transfer minimizes contamination of non-hybridized (non-target) nucleic acids with target nucleic acids. In some instances, a controlled transfer decreases local non-uniform concentration of nucleic acids in a solution, such as at a gas-liquid interface. In some instances, non-target nucleic acids are present at a higher concentration near a gas-liquid interface 3005. In some instances, the interface is an air-water interface. In this method, controlled fluid transfer of liquid near or in the local area 3003 adjacent to the gas-liquid interface provides for selective removal of off-target nucleic acids during hybridization and/or capture steps. For example, liquid is removed only from this local area in a continuous fashion, until all liquid 3002 is removed. The local area is in some instances defined as a volume of liquid near the gas-liquid interface, and related to the total volume of the liquid. For example, the local area volume is about the upper 10% of the total volume. In some instances, the local area volume is about the upper 1%, 2%, 5%, 8%, 10%, 15%, 20%, or about 25% of the total volume. In some instances, the local area volume is about the upper 1%-25%, 2%-20%, 5%-15%, 8%-12%, 10%-25%, 1%-10%, 20%, or about 25% of the total volume. The location of liquid removal in some instances depends on the surface area of the gas-liquid interface. In some instances, a higher interface surface area decreases the local area volume from which liquid is removed.

Various temperatures and times are used for hybridization of probes to target nucleic acids. In some instances, the hybridization temperature is at least 50, 60, 70, 80, 90, or at least 95 C. In some instances, the hybridization temperature is about 50, 55, 60, 65, 70, 75, 80, 85, or 90 C. In some instances, the hybridization temperature is 40-50 C, 40-80 C, 50-70 C, 50-80 C, 60-90 C, 55-70 C, or 60-80 C. In some instances, probes are hybridized for no more than 5, 10, 15, 20, 30, 45, 60, or no more than 60 minutes. In some instances, probes are hybridized for about 0.1, 0.2, 0.3, 0.5, 0.75, 1, 2, 3, 4, 5, 6, 7, 8, 9, 10 or about 12 hours. In some instances, probes are hybridized for about 10 min to 8 hours, 15 min to 6 hours, 20 min to 4 hrs, 15 min to 2 hrs, 10 min to 6 hrs, 30 min to 5 hrs, 1 hr to 8 hrs, or 2 hrs to 10 hrs.

Various temperatures and times are used for wash buffers used with the methods and compositions described herein. Washes in some instances are performed when hybridized nucleic acids are bound to a solid support. In some instances a wash buffer is pre-heated to about 50, 55, 57, 60, 62, 64, 66, 68, 70, 72, 74, 76, 78, or 80 C prior to use. In some instances a wash buffer is pre-heated to 50-80, 50-75, 50-70, 60-75, 60-70, 65-75, 70-80, 67-74, or 55-75 C prior to use. In some instances, more than one wash is performed, and each wash buffer used is the same or a different temperature. In some instances a first wash buffer (or wash buffer 1) is pre-heated to about 50, 55, 57, 60, 62, 64, 66, 68, 70, 72, 74, 76, 78, or 80 C prior to use. In some instances a first wash buffer is pre-heated to 50-80, 50-75, 50-70, 60-75, 60-70, 65-75, 70-80, 67-74, or 55-75 C prior to use.

Hybridization Blockers

Blockers may comprise any number of nucleobase analogues (such as LNAs or BNAs), depending on the desired hybridization $T_m$. For example, a blocker comprises 20 to 40 nucleobase analogues. In some instances, a blocker comprises 8 to 16 nucleobase analogues. In some instances, a blocker comprises at least 1, 2, 3, 4, 5, 6, 7, 8, 9, 10, 11, 12, or at least 12 nucleobase analogues. In some instances, a blocker comprises about 1, 2, 3, 4, 5, 6, 7, 8, 9, 10, 11, 12, 13, 14, 15, or about 16 nucleobase analogues. In some instances, the number of nucleobase analogous is expressed as a percent of the total bases in the blocker. For example, a blocker comprises at least 1%, 2%, 5%, 10%, 12%, 18%, 24%, 30%, or more than 30% nucleobase analogues. In some instances, the blocker comprising a nucleobase analogue raises the $T_m$ in a range of about 2° C. to about 8° C. for each nucleobase analogue. In some instances, the $T_m$ is raised by at least or about 1° C., 2° C., 3° C., 4° C., 5° C., 6° C., 7° C., 8° C., 9° C., 10° C., 12° C., 14° C., or 16° C. for each nucleobase analogue. Such blockers in some instances are configured to bind to the top or "sense" strand of an adapter. Blockers in some instances are configured to bind to the bottom or "anti-sense" strand of an adapter. In some instances a set of blockers includes sequences which are configured to bind to both top and bottom strands of an adapter. Additional blockers in some instances are configured to the complement, reverse, forward, or reverse complement of an adapter sequence. In some instances, a set of blockers targeting a top (binding to the top) or bottom strand (or both) is designed and tested, followed by optimization, such as replacing a top blocker with a bottom blocker, or a bottom blocker with a top blocker.

Blockers may be any length, depending on the size of the adapter or hybridization $T_m$. For example, blockers are 20 to 50 bases in length. In some instances, blockers are 25 to 45 bases, 30 to 40 bases, 20 to 40 bases, or 30 to 50 bases in length. In some instances, blockers are 25 to 35 bases in length. In some instances blockers are at least 25, 26, 27, 28, 29, 30, 31, 32, 33, 34, or at least 35 bases in length. In some instances, blockers are no more than 25, 26, 27, 28, 29, 30, 31, 32, 33, 34, or no more than 35 bases in length. In some instances, blockers are about 25, 26, 27, 28, 29, 30, 31, 32, 33, 34, or about 35 bases in length. In some instances, blockers are about 50 bases in length. A set of blockers targeting an adapter-tagged genomic library fragment in some instances comprises blockers of more than one length. Two blockers are in some instances tethered together with a linker. Various linkers are well known in the art, and in some instances comprise alkyl groups, polyether groups, amine groups, amide groups, or other chemical group. In some instances, linkers comprise individual linker units, which are connected together (or attached to blocker polynucleotides) through a backbone such as phosphate, thiophosphate, amide, or other backbone. In an exemplary arrangement, a linker spans the index region between a first blocker that each targets the 5' end of the adapter sequence and a second blocker that targets the 3' end of the adapter sequence. In some instances, capping groups are added to the 5' or 3' end of the blocker to prevent downstream amplification. Capping groups variously comprise polyethers, polyalcohols, alkanes, or other non-hybridizable group that prevents amplification. Such groups are in some instances connected through phosphate, thiophosphate, amide, or other backbone. In some instances, one or more blockers are used. In some instances, at least 4 non-identical blockers are used. In some instances, a first blocker spans a first 3' end of an adaptor sequence, a second blocker spans a first 5' end of an adaptor sequence, a third blocker spans a second 3' end of an adaptor sequence, and a fourth blockers spans a second 5' end of an adaptor sequence. In some instances a first blocker is at least 20, 21, 22, 23, 24, 25, 26, 27, 28, 29, 30, 31, 32, 33, 34, or at least 35 bases in length. In some instances a second blocker is at least 20, 21, 22, 23, 24, 25, 26, 27, 28, 29, 30, 31, 32, 33, 34, or at least 35 bases in length. In some instances a third blocker is at least 20, 21, 22, 23, 24, 25, 26, 27, 28, 29, 30, 31, 32, 33, 34, or at least 35 bases in length. In some instances a fourth blocker is at least 20, 21, 22, 23, 24, 25, 26, 27, 28, 29, 30, 31, 32, 33, 34, or at least 35 bases in length. In some instances, a first blocker, second blocker, third blocker, or fourth blocker comprises a nucleobase analogue. In some instances, the nucleobase analogue is LNA.

The design of blockers may be influenced by the desired hybridization $T_m$ to the adapter sequence. In some instances, non-canonical nucleic acids (for example locked nucleic acids, bridged nucleic acids, or other non-canonical nucleic acid or analog) are inserted into blockers to increase or decrease the blocker's $T_m$. In some instances, the $T_m$ of a blocker is calculated using a tool specific to calculating $T_m$ for polynucleotides comprising a non-canonical amino acid. In some instances, a $T_m$ is calculated using the Exiqon™ online prediction tool. In some instances, blocker $T_m$ described herein are calculated in-silico. In some instances, the blocker $T_m$ is calculated in-silico, and is correlated to experimental in-vitro conditions. Without being bound by theory, an experimentally determined $T_m$ may be further influenced by experimental parameters such as salt concentration, temperature, presence of additives, or other factor. In some instances, $T_m$ described herein are in-silico determined $T_m$ that are used to design or optimize blocker performance. In some instances, $T_m$ values are predicted, estimated, or determined from melting curve analysis experiments. In some instances, blockers have a $T_m$ of 70 degrees C. to 99 degrees C. In some instances, blockers have a $T_m$ of 75 degrees C. to 90 degrees C. In some instances, blockers have a $T_m$ of at least 85 degrees C. In some instances, blockers have a $T_m$ of at least 70, 72, 75, 77, 80, 82, 85, 88, 90, or at least 92 degrees C. In some instances, blockers have a $T_m$ of about 70, 72, 75, 77, 80, 82, 85, 88, 90, 92, or about 95 degrees C. In some instances, blockers have a $T_m$ of 78 degrees C. to 90 degrees C. In some instances, blockers have a $T_m$ of 79 degrees C. to 90 degrees C. In some instances, blockers have a $T_m$ of 80 degrees C. to 90 degrees C. In some instances, blockers have a $T_m$ of 81 degrees C. to 90 degrees C. In some instances, blockers have a $T_m$ of 82 degrees C. to 90 degrees C. In some instances, blockers have a $T_m$ of 83 degrees C. to 90 degrees C. In some instances, blockers have a $T_m$ of 84 degrees C. to 90 degrees C. In some instances, a set of blockers have an average $T_m$ of 78 degrees C. to 90 degrees C. In some instances, a set of blockers have an average $T_m$ of 80 degrees C. to 90 degrees C. In some instances, a set of blockers have an average $T_m$ of at least 80 degrees C. In some instances, a set of blockers have an average $T_m$ of at least 81 degrees C. In some instances, a set of blockers have an average $T_m$ of at least 82 degrees C. In some instances, a set of blockers have an average $T_m$ of at least 83 degrees C. In some instances, a set of blockers have an average $T_m$ of at least 84 degrees C. In some instances, a set of blockers have an average $T_m$ of at least 86 degrees C. Blocker $T_m$ are in some instances modified as a result of other components described herein, such as use of a fast hybridization buffer and/or hybridization enhancer.

The molar ratio of blockers to adapter targets may influence the off-bait (and subsequently off-target) rates during hybridization. The more efficient a blocker is at binding to the target adapter, the less blocker is required. Blockers described herein in some instances achieve sequencing outcomes of no more than 20% off-target reads with a molar ratio of less than 20:1 (blocker:target). In some instances, no more than 20% off-target reads are achieved with a molar ratio of less than 10:1 (blocker:target). In some instances, no more than 20% off-target reads are achieved with a molar ratio of less than 5:1 (blocker:target). In some instances, no more than 20% off-target reads are achieved with a molar ratio of less than 2:1 (blocker:target). In some instances, no more than 20% off-target reads are achieved with a molar ratio of less than 1.5:1 (blocker:target). In some instances, no more than 20% off-target reads are achieved with a molar ratio of less than 1.2:1 (blocker:target). In some instances, no more than 20% off-target reads are achieved with a molar ratio of less than 1.05:1 (blocker:target).

Figure 1C:
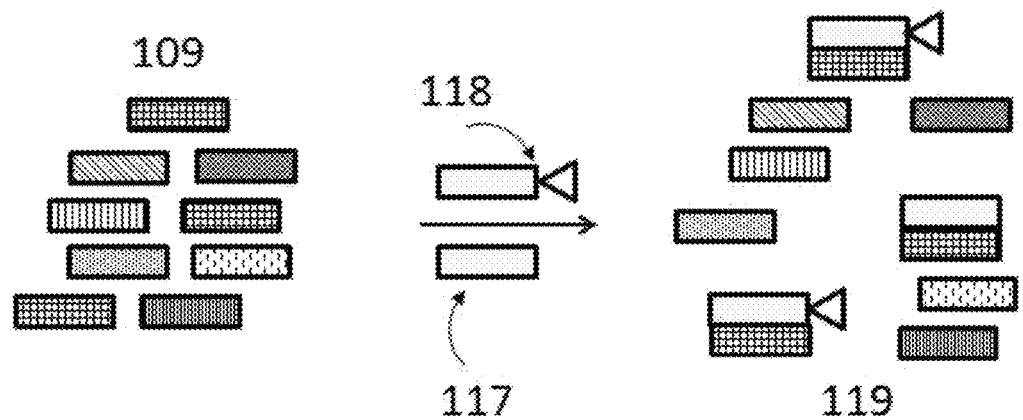
FIG. 1C depicts an exemplary workflow for enrichment and sequencing of a nucleic acid sample using partially labeled capture probes.

A third method described herein comprises improving the efficiency of polynucleotide probe libraries by selectively labeling only a portion of the probes (FIG. 1C). If a library of polynucleotide probes that is fully labeled is diluted, the result is often an increase in off bait, and a decrease in HS library size. By keeping the total ratio of polynucleotides to target genomic sequences constant, all target genomic sequences are still bound to a complementary probe and inter or intramolecular hybridization of such sequences is reduced. In an exemplary workflow, a library of sample polynucleotides 109 is hybridized with a plurality of probes, some of which are labeled probes 118 or unlabeled probes 117. The hybridization mixture 119 can then be subjected to further purification to isolate target polynucleotides binding to labeled probes 118. The percentage of labeled probes may vary depending on the application, library size, and genomic targets. For example, about 1%, 5%, 10%, 20%, 30%, 40%, 50%, 60%, 70%, 80%, or 90% of all probes are labeled. In some instances at least 1%, 5%, 10%, 20%, 30%, 40%, 50%, 60%, 70%, 80%, or at least 90% of all probes are labeled. In some instances no more than 1%, 5%, 10%, 20%, 30%, 40%, 50%, 60%, 70%, 80%, or no more than 90% of all probes are labeled. In some instances, 10-90%, 20-80%, 30-70%, 40-50%, 1-40%, 20-60%, 40-70%, 50-90%, 60-99%, 70-99%, or 80-99% of all probes are labeled. In some instances, the label is a molecular tag, such as biotin or other molecular tag. In some instances, polynucleotide probe libraries comprising less than 15% labeled probes results in less than 40% off bait. In some instances, polynucleotide probe libraries comprising less than 15% labeled probes results in less than 40% off bait. Partial labeling of probes may also result in a decrease in AT and GC dropouts. For example, polynucleotide probe libraries comprising 1-50% labeled probes results in less than 1.9% AT dropout. In some instances, polynucleotide probe libraries comprising 1-50% labeled probes results in less than 1.3% GC dropout. In some instances, polynucleotide probe libraries comprising 12.5-50% labeled probes results in less than 1.3% GC dropout. In some instances, polynucleotide probe libraries comprising 12.5-50% labeled probes results in less than 1.9% AT dropout.

Hybridization Buffers

Any number of buffers may be used with the hybridization methods described herein. For example, a buffer comprises numerous chemical components, such as polymers, solvents, salts, surfactants, or other component. In some instances, hybridization buffers decrease the hybridization times (e.g., "fast" hybridization buffers) required to achieve a given sequencing result or level of quality. Such components in some instances lead to improved hybridization outcomes, such as increased on-target rate, improved sequencing outcomes (e.g., sequencing depth or other metric), or decreased off-target rates. Such components may be introduced at any concentration to achieve such outcomes. In some instances, buffer components are added in specific order. For example, water is added first. In some instances, salts are added after water. In some instances, salts are added after thickening agents and surfactants. In some instances, hybridization buffers such as "fast" hybridization buffers described herein are used in conjunction with universal blockers and liquid polymer additives.

Hybridization buffers described herein may comprise solvents, or mixtures of two or more solvents. In some instances, a hybridization buffer comprises a mixture of two solvents, three solvents or more than three solvents. In some instances, a hybridization buffer comprises a mixture of an alcohol and water. In some instances, a hybridization buffer comprises a mixture of a ketone containing solvent and water. In some instances, a hybridization buffer comprises a mixture of an ethereal solvent and water. In some instances, a hybridization buffer comprises a mixture of a sulfoxide-containing solvent and water. In some instances, a hybridization buffer comprises a mixture of am amide-containing solvent and water. In some instances, a hybridization buffer comprises a mixture of an ester-containing solvent and water. In some instances, hybridization buffers comprise solvents such as water, ethanol, methanol, propanol, butanol, other alcohol solvent, or a mixture thereof. In some instances, hybridization buffers comprise solvents such as acetone, methyl ethyl ketone, 2-butanone, ethyl acetate, methyl acetate, tetrahydrofuran, diethyl ether, or a mixture thereof. In some instances, hybridization buffers comprise solvents such as DMSO, DMF, DMA, HMPA, or a mixture thereof. In some instances, hybridization buffers comprise a mixture of water, HMPA, and an alcohol. In some instances, two solvents are present at a 1:1, 1:2, 1:3, 1:4, 1:5, 1:8, 1:9, 1:10, 1:20, 1:50, 1:100, or 1:500 ratio.

Hybridization buffers described herein may comprise polymers. Polymers include but are not limited to thickening agents, polymeric solvents, dielectric materials, or other polymer. Polymers are in some instances hydrophobic or hydrophilic. In some instances, polymers are silicon polymers. In some instances, polymers comprise repeating polyethylene or polypropylene units, or a mixture thereof. In some instances, polymers comprise polyvinylpyrrolidone or polyvinylpyridine. In some instances, polymers comprise amino acids. For example, in some instances polymers comprise proteins. In some instances, polymers comprise casein, milk proteins, bovine serum albumin, or other protein. In some instances, polymers comprise nucleotides, for example, DNA or RNA. In some instances, polymers comprise polyA, polyT, Cot-1 DNA, or other nucleic acid. In some instances, polymers comprise sugars. For example, in some instances a polymer comprises glucose, arabinose, galactose, mannose, or other sugar. In some instances, a polymer comprises cellulose or starch. In some instances, a polymer comprises agar, carboxyalkyl cellulose, xanthan, guar gum, locust bean gum, gum karaya, gum tragacanth, gum Arabic. In some instances, a polymer comprises a derivative of cellulose or starch, or nitrocellulose, dextran, hydroxyethyl starch, ficoll, or a combination thereof. In some instances, mixtures of polymers are used in hybridization buffers described herein. In some instances, hybridization buffers comprise Denhardt's solution. Polymers described herein may be present at any concentration suitable for reducing off-target binding. Such concentrations are often represented as a percent by weight, percent by volume, or percent weight per volume. For example, a polymer is present at about 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or about 30%. In some instances, a polymer is present at no more than 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or no more than 30%. In some instances, a polymer is present in at least 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or at least 30%. In some instances, a polymer is present at 0.0001%-10%, 0.0002%-5%, 0.0005%-1.5%, 0.0008%-1%, 0.001%-0.2%, 0.002%-0.08%, 0.005%-0.02%, or 0.008%-0.05%. In some instances, a polymer is present at 0.005%-0.1%. In some instances, a polymer is present at 0.05%-0.1%. In some instances, a polymer is present at 0.005%-0.6%. In some instances, a polymer is present at 1%-30%, 5%-25%, 10%-30%, 15%-30%, or 1%-15%. Liquid polymers may be present as a percentage of the total reaction volume. In some instances, a polymer is about 10%, 20%, 30%, 40%, 50%, 60%, 75%, or about 90% of the total volume. In some instances, a polymer is at least 10%, 20%, 30%, 40%, 50%, 60%, 75%, or at least 90% of the total volume. In some instances, a polymer is no more than 10%, 20%, 30%, 40%, 50%, 60%, 75%, or no more than 90% of the total volume. In some instances, a polymer is 5%-75%, 5%-65%, 5%-55%, 10%-50%, 15%-40%, 20%-50%, 20%-30%, 25%-35%, 5%-35%, 10%-35%, or 20%-40% of the total volume. In some instances, a polymer is 25%-45% of the total volume. In some instances, hybridization buffers described herein are used in conjunction with universal blockers and liquid polymer additives.

Hybridization buffers described herein may comprise salts such as cations or anions. For example, hybridization buffer comprises a monovalent or divalent cation. In some instances, a hybridization buffer comprises a monovalent or divalent anion. Cations in some instances comprise sodium, potassium, magnesium, lithium, tris, or other salt. Anions in some instances comprise sulfate, bisulfite, hydrogensulfate, nitrate, chloride, bromide, citrate, ethylenediaminetetraacetate, dihydrogenphosphate, hydrogenphosphate, or phosphate. In some instances, hybridization buffers comprise salts comprising any combination of anions and cations (e.g. sodium chloride, sodium sulfate, potassium phosphate, or other salt). In some instance, a hybridization buffer comprises an ionic liquid. Salts described herein may be present at any concentration suitable for reducing off-target binding. Such concentrations are often represented as a percent by weight, percent by volume, or percent weight per volume. For example, a salt is present at about 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or about 30%. In some instances, a salt is present at no more than 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or no more than 30%. In some instances, a salt is present in at least 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or at least 30%. In some instances, a salt is present at 0.0001%-10%, 0.0002%-5%, 0.0005%-1.5%, 0.0008%-1%, 0.001%-0.2%, 0.002%-0.08%, 0.005%-0.02%, or 0.008%-0.05%. In some instances, a salt is present at 0.005%-0.1%. In some instances, a salt is present at 0.05%-0.1%. In some instances, a salt is present at 0.005%-0.6%. In some instances, a salt is present at 1%-30%, 5%-25%, 10%-30%, 15%-30%, or 1%-15%. Liquid polymers may be present as a percentage of the total reaction volume. In some instances, a salt is about 10%, 20%, 30%, 40%, 50%, 60%, 75%, or about 90% of the total volume. In some instances, a salt is at least 10%, 20%, 30%, 40%, 50%, 60%, 75%, or at least 90% of the total volume. In some instances, a salt is no more than 10%, 20%, 30%, 40%, 50%, 60%, 75%, or no more than 90% of the total volume. In some instances, a salt is 5%-75%, 5%-65%, 5%-55%, 10%-50%, 15%-40%, 20%-50%, 20%-30%, 25%-35%, 5%-35%, 10%-35%, or 20%-40% of the total volume. In some instances, a salt is 25%-45% of the total volume.

Hybridization buffers described herein may comprise surfactants (or emulsifiers). For example, a hybridization buffer comprises SDS (sodium dodecyl sulfate), CTAB, cetylpyridinium, benzalkonium tergitol, fatty acid sulfonates (e.g., sodium lauryl sulfate), ethyloxylated propylene glycol, lignin sulfonates, benzene sulfonate, lecithin, phospholipids, dialkyl sulfosuccinates (e.g., dioctyl sodium sulfosuccinate), glycerol diester, polyethoxylated octyl phenol, abietic acid, sorbitan monoester, perfluoro alkanols, sulfonated polystyrene, betaines, dimethyl polysiloxanes, or other surfactant. In some instances, a hybridization buffer comprises a sulfate, phosphate, or tetralkyl ammonium group. Surfactants described herein may be present at any concentration suitable for reducing off-target binding. Such concentrations are often represented as a percent by weight, percent by volume, or percent weight per volume. For example, a surfactant is present at about 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or about 30%. In some instances, a surfactant is present at no more than 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or no more than 30%. In some instances, a surfactant is present in at least 0.0001%, 0.0002%, 0.0005%, 0.0008%, 0.001%, 0.002%, 0.005%, 0.008%, 0.01%, 0.02%, 0.05%, 0.08%, 0.1%, 0.2%, 0.5%, 0.8%, 1%, 1.2%, 1.5%, 1.8%, 2%, 5%, 10%, 20%, or at least 30%. In some instances, a surfactant is present at 0.0001%-10%, 0.0002%-5%, 0.0005%-1.5%, 0.0008%-1%, 0.001%-0.2%, 0.002%-0.08%, 0.005%-0.02%, or 0.008%-0.05%. In some instances, a surfactant is present at 0.005%-0.1%. In some instances, a surfactant is present at 0.05%-0.1%. In some instances, a surfactant is present at 0.005%-0.6%. In some instances, a surfactant is present at 1%-30%, 5%-25%, 10%-30%, 15%-30%, or 1%-15%. Liquid polymers may be present as a percentage of the total reaction volume. In some instances, a surfactant is about 10%, 20%, 30%, 40%, 50%, 60%, 75%, or about 90% of the total volume. In some instances, a surfactant is at least 10%, 20%, 30%, 40%, 50%, 60%, 75%, or at least 90% of the total volume. In some instances, a surfactant is no more than 10%, 20%, 30%, 40%, 50%, 60%, 75%, or no more than 90% of the total volume. In some instances, a surfactant is 5%-75%, 5%-65%, 5%-55%, 10%-50%, 15%-40%, 20%-50%, 20%-30%, 25%-35%, 5%-35%, 10%-35%, or 20%-40% of the total volume. In some instances, a surfactant is 25%-45% of the total volume.

Buffers used in the methods described herein may comprise any combination of components. In some instances, a buffer described herein is a hybridization buffer. In some instances, a hybridization buffer described herein is a fast hybridization buffer. Such fast hybridization buffers allow for lower hybridization times such as less than 8 hours, 6 hours, 4 hours, 2 hours, 1 hour, 45 minutes, 30 minutes, or less than 15 minutes. Hybridization buffers described herein in some instances comprise a buffer described in Tables 2A-2G. In some instances, the buffers described in Tables 1A-1I may be used as fast hybridization buffers. In some instances, the buffers described in Tables 1B, 1C, and 1D may be used as fast hybridization buffers. In some instances, a fast hybridization buffer as described herein is described in Table 1B. In some instances, a fast hybridization buffer as described herein is described in Table 1C. In some instances, a fast hybridization buffer as described herein is described in Table 1D.

TABLE 2A

Buffers A

| Buffer Component | Volume (mL) | Buffer Component | Volume (mL) |
|---|---|---|---|
| Water | 5-300 | Water | 100-300 |
| DMF | 0-3 | DMSO | 0-3 |
| NaCl (5M) | 0.01-0.5 | NaCl (5M) | 0.01-0.5 |
| 20% SDS | 0.05-0.5 | 20% SDS | 0.05-0.5 |
| Tergitol (1% by weight) | 0.2-3 | EDTA (1M) | 0-2 |
| Denhardt's Solution (50X) | 1-10 | Denhardt's Solution (50X) | 1-10 |
| $NaH_2PO_4$ (5M) | 0.01-1.5 | $NaH_2PO_4$ (5M) | 0.01-1.5 |

TABLE 2B

Buffers B

| Buffer Component | Volume (mL) | Buffer Component | Volume (mL) |
|---|---|---|---|
| Water | 5-30 | Water | 5-30 |
| DMSO | 0.5-3 | DMSO | 0.5-3 |
| NaCl (5M) | 0.01-0.5 | NaCl (5M) | 0.01-0.5 |
| 20% SDS | 0.05-0.5 | 20% CTAB | 0.05-0.5 |
| EDTA (1M) | 0.05-2 | EDTA (1M) | 0.05-2 |
| Denhardt's Solution (50X) | 1-10 | Denhardt's Solution (50X) | 1-10 |
| $NaH_2PO_4$ (5M) | 0.01-1.5 | $NaH_2PO_4$ (5M) | 0.01-1.5 |

TABLE 2C

Buffers C

| Buffer Component | Volume (mL) | Buffer Component | Volume (mL) |
|---|---|---|---|
| Water | 5-30 | Water | 5-30 |
| DMSO | 0.5-3 | DMSO | 0.5-3 |
| NaCl (1M) | 0.01-0.5 | NaCl (5M) | 0.01-0.5 |
| 20% SDS | 0.05-0.5 | 20% SDS | 0.05-0.5 |
| TrisHCl (1M) | 0.01-2.5 | Dextran Sulfate (50%) | 0.05-2 |
| Denhardt's Solution (50X) | 1-10 | Denhardt's Solution (50X) | 1-10 |
| $NaH_2PO_4$ (5M) | 0.01-1.5 | $NaH_2PO_4$ (5M) | 0.01-1.5 |
| EDTA (0.5M) | 0.05-1.5 | EDTA (0.5M) | 0.05-1.5 |

TABLE 2D

Buffers D

| Buffer Component | Volume (mL) | Buffer Component | Volume (mL) |
|---|---|---|---|
| Water | 5-30 | Water | 5-30 |
| Methanol | 0.1-3 | DMSO | 0.5-3 |
| NaCl (1M) | 0.01-0.5 | NaCl (5M) | 0.01-0.5 |
| 20% Dextran Sulfate | 0.05-0.5 | 20% SDS | 0.05-0.5 |
| TrisHCl (1M) | 0.01-2.5 | hydroxyethyl starch (20%) | 0.05-2 |
| Denhardt's Solution (50X) | 1-10 | Denhardt's Solution (50X) | 1-10 |
| $NaH_2PO_4$ (1M) | 0.01-1.5 | $NaH_2PO_4$ (5M) | 0.01-1.5 |
| EDTA (0.5M) | 0.05-1.5 | EDTA (0.5M) | 0.05-1.5 |

TABLE 2E

Buffers E

| Buffer Component | Volume (mL) | Buffer Component | Volume (mL) |
|---|---|---|---|
| Water | 5-300 | Water | 5-300 |
| DMF | 0.1-30 | DMSO | 0.5-30 |
| NaCl (1M) | 0.01-0.5 | NaCl (5M) | 0.01-1.0 |
| hydroxyethyl starch (20%) | 0.01-2.5 | hydroxyethyl starch (20%) | 0.01-2.5 |
| Denhardt's Solution (50X) | 1-10 | Denhardt's Solution (50X) | 0.05-2 |
| $NaH_2PO_4$ (1M) | 0.01-1.5 | $NaH_2PO_4$ (5M) | 1-10 |

TABLE 2F

Buffers F

| Buffer Component | Volume (mL) | Buffer Component | Volume (mL) |
|---|---|---|---|
| Water | 50-300 | Water | 50-300 |
| DMF | 15-300 | DMSO | 15-300 |
| NaCl (5M) | 2-100 | NaCl (5M) | 2-100 |
| Denhardt's Solution (50X) | 1-10 | saline-sodium citrate 20X | 1-50 |
| Tergitol (1% by weight) | 0.2-2.0 | 20% SDS | 0-2 |

TABLE 2G

Buffers G

| Buffer Component | Volume (mL) | Buffer Component | Volume (mL) |
|---|---|---|---|
| Water | 5-30 | Water | 5-30 |
| Ethanol | 0-3 | Methanol | 0-3 |
| NaCl (1M) | 0.01-0.5 | NaCl (5M) | 0.01-0.5 |
| $NaH_2PO_4$ (5M) | 0.01-1.5 | $NaH_2PO_4$ (5M) | 0-2 |
| EDTA (0.5M) | 0-1.5 | EDTA (0.5M) | 1-10 |

TABLE 2H

Buffers H

| Buffer Component | Volume (mL) | Buffer Component | Volume (mL) |
|---|---|---|---|
| Water | 50-300 | Water | 10-300 |
| EDTA (0.5M) | 0-1.5 | NaCl (5M) | 0.01-0.5 |
| NaCl (5M) | 5-70 | 10% Triton X-100 | 0.05-0.5 |
| Tergitol (1% by weight) | 0.2-2.0 | EDTA (1M) | 0-2 |
| TrisHCl (1M) | 0.01-2.5 | TrisHCl (1M) | 0.1-5 |

TABLE 2I

Buffers I

| Buffer Component | Volume (mL) | Buffer Component | Volume (mL) |
|---|---|---|---|
| Water | 5-200 | Water | 10-200 |
| EDTA (0.5M) | 0-1.5 | NaCl (5M) | 0.01-0.5 |
| NaCl (5M) | 5-100 | Sodium Lauryl sulfate (10%) | 0.05-0.5 |
| CTAB (0.2M) | 0.05-0.5 | EDTA (1M) | 0-2 |

Buffers such as binding buffers and wash buffers are described herein. Binding buffers in some instances are used to prepare mixtures of sample polynucleotides and probes after hybridization. In some instances, binding buffers facilitate capture of sample polynucleotides on a column or other solid support. In some instances, the buffers described in Tables 2A-2I may be used as binding buffers. Binding buffers in some instances comprise a buffer described in Tables 2A, 2H, and 2I. In some instances, a binding buffer as described herein is described in Table 2A. In some instances, a binding buffer as described herein is described in Table 2H. In some instances, a binding buffer as described herein is described in Table 2I. In some instances, the buffers described herein may be used as wash buffers. Wash buffers in some instances are used to remove non-binding polynucleotides from a column or solid support. In some instances, the buffers described in Tables 2A-2I may be used as wash buffers. In some instances, a wash buffer comprises a buffer as described in Tables 2E, 2F, and 2G. In some instances, a wash buffer as described herein is described in Table 2E. In some instances, a wash buffer as described herein is described in Table 2F. In some instances, a wash buffer as described herein is described in Table 2G. Wash buffers used with the compositions and methods described herein are in some instances described as a first wash buffer (wash buffer 1), second wash buffer (wash buffer 2), etc.

Figure 8:
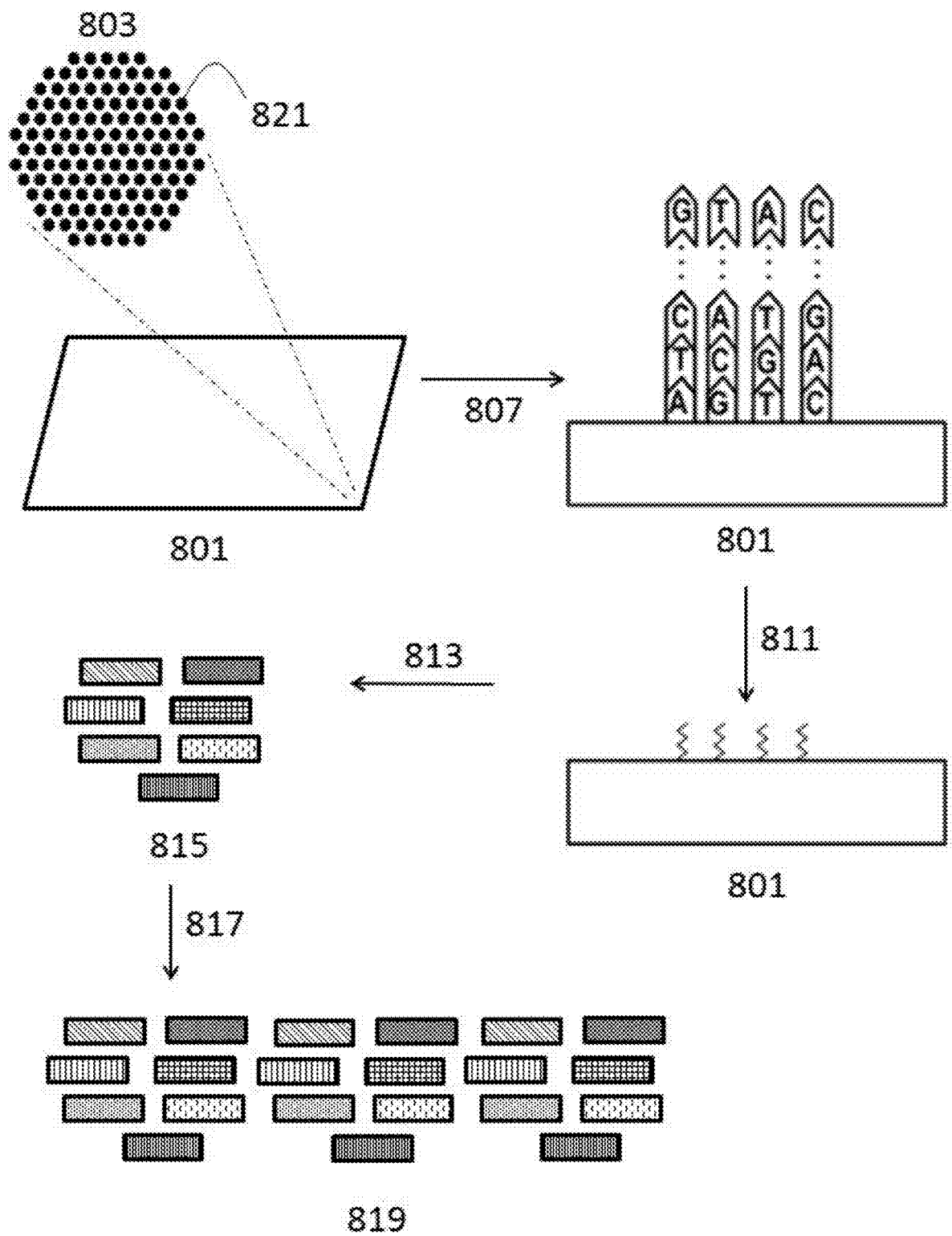
FIG. 8 depicts a schematic for generation of polynucleotide libraries from cluster amplification.

De Novo Synthesis of Small Polynucleotide Populations for Amplification Reactions Described herein are methods of synthesis of polynucleotides from a surface, e.g., a plate. In some instances, the polynucleotides are synthesized on a cluster of loci for polynucleotide extension, released and then subsequently subjected to an amplification reaction, e.g., PCR. An exemplary workflow of synthesis of polynucleotides from a cluster is depicted in FIG. 8. A silicon plate 801 includes multiple clusters 803. Within each cluster are multiple loci 821. Polynucleotides are synthesized 807 de novo on a plate 801 from the cluster 803. Polynucleotides are cleaved 811 and removed 813 from the plate to form a population of released polynucleotides 815. The population of released polynucleotides 815 is then amplified 817 to form a library of amplified polynucleotides 219.

Provided herein are methods where amplification of polynucleotides synthesized on a cluster provide for enhanced control over polynucleotide representation compared to amplification of polynucleotides across an entire surface of a structure without such a clustered arrangement. In some instances, amplification of polynucleotides synthesized from a surface having a clustered arrangement of loci for polynucleotides extension provides for overcoming the negative effects on representation due to repeated synthesis of large polynucleotide populations. Exemplary negative effects on representation due to repeated synthesis of large polynucleotide populations include, without limitation, amplification bias resulting from high/low GC content, repeating sequences, trailing adenines, secondary structure, affinity for target sequence binding, or modified nucleotides in the polynucleotide sequence.

Cluster amplification as opposed to amplification of polynucleotides across an entire plate without a clustered arrangement can result in a tighter distribution around the mean. For example, if 100,000 reads are randomly sampled, an average of 8 reads per sequence would yield a library with a distribution of about 1.5× from the mean. In some cases, single cluster amplification results in at most about 1.5×, 1.6×, 1.7×, 1.8×, 1.9×, or 2.0× from the mean. In some cases, single cluster amplification results in at least about 1.0×, 1.2×, 1.3×, 1.5× 1.6×, 1.7×, 1.8×, 1.9×, or 2.0× from the mean.

Cluster amplification methods described herein when compared to amplification across a plate can result in a polynucleotide library that requires less sequencing for equivalent sequence representation. In some instances at least 10%, at least 20%, at least 30%, at least 40%, at least 50%, at least 60%, at least 70%, at least 80%, at least 90%, or at least 95% less sequencing is required. In some instances up to 10%, up to 20%, up to 30%, up to 40%, up to 50%, up to 60%, up to 70%, up to 80%, up to 90%, or up to 95% less sequencing is required. Sometimes 30% less sequencing is required following cluster amplification compared to amplification across a plate. Sequencing of polynucleotides in some instances is verified by high-throughput sequencing such as by next generation sequencing. Sequencing of the sequencing library can be performed with any appropriate sequencing technology, including but not limited to single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis. The number of times a single nucleotide or polynucleotide is identified or "read" is defined as the sequencing depth or read depth. In some cases, the read depth is referred to as a fold coverage, for example, 55 fold (or 55×) coverage, optionally describing a percentage of bases.

Libraries described herein may have a reduced number of dropouts after amplification. In some instances, amplification from a clustered arrangement compared to amplification across a plate results in less dropouts, or sequences which are not detected after sequencing of amplification product. Dropouts can be of AT and/or GC. In some instances, a number of dropouts is at most about 1%, 2%, 3%, 4%, or 5% of a polynucleotide population. In some cases, the number of dropouts is zero.

A cluster as described herein comprises a collection of discrete, non-overlapping loci for polynucleotide synthesis. A cluster can comprise about 50-1000, 75-900, 100-800, 125-700, 150-600, 200-500, or 300-400 loci. In some instances, each cluster includes 121 loci. In some instances, each cluster includes about 50-500, 50-200, 100-150 loci. In some instances, each cluster includes at least about 50, 100, 150, 200, 500, 1000 or more loci. In some instances, a single plate includes 100, 500, 10000, 20000, 30000, 50000, 100000, 500000, 700000, 1000000 or more loci. A locus can be a spot, well, microwell, channel, or post. In some instances, each cluster has at least 1×, 2×, 3×, 4×, 5×, 6×, 7×, 8×, 9×, 10×, or more redundancy of separate features supporting extension of polynucleotides having identical sequence.

Generation of Polynucleotide Libraries with Controlled Stoichiometry of Sequence Content Provided herein are polynucleotide libraries synthesized with a specified distribution of desired polynucleotide sequences. Adjusting polynucleotide libraries for enrichment of specific desired sequences may provide for improved downstream application outcomes. For example, one or more specific sequences can be selected based on their evaluation in a downstream application. In some instances, the evaluation is binding affinity to target sequences for amplification, enrichment, or detection, stability, melting temperature, biological activity, ability to assemble into larger fragments, or other property of polynucleotides. In some instances, the evaluation is empirical or predicted from prior experiments and/or computer algorithms. An exemplary application includes increasing sequences in a probe library which correspond to areas of a genomic target having less than average read depth. The selected sequences for adjustment in a polynucleotide library can be at least 10%, 20%, 30%, 40%, 50%, 60%, 70%, 80%, 90%, 95%, or more than 95% of the sequences. In some instances, selected sequences for adjustment in a polynucleotide library are at most 10%, 20%, 30%, 40%, 50%, 60%, 70%, 80%, 90%, 95%, or at most 100% of the sequences. In some cases, selected sequences are in a range of about 5-95%, 10-90%, 30-80%, 40-75%, or 50-70% of the sequences. Polynucleotide libraries can be adjusted for the frequency of each selected sequence for adjustment. In some instances, polynucleotide libraries favor a higher number of selected sequences. For example, a library is designed where increased polynucleotide frequency of selected sequences is in a range of about 40% to about 90%. In some instances, polynucleotide libraries contain a low number of selected sequences. For example, a library is designed where increased polynucleotide frequency of the selected sequences is in a range of about 10% to about 60%. A library can be designed to favor a higher and lower frequency of selected sequences. In some instances, a library favors uniform sequence representation. For example, polynucleotide frequency is uniform with regard to selected sequence frequency, in a range of about 10% to about 90%. In some instances, a library comprises polynucleotides with a selected sequence frequency of about 10% to about 95% of the sequences.

Generation of polynucleotide libraries with a specified selected sequence for adjustment frequency may occur by combining at least 2 polynucleotide libraries with different selected sequence for adjustment frequency content. In some instances, at least 2, 3, 4, 5, 6, 7, 10, or more than 10 polynucleotide libraries are combined to generate a population of polynucleotides with a specified selected sequence frequency. In some cases, no more than 2, 3, 4, 5, 6, 7, or 10 polynucleotide libraries are combined to generate a population of non-identical polynucleotides with a specified selected sequence frequency.

As described herein, selected sequence for adjustment frequency is adjusted by synthesizing fewer or more polynucleotides per cluster. For example, at least 25, 50, 100, 200, 300, 400, 500, 600, 700, 800, 900, 1000, or more than 1000 non-identical polynucleotides are synthesized on a single cluster. In some cases, no more than about 50, 100, 200, 300, 400, 500, 600, 700, 800, 900, 1000 non-identical polynucleotides are synthesized on a single cluster. In some instances, 50 to 500 non-identical polynucleotides are synthesized on a single cluster. In some instances, 100 to 200 non-identical polynucleotides are synthesized on a single cluster. In some instances, about 100, about 120, about 125, about 130, about 150, about 175, or about 200 non-identical polynucleotides are synthesized on a single cluster.

In some cases, selected sequence for adjustment frequency is adjusted by synthesizing non-identical polynucleotides of varying length. For example, the length of each of the non-identical polynucleotides synthesized may be at least or about at least 10, 15, 20, 25, 30, 35, 40, 45, 50, 100, 150, 200, 300, 400, 500, 2000 nucleotides, or more. The length of the non-identical polynucleotides synthesized may be at most or about at most 2000, 500, 400, 300, 200, 150, 100, 50, 45, 35, 30, 25, 20, 19, 18, 17, 16, 15, 14, 13, 12, 11, 10 nucleotides, or less. The length of each of the non-identical polynucleotides synthesized may fall from 10-2000, 10-500, 9-400, 11-300, 12-200, 13-150, 14-100, 15-50, 16-45, 17-40, 18-35, and 19-25.

Polynucleotide Probe Structures

Libraries of polynucleotide probes can be used to enrich particular target sequences in a larger population of sample polynucleotides. In some instances, polynucleotide probes each comprise a target binding sequence complementary to one or more target sequences, one or more non-target binding sequences, and one or more primer binding sites, such as universal primer binding sites. Target binding sequences that are complementary or at least partially complementary in some instances bind (hybridize) to target sequences. Primer binding sites, such as universal primer binding sites facilitate simultaneous amplification of all members of the probe library, or a subpopulation of members. In some instances, the probes or adapters further comprise a barcode or index sequence. Barcodes are nucleic acid sequences that allow some feature of a polynucleotide with which the barcode is associated to be identified. After sequencing, the barcode region provides an indicator for identifying a characteristic associated with the coding region or sample source. Barcodes can be designed at suitable lengths to allow sufficient degree of identification, e.g., at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or more bases in length. Multiple barcodes, such as about 2, 3, 4, 5, 6, 7, 8, 9, 10, or more barcodes, may be used on the same molecule, optionally separated by non-barcode sequences. In some embodiments, each barcode in a plurality of barcodes differ from every other barcode in the plurality at least three base positions, such as at least about 3, 4, 5, 6, 7, 8, 9, 10, or more positions. Use of barcodes allows for the pooling and simultaneous processing of multiple libraries for downstream applications, such as sequencing (multiplex). In some instances, at least 4, 8, 16, 32, 48, 64, 128, or more 512 barcoded libraries are used. In some instances, the polynucleotides are ligated to one or more molecular (or affinity) tags such as a small molecule, peptide, antigen, metal, or protein to form a probe for subsequent capture of the target sequences of interest. In some instances, only a portion of the polynucleotides are ligated to a molecular tag. In some instances, two probes that possess complementary target binding sequences which are capable of hybridization form a double stranded probe pair. Polynucleotide probes or adapters may comprise unique molecular identifiers (UMI). UMIs allow for internal measurement of initial sample concentrations or stoichiometry prior to downstream sample processing (e.g., PCR or enrichment steps) which can introduce bias. In some instances, UMIs comprise one or more barcode sequences.

Probes described here may be complementary to target sequences which are sequences in a genome. Probes described here may be complementary to target sequences which are exome sequences in a genome. Probes described here may be complementary to target sequences which are intron sequences in a genome. In some instances, probes comprise a target binding sequence complementary to a target sequence, and at least one non-target binding sequence that is not complementary to the target. In some instances, the target binding sequence of the probe is about 120 nucleotides in length, or at least 10, 15, 20, 25, 50, 75, 100, 110, 120, 125, 140, 150, 160, 175, 200, 300, 400, 500, or more than 500 nucleotides in length. The target binding sequence is in some instances no more than 10, 15, 20, 25, 50, 75, 100, 125, 150, 175, 200, or no more than 500 nucleotides in length. The target binding sequence of the probe is in some instances about 120 nucleotides in length, or about 10, 15, 20, 25, 40, 50, 60, 70, 80, 85, 87, 90, 95, 97, 100, 105, 110, 115, 117, 118, 119, 120, 121, 122, 123, 124, 125, 126, 127, 128, 129, 130, 135, 140, 145, 150, 155, 157, 158, 159, 160, 161, 162, 163, 164, 165, 166, 167, 168, 169, 170, 175, 180, 190, 200, 210, 220, 230, 240, 250, 300, 400, or about 500 nucleotides in length. The target binding sequence is in some instances about 20 to about 400 nucleotides in length, or about 30 to about 175, about 40 to about 160, about 50 to about 150, about 75 to about 130, about 90 to about 120, or about 100 to about 140 nucleotides in length. The non-target binding sequence(s) of the probe is in some instances at least about 20 nucleotides in length, or at least about 1, 5, 10, 15, 17, 20, 23, 25, 50, 75, 100, 110, 120, 125, 140, 150, 160, 175, or more than about 175 nucleotides in length. The non-target binding sequence often is no more than about 5, 10, 15, 20, 25, 50, 75, 100, 125, 150, 175, or no more than about 200 nucleotides in length. The non-target binding sequence of the probe often is about 20 nucleotides in length, or about 1, 2, 3, 4, 5, 6, 7, 8, 9, 10, 11, 12, 13, 14, 15, 16, 17, 18, 19, 20, 21, 22, 23, 25, 40, 50, 60, 70, 80, 90, 100, 110, 120, 130, 140, 150, or about 200 nucleotides in length. The non-target binding sequence in some instances is about 1 to about 250 nucleotides in length, or about 20 to about 200, about 10 to about 100, about 10 to about 50, about 30 to about 100, about 5 to about 40, or about 15 to about 35 nucleotides in length. The non-target binding sequence often comprises sequences that are not complementary to the target sequence, and/or comprise sequences that are not used to bind primers. In some instances, the non-target binding sequence comprises a repeat of a single nucleotide, for example polyadenine or polythymidine. A probe often comprises none or at least one non-target binding sequence. In some instances, a probe comprises one or two non-target binding sequences. The non-target binding sequence may be adjacent to one or more target binding sequences in a probe. For example, a non-target binding sequence is located on the 5' or 3' end of the probe. In some instances, the non-target binding sequence is attached to a molecular tag or spacer.

Figure 9A:
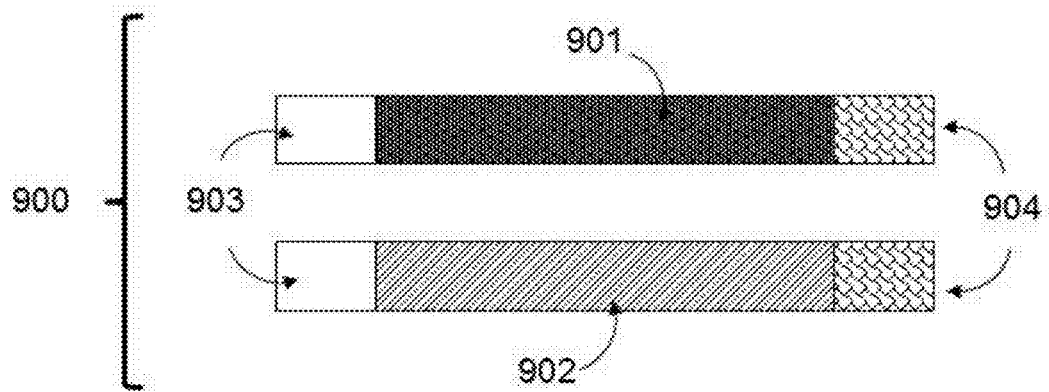
FIG. 9A depicts a pair of polynucleotides for targeting and enrichment. The polynucleotides comprise complementary target binding (insert) sequences, as well as primer binding sites.

As described herein, non-target binding sequence(s) may be a primer binding site. The primer binding sites often are each at least about 20 nucleotides in length, or at least about 10, 12, 14, 16, 18, 20, 22, 24, 26, 28, 30, 32, 34, 36, 38, or at least about 40 nucleotides in length. Each primer binding site in some instances is no more than about 10, 12, 14, 16, 18, 20, 22, 24, 26, 28, 30, 32, 34, 36, 38, or no more than about 40 nucleotides in length. Each primer binding site in some instances is about 10 to about 50 nucleotides in length, or about 15 to about 40, about 20 to about 30, about 10 to about 40, about 10 to about 30, about 30 to about 50, or about 20 to about 60 nucleotides in length. In some instances the polynucleotide probes comprise at least two primer binding sites. In some instances, primer binding sites may be universal primer binding sites, wherein all probes comprise identical primer binding sequences at these sites. In some instances, a pair of polynucleotide probes targeting a particular sequence and its reverse complement (e.g., a region of genomic DNA) are represented by 900 in FIG. 9A, comprising a first target binding sequence 901, a second target binding sequence 902, a first non-target binding sequence 903, and a second non-target binding sequence 904. For example, a pair of polynucleotide probes complementary to a particular sequence (e.g., a region of genomic DNA).

Figure 9B:
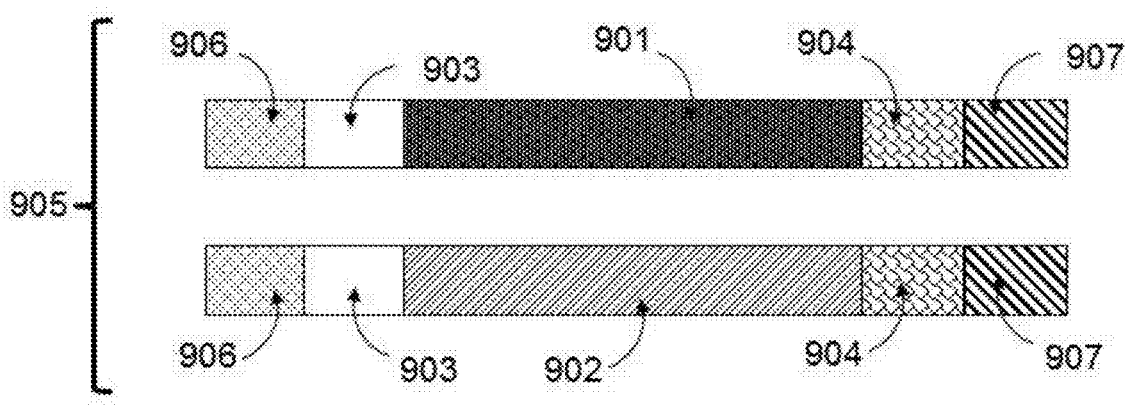
FIG. 9B depicts a pair of polynucleotides for targeting and enrichment. The polynucleotides comprise complementary target sequence binding (insert) sequences, primer binding sites, and non-target sequences.

In some instances, the first target binding sequence 901 is the reverse complement of the second target binding sequence 902. In some instances, both target binding sequences are chemically synthesized prior to amplification. In an alternative arrangement, a pair of polynucleotide probes targeting a particular sequence and its reverse complement (e.g., a region of genomic DNA) are represented by 905 in FIG. 9B, comprising a first target binding sequence 901, a second target binding sequence 902, a first non-target binding sequence 903, a second non-target binding sequence 904, a third non-target binding sequence 906, and a fourth non-target binding sequence 907. In some instances, the first target binding sequence 901 is the reverse complement of the second target binding sequence 902. In some instances, one or more non-target binding sequences comprise polyadenine or polythymidine.

Probes described herein may comprise molecular tags. In some instances, both probes in the pair are labeled with at least one molecular tag. In some instances, PCR is used to introduce molecular tags (via primers comprising the molecular tag) onto the probes during amplification. In some instances, the molecular tag comprises one or more biotin, folate, a polyhistidine, a FLAG tag, glutathione, or other molecular tag consistent with the specification. In some instances probes are labeled at the 5' terminus. In some instances, the probes are labeled at the 3' terminus. In some instances, both the 5' and 3' termini are labeled with a molecular tag. In some instances, the 5' terminus of a first probe in a pair is labeled with at least one molecular tag, and the 3' terminus of a second probe in the pair is labeled with at least one molecular tag. In some instances, a spacer is present between one or more molecular tags and the nucleic acids of the probe. In some instances, the spacer may comprise an alkyl, polyol, or polyamino chain, a peptide, or a polynucleotide. The solid support used to capture probe-target nucleic acid complexes in some instances, is a bead or a surface. The solid support in some instances comprises glass, plastic, or other material capable of comprising a capture moiety that will bind the molecular tag. In some instances, a bead is a magnetic bead. For example, probes labeled with biotin are captured with a magnetic bead comprising streptavidin. The probes are contacted with a library of nucleic acids to allow binding of the probes to target sequences. In some instances, blocking polynucleic acids are added to prevent binding of the probes to one or more adapter sequences attached to the target nucleic acids. In some instances, blocking polynucleic acids comprise one or more nucleic acid analogues. In some instances, blocking polynucleic acids have a uracil substituted for thymine at one or more positions.

Probes described herein may comprise complementary target binding sequences which bind to one or more target nucleic acid sequences. In some instances, the target sequences are any DNA or RNA nucleic acid sequence. In some instances, target sequences may be longer than the probe insert. In some instance, target sequences may be shorter than the probe insert. In some instance, target sequences may be the same length as the probe insert. For example, the length of the target sequence may be at least or about at least 2, 10, 15, 20, 25, 30, 35, 40, 45, 50, 100, 150, 200, 300, 400, 500, 1000, 2000, 5,000, 12,000, 20,000 nucleotides, or more. The length of the target sequence may be at most or about at most 20,000, 12,000, 5,000, 2,000, 1,000, 500, 400, 300, 200, 150, 100, 50, 45, 35, 30, 25, 20, 19, 18, 17, 16, 15, 14, 13, 12, 11, 10, 2 nucleotides, or less. The length of the target sequence may fall from 2-20,000, 3-12,000, 5-5, 5000, 10-2,000, 10-1,000, 10-500, 9-400, 11-300, 12-200, 13-150, 14-100, 15-50, 16-45, 17-40, 18-35, and 19-25. The probe sequences may target sequences associated with specific genes, diseases, regulatory pathways, or other biological functions consistent with the specification.

Figures 10A, 10B, 10C, 10D, 10E, 10F, 10G:
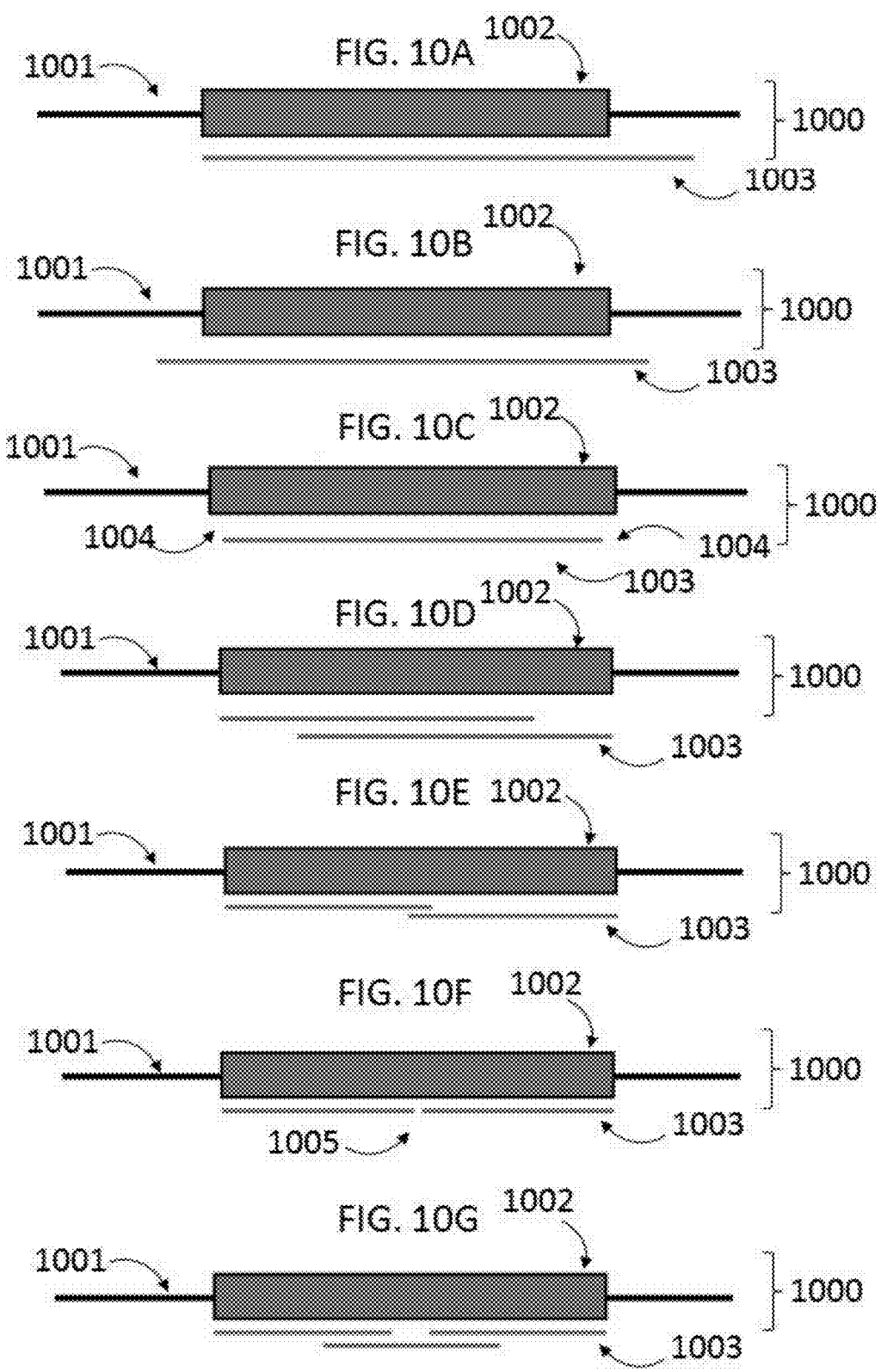
FIG. 10A depicts a polynucleotide binding configuration to a target sequence of a larger polynucleotide. The target sequence is shorter than the polynucleotide binding region, and the polynucleotide binding region (or insert sequence) is offset relative to the target sequence, and also binds to a portion of adjacent sequence.
FIG. 10B depicts a polynucleotide binding configuration to a target sequence of a larger polynucleotide. The target sequence length is less than or equal to the polynucleotide binding region, and the polynucleotide binding region is centered with the target sequence, and also binds to a portion of adjacent sequence.
FIG. 10C depicts a polynucleotide binding configuration to a target sequence of a larger polynucleotide. The target sequence is slightly longer than the polynucleotide binding region, and the polynucleotide binding region is centered on the target sequence with a buffer region on each side.
FIG. 10D depicts a polynucleotide binding configuration to a target sequence of a larger polynucleotide. The target sequence is longer than the polynucleotide binding region, and the binding regions of two polynucleotides are overlapped to span the target sequence.
FIG. 10E depicts a polynucleotide binding configuration to a target sequence of a larger polynucleotide. The target sequence is longer than the polynucleotide binding region, and the binding regions of two polynucleotides are overlapped to span the target sequence.
FIG. 10F depicts a polynucleotide binding configuration to a target sequence of a larger polynucleotide. The target sequence is longer than the polynucleotide binding region, and the binding regions of two polynucleotides are not overlapped to span the target sequence, leaving a gap 405.
FIG. 10G depicts a polynucleotide binding configuration to a target sequence of a larger polynucleotide. The target sequence is longer than the polynucleotide binding region, and the binding regions of three polynucleotides are overlapped to span the target sequence.

A probe described herein may bind to a target sequences in any number of suitable arrangements. In some instances, a single probe insert 1003 is complementary to one or more target sequences 1002 (FIGS. 10A-10G) in a larger polynucleic acid 1000. An exemplary target sequence is an exon. In some instances, one or more probes target a single target sequence (FIGS. 10A-10G). In some instances, a single probe may target more than one target sequence. In some instances, the target binding sequence of the probe targets both a target sequence 1002 and an adjacent sequence 1001 (FIGS. 10A and 10B). In some instances, a first probe targets a first region and a second region of a target sequence, and a second probe targets the second region and a third region of the target sequence (FIG. 10D and FIG. 10E). In some instances, a plurality of probes targets a single target sequence, wherein the target binding sequences of the plurality of probes contain one or more sequences which overlap with regard to complementarity to a region of the target sequence (FIG. 10G). In some instances, probe inserts do not overlap with regard to complementarity to a region of the target sequence. In some instances, at least at least 2, 10, 15, 20, 25, 30, 35, 40, 45, 50, 100, 150, 200, 300, 400, 500, 1000, 2000, 5,000, 12,000, 20,000, or more than 20,000 probes target a single target sequence. In some instances no more than 4 probes directed to a single target sequence overlap, or no more than 3, 2, 1, or no probes targeting a single target sequence overlap. In some instances, one or more probes do not target all bases in a target sequence, leaving one or more gaps (FIG. 10C and FIG. 10F). In some instances, the gaps are near the middle of the target sequence 1005 (FIG. 10F). In some instances, the gaps 1004 are at the 5' or 3' ends of the target sequence (FIG. 10C). In some instances, the gaps are 6 nucleotides in length. In some instances, the gaps are no more than 1, 2, 3, 4, 5, 6, 7, 8, 9, 10, 20, 30, 40, or no more than 50 nucleotides in length. In some instances, the gaps are at least 1, 2, 3, 4, 5, 6, 7, 8, 9, 10, 20, 30, 40, or at least 50 nucleotides in length. In some instances, the gaps length falls within 1-50, 1-40, 1-30, 1-20, 1-10, 2-30, 2-20, 2-10, 3-50, 3-25, 3-10, or 3-8 nucleotides in length. In some instances, a set of probes targeting a sequence do not comprise overlapping regions amongst probes in the set when hybridized to complementary sequence. In some instances, a set of probes targeting a sequence do not have any gaps amongst probes in the set when hybridized to complementary sequence. Probes may be designed to maximize uniform binding to target sequences. In some instances, probes are designed to minimize target binding sequences of high or low GC content, secondary structure, repetitive/palindromic sequences, or other sequence feature that may interfere with probe binding to a target. In some instances, a single probe may target a plurality of target sequences.

A probe library described herein may comprise at least 10, 20, 50, 100, 200, 500, 1,000, 2,000, 5,000, 10,000, 20,000, 50,000, 100,000, 200,000, 500,000, 1,000,000 or more than 1,000,000 probes. A probe library may have no more than 10, 20, 50, 100, 200, 500, 1,000, 2,000, 5,000, 10,000, 20,000, 50,000, 100,000, 200,000, 500,000, or no more than 1,000,000 probes. A probe library may comprise 10 to 500, 20 to 1000, 50 to 2000, 100 to 5000, 500 to 10,000, 1,000 to 5,000, 10,000 to 50,000, 100,000 to 500,000, or to 50,000 to 1,000,000 probes. A probe library may comprise about 370,000; 400,000; 500,000 or more different probes.

Next Generation Sequencing Applications

Downstream applications of polynucleotide libraries may include next generation sequencing. For example, enrichment of target sequences with a controlled stoichiometry polynucleotide probe library results in more efficient sequencing. The performance of a polynucleotide library for capturing or hybridizing to targets may be defined by a number of different metrics describing efficiency, accuracy, and precision. For example, Picard metrics comprise variables such as HS library size (the number of unique molecules in the library that correspond to target regions, calculated from read pairs), mean target coverage (the percentage of bases reaching a specific coverage level), depth of coverage (number of reads including a given nucleotide) fold enrichment (sequence reads mapping uniquely to the target/reads mapping to the total sample, multiplied by the total sample length/target length), percent off-bait bases (percent of bases not corresponding to bases of the probes/baits), percent off-target (percent of bases not corresponding to bases of interest), usable bases on target, AT or GC dropout rate, fold 80 base penalty (fold overcoverage needed to raise 80 percent of non-zero targets to the mean coverage level), percent zero coverage targets, PF reads (the number of reads passing a quality filter), percent selected bases (the sum of on-bait bases and near-bait bases divided by the total aligned bases), percent duplication, or other variable consistent with the specification.

Read depth (sequencing depth, or sampling) represents the total number of times a sequenced nucleic acid fragment (a "read") is obtained for a sequence. Theoretical read depth is defined as the expected number of times the same nucleotide is read, assuming reads are perfectly distributed throughout an idealized genome. Read depth is expressed as function of % coverage (or coverage breadth). For example, 10 million reads of a 1 million base genome, perfectly distributed, theoretically results in 10× read depth of 100% of the sequences. In practice, a greater number of reads (higher theoretical read depth, or oversampling) may be needed to obtain the desired read depth for a percentage of the target sequences. In some instances, the efficiency in sequencing is defined as a ratio of reads for a population of bases in a sample vs. the total reads obtained for the sample. In some instances, a population of bases is selected using probes described herein. In some instances, the ratio of reads for a population of bases in a sample vs. the total reads is at least 0.1, 0.15, 0.2, 0.25, 0.3, 0.35, 0.4, 0.45, 0.5, 0.55, 0.6, 0.65, 0.7, 0.75, 0.8, 0.85, 0.9, or at least 0.95. In some instances, the ratio of reads for a population of bases in a sample vs. the total reads is about 0.1, 0.15, 0.2, 0.25, 0.3, 0.35, 0.4, 0.45, 0.5, 0.55, 0.6, 0.65, 0.7, 0.75, 0.8, 0.85, 0.9, or about 0.95. In some instances, the ratio of reads for a population of bases in a sample vs. the total reads is 0.1 to 0.9, 0.2 to 0.8, 0.3 to 0.7, 0.2 to 0.8, 0.3 to 0.7, 0.5-0.7, or 0.4-0.7. In some instances, the ratio of reads for a population of bases in a sample vs. the total reads is at least 0.5. In some instances, the ratio of reads for a population of bases in a sample vs. the total reads is at least 0.6. In some instances, the ratio of reads for a population of bases in a sample vs. the total reads is at least 0.7. In some instances, the ratio of reads for a population of bases in a sample vs. the total reads is at least 0.8. Enrichment of target sequences with a controlled stoichiometry probe library increases the efficiency of downstream sequencing, as fewer total reads will be required to obtain an outcome with an acceptable number of reads over a desired % of target sequences. For example, in some instances 55×theoretical read depth of target sequences results in at least 30× coverage of at least 90% of the sequences. In some instances no more than 55× theoretical read depth of target sequences results in at least 30×read depth of at least 80% of the sequences. In some instances no more than 55× theoretical read depth of target sequences results in at least 30× read depth of at least 95% of the sequences. In some instances no more than 55× theoretical read depth of target sequences results in at least 10× read depth of at least 98% of the sequences. In some instances, 55× theoretical read depth of target sequences results in at least 20×read depth of at least 98% of the sequences. In some instances no more than 55× theoretical read depth of target sequences results in at least 5× read depth of at least 98% of the sequences. Increasing the concentration of probes during hybridization with targets can lead to an increase in read depth. In some instances, the concentration of probes is increased by at least 1.5×, 2.0×, 2.5×, 3×, 3.5×, 4×, 5×, or more than 5×. In some instances, increasing the probe concentration results in at least a 1000% increase, or a 20%, 30%, 40%, 50%, 60%, 70%, 80%, 90%, 100%, 200%, 300%, 500%, 750%, 1000%, or more than a 1000% increase in read depth. In some instances, increasing the probe concentration by 3× results in a 1000% increase in read depth.

On-target rate represents the percentage of sequencing reads that correspond with the desired target sequences. In some instances, a controlled stoichiometry polynucleotide probe library results in an on-target rate of at least 30%, or at least 35%, 40%, 45%, 50%, 55%, 60%, 65%, 70%, 75%, 80%, 85%, or at least 90%. Increasing the concentration of polynucleotide probes during contact with target nucleic acids leads to an increase in the on-target rate. In some instances, the concentration of probes is increased by at least 1.5×, 2.0×, 2.5×, 3×, 3.5×, 4×, 5×, or more than 5×. In some instances, increasing the probe concentration results in at least a 20% increase, or a 10%, 20%, 30%, 40%, 50%, 60%, 70%, 80%, 90%, 100%, 200%, 300%, or at least a 500% increase in on-target binding. In some instances, increasing the probe concentration by 3× results in a 20% increase in on-target rate.

Coverage uniformity is in some cases calculated as the read depth as a function of the target sequence identity. Higher coverage uniformity results in a lower number of sequencing reads needed to obtain the desired read depth. For example, a property of the target sequence may affect the read depth, for example, high or low GC or AT content, repeating sequences, trailing adenines, secondary structure, affinity for target sequence binding (for amplification, enrichment, or detection), stability, melting temperature, biological activity, ability to assemble into larger fragments, sequences containing modified nucleotides or nucleotide analogues, or any other property of polynucleotides. Enrichment of target sequences with controlled stoichiometry polynucleotide probe libraries results in higher coverage uniformity after sequencing. In some instances, 95% of the sequences have a read depth that is within 1× of the mean library read depth, or about 0.05, 0.1, 0.2, 0.5, 0.7, 1, 1.2, 1.5, 1.7 or about within 2× the mean library read depth. In some instances, 80%, 85%, 90%, 95%, 97%, or 99% of the sequences have a read depth that is within 1× of the mean.

The methods and compositions described herein may be used for specific sample types, including but not limited to DNA, RNA, mRNA, cfDNA, fetal cfDNA, siRNA, rRNA, miRNA, FFPE or other nucleic acid sample. In some instances, mechanical shearing is used to prepare nucleic acid samples for ligation of adapters, capture, enrichment, and sequencing. In some instances, enzymatic cleavage is used to prepare nucleic acid samples for ligation of adapters, capture, enrichment, and sequencing. In some instances, FFPE samples are analyzed, such as FFPE samples from different tissues. Tissues include but are not limited to brain, neck, lymph node, lung, liver, spleen, heart, kidney, skin, uterus, testis, pancreas, intestine, colon, stomach, prostate, or other tissue. In some instances, the tissue is a cancer, such as a solid tumor. In some instances, the solid tumor is a carcinoma. In some instances, use of probes described herein result in increased uniformity and sensitivity of sequencing data obtained using the methods described herein.

Enrichment of Target Nucleic Acids with a Polynucleotide Probe Library

A probe library described herein may be used to enrich target polynucleotides present in a population of sample polynucleotides, for a variety of downstream applications. In one some instances, a sample is obtained from one or more sources, and the population of sample polynucleotides is isolated. Samples are obtained (by way of non-limiting example) from biological sources such as saliva, blood, tissue, skin, or completely synthetic sources. The plurality of polynucleotides obtained from the sample are fragmented, end-repaired, and adenylated to form a double stranded sample nucleic acid fragment. In some instances, end repair is accomplished by treatment with one or more enzymes, such as T4 DNA polymerase, klenow enzyme, and T4 polynucleotide kinase in an appropriate buffer. A nucleotide overhang to facilitate ligation to adapters is added, in some instances with 3' to 5' exo minus klenow fragment and dATP.

Adapters may be ligated to both ends of the sample polynucleotide fragments with a ligase, such as T4 ligase, to produce a library of adapter-tagged polynucleotide strands, and the adapter-tagged polynucleotide library is amplified with primers, such as universal primers. In some instances, the adapters are Y-shaped adapters comprising one or more primer binding sites, one or more grafting regions, and one or more index (or barcode) regions. In some instances, the one or more index region is present on each strand of the adapter. In some instances, grafting regions are complementary to a flowcell surface, and facilitate next generation sequencing of sample libraries. In some instances, Y-shaped adapters comprise partially complementary sequences. In some instances, Y-shaped adapters comprise a single thymidine overhang which hybridizes to the overhanging adenine of the double stranded adapter-tagged polynucleotide strands. Y-shaped adapters may comprise modified nucleic acids, that are resistant to cleavage. For example, a phosphorothioate backbone is used to attach an overhanging thymidine to the 3' end of the adapters. The library of double stranded sample nucleic acid fragments is then denatured in the presence of adapter blockers. Adapter blockers minimize off-target hybridization of probes to the adapter sequences (instead of target sequences) present on the adapter-tagged polynucleotide strands, and/or prevent intermolecular hybridization of adapters (i.e., "daisy chaining"). Denaturation is carried out in some instances at 96° C., or at about 85, 87, 90, 92, 95, 97, 98 or about 99° C. A polynucleotide targeting library (probe library) is denatured in a hybridization solution, in some instances at 96° C., at about 85, 87, 90, 92, 95, 97, 98 or 99° C. The denatured adapter-tagged polynucleotide library and the hybridization solution are incubated for a suitable amount of time and at a suitable temperature to allow the probes to hybridize with their complementary target sequences. In some instances, a suitable hybridization temperature is about 45 to 80° C., or at least 45, 50, 55, 60, 65, 70, 75, 80, 85, or 90° C. In some instances, the hybridization temperature is 70° C. In some instances, a suitable hybridization time is 16 hours, or at least 4, 6, 8, 10, 12, 14, 16, 18, 20, 22, or more than 22 hours, or about 12 to 20 hours. Binding buffer is then added to the hybridized adapter-tagged-polynucleotide probes, and a solid support comprising a capture moiety are used to selectively bind the hybridized adapter-tagged polynucleotide-probes. The solid support is washed with buffer to remove unbound polynucleotides before an elution buffer is added to release the enriched, tagged polynucleotide fragments from the solid support. In some instances, the solid support is washed 2 times, or 1, 2, 3, 4, 5, or 6 times. The enriched library of adapter-tagged polynucleotide fragments is amplified and the enriched library is sequenced.

A plurality of nucleic acids (i.e. genomic sequence) may obtained from a sample, and fragmented, optionally end-repaired, and adenylated. Adapters are ligated to both ends of the polynucleotide fragments to produce a library of adapter-tagged polynucleotide strands, and the adapter-tagged polynucleotide library is amplified. The adapter-tagged polynucleotide library is then denatured at high temperature, preferably 96° C., in the presence of adapter blockers. A polynucleotide targeting library (probe library) is denatured in a hybridization solution at high temperature, preferably about 90 to 99° C., and combined with the denatured, tagged polynucleotide library in hybridization solution for about 10 to 24 hours at about 45 to 80° C. Binding buffer is then added to the hybridized tagged polynucleotide probes, and a solid support comprising a capture moiety are used to selectively bind the hybridized adapter-tagged polynucleotide-probes. The solid support is washed one or more times with buffer, preferably about 2 and 5 times to remove unbound polynucleotides before an elution buffer is added to release the enriched, adapter-tagged polynucleotide fragments from the solid support. The enriched library of adapter-tagged polynucleotide fragments is amplified and then the library is sequenced. Alternative variables such as incubation times, temperatures, reaction volumes/concentrations, number of washes, or other variables consistent with the specification are also employed in the method.

A population of polynucleotides may be enriched prior to adapter ligation. In one example, a plurality of polynucleotides is obtained from a sample, fragmented, optionally end-repaired, and denatured at high temperature, preferably 90-99° C. A polynucleotide targeting library (probe library) is denatured in a hybridization solution at high temperature, preferably about 90 to 99° C., and combined with the denatured, tagged polynucleotide library in hybridization solution for about 10 to 24 hours at about 45 to 80° C. Binding buffer is then added to the hybridized tagged polynucleotide probes, and a solid support comprising a capture moiety are used to selectively bind the hybridized adapter-tagged polynucleotide-probes. The solid support is washed one or more times with buffer, preferably about 2 and 5 times to remove unbound polynucleotides before an elution buffer is added to release the enriched, adapter-tagged polynucleotide fragments from the solid support. The enriched polynucleotide fragments are then polyadenylated, adapters are ligated to both ends of the polynucleotide fragments to produce a library of adapter-tagged polynucleotide strands, and the adapter-tagged polynucleotide library is amplified. The adapter-tagged polynucleotide library is then sequenced.

A polynucleotide targeting library may also be used to filter undesired sequences from a plurality of polynucleotides, by hybridizing to undesired fragments. For example, a plurality of polynucleotides is obtained from a sample, and fragmented, optionally end-repaired, and adenylated. Adapters are ligated to both ends of the polynucleotide fragments to produce a library of adapter-tagged polynucleotide strands, and the adapter-tagged polynucleotide library is amplified. Alternatively, adenylation and adapter ligation steps are instead performed after enrichment of the sample polynucleotides. The adapter-tagged polynucleotide library is then denatured at high temperature, preferably 90-99° C., in the presence of adapter blockers. A polynucleotide filtering library (probe library) designed to remove undesired, non-target sequences is denatured in a hybridization solution at high temperature, preferably about 90 to 99° C., and combined with the denatured, tagged polynucleotide library in hybridization solution for about 10 to 24 hours at about 45 to 80° C. Binding buffer is then added to the hybridized tagged polynucleotide probes, and a solid support comprising a capture moiety are used to selectively bind the hybridized adapter-tagged polynucleotide-probes. The solid support is washed one or more times with buffer, preferably about 1 and 5 times to elute unbound adapter-tagged polynucleotide fragments. The enriched library of unbound adapter-tagged polynucleotide fragments is amplified and then the amplified library is sequenced.

A polynucleotide targeting library may be designed to target genes with specific functions. For example, the target genes are mitochondrial genes. In some instances, the target genes are involved in a disease such as cancer or a neurodegenerative disease.

A polynucleotide targeting library may be designed to target a number of genes. In some instances, the number of genes comprises at least or about 10, 20, 30, 40, 50, 60, 70, 80, 90, 100, 120, 140, 160, 180, 200, 300, 400, 500, 600, 700, 800, 900, 1000, or more than 1000 genes. In some instances, a size of the target gene is at least or about 0.01, 0.02, 0.03, 0.04, 0.05, 0.06, 0.07, 0.08, 0.09, 1.0, 2.0, 4.0, 8.0, 10.0, 12.0, 14.0, 16.0, 18.0, 20.0, 22.0, 24.0, 26.0, 28.0, 30.0, 40.0, 50.0, 60.0, or more than 60.0 megabases (Mb). A number of probes in the polynucleotide targeting library, in some instances, comprises at least or about 100, 200, 300, 400, 500, 600, 700, 800, 900, 1000, 2000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, or more than 1000000 probes.

Described herein are polynucleotide targeting libraries with improved performance. In some instances, the polynucleotide targeting library comprises sequences that are highly uniform. In some instances, polynucleotide sequences are within at least or about 0.05, 0.1, 0.2, 0.5, 0.7, 1, 1.2, 1.5, 1.7, or 2× the mean. In some instances, 80%, 85%, 90%, 95%, 97%, or 99% of the sequences are within 1× of the mean. In some instances, the polynucleotide targeting libraries result in an on-target rate of at least 35%, 40%, 45%, 50%, 55%, 60%, 65%, 70%, 75%, 80%, 85%, or at least 90%. In some instances, the polynucleotide targeting libraries result in a duplication rate of at most or about 0.5%, 1.0%, 1.5%, 2.0%, 2.5%, 3.0%, 3.5%, 4.0%, 4.5%, or 5.0%. In some instances, the polynucleotide targeting libraries result in at least 30× coverage of at least 80%, 85%, 90%, 95%, or 99% of the sequences. In some instances, the polynucleotide targeting libraries result in at least 30× coverage of at least 95% of the sequences. In some instances, the polynucleotide targeting libraries result in at least 30× coverage of at least 99% of the sequences.

A polynucleotide targeting library as described herein may be used for multiplexed reactions. In some instances, the polynucleotide targeting library is used for a 1-, 2-, 3-, 4-, 5-, 6-, 7-, 8-, 9-, 10-, 11-, 12-, 13-, 14-, 15-, 16-, 17-, 18-, 19-, or a 20-plex enrichment reaction. In some instances, the polynucleotide targeting library used for multiplexed reactions result in improved performance. In some instances, the polynucleotide targeting library used for multiplexed reactions comprises sequences that are highly uniform. In some instances, polynucleotide sequences are within at least or about 0.05, 0.1, 0.2, 0.5, 0.7, 1, 1.2, 1.5, 1.7, or 2×the mean. In some instances, 80%, 85%, 90%, 95%, 97%, or 99% of the sequences are within 1× of the mean. In some instances, the polynucleotide targeting library used for multiplexed reactions result in an on-target rate of at least 35%, 40%, 45%, 50%, 55%, 60%, 65%, 70%, 75%, 80%, 85%, or at least 90%. In some instances, the polynucleotide targeting library used for multiplexed reactions result in a duplication rate of at most or about 0.5%, 1.0%, 1.5%, 2.0%, 2.5%, 3.0%, 3.5%, 4.0%, 4.5%, or 5.0%. In some instances, the polynucleotide targeting library used for multiplexed reactions result in a duplication rate of at most or about 2.0%. In some instances, the polynucleotide targeting library used for multiplexed reactions result in a duplication rate of at most or about 3.0%. In some instances, the improved performance is regardless of panel size. In some instances, the polynucleotide library results in improved performance for panels comprising at least or about 0.01, 0.02, 0.03, 0.04, 0.05, 0.06, 0.07, 0.08, 0.09, 1.0, 2.0, 4.0, 8.0, 10.0, 12.0, 14.0, 16.0, 18.0, 20.0, 22.0, 24.0, 26.0, 28.0, 30.0, 40.0, 50.0, 60.0, or more than 60.0 megabases (Mb). In some instances, the improved performance is regardless of sample mass. In some instances, the polynucleotide library results in improved performance for panels comprising at least or about 10, 20, 30, 40, 50, 60, 70, 80, 90, 100, 110, 120, 130, 140, 150, 160, 170, 180, 190, 200, 300, 400, 500, 600, 700, 800, 900, 1000, 1500, 2000, 2500, 3000, 3500, 4000, 4500, 5000, or more than 500 nanograms (ng).

Polynucleotide targeting libraries as described herein are highly accurate. In some instances, a first polynucleotide targeting library and a second polynucleotide targeting library comprise similar target enrichment. In some instances, a first polynucleotide targeting library and a second polynucleotide targeting library comprise similar probe abundance.

Polynucleotide targeting libraries as described herein are highly flexible and modular. For example, content of the polynucleotide targeting libraries may be added or enhanced. Adding content can increase a number of targets covered or enhancing content can augment the coverage of specific regions. In some instances, at least or about 0.01, 0.02, 0.03, 0.04, 0.05, 0.06, 0.07, 0.08, 0.09, 1.0, 2.0, 4.0, 8.0, 10.0, 12.0, 14.0, 16.0, 18.0, 20.0 megabases (Mb) of content is added or enhanced. In some instances, addition or enhancement of content results in increased coverage. In some instances, coverage is improved to at least 80%, 85%, 90%, 95%, 99%, or more than 99%. In some instances, polynucleotide targeting libraries comprising added or enhanced content have high uniformity, high on-target rate, low duplicate rate, or a combination thereof. In some instances, the polynucleotide targeting library comprising added or enhanced content comprises sequences that are highly uniform. In some instances, polynucleotide sequences are within at least or about 0.05, 0.1, 0.2, 0.5, 0.7, 1, 1.2, 1.5, 1.7, or 2×the mean. In some instances, 80%, 85%, 90%, 95%, 97%, or 99% of the sequences are within 1× of the mean. In some instances, the polynucleotide targeting libraries comprising added or enhanced content result in an on-target rate of at least 35%, 40%, 45%, 50%, 55%, 60%, 65%, 70%, 75%, 80%, 85%, or at least 90%. In some instances, the polynucleotide targeting libraries comprising added or enhanced content result in a duplication rate of at most or about 0.5%, 1.0%, 1.5%, 2.0%, 2.5%, 3.0%, 3.5%, 4.0%, 4.5%, or 5.0%.

Polynucleotide targeting libraries as described herein may be designed to improve capture uniformity. For example, polynucleotide targeting libraries are designed to result in less than 1.0%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10% AT dropout. In some instances, polynucleotide targeting libraries are designed to result in less than 1.0%, 1.5%, 2.0%, 2.5%, 3.0%, 3.5%, 4.0%, 4.5%, or 5.0% AT dropout. In some instances, polynucleotide targeting libraries are designed to result in less than 1.0%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10% GC dropout. In some instances, polynucleotide targeting libraries are designed to result in less than 1.0%, 1.5%, 2.0%, 2.5%, 3.0%, 3.5%, 4.0%, 4.5%, or 5.0% GC dropout. In some instances, the polynucleotide targeting libraries designed for improved capture uniformity result in polynucleotide sequences are within at least or about 0.05, 0.1, 0.2, 0.5, 0.7, 1, 1.2, 1.5, 1.7, or 2×the mean. In some instances, 80%, 85%, 90%, 95%, 97%, or 99% of the sequences are within 1× of the mean. In some instances, the polynucleotide targeting libraries designed for improved capture uniformity result in an on-target rate of at least 35%, 40%, 45%, 50%, 55%, 60%, 65%, 70%, 75%, 80%, 85%, or at least 90%. In some instances, the polynucleotide targeting libraries designed for improved capture uniformity result in a duplication rate of at most or about 0.5%, 1.0%, 1.5%, 2.0%, 2.5%, 3.0%, 3.5%, 4.0%, 4.5%, or 5.0%. In some instances, the polynucleotide targeting libraries designed for improved capture uniformity result in at least 30× coverage of at least 80%, 85%, 90%, 95%, or 99% of the sequences. In some instances, the polynucleotide targeting libraries designed for improved capture uniformity result in at least 30× coverage of at least 95% of the sequences. In some instances, the polynucleotide targeting libraries designed for improved capture uniformity result in at least 30× coverage of at least 99% of the sequences. In some instances, the polynucleotide targeting libraries designed for improved capture uniformity result in at least 20× coverage of at least 80%, 85%, 90%, 95%, or 99% of the sequences. In some instances, the polynucleotide targeting libraries designed for improved capture uniformity result in at least 20× coverage of at least 95% of the sequences. In some instances, the polynucleotide targeting libraries result in at least 30× coverage of at least 99% of the sequences.

Polynucleotide targeting libraries may iteratively optimized based on performance of the library. In some instances, polynucleotides are removed from a library. In some instances, removal of a portion of the polynucleotides results in increased on-target rates or a decrease in off-target rates. In some instances, about 0.1%, 0.2%, 0.5%, 1%, 2%, 3%, 4%, or about 5% of the polynucleotides are removed. In some instances, no more than 0.1%, 0.2%, 0.5%, 1%, 2%, 3%, 4%, or no more than 5% of the polynucleotides are removed. In some instances, 0.0.1%-1%, 0.02-0.4%, 0.3-0.5%, 0.2-1.5%, 0.5-2%, 1-2%, 1-5%, 2-4% or 0.7-3% of the polynucleotides are removed. In some instances, removal of one or more probes from a polynucleotide library used in a method described herein results in enhanced enrichment performance of the library (e.g., on target rate, off target rate, 80-fold base penalty, off-bait rate, % bases >30× coverage, or other sequencing metric).

Highly Parallel De Novo Nucleic Acid Synthesis

Described herein is a platform approach utilizing miniaturization, parallelization, and vertical integration of the end-to-end process from polynucleotide synthesis to gene assembly within Nano wells on silicon to create a revolutionary synthesis platform. Devices described herein provide, with the same footprint as a 96-well plate, a silicon synthesis platform is capable of increasing throughput by a factor of 100 to 1,000 compared to traditional synthesis methods, with production of up to approximately 1,000,000 polynucleotides in a single highly-parallelized run. In some instances, a single silicon plate described herein provides for synthesis of about 6,100 non-identical polynucleotides. In some instances, each of the non-identical polynucleotides is located within a cluster. A cluster may comprise 50 to 500 non-identical polynucleotides.

Methods described herein provide for synthesis of a library of polynucleotides each encoding for a predetermined variant of at least one predetermined reference nucleic acid sequence. In some cases, the predetermined reference sequence is nucleic acid sequence encoding for a protein, and the variant library comprises sequences encoding for variation of at least a single codon such that a plurality of different variants of a single residue in the subsequent protein encoded by the synthesized nucleic acid are generated by standard translation processes. The synthesized specific alterations in the nucleic acid sequence can be introduced by incorporating nucleotide changes into overlapping or blunt ended polynucleotide primers. Alternatively, a population of polynucleotides may collectively encode for a long nucleic acid (e.g., a gene) and variants thereof. In this arrangement, the population of polynucleotides can be hybridized and subject to standard molecular biology techniques to form the long nucleic acid (e.g., a gene) and variants thereof. When the long nucleic acid (e.g., a gene) and variants thereof are expressed in cells, a variant protein library is generated. Similarly, provided here are methods for synthesis of variant libraries encoding for RNA sequences (e.g., miRNA, shRNA, and mRNA) or DNA sequences (e.g., enhancer, promoter, UTR, and terminator regions). Also provided here are downstream applications for variants selected out of the libraries synthesized using methods described here. Downstream applications include identification of variant nucleic acid or protein sequences with enhanced biologically relevant functions, e.g., biochemical affinity, enzymatic activity, changes in cellular activity, and for the treatment or prevention of a disease state.

Substrates

Provided herein are substrates comprising a plurality of clusters, wherein each cluster comprises a plurality of loci that support the attachment and synthesis of polynucleotides. The term "locus" as used herein refers to a discrete region on a structure which provides support for polynucleotides encoding for a single predetermined sequence to extend from the surface. In some instances, a locus is on a two dimensional surface, e.g., a substantially planar surface. In some instances, a locus refers to a discrete raised or lowered site on a surface e.g., a well, micro well, channel, or post. In some instances, a surface of a locus comprises a material that is actively functionalized to attach to at least one nucleotide for polynucleotide synthesis, or preferably, a population of identical nucleotides for synthesis of a population of polynucleotides. In some instances, polynucleotide refers to a population of polynucleotides encoding for the same nucleic acid sequence. In some instances, a surface of a device is inclusive of one or a plurality of surfaces of a substrate.

Provided herein are structures that may comprise a surface that supports the synthesis of a plurality of polynucleotides having different predetermined sequences at addressable locations on a common support. In some instances, a device provides support for the synthesis of more than 2,000; 5,000; 10,000; 20,000; 30,000; 50,000; 75,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical polynucleotides. In some instances, the device provides support for the synthesis of more than 2,000; 5,000; 10,000; 20,000; 30,000; 50,000; 75,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more polynucleotides encoding for distinct sequences. In some instances, at least a portion of the polynucleotides have an identical sequence or are configured to be synthesized with an identical sequence.

Provided herein are methods and devices for manufacture and growth of polynucleotides about 5, 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, or 2000 bases in length. In some instances, the length of the polynucleotide formed is about 5, 10, 20, 30, 40, 50, 60, 70, 80, 90, 100, 125, 150, 175, 200, or 225 bases in length. A polynucleotide may be at least 5, 10, 20, 30, 40, 50, 60, 70, 80, 90, or 100 bases in length. A polynucleotide may be from 10 to 225 bases in length, from 12 to 100 bases in length, from 20 to 150 bases in length, from 20 to 130 bases in length, or from 30 to 100 bases in length.

In some instances, polynucleotides are synthesized on distinct loci of a substrate, wherein each locus supports the synthesis of a population of polynucleotides. In some instances, each locus supports the synthesis of a population of polynucleotides having a different sequence than a population of polynucleotides grown on another locus. In some instances, the loci of a device are located within a plurality of clusters. In some instances, a device comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a device comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some instances, a device comprises about 10,000 distinct loci. The amount of loci within a single cluster is varied in different instances. In some instances, each cluster includes 1, 2, 3, 4, 5, 6, 7, 8, 9, 10, 20, 30, 40, 50, 60, 70, 80, 90, 100, 120, 130, 150, 200, 300, 400, 500, 1000 or more loci. In some instances, each cluster includes about 50-500 loci. In some instances, each cluster includes about 100-200 loci. In some instances, each cluster includes about 100-150 loci. In some instances, each cluster includes about 109, 121, 130 or 137 loci. In some instances, each cluster includes about 19, 20, 61, 64 or more loci.

The number of distinct polynucleotides synthesized on a device may be dependent on the number of distinct loci available in the substrate. In some instances, the density of loci within a cluster of a device is at least or about 1 locus per mm$^2$, 10 loci per mm$^2$, 25 loci per mm$^2$, 50 loci per mm$^2$, 65 loci per mm$^2$, 75 loci per mm$^2$, 100 loci per mm$^2$, 130 loci per mm$^2$, 150 loci per mm$^2$, 175 loci per mm$^2$, 200 loci per mm$^2$, 300 loci per mm$^2$, 400 loci per mm$^2$, 500 loci per mm$^2$, 1,000 loci per mm$^2$ or more. In some instances, a device comprises from about 10 loci per mm$^2$ to about 500 mm$^2$, from about 25 loci per mm$^2$ to about 400 mm$^2$, from about 50 loci per mm$^2$ to about 500 mm$^2$, from about 100 loci per mm$^2$ to about 500 mm$^2$, from about 150 loci per mm$^2$ to about 500 mm$^2$, from about 10 loci per mm$^2$ to about 250 mm$^2$, from about 50 loci per mm$^2$ to about 250 mm$^2$, from about 10 loci per mm$^2$ to about 200 mm$^2$, or from about 50 loci per mm$^2$ to about 200 mm$^2$. In some instances, the distance from the centers of two adjacent loci within a cluster is from about 10 um to about 500 um, from about 10 um to about 200 um, or from about 10 um to about 100 um. In some instances, the distance from two centers of adjacent loci is greater than about 10 um, 20 um, 30 um, 40 um, 50 um, 60 um, 70 um, 80 um, 90 um or 100 um. In some instances, the distance from the centers of two adjacent loci is less than about 200 um, 150 um, 100 um, 80 um, 70 um, 60 um, 50 um, 40 um, 30 um, 20 um or 10 um. In some instances, each locus has a width of about 0.5 um, 1 um, 2 um, 3 um, 4 um, 5 um, 6 um, 7 um, 8 um, 9 um, 10 um, 20 um, 30 um, 40 um, 50 um, 60 um, 70 um, 80 um, 90 um or 100 um. In some instances, the each locus is has a width of about 0.5 um to 100 um, about 0.5 um to 50 um, about 10 um to 75 um, or about 0.5 um to 50 um.

In some instances, the density of clusters within a device is at least or about 1 cluster per 100 mm$^2$, 1 cluster per 10 mm$^2$, 1 cluster per 5 mm$^2$, 1 cluster per 4 mm$^2$, 1 cluster per 3 mm$^2$, 1 cluster per 2 mm$^2$, 1 cluster per 1 mm$^2$, 2 clusters per 1 mm$^2$, 3 clusters per 1 mm$^2$, 4 clusters per 1 mm$^2$, 5 clusters per 1 mm$^2$, 10 clusters per 1 mm$^2$, 50 clusters per 1 mm$^2$ or more. In some instances, a device comprises from about 1 cluster per 10 mm$^2$ to about 10 clusters per 1 mm$^2$. In some instances, the distance from the centers of two adjacent clusters is less than about 50 um, 100 um, 200 um, 500 um, 1000 um, or 2000 um or 5000 um. In some instances, the distance from the centers of two adjacent clusters is from about 50 um and about 100 um, from about 50 um and about 200 um, from about 50 um and about 300 um, from about 50 um and about 500 um, and from about 100 um to about 2000 um. In some instances, the distance from the centers of two adjacent clusters is from about 0.05 mm to about 50 mm, from about 0.05 mm to about 10 mm, from about 0.05 mm and about 5 mm, from about 0.05 mm and about 4 mm, from about 0.05 mm and about 3 mm, from about 0.05 mm and about 2 mm, from about 0.1 mm and 10 mm, from about 0.2 mm and 10 mm, from about 0.3 mm and about 10 mm, from about 0.4 mm and about 10 mm, from about 0.5 mm and 10 mm, from about 0.5 mm and about 5 mm, or from about 0.5 mm and about 2 mm. In some instances, each cluster has a diameter or width along one dimension of about 0.5 to 2 mm, about 0.5 to 1 mm, or about 1 to 2 mm. In some instances, each cluster has a diameter or width along one dimension of about 0.5, 0.6, 0.7, 0.8, 0.9, 1, 1.1, 1.2, 1.3, 1.4, 1.5, 1.6, 1.7, 1.8, 1.9 or 2 mm. In some instances, each cluster has an interior diameter or width along one dimension of about 0.5, 0.6, 0.7, 0.8, 0.9, 1, 1.1, 1.15, 1.2, 1.3, 1.4, 1.5, 1.6, 1.7, 1.8, 1.9 or 2 mm.

A device may be about the size of a standard 96 well plate, for example from about 100 and 200 mm by from about 50 and 150 mm. In some instances, a device has a diameter less than or equal to about 1000 mm, 500 mm, 450 mm, 400 mm, 300 mm, 250 nm, 200 mm, 150 mm, 100 mm or 50 mm. In some instances, the diameter of a device is from about 25 mm and 1000 mm, from about 25 mm and about 800 mm, from about 25 mm and about 600 mm, from about 25 mm and about 500 mm, from about 25 mm and about 400 mm, from about 25 mm and about 300 mm, or from about 25 mm and about 200. Non-limiting examples of device size include about 300 mm, 200 mm, 150 mm, 130 mm, 100 mm, 76 mm, 51 mm and 25 mm. In some instances, a device has a planar surface area of at least about 100 mm$^2$; 200 mm$^2$; 500 mm$^2$; 1,000 mm$^2$; 2,000 mm$^2$; 5,000 mm$^2$; 10,000 mm$^2$; 12,000 mm$^2$; 15,000 mm$^2$; 20,000 mm$^2$; 30,000 mm$^2$; 40,000 mm$^2$; 50,000 mm$^2$ or more. In some instances, the thickness of a device is from about 50 mm and about 2000 mm, from about 50 mm and about 1000 mm, from about 100 mm and about 1000 mm, from about 200 mm and about 1000 mm, or from about 250 mm and about 1000 mm. Non-limiting examples of device thickness include 275 mm, 375 mm, 525 mm, 625 mm, 675 mm, 725 mm, 775 mm and 925 mm. In some instances, the thickness of a device varies with diameter and depends on the composition of the substrate. For example, a device comprising materials other than silicon has a different thickness than a silicon device of the same diameter. Device thickness may be determined by the mechanical strength of the material used and the device must be thick enough to support its own weight without cracking during handling. In some instances, a structure comprises a plurality of devices described herein.

Surface Materials

Provided herein is a device comprising a surface, wherein the surface is modified to support polynucleotide synthesis at predetermined locations and with a resulting low error rate, a low dropout rate, a high yield, and a high oligo representation. In some embodiments, surfaces of a device for polynucleotide synthesis provided herein are fabricated from a variety of materials capable of modification to support a de novo polynucleotide synthesis reaction. In some cases, the devices are sufficiently conductive, e.g., are able to form uniform electric fields across all or a portion of the device. A device described herein may comprise a flexible material. Exemplary flexible materials include, without limitation, modified nylon, unmodified nylon, nitrocellulose, and polypropylene. A device described herein may comprise a rigid material. Exemplary rigid materials include, without limitation, glass, fuse silica, silicon, silicon dioxide, silicon nitride, plastics (for example, polytetrafluoroethylene, polypropylene, polystyrene, polycarbonate, and blends thereof, and metals (for example, gold, platinum). Device disclosed herein may be fabricated from a material comprising silicon, polystyrene, agarose, dextran, cellulosic polymers, polyacrylamides, polydimethylsiloxane (PDMS), glass, or any combination thereof. In some cases, a device disclosed herein is manufactured with a combination of materials listed herein or any other suitable material known in the art.

A listing of tensile strengths for exemplary materials described herein is provides as follows: nylon (70 MPa), nitrocellulose (1.5 MPa), polypropylene (40 MPa), silicon (268 MPa), polystyrene (40 MPa), agarose (1-10 MPa), polyacrylamide (1-10 MPa), polydimethylsiloxane (PDMS) (3.9-10.8 MPa). Solid supports described herein can have a tensile strength from 1 to 300, 1 to 40, 1 to 10, 1 to 5, or 3 to 11 MPa. Solid supports described herein can have a tensile strength of about 1, 1.5, 2, 3, 4, 5, 6, 7, 8, 9, 10, 11, 20, 25, 40, 50, 60, 70, 80, 90, 100, 150, 200, 250, 270, or more MPa. In some instances, a device described herein comprises a solid support for polynucleotide synthesis that is in the form of a flexible material capable of being stored in a continuous loop or reel, such as a tape or flexible sheet.

Young's modulus measures the resistance of a material to elastic (recoverable) deformation under load. A listing of Young's modulus for stiffness of exemplary materials described herein is provides as follows: nylon (3 GPa), nitrocellulose (1.5 GPa), polypropylene (2 GPa), silicon (150 GPa), polystyrene (3 GPa), agarose (1-10 GPa), polyacrylamide (1-10 GPa), polydimethylsiloxane (PDMS) (1-10 GPa). Solid supports described herein can have a Young's moduli from 1 to 500, 1 to 40, 1 to 10, 1 to 5, or 3 to 11 GPa. Solid supports described herein can have a Young's moduli of about 1, 1.5, 2, 3, 4, 5, 6, 7, 8, 9, 10, 11, 20, 25, 40, 50, 60, 70, 80, 90, 100, 150, 200, 250, 400, 500 GPa, or more. As the relationship between flexibility and stiffness are inverse to each other, a flexible material has a low Young's modulus and changes its shape considerably under load.

In some cases, a device disclosed herein comprises a silicon dioxide base and a surface layer of silicon oxide. Alternatively, the device may have a base of silicon oxide.

Surface of the device provided here may be textured, resulting in an increase overall surface area for polynucleotide synthesis. Device disclosed herein may comprise at least 5%, 10%, 25%, 50%, 80%, 90%, 95%, or 99% silicon. A device disclosed herein may be fabricated from a silicon on insulator (SOI) wafer.

Surface Architecture

Provided herein are devices comprising raised and/or lowered features. One benefit of having such features is an increase in surface area to support polynucleotide synthesis. In some instances, a device having raised and/or lowered features is referred to as a three-dimensional substrate. In some instances, a three-dimensional device comprises one or more channels. In some instances, one or more loci comprise a channel. In some instances, the channels are accessible to reagent deposition via a deposition device such as a polynucleotide synthesizer. In some instances, reagents and/or fluids collect in a larger well in fluid communication one or more channels. For example, a device comprises a plurality of channels corresponding to a plurality of loci with a cluster, and the plurality of channels are in fluid communication with one well of the cluster. In some methods, a library of polynucleotides is synthesized in a plurality of loci of a cluster.

In some instances, the structure is configured to allow for controlled flow and mass transfer paths for polynucleotide synthesis on a surface. In some instances, the configuration of a device allows for the controlled and even distribution of mass transfer paths, chemical exposure times, and/or wash efficacy during polynucleotide synthesis. In some instances, the configuration of a device allows for increased sweep efficiency, for example by providing sufficient volume for a growing a polynucleotide such that the excluded volume by the growing polynucleotide does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing the polynucleotide. In some instances, a three-dimensional structure allows for managed flow of fluid to allow for the rapid exchange of chemical exposure.

Provided herein are methods to synthesize an amount of DNA of 1 fM, 5 fM, 10 fM, 25 fM, 50 fM, 75 fM, 100 fM, 200 fM, 300 fM, 400 fM, 500 fM, 600 fM, 700 fM, 800 fM, 900 fM, 1 pM, 5 pM, 10 pM, 25 pM, 50 pM, 75 pM, 100 pM, 200 pM, 300 pM, 400 pM, 500 pM, 600 pM, 700 pM, 800 pM, 900 pM, or more. In some instances, a polynucleotide library may span the length of about 1%, 2%, 3%, 4%, 5%, 10%, 15%, 20%, 30%, 40%, 50%, 60%, 70%, 80%, 90%, 95%, or 100% of a gene. A gene may be varied up to about 1%, 2%, 3%, 4%, 5%, 10%, 15%, 20%, 30%, 40%, 50%, 60%, 70%, 80%, 85%, 90%, 95%, or 100%.

Non-identical polynucleotides may collectively encode a sequence for at least 1%, 2%, 3%, 4%, 5%, 10%, 15%, 20%, 30%, 40%, 50%, 60%, 70%, 80%, 85%, 90%, 95%, or 100% of a gene. In some instances, a polynucleotide may encode a sequence of 50%, 60%, 70%, 80%, 85%, 90%, 95%, or more of a gene. In some instances, a polynucleotide may encode a sequence of 80%, 85%, 90%, 95%, or more of a gene.

In some instances, segregation is achieved by physical structure. In some instances, segregation is achieved by differential functionalization of the surface generating active and passive regions for polynucleotide synthesis. Differential functionalization is also be achieved by alternating the hydrophobicity across the device surface, thereby creating water contact angle effects that cause beading or wetting of the deposited reagents. Employing larger structures can decrease splashing and cross-contamination of distinct polynucleotide synthesis locations with reagents of the neighboring spots. In some instances, a device, such as a polynucleotide synthesizer, is used to deposit reagents to distinct polynucleotide synthesis locations. Substrates having three-dimensional features are configured in a manner that allows for the synthesis of a large number of polynucleotides (e.g., more than about 10,000) with a low error rate (e.g., less than about 1:500, 1:1000, 1:1500, 1:2,000; 1:3,000; 1:5,000; or 1:10,000). In some instances, a device comprises features with a density of about or greater than about 1, 5, 10, 20, 30, 40, 50, 60, 70, 80, 100, 110, 120, 130, 140, 150, 160, 170, 180, 190, 200, 300, 400 or 500 features per $mm^2$.

A well of a device may have the same or different width, height, and/or volume as another well of the substrate. A channel of a device may have the same or different width, height, and/or volume as another channel of the substrate. In some instances, the width of a cluster is from about 0.05 mm to about 50 mm, from about 0.05 mm to about 10 mm, from about 0.05 mm and about 5 mm, from about 0.05 mm and about 4 mm, from about 0.05 mm and about 3 mm, from about 0.05 mm and about 2 mm, from about 0.05 mm and about 1 mm, from about 0.05 mm and about 0.5 mm, from about 0.05 mm and about 0.1 mm, from about 0.1 mm and 10 mm, from about 0.2 mm and 10 mm, from about 0.3 mm and about 10 mm, from about 0.4 mm and about 10 mm, from about 0.5 mm and 10 mm, from about 0.5 mm and about 5 mm, or from about 0.5 mm and about 2 mm. In some instances, the width of a well comprising a cluster is from about 0.05 mm to about 50 mm, from about 0.05 mm to about 10 mm, from about 0.05 mm and about 5 mm, from about 0.05 mm and about 4 mm, from about 0.05 mm and about 3 mm, from about 0.05 mm and about 2 mm, from about 0.05 mm and about 1 mm, from about 0.05 mm and about 0.5 mm, from about 0.05 mm and about 0.1 mm, from about 0.1 mm and 10 mm, from about 0.2 mm and 10 mm, from about 0.3 mm and about 10 mm, from about 0.4 mm and about 10 mm, from about 0.5 mm and 10 mm, from about 0.5 mm and about 5 mm, or from about 0.5 mm and about 2 mm. In some instances, the width of a cluster is less than or about 5 mm, 4 mm, 3 mm, 2 mm, 1 mm, 0.5 mm, 0.1 mm, 0.09 mm, 0.08 mm, 0.07 mm, 0.06 mm or 0.05 mm. In some instances, the width of a cluster is from about 1.0 and 1.3 mm. In some instances, the width of a cluster is about 1.150 mm. In some instances, the width of a well is less than or about 5 mm, 4 mm, 3 mm, 2 mm, 1 mm, 0.5 mm, 0.1 mm, 0.09 mm, 0.08 mm, 0.07 mm, 0.06 mm or 0.05 mm. In some instances, the width of a well is from about 1.0 and 1.3 mm. In some instances, the width of a well is about 1.150 mm. In some instances, the width of a cluster is about 0.08 mm. In some instances, the width of a well is about 0.08 mm. The width of a cluster may refer to clusters within a two-dimensional or three-dimensional substrate.

In some instances, the height of a well is from about 20 um to about 1000 um, from about 50 um to about 1000 um, from about 100 um to about 1000 um, from about 200 um to about 1000 um, from about 300 um to about 1000 um, from about 400 um to about 1000 um, or from about 500 um to about 1000 um. In some instances, the height of a well is less than about 1000 um, less than about 900 um, less than about 800 um, less than about 700 um, or less than about 600 um.

In some instances, a device comprises a plurality of channels corresponding to a plurality of loci within a cluster, wherein the height or depth of a channel is from about 5 um to about 500 um, from about 5 um to about 400 um, from about 5 um to about 300 um, from about 5 um to about 200 um, from about 5 um to about 100 um, from about 5 um to about 50 um, or from about 10 um to about 50 um. In some instances, the height of a channel is less than 100 um, less than 80 um, less than 60 um, less than 40 um or less than 20 um.

In some instances, the diameter of a channel, locus (e.g., in a substantially planar substrate) or both channel and locus (e.g., in a three-dimensional device wherein a locus corresponds to a channel) is from about 1 um to about 1000 um, from about 1 um to about 500 um, from about 1 um to about 200 um, from about 1 um to about 100 um, from about 5 um to about 100 um, or from about 10 um to about 100 um, for example, about 90 um, 80 um, 70 um, 60 um, 50 um, 40 um, 30 um, 20 um or 10 um. In some instances, the diameter of a channel, locus, or both channel and locus is less than about 100 um, 90 um, 80 um, 70 um, 60 um, 50 um, 40 um, 30 um, 20 um or 10 um. In some instances, the distance from the center of two adjacent channels, loci, or channels and loci is from about 1 um to about 500 um, from about 1 um to about 200 um, from about 1 um to about 100 um, from about 5 um to about 200 um, from about 5 um to about 100 um, from about 5 um to about 50 um, or from about 5 um to about 30 um, for example, about 20 um.

Surface Modifications

In various instances, surface modifications are employed for the chemical and/or physical alteration of a surface by an additive or subtractive process to change one or more chemical and/or physical properties of a device surface or a selected site or region of a device surface. For example, surface modifications include, without limitation, (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

In some instances, the addition of a chemical layer on top of a surface (referred to as adhesion promoter) facilitates structured patterning of loci on a surface of a substrate. Exemplary surfaces for application of adhesion promotion include, without limitation, glass, silicon, silicon dioxide and silicon nitride. In some instances, the adhesion promoter is a chemical with a high surface energy. In some instances, a second chemical layer is deposited on a surface of a substrate. In some instances, the second chemical layer has a low surface energy. In some instances, surface energy of a chemical layer coated on a surface supports localization of droplets on the surface. Depending on the patterning arrangement selected, the proximity of loci and/or area of fluid contact at the loci are alterable.

In some instances, a device surface, or resolved loci, onto which nucleic acids or other moieties are deposited, e.g., for polynucleotide synthesis, are smooth or substantially planar (e.g., two-dimensional) or have irregularities, such as raised or lowered features (e.g., three-dimensional features). In some instances, a device surface is modified with one or more different layers of compounds. Such modification layers of interest include, without limitation, inorganic and organic layers such as metals, metal oxides, polymers, small organic molecules and the like. Non-limiting polymeric layers include peptides, proteins, nucleic acids or mimetics thereof (e.g., peptide nucleic acids and the like), polysaccharides, phospholipids, polyurethanes, polyesters, polycarbonates, polyureas, polyamides, polyethyleneamines, polyarylene sulfides, polysiloxanes, polyimides, polyacetates, and any other suitable compounds described herein or otherwise known in the art. In some instances, polymers are heteropolymeric. In some instances, polymers are homopolymeric. In some instances, polymers comprise functional moieties or are conjugated.

In some instances, resolved loci of a device are functionalized with one or more moieties that increase and/or decrease surface energy. In some instances, a moiety is chemically inert. In some instances, a moiety is configured to support a desired chemical reaction, for example, one or more processes in a polynucleotide synthesis reaction. The surface energy, or hydrophobicity, of a surface is a factor for determining the affinity of a nucleotide to attach onto the surface. In some instances, a method for device functionalization may comprise: (a) providing a device having a surface that comprises silicon dioxide; and (b) silanizing the surface using, a suitable silanizing agent described herein or otherwise known in the art, for example, an organofunctional alkoxysilane molecule.

In some instances, the organofunctional alkoxysilane molecule comprises dimethylchloro-octodecyl-silane, methyldichloro-octodecyl-silane, trichloro-octodecyl-silane, trimethyl-octodecyl-silane, triethyl-octodecyl-silane, or any combination thereof. In some instances, a device surface comprises functionalized with polyethylene/polypropylene (functionalized by gamma irradiation or chromic acid oxidation, and reduction to hydroxyalkyl surface), highly cross-linked polystyrene-divinylbenzene (derivatized by chloromethylation, and aminated to benzylamine functional surface), nylon (the terminal aminohexyl groups are directly reactive), or etched with reduced polytetrafluoroethylene. Other methods and functionalizing agents are described in U.S. Pat. No. 5,474,796, which is herein incorporated by reference in its entirety.

In some instances, a device surface is functionalized by contact with a derivatizing composition that contains a mixture of silanes, under reaction conditions effective to couple the silanes to the device surface, typically via reactive hydrophilic moieties present on the device surface. Silanization generally covers a surface through self-assembly with organofunctional alkoxysilane molecules.

A variety of siloxane functionalizing reagents can further be used as currently known in the art, e.g., for lowering or increasing surface energy. The organofunctional alkoxysilanes can be classified according to their organic functions.

Provided herein are devices that may contain patterning of agents capable of coupling to a nucleoside. In some instances, a device may be coated with an active agent. In some instances, a device may be coated with a passive agent. Exemplary active agents for inclusion in coating materials described herein includes, without limitation, N-(3-triethoxysilylpropyl)-4-hydroxybutyramide (HAPS), 11-acetoxyundecyltriethoxysilane, n-decyltriethoxysilane, (3-aminopropyl)trimethoxysilane, (3-aminopropyl)triethoxysilane, 3-glycidoxypropyltrimethoxysilane (GOPS), 3-iodo-propyltrimethoxysilane, butyl-aldehydr-trimethoxysilane, dimeric secondary aminoalkyl siloxanes, (3-aminopropyl)-diethoxymethylsilane, (3-aminopropyl)-dimethyl-ethoxysilane, and (3-aminopropyl)-trimethoxysilane, (3-glycidoxypropyl)-dimethyl-ethoxysilane, glycidoxy-trimethoxysilane, (3-mercaptopropyl)-trimethoxysilane, 3-4 epoxycyclohexyl-ethyl-trimethoxysilane, and (3-mercaptopropyl)-methyl-dimethoxysilane, allyl trichlorochlorosilane, 7-oct-1-enyl trichlorochlorosilane, or bis (3-trimethoxysilylpropyl) amine.

Exemplary passive agents for inclusion in a coating material described herein includes, without limitation, perfluorooctyltrichlorosilane; tridecafluoro-1,1,2,2-tetrahydrooctyl)trichlorosilane; 1H, 1H, 2H, 2H-fluorooctyltriethoxysilane (FOS); trichloro(1H, 1H, 2H, 2H-perfluorooctyl)silane; tert-butyl-[5-fluoro-4-(4,4,5,5-tetramethyl-1,3,2-dioxaborolan-2-yl)indol-1-yl]-dimethyl-silane; CYTOP™; Fluorinert™; perfluorooctyltrichlorosilane (PFOTCS); perfluorooctyldimethylchlorosilane (PFODCS); perfluorodecyltriethoxysilane (PFDTES); pentafluorophenyl-dimethylpropylchloro-silane (PFPTES); perfluorooctyl-triethoxysilane; perfluorooctyltrimethoxysilane; octylchlorosilane; dimethylchloro-octodecyl-silane; methyldichloro-octodecyl-silane; trichloro-octodecyl-silane; trimethyl-octodecyl-silane; triethyl-octodecyl-silane; or octadecyltrichlorosilane.

In some instances, a functionalization agent comprises a hydrocarbon silane such as octadecyltrichlorosilane. In some instances, the functionalizing agent comprises 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide.

Polynucleotide Synthesis

Methods of the current disclosure for polynucleotide synthesis may include processes involving phosphoramidite chemistry. In some instances, polynucleotide synthesis comprises coupling a base with phosphoramidite. Polynucleotide synthesis may comprise coupling a base by deposition of phosphoramidite under coupling conditions, wherein the same base is optionally deposited with phosphoramidite more than once, i.e., double coupling. Polynucleotide synthesis may comprise capping of unreacted sites. In some instances, capping is optional. Polynucleotide synthesis may also comprise oxidation or an oxidation step or oxidation steps. Polynucleotide synthesis may comprise deblocking, detritylation, and sulfurization. In some instances, polynucleotide synthesis comprises either oxidation or sulfurization. In some instances, between one or each step during a polynucleotide synthesis reaction, the device is washed, for example, using tetrazole or acetonitrile. Time frames for any one step in a phosphoramidite synthesis method may be less than about 2 minutes, 1 minute, 50 seconds, 40 seconds, 30 seconds, 20 seconds and 10 seconds.

Polynucleotide synthesis using a phosphoramidite method may comprise a subsequent addition of a phosphoramidite building block (e.g., nucleoside phosphoramidite) to a growing polynucleotide chain for the formation of a phosphite triester linkage. Phosphoramidite polynucleotide synthesis proceeds in the 3' to 5' direction. Phosphoramidite polynucleotide synthesis allows for the controlled addition of one nucleotide to a growing nucleic acid chain per synthesis cycle. In some instances, each synthesis cycle comprises a coupling step. Phosphoramidite coupling involves the formation of a phosphite triester linkage between an activated nucleoside phosphoramidite and a nucleoside bound to the substrate, for example, via a linker. In some instances, the nucleoside phosphoramidite is provided to the device activated. In some instances, the nucleoside phosphoramidite is provided to the device with an activator. In some instances, nucleoside phosphoramidites are provided to the device in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition of a nucleoside phosphoramidite, the device is optionally washed. In some instances, the coupling step is repeated one or more additional times, optionally with a wash step between nucleoside phosphoramidite additions to the substrate. In some instances, a polynucleotide synthesis method used herein comprises 1, 2, 3 or more sequential coupling steps. Prior to coupling, in many cases, the nucleoside bound to the device is de-protected by removal of a protecting group, where the protecting group functions to prevent polymerization. A common protecting group is 4,4'-dimethoxytrityl (DMT).

Following coupling, phosphoramidite polynucleotide synthesis methods optionally comprise a capping step. In a capping step, the growing polynucleotide is treated with a capping agent. A capping step is useful to block unreacted substrate-bound 5'-OH groups after coupling from further chain elongation, preventing the formation of polynucleotides with internal base deletions. Further, phosphoramidites activated with 1H-tetrazole may react, to a small extent, with the O6 position of guanosine. Without being bound by theory, upon oxidation with $I_2$/water, this side product, possibly via O6-N7 migration, may undergo depurination. The apurinic sites may end up being cleaved in the course of the final deprotection of the polynucleotide thus reducing the yield of the full-length product. The O6 modifications may be removed by treatment with the capping reagent prior to oxidation with $I_2$/water. In some instances, inclusion of a capping step during polynucleotide synthesis decreases the error rate as compared to synthesis without capping. As an example, the capping step comprises treating the substrate-bound polynucleotide with a mixture of acetic anhydride and 1-methylimidazole. Following a capping step, the device is optionally washed.

In some instances, following addition of a nucleoside phosphoramidite, and optionally after capping and one or more wash steps, the device bound growing nucleic acid is oxidized. The oxidation step comprises the phosphite triester is oxidized into a tetracoordinated phosphate triester, a protected precursor of the naturally occurring phosphate diester internucleoside linkage. In some instances, oxidation of the growing polynucleotide is achieved by treatment with iodine and water, optionally in the presence of a weak base (e.g., pyridine, lutidine, collidine). Oxidation may be carried out under anhydrous conditions using, e.g. tert-Butyl hydroperoxide or (1S)-(+)-(10-camphorsulfonyl)-oxaziridine (CSO). In some methods, a capping step is performed following oxidation. A second capping step allows for device drying, as residual water from oxidation that may persist can inhibit subsequent coupling. Following oxidation, the device and growing polynucleotide is optionally washed. In some instances, the step of oxidation is substituted with a sulfurization step to obtain polynucleotide phosphorothioates, wherein any capping steps can be performed after the sulfurization. Many reagents are capable of the efficient sulfur transfer, including but not limited to 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

In order for a subsequent cycle of nucleoside incorporation to occur through coupling, the protected 5' end of the device bound growing polynucleotide is removed so that the primary hydroxyl group is reactive with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound polynucleotide and thus reduces the yield of the desired full-length product. Methods and compositions of the disclosure described herein provide for controlled deblocking conditions limiting undesired depurination reactions. In some instances, the device bound polynucleotide is washed after deblocking. In some instances, efficient washing after deblocking contributes to synthesized polynucleotides having a low error rate.

Methods for the synthesis of polynucleotides typically involve an iterating sequence of the following steps: application of a protected monomer to an actively functionalized surface (e.g., locus) to link with either the activated surface, a linker or with a previously deprotected monomer; deprotection of the applied monomer so that it is reactive with a subsequently applied protected monomer; and application of another protected monomer for linking. One or more intermediate steps include oxidation or sulfurization. In some instances, one or more wash steps precede or follow one or all of the steps.

Methods for phosphoramidite-based polynucleotide synthesis comprise a series of chemical steps. In some instances, one or more steps of a synthesis method involve reagent cycling, where one or more steps of the method comprise application to the device of a reagent useful for the step. For example, reagents are cycled by a series of liquid deposition and vacuum drying steps. For substrates comprising three-dimensional features such as wells, microwells, channels and the like, reagents are optionally passed through one or more regions of the device via the wells and/or channels.

Methods and systems described herein relate to polynucleotide synthesis devices for the synthesis of polynucleotides. The synthesis may be in parallel. For example at least or about at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 100, 150, 200, 250, 300, 350, 400, 450, 500, 550, 600, 650, 700, 750, 800, 850, 900, 1000, 10000, 50000, 75000, 100000 or more polynucleotides can be synthesized in parallel. The total number polynucleotides that may be synthesized in parallel may be from 2-100000, 3-50000, 4-10000, 5-1000, 6-900, 7-850, 8-800, 9-750, 10-700, 11-650, 12-600, 13-550, 14-500, 15-450, 16-400, 17-350, 18-300, 19-250, 20-200, 21-150, 22-100, 23-50, 24-45, 25-40, 30-35. Those of skill in the art appreciate that the total number of polynucleotides synthesized in parallel may fall within any range bound by any of these values, for example 25-100. The total number of polynucleotides synthesized in parallel may fall within any range defined by any of the values serving as endpoints of the range. Total molar mass of polynucleotides synthesized within the device or the molar mass of each of the polynucleotides may be at least or at least about 10, 20, 30, 40, 50, 100, 250, 500, 750, 1000, 2000, 3000, 4000, 5000, 6000, 7000, 8000, 9000, 10000, 25000, 50000, 75000, 100000 picomoles, or more. The length of each of the polynucleotides or average length of the polynucleotides within the device may be at least or about at least 10, 15, 20, 25, 30, 35, 40, 45, 50, 100, 150, 200, 300, 400, 500 nucleotides, or more. The length of each of the polynucleotides or average length of the polynucleotides within the device may be at most or about at most 500, 400, 300, 200, 150, 100, 50, 45, 35, 30, 25, 20, 19, 18, 17, 16, 15, 14, 13, 12, 11, 10 nucleotides, or less. The length of each of the polynucleotides or average length of the polynucleotides within the device may fall from 10-500, 9-400, 11-300, 12-200, 13-150, 14-100, 15-50, 16-45, 17-40, 18-35, 19-25. Those of skill in the art appreciate that the length of each of the polynucleotides or average length of the polynucleotides within the device may fall within any range bound by any of these values, for example 100-300. The length of each of the polynucleotides or average length of the polynucleotides within the device may fall within any range defined by any of the values serving as endpoints of the range.

Methods for polynucleotide synthesis on a surface provided herein allow for synthesis at a fast rate. As an example, at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200 nucleotides per hour, or more are synthesized. Nucleotides include adenine, guanine, thymine, cytosine, uridine building blocks, or analogs/modified versions thereof. In some instances, libraries of polynucleotides are synthesized in parallel on substrate. For example, a device comprising about or at least about 100; 1,000; 10,000; 30,000; 75,000; 100,000; 1,000,000; 2,000,000; 3,000,000; 4,000,000; or 5,000,000 resolved loci is able to support the synthesis of at least the same number of distinct polynucleotides, wherein polynucleotide encoding a distinct sequence is synthesized on a resolved locus. In some instances, a library of polynucleotides are synthesized on a device with low error rates described herein in less than about three months, two months, one month, three weeks, 15, 14, 13, 12, 11, 10, 9, 8, 7, 6, 5, 4, 3, 2 days, 24 hours or less. In some instances, larger nucleic acids assembled from a polynucleotide library synthesized with low error rate using the substrates and methods described herein are prepared in less than about three months, two months, one month, three weeks, 15, 14, 13, 12, 11, 10, 9, 8, 7, 6, 5, 4, 3, 2 days, 24 hours or less.

In some instances, methods described herein provide for generation of a library of polynucleotides comprising variant polynucleotides differing at a plurality of codon sites. In some instances, a polynucleotide may have 1 site, 2 sites, 3 sites, 4 sites, 5 sites, 6 sites, 7 sites, 8 sites, 9 sites, 10 sites, 11 sites, 12 sites, 13 sites, 14 sites, 15 sites, 16 sites, 17 sites 18 sites, 19 sites, 20 sites, 30 sites, 40 sites, 50 sites, or more of variant codon sites.

In some instances, the one or more sites of variant codon sites may be adjacent. In some instances, the one or more sites of variant codon sites may be not be adjacent and separated by 1, 2, 3, 4, 5, 6, 7, 8, 9, 10, or more codons.

In some instances, a polynucleotide may comprise multiple sites of variant codon sites, wherein all the variant codon sites are adjacent to one another, forming a stretch of variant codon sites. In some instances, a polynucleotide may comprise multiple sites of variant codon sites, wherein none the variant codon sites are adjacent to one another. In some instances, a polynucleotide may comprise multiple sites of variant codon sites, wherein some the variant codon sites are adjacent to one another, forming a stretch of variant codon sites, and some of the variant codon sites are not adjacent to one another.

Figure 11:
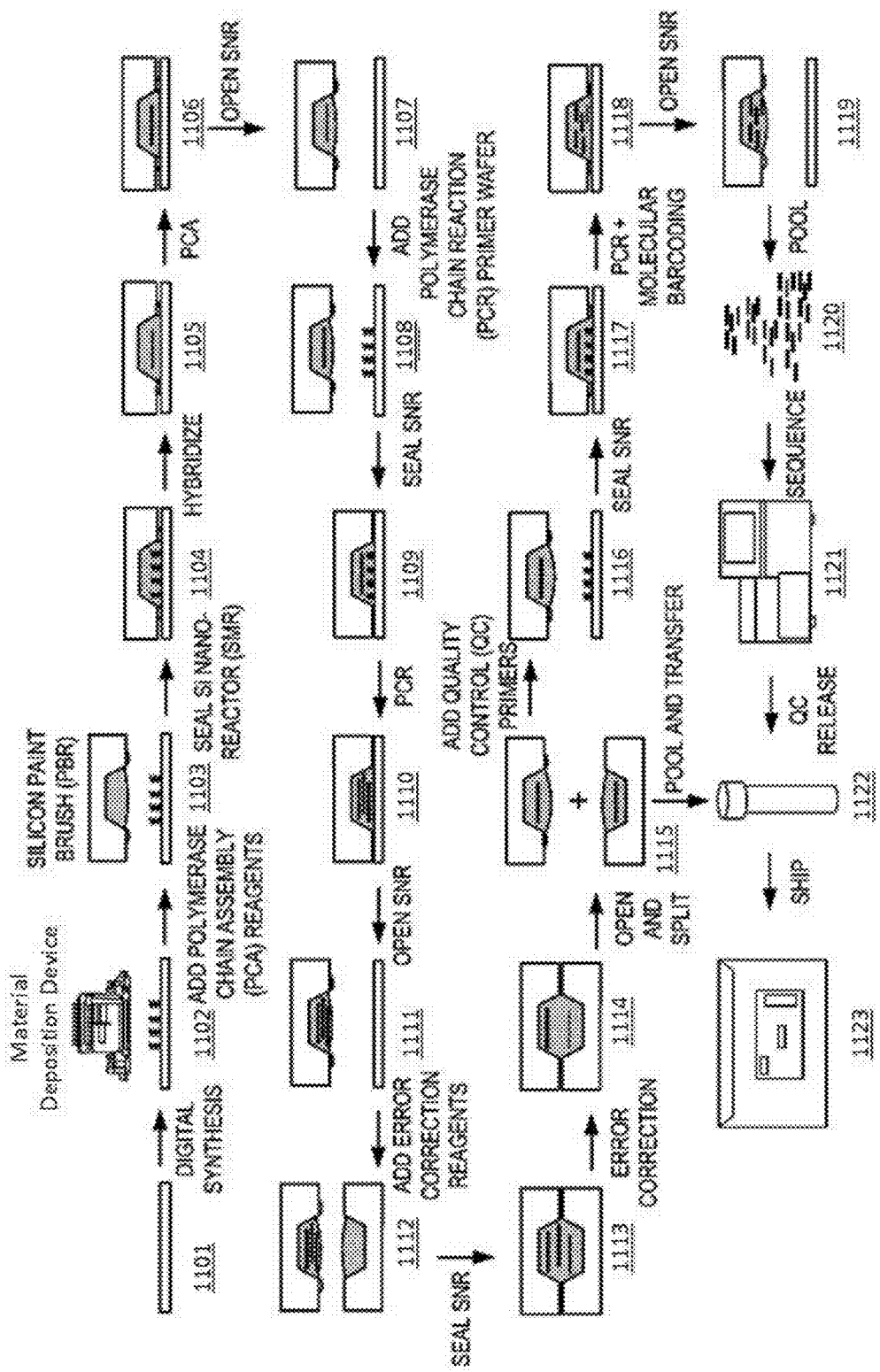
FIG. 11 presents a diagram of steps demonstrating an exemplary process workflow for gene synthesis as disclosed herein.

Referring to the Figures, FIG. 11 illustrates an exemplary process workflow for synthesis of nucleic acids (e.g., genes) from shorter polynucleotides. The workflow is divided generally into phases: (1) de novo synthesis of a single stranded polynucleotide library, (2) joining polynucleotides to form larger fragments, (3) error correction, (4) quality control, and (5) shipment. Prior to de novo synthesis, an intended nucleic acid sequence or group of nucleic acid sequences is preselected. For example, a group of genes is preselected for generation.

Once large polynucleotides for generation are selected, a predetermined library of polynucleotides is designed for de novo synthesis. Various suitable methods are known for generating high density polynucleotide arrays. In the workflow example, a device surface layer 1101 is provided. In the example, chemistry of the surface is altered in order to improve the polynucleotide synthesis process. Areas of low surface energy are generated to repel liquid while areas of high surface energy are generated to attract liquids. The surface itself may be in the form of a planar surface or contain variations in shape, such as protrusions or microwells which increase surface area. In the workflow example, high surface energy molecules selected serve a dual function of supporting DNA chemistry, as disclosed in International Patent Application Publication WO/2015/021080, which is herein incorporated by reference in its entirety.

In situ preparation of polynucleotide arrays is generated on a solid support and utilizes single nucleotide extension process to extend multiple oligomers in parallel. A material deposition device, such as a polynucleotide synthesizer, is designed to release reagents in a step wise fashion such that multiple polynucleotides extend, in parallel, one residue at a time to generate oligomers with a predetermined nucleic acid sequence 1102. In some instances, polynucleotides are cleaved from the surface at this stage. Cleavage includes gas cleavage, e.g., with ammonia or methylamine.

The generated polynucleotide libraries are placed in a reaction chamber. In this exemplary workflow, the reaction chamber (also referred to as "nanoreactor") is a silicon coated well, containing PCR reagents and lowered onto the polynucleotide library 1103. Prior to or after the sealing 1104 of the polynucleotides, a reagent is added to release the polynucleotides from the substrate. In the exemplary workflow, the polynucleotides are released subsequent to sealing of the nanoreactor 1105. Once released, fragments of single stranded polynucleotides hybridize in order to span an entire long range sequence of DNA. Partial hybridization 1105 is possible because each synthesized polynucleotide is designed to have a small portion overlapping with at least one other polynucleotide in the population.

After hybridization, a PCR reaction is commenced. During the polymerase cycles, the polynucleotides anneal to complementary fragments and gaps are filled in by a polymerase. Each cycle increases the length of various fragments randomly depending on which polynucleotides find each other. Complementarity amongst the fragments allows for forming a complete large span of double stranded DNA 1106.

After PCR is complete, the nanoreactor is separated from the device 1107 and positioned for interaction with a device having primers for PCR 1108. After sealing, the nanoreactor is subject to PCR 1109 and the larger nucleic acids are amplified. After PCR 1110, the nanochamber is opened 1111, error correction reagents are added 1112, the chamber is sealed 1113 and an error correction reaction occurs to remove mismatched base pairs and/or strands with poor complementarity from the double stranded PCR amplification products 1114. The nanoreactor is opened and separated 1115. Error corrected product is next subject to additional processing steps, such as PCR and molecular bar coding, and then packaged 1122 for shipment 1123.

In some instances, quality control measures are taken. After error correction, quality control steps include for example interaction with a wafer having sequencing primers for amplification of the error corrected product 1116, sealing the wafer to a chamber containing error corrected amplification product 1117, and performing an additional round of amplification 1118. The nanoreactor is opened 1119 and the products are pooled 1120 and sequenced 1121. After an acceptable quality control determination is made, the packaged product 1122 is approved for shipment 1123.

In some instances, a nucleic acid generate by a workflow such as that in FIG. 11 is subject to mutagenesis using overlapping primers disclosed herein. In some instances, a library of primers are generated by in situ preparation on a solid support and utilize single nucleotide extension process to extend multiple oligomers in parallel. A deposition device, such as a polynucleotide synthesizer, is designed to release reagents in a step wise fashion such that multiple polynucleotides extend, in parallel, one residue at a time to generate oligomers with a predetermined nucleic acid sequence 1102.

Large Polynucleotide Libraries Having Low Error Rates

Average error rates for polynucleotides synthesized within a library using the systems and methods provided may be less than 1 in 1000, less than 1 in 1250, less than 1 in 1500, less than 1 in 2000, less than 1 in 3000 or less often. In some instances, average error rates for polynucleotides synthesized within a library using the systems and methods provided are less than 1/500, 1/600, 1/700, 1/800, 1/900, 1/1000, 1/1100, 1/1200, 1/1250, 1/1300, 1/1400, 1/1500, 1/1600, 1/1700, 1/1800, 1/1900, 1/2000, 1/3000, or less. In some instances, average error rates for polynucleotides synthesized within a library using the systems and methods provided are less than 1/1000.

In some instances, aggregate error rates for polynucleotides synthesized within a library using the systems and methods provided are less than 1/500, 1/600, 1/700, 1/800, 1/900, 1/1000, 1/1100, 1/1200, 1/1250, 1/1300, 1/1400, 1/1500, 1/1600, 1/1700, 1/1800, 1/1900, 1/2000, 1/3000, or less compared to the predetermined sequences. In some instances, aggregate error rates for polynucleotides synthesized within a library using the systems and methods provided are less than 1/500, 1/600, 1/700, 1/800, 1/900, or 1/1000. In some instances, aggregate error rates for polynucleotides synthesized within a library using the systems and methods provided are less than 1/1000.

In some instances, an error correction enzyme may be used for polynucleotides synthesized within a library using the systems and methods provided can use. In some instances, aggregate error rates for polynucleotides with error correction can be less than 1/500, 1/600, 1/700, 1/800, 1/900, 1/1000, 1/1100, 1/1200, 1/1300, 1/1400, 1/1500, 1/1600, 1/1700, 1/1800, 1/1900, 1/2000, 1/3000, or less compared to the predetermined sequences. In some instances, aggregate error rates with error correction for polynucleotides synthesized within a library using the systems and methods provided can be less than 1/500, 1/600, 1/700, 1/800, 1/900, or 1/1000. In some instances, aggregate error rates with error correction for polynucleotides synthesized within a library using the systems and methods provided can be less than 1/1000.

Error rate may limit the value of gene synthesis for the production of libraries of gene variants. With an error rate of 1/300, about 0.7% of the clones in a 1500 base pair gene will be correct. As most of the errors from polynucleotide synthesis result in frame-shift mutations, over 99% of the clones in such a library will not produce a full-length protein. Reducing the error rate by 75% would increase the fraction of clones that are correct by a factor of 40. The methods and compositions of the disclosure allow for fast de novo synthesis of large polynucleotide and gene libraries with error rates that are lower than commonly observed gene synthesis methods both due to the improved quality of synthesis and the applicability of error correction methods that are enabled in a massively parallel and time-efficient manner. Accordingly, libraries may be synthesized with base insertion, deletion, substitution, or total error rates that are under 1/300, 1/400, 1/500, 1/600, 1/700, 1/800, 1/900, 1/1000, 1/1250, 1/1500, 1/2000, 1/2500, 1/3000, 1/4000, 1/5000, 1/6000, 1/7000, 1/8000, 1/9000, 1/10000, 1/12000, 1/15000, 1/20000, 1/25000, 1/30000, 1/40000, 1/50000, 1/60000, 1/70000, 1/80000, 1/90000, 1/100000, 1/125000, 1/150000, 1/200000, 1/300000, 1/400000, 1/500000, 1/600000, 1/700000, 1/800000, 1/900000, 1/1000000, or less, across the library, or across more than 80%, 85%, 90%, 93%, 95%, 96%, 97%, 98%, 99%, 99.5%, 99.8%, 99.9%, 99.95%, 99.98%, 99.99%, or more of the library. The methods and compositions of the disclosure further relate to large synthetic polynucleotide and gene libraries with low error rates associated with at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of the polynucleotides or genes in at least a subset of the library to relate to error free sequences in comparison to a predetermined/preselected sequence. In some instances, at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of the polynucleotides or genes in an isolated volume within the library have the same sequence. In some instances, at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of any polynucleotides or genes related with more than 95%, 96%, 97%, 98%, 99%, 99.5%, 99.6%, 99.7%, 99.8%, 99.9% or more similarity or identity have the same sequence. In some instances, the error rate related to a specified locus on a polynucleotide or gene is optimized. Thus, a given locus or a plurality of selected loci of one or more polynucleotides or genes as part of a large library may each have an error rate that is less than 1/300, 1/400, 1/500, 1/600, 1/700, 1/800, 1/900, 1/1000, 1/1250, 1/1500, 1/2000, 1/2500, 1/3000, 1/4000, 1/5000, 1/6000, 1/7000, 1/8000, 1/9000, 1/10000, 1/12000, 1/15000, 1/20000, 1/25000, 1/30000, 1/40000, 1/50000, 1/60000, 1/70000, 1/80000, 1/90000, 1/100000, 1/125000, 1/150000, 1/200000, 1/300000, 1/400000, 1/500000, 1/600000, 1/700000, 1/800000, 1/900000, 1/1000000, or less. In various instances, such error optimized loci may comprise at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 1500, 2000, 2500, 3000, 4000, 5000, 6000, 7000, 8000, 9000, 10000, 30000, 50000, 75000, 100000, 500000, 1000000, 2000000, 3000000 or more loci. The error optimized loci may be distributed to at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 1500, 2000, 2500, 3000, 4000, 5000, 6000, 7000, 8000, 9000, 10000, 30000, 75000, 100000, 500000, 1000000, 2000000, 3000000 or more polynucleotides or genes.

The error rates can be achieved with or without error correction. The error rates can be achieved across the library, or across more than 80%, 85%, 90%, 93%, 95%, 96%, 97%, 98%, 99%, 99.5%, 99.8%, 99.9%, 99.95%, 99.98%, 99.99%, or more of the library.

Computer Systems

Any of the systems described herein, may be operably linked to a computer and may be automated through a computer either locally or remotely. In various instances, the methods and systems of the disclosure may further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the disclosure. The computer systems may be programmed to interface between the user specified base sequence and the position of a material deposition device to deliver the correct reagents to specified regions of the substrate.

Figure 12:
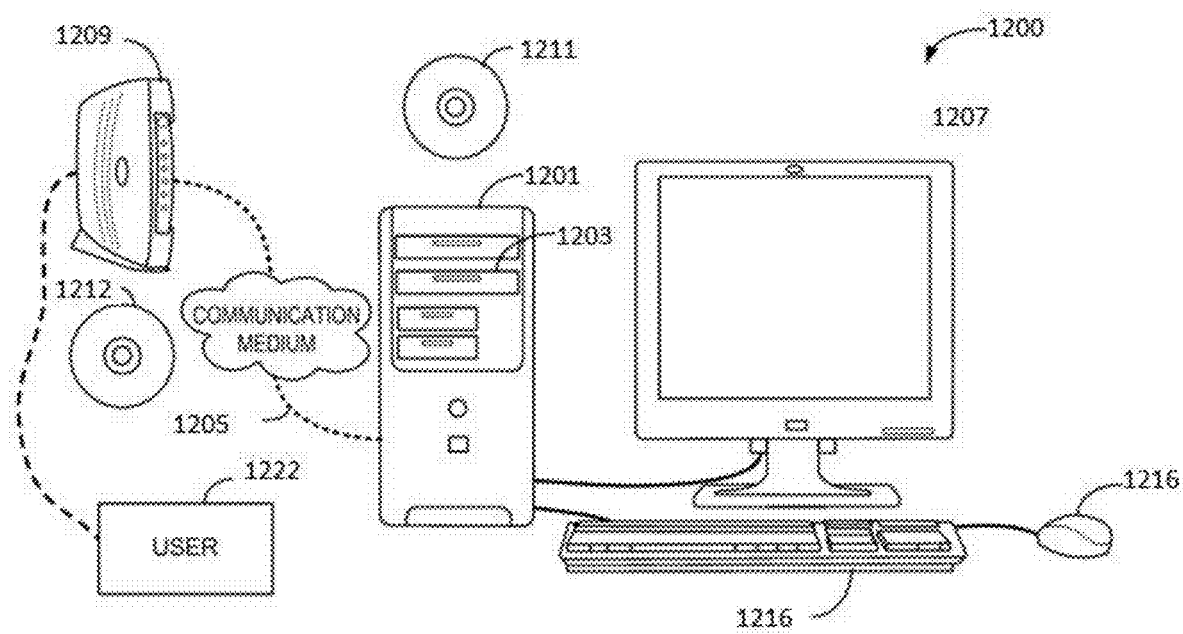
FIG. 12 illustrates a computer system.

The computer system 1200 illustrated in FIG. 12 may be understood as a logical apparatus that can read instructions from media 1211 and/or a network port 1205, which can optionally be connected to server 1209 having fixed media 1212. The system, such as shown in FIG. 12 can include a CPU 1201, disk drives 1203, optional input devices such as keyboard 1215 and/or mouse 1216 and optional monitor 1207. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 1222 as illustrated in FIG. 12.

Figure 13:
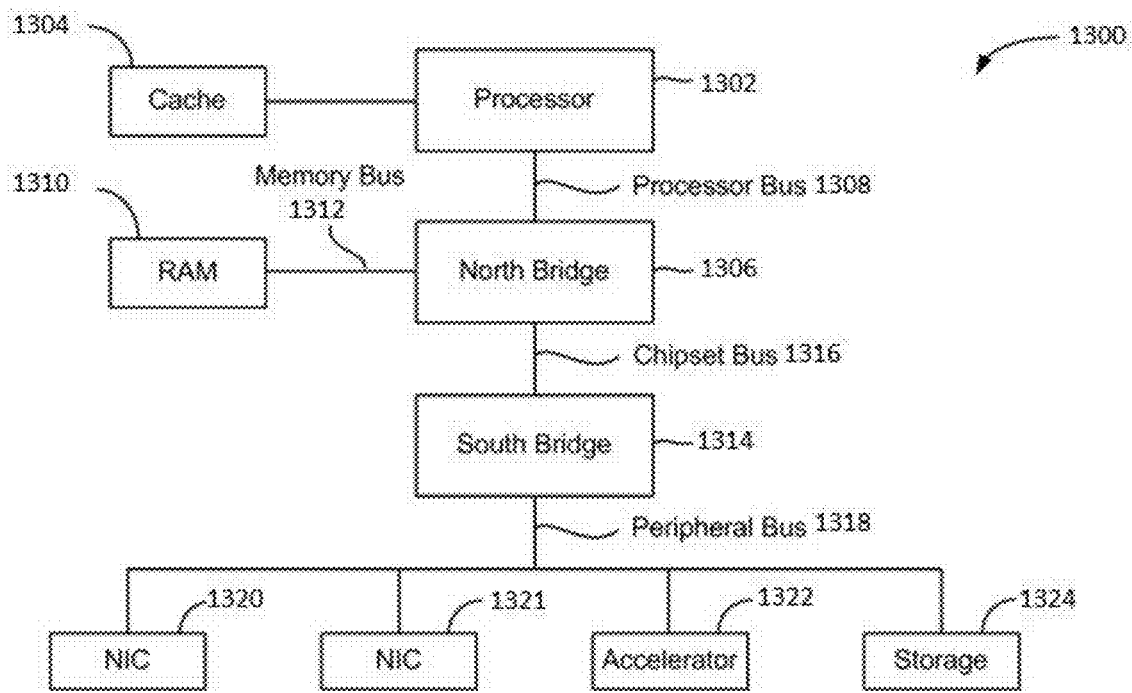
FIG. 13 is a block diagram illustrating an architecture of a computer system.

FIG. 13 is a block diagram illustrating a first example architecture of a computer system 1300 that can be used in connection with example instances of the present disclosure. As depicted in FIG. 13, the example computer system can include a processor 1302 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices.

As illustrated in FIG. 13, a high speed cache 1304 can be connected to, or incorporated in, the processor 1302 to provide a high speed memory for instructions or data that have been recently, or are frequently, used by processor 1302. The processor 1302 is connected to a north bridge 1306 by a processor bus 1308. The north bridge 1306 is connected to random access memory (RAM) 1310 by a memory bus 1312 and manages access to the RAM 1310 by the processor 1302. The north bridge 1306 is also connected to a south bridge 1314 by a chipset bus 1316. The south bridge 1314 is, in turn, connected to a peripheral bus 1318. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 1318. In some alternative architectures, the functionality of the north bridge can be incorporated into the processor instead of using a separate north bridge chip. In some instances, system 1300 can include an accelerator card 1322 attached to the peripheral bus 1318. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 1324 and can be loaded into RAM 1310 and/or cache 1304 for use by the processor. The system 1300 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example instances of the present disclosure. In this example, system 1300 also includes network interface cards (NICs) 1320 and 1321 connected to the peripheral bus for providing network interfaces to external storage, such as Network Attached Storage (NAS) and other computer systems that can be used for distributed parallel processing.

Figure 14:
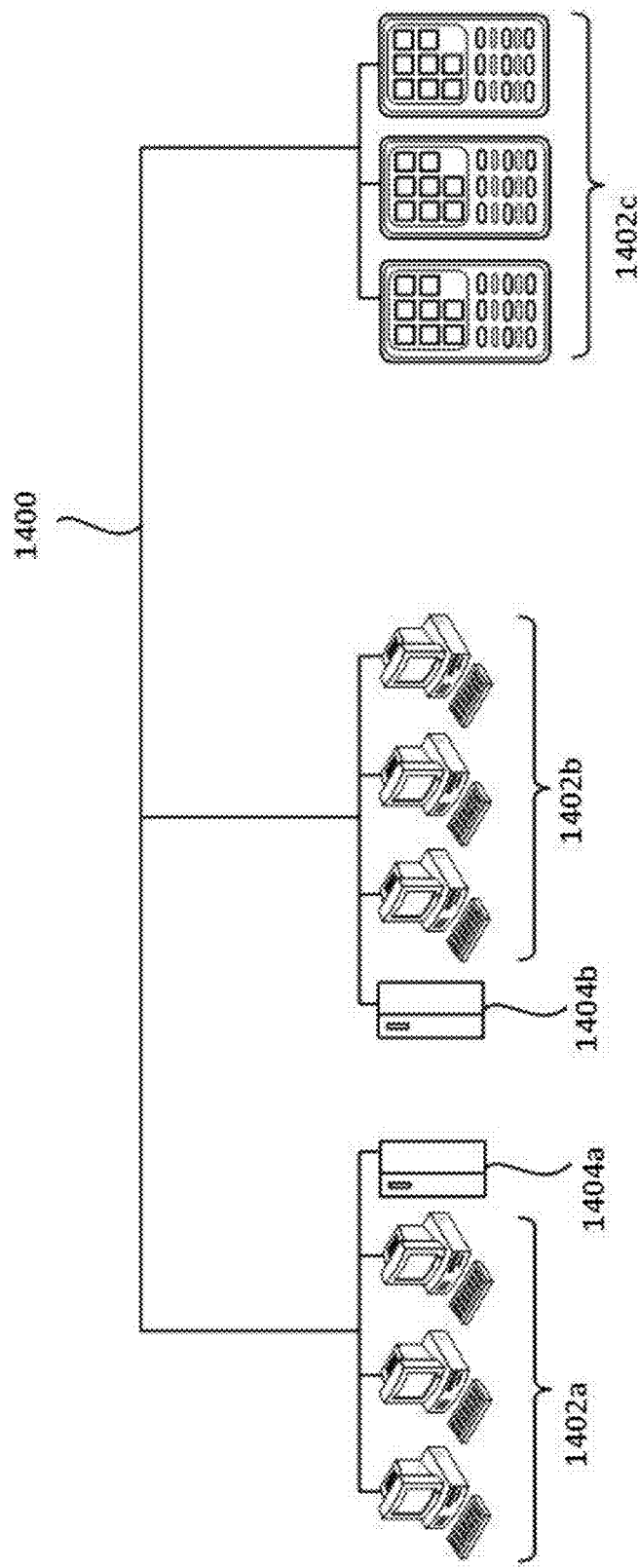
FIG. 14 is a diagram demonstrating a network configured to incorporate a plurality of computer systems, a plurality of cell phones and personal data assistants, and Network Attached Storage (NAS).

FIG. 14 is a diagram showing a network 1400 with a plurality of computer systems 1402a, and 1402b, a plurality of cell phones and personal data assistants 1402c, and Network Attached Storage (NAS) 1404a, and 1404b. In example instances, systems 1402a, 1402b, and 1402c can manage data storage and optimize data access for data stored in Network Attached Storage (NAS) 1404a and 1404b. A mathematical model can be used for the data and be evaluated using distributed parallel processing across computer systems 1402a, and 1402b, and cell phone and personal data assistant systems 1402c. Computer systems 1402a, and 1402b, and cell phone and personal data assistant systems 1402c can also provide parallel processing for adaptive data restructuring of the data stored in Network Attached Storage (NAS) 1404a and 1404b. FIG. 14 illustrates an example only, and a wide variety of other computer architectures and systems can be used in conjunction with the various instances of the present disclosure. For example, a blade server can be used to provide parallel processing. Processor blades can be connected through a back plane to provide parallel processing. Storage can also be connected to the back plane or as Network Attached Storage (NAS) through a separate network interface. In some example instances, processors can maintain separate memory spaces and transmit data through network interfaces, back plane or other connectors for parallel processing by other processors. In other instances, some or all of the processors can use a shared virtual address memory space.

Figure 15:
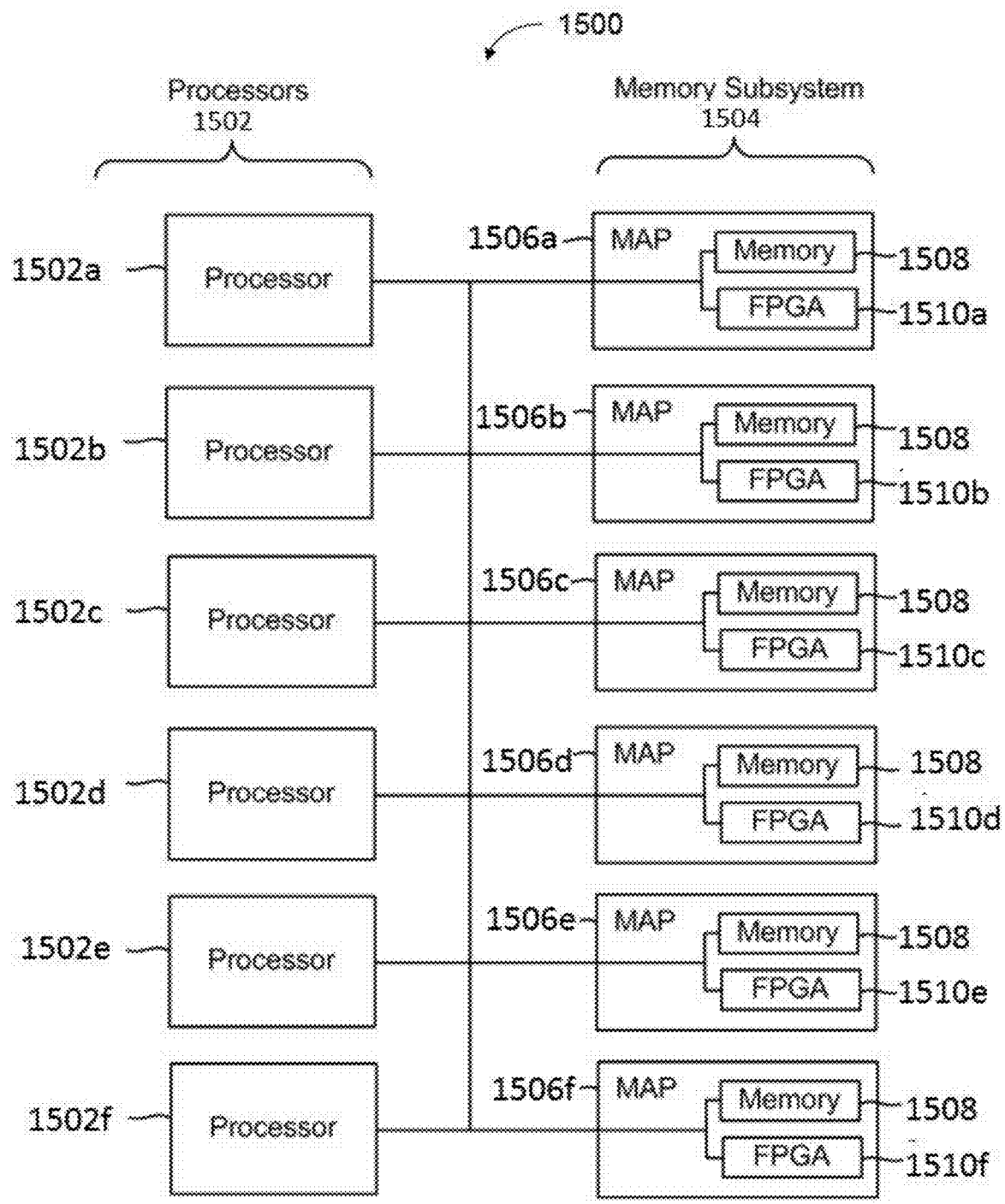
FIG. 15 is a block diagram of a multiprocessor computer system using a shared virtual address memory space.

FIG. 15 is a block diagram of a multiprocessor computer system 1500 using a shared virtual address memory space in accordance with an example instance. The system includes a plurality of processors 1502a-f that can access a shared memory subsystem 1504. The system incorporates a plurality of programmable hardware memory algorithm processors (MAPs) 1506a-f in the memory subsystem 1504. Each MAP 1506a-f can comprise a memory 1508a-f and one or more field programmable gate arrays (FPGAs) 1510a-f. The MAP provides a configurable functional unit and particular algorithms or portions of algorithms can be provided to the FPGAs 1510a-f for processing in close coordination with a respective processor. For example, the MAPs can be used to evaluate algebraic expressions regarding the data model and to perform adaptive data restructuring in example instances. In this example, each MAP is globally accessible by all of the processors for these purposes. In one configuration, each MAP can use Direct Memory Access (DMA) to access an associated memory 1508a-f, allowing it to execute tasks independently of, and asynchronously from the respective microprocessor 1502a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example instances, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example instances, including random access memory, hard drives, flash memory, tape drives, disk arrays, Network Attached Storage (NAS) and other local or distributed data storage devices and systems.

In example instances, the computer system can be implemented using software modules executing on any of the above or other computer architectures and systems. In other instances, the functions of the system can be implemented partially or completely in firmware, programmable logic devices such as field programmable gate arrays (FPGAs) as referenced in FIG. 15, system on chips (SOCs), application specific integrated circuits (ASICs), or other processing and logic elements. For example, the Set Processor and Optimizer can be implemented with hardware acceleration through the use of a hardware accelerator card, such as accelerator card 1322 illustrated in FIG. 13.

EMBODIMENTS

Provided herein are polynucleotide libraries comprising: a first polynucleotide library comprising at least 30,000 polynucleotides, wherein each of the at least 30,000 polynucleotides is present in an amount such that, following hybridization with genomic fragments and sequencing of the hybridized genomic fragments, the polynucleotide library provides for at least 25 fold read depth of at least 80 percent of the bases of a first set of hybridized genomic fragments and at least 40 fold average read depth; and a second polynucleotide library comprising at least 1500 polynucleotides, wherein each of the at least 1500 polynucleotides is present in an amount such that, following hybridization with genomic fragments and sequencing of the hybridized genomic fragments, the polynucleotide library provides for at least 15 fold read depth of at least 80 percent of the bases of a second set of hybridized genomic fragments and at least 24 fold average read depth. Further provided herein are polynucleotide libraries, wherein the first polynucleotide library comprises at least 100,000 polynucleotides. Further provided herein are polynucleotide libraries wherein the second polynucleotide library comprises at least 5,000 polynucleotides. Further provided herein are polynucleotide libraries wherein the first polynucleotide library comprises at least 100,000 polynucleotides and the second polynucleotide library comprises at least 5,000 polynucleotides. Further provided herein are polynucleotide libraries wherein the first polynucleotide library provides for at least 25 fold read depth of at least 90 percent of the bases of the first set of hybridized genomic fragments and at least 40 fold average read depth. Further provided herein are polynucleotide libraries wherein the first polynucleotide library provides for at least 40 fold read depth of at least 80 percent of the bases of the first set of hybridized genomic fragments and at least 50 fold average read depth. Further provided herein are polynucleotide libraries wherein the second polynucleotide library provides for at least 15 fold read depth of at least 90 percent of the bases of the second set of hybridized genomic fragments and at least 24 fold average read depth. Further provided herein are polynucleotide libraries wherein the second polynucleotide library provides for at least 20 fold read depth of at least 80 percent of the bases of the second set of hybridized genomic fragments and at least 30 fold average read depth. Further provided herein are polynucleotide libraries wherein at least 90% of the bases sequenced are at least 99.5% correct. Further provided herein are polynucleotide libraries wherein at least 90% of the bases sequenced are at least 99.9% correct. Further provided herein are polynucleotide libraries wherein at least 90% of the bases sequenced are at least 99.95% correct. Further provided herein are polynucleotide libraries wherein each of the genomic fragments is about 100 bases to about 500 bases in length. Further provided herein are polynucleotide libraries wherein the at least 30,000 polynucleotides encode for at least 1000 genes. Further provided herein are polynucleotide libraries wherein the at least 30,000 polynucleotides encode for at least one exon sequence. Further provided herein are polynucleotide libraries wherein the at least 1500 polynucleotides encode for at least one exon sequence. Further provided herein are polynucleotide libraries wherein the at least 1500 polynucleotides encode for at least 10 genes. Further provided herein are polynucleotide libraries wherein the at least 1500 polynucleotides encode for at least 100 genes. Further provided herein are polynucleotide libraries wherein the at least 1500 polynucleotides encode for at least one intron. Further provided herein are polynucleotide libraries wherein the at least 1500 polynucleotides encode for at least one single nucleotide polymorphism (SNP). Further provided herein are polynucleotide libraries wherein the single nucleotide polymorphism (SNP) is heterozygous.

Provided herein are methods for sequencing genomic DNA, comprising: contacting the first library and the second library of the polynucleotide libraries described herein with a plurality of genomic fragments; enriching at least one genomic fragment that binds to the first library or the second library to generate at least one enriched target polynucleotide; and sequencing the at least one enriched polynucleotide.

Provided herein are methods for sequencing genomic DNA, comprising: contacting a composition comprising a first polynucleotide library of the polynucleotide libraries described herein with a plurality of genomic fragments; enriching at least one genomic fragment that binds to the first polynucleotide library to generate at least one enriched target polynucleotide; sequencing the at least one enriched target polynucleotide; identifying one or more positions of the at least one enriched polynucleotide having less than average read depth; repeating steps a-c, wherein the second polynucleotide library of the polynucleotide libraries described herein is added to the composition, wherein the second polynucleotide library comprises at least one polynucleotide that binds to genomic fragments comprising the one or more positions having less than average read depth, wherein the presence of the second polynucleotide library increases the read depth at the one or more positions having less than average read depth. Further provided herein are methods wherein the first polynucleotide library and the second polynucleotide library do not comprise any common sequences. Further provided herein are methods wherein the first polynucleotide library and the second polynucleotide library comprise at least one common sequence. Further provided herein are methods wherein the presence of the second polynucleotide library increases the read depth at the one or more positions of the least one enriched target polynucleotide having less than average read depth by at least 10 fold. Further provided herein are methods wherein the presence of the second polynucleotide library increases the read depth at the one or more positions of the at least one enriched target polynucleotide having less than average read depth by at least 100 fold.

Provided herein are polynucleotide libraries, the polynucleotide library comprising at least 1500 polynucleotides, wherein less than all polynucleotides comprises a molecular tag, wherein each of the at least 5000 polynucleotides are present in an amount such that, following hybridization with genomic fragments and sequencing of the hybridized genomic fragments, the polynucleotide library provides for at least 30 fold read depth of at least 90 percent of the bases of the hybridized genomic fragments under conditions wherein the total number of reads is no more than 55 fold higher than the total number of bases of the hybridized genomic fragments. Further provided herein are polynucleotide libraries wherein no more than 90% of the polynucleotides comprise a molecular tag. Further provided herein are polynucleotide libraries wherein no more than 80% of the polynucleotides comprise a molecular tag. Further provided herein are polynucleotide libraries wherein no more than 50% of the polynucleotides comprise a molecular tag. Further provided herein are polynucleotide libraries wherein no more than 25% of the polynucleotides comprise a molecular tag. Further provided herein are polynucleotide libraries wherein the molecular tag is biotin. Further provided herein are polynucleotide libraries wherein the at least 5000 polynucleotides encode for at least 5000 genes. Further provided herein are polynucleotide libraries wherein the polynucleotide library comprises at least 30,000 polynucleotides. Further provided herein are polynucleotide libraries wherein the polynucleotide library comprises at least 100,000 polynucleotides.

Provided herein are methods for enriching nucleic acids comprising: contacting the polynucleotide library described herein with a plurality of genomic fragments; enriching at least one genomic fragment that binds to the polynucleotide library to generate at least one enriched target polynucleotide; and sequencing the at least one enriched target polynucleotide. Further provided herein are methods wherein the polynucleotide library provides for at least 90 percent unique reads for the bases of the enriched target polynucleotide after sequencing. Further provided herein are methods wherein the polynucleotide library provides for at least 95 percent unique reads for the bases of the enriched target polynucleotide after sequencing. Further provided herein are methods wherein the polynucleotide library provides for at least 80 percent of the bases of the enriched target polynucleotide having a read depth within about 1.5 times the mean read depth. Further provided herein are methods wherein the polynucleotide library provides for at least 90 percent of the bases of the enriched target polynucleotide having a read depth within about 1.5 times the mean read depth.

Provided herein are polynucleotide libraries, the polynucleotide library comprising at least 5000 polynucleotides, wherein each of the at least 5000 polynucleotides is present in an amount such that, following hybridization with a composition comprising i) a genomic library, wherein the genomic library comprises polynucleotides each comprising genomic fragments, at least one index sequence, and at least one adapter; and ii) at least one polynucleotide blocker, wherein the polynucleotide blocker is complementary to at least a portion of the adapter sequence, but not complementary to the at least one index sequence; and sequencing of the hybridized genomic fragments, the polynucleotide library provides for at least 30 fold read depth of at least 90 percent of the bases of the genomic fragments under conditions wherein the total number of reads is no more than 55 fold higher than the total number of bases of the hybridized genomic fragments. Further provided herein are polynucleotide libraries wherein the composition comprises no more than four polynucleotide blockers. Further provided herein are polynucleotide libraries wherein the polynucleotide blocker comprises one or more nucleotide analogues.

Further provided herein are polynucleotide libraries wherein the polynucleotide blocker comprises one or more locked nucleic acids (LNAs). Further provided herein are polynucleotide libraries wherein the polynucleotide blocker comprises one or more bridged nucleic acids (BNAs). Further provided herein are polynucleotide libraries wherein the polynucleotide blocker comprises at least 2 nucleotide analogues. Further provided herein are polynucleotide libraries wherein the polynucleotide blocker comprises at least 5 nucleotide analogues. Further provided herein are polynucleotide libraries wherein the polynucleotide blocker comprises at least 10 nucleotide analogues. Further provided herein are polynucleotide libraries wherein the polynucleotide blocker has a $T_m$ of at least 70 degrees C. Further provided herein are polynucleotide libraries wherein the polynucleotide blocker has a Tm of at least 75 degrees C. Further provided herein are polynucleotide libraries wherein the polynucleotide blocker has a $T_m$ of at least 80 degrees C. Further provided herein are polynucleotide libraries wherein the genomic library comprises genomic fragments from at least 2 different samples. Further provided herein are polynucleotide libraries wherein the genomic library comprises genomic fragments from at least 10 different samples. Further provided herein are polynucleotide libraries wherein the genomic library comprises genomic fragments from at least 2 non-identical index sequences. Further provided herein are polynucleotide libraries wherein the genomic library comprises genomic fragments from at least 16 non-identical index sequences. Further provided herein are polynucleotide libraries wherein the genomic library comprises genomic fragments further comprising at least one unique molecular identifier (UMI).

Provided herein are methods for enriching nucleic acids comprising: contacting the polynucleotide libraries described herein with a plurality of genomic fragments; enriching at least one genomic fragment that binds to the polynucleotide library to generate at least one enriched target polynucleotide; and sequencing the at least one enriched target polynucleotide. Further provided herein are methods wherein the off-target rate is less than 25%. Further provided herein are methods wherein the off-target rate is less than 20%. Further provided herein are methods wherein the molar ratio between at least one polynucleotide blocker and the complementary adapter is no more than 5:1. Further provided herein are methods wherein the molar ratio between at least one polynucleotide blocker and the complementary adapter is no more than 2:1. Further provided herein are methods wherein the molar ratio between at least one polynucleotide blocker and the complementary adapter is no more than 1.5:1.

Provided [A1] herein are compositions for nucleic acid hybridization comprising: a first polynucleotide library; a second polynucleotide library, wherein at least one polynucleotide in the first library is at least partially complimentary to at least one polynucleotide of the second library; and an additive, wherein the additive reduces off-target hybridization of the at least one polynucleotide of the first library with the at least one polynucleotide of the second library by decreasing a local concentration of the first polynucleotide library or the second polynucleotide library at an air-liquid interface. Further provided herein are compositions wherein the additive is mineral oil, a nucleotide triphosphate, polyether, or urea. Further provided herein are compositions wherein the additive is a hydrocarbon comprising at least six carbon atoms. Further provided herein are compositions wherein the additive is silicon oil. Further provided herein are compositions wherein the oil is derived from plant sources. Further provided herein are compositions wherein the composition further comprises dimethyl sulfoxide. Further provided herein are compositions wherein the composition does not comprise a formamide. Further provided herein are compositions wherein the size of the first polynucleotide library is less than 10 million bases. Further provided herein are compositions wherein the size of the first polynucleotide library is less than 1 million bases. Further provided herein are compositions wherein the size of the first polynucleotide library is less than 0.5 million bases. Further provided herein are compositions wherein the first polynucleotide library comprises as least one exon sequence. Further provided herein are compositions wherein first polynucleotide library comprises polynucleotides encoding for at least 10 genes. Further provided herein are compositions wherein the first polynucleotide library comprises polynucleotides encoding for at least 100 genes. Further provided herein are compositions wherein the first polynucleotide library comprises at least one genomic fragment. Further provided herein are compositions wherein the first polynucleotide library comprises RNA, DNA, cDNA, or genomic DNA. Further provided herein are compositions wherein the first polynucleotide library comprises genomic DNA.

Provided herein are compositions for nucleic acid hybridization comprising: a first polynucleotide library and a second polynucleotide library each comprising a plurality of polynucleotides, wherein at least one polynucleotide in the first library is at least partially complimentary to at least one polynucleotide of the second library; and an oil, wherein the oil reduces off-target hybridization of the at least one polynucleotide of the first library with the at least one polynucleotide of the second library by decreasing a local concentration of the first polynucleotide library or the second polynucleotide library at an air-liquid interface. Further provided herein are compositions wherein the additive is mineral oil, a nucleotide triphosphate, polyether, or urea. Further provided herein are compositions wherein the additive is a hydrocarbon comprising at least six carbon atoms. Further provided herein are compositions wherein the additive is silicon oil. Further provided herein are compositions wherein the oil is derived from plant sources. Further provided herein are compositions wherein the composition further comprises dimethyl sulfoxide. Further provided herein are compositions wherein the composition does not comprise a formamide. Further provided herein are compositions wherein the size of the first polynucleotide library is less than 10 million bases. Further provided herein are compositions wherein the size of the first polynucleotide library is less than 1 million bases. Further provided herein are compositions wherein the size of the first polynucleotide library is less than 0.5 million bases. Further provided herein are compositions wherein first polynucleotide library comprises as least one exon sequence. Further provided herein are compositions wherein first polynucleotide library comprises polynucleotides encoding for at least 10 genes. Further provided herein are compositions wherein first polynucleotide library comprises polynucleotides encoding for at least 100 genes. Further provided herein are compositions wherein the first polynucleotide library comprises at least one genomic fragment. Further provided herein are compositions wherein the first polynucleotide library comprises RNA, DNA, cDNA, or genomic DNA. Further provided herein are compositions wherein the first polynucleotide library comprises genomic DNA.

Provided herein are methods for reducing off-target nucleic acid hybridization, comprising: contacting a first polynucleotide library with a second polynucleotide library, wherein the first polynucleotide library and the second polynucleotide library each comprise a plurality of polynucleotides, and wherein at least one polynucleotide in the first library is at least partially complimentary to at least one polynucleotide in the second library; enriching at least one genomic fragment that binds to the second polynucleotide library to generate at least one enriched target polynucleotide, wherein enriching comprises at least one aspiration step, and wherein the at least one aspiration step comprises aspirating only liquid from the area near the air/liquid interface; and sequencing the at least one enriched target polynucleotide. Further provided herein are methods wherein the additive is oil, a nucleotide triphosphate, polyether, or urea. Further provided herein are methods wherein the additive is mineral oil. Further provided herein are methods wherein the presence of the additive decreases off-target binding. Further provided herein are methods wherein the presence of the additive decreases off-target binding by at least 10%. Further provided herein are methods wherein the presence of the additive decreases off-target binding by at least 20%. Further provided herein are methods wherein the presence of the additive decreases off-target binding by at least 30%. Further provided herein are methods wherein the off-target binding is random off-target binding. Further provided herein are methods wherein the size of the first polynucleotide library is less than 10 million bases. Further provided herein are methods wherein the size of the first polynucleotide library is less than 1 million bases. Further provided herein are methods wherein the size of the first polynucleotide library is less than 0.5 million bases. Further provided herein are methods wherein first polynucleotide library comprises as least one exon sequence. Further provided herein are methods wherein first polynucleotide library comprises polynucleotides encoding for at least 10 genes. Further provided herein are methods wherein first polynucleotide library comprises polynucleotides encoding for at least 100 genes. Further provided herein are methods wherein the first polynucleotide library comprises at least one genomic fragment. Further provided herein are methods wherein the first polynucleotide library comprises RNA, DNA, cDNA, or genomic DNA. Further provided herein are methods wherein the first polynucleotide library comprises genomic DNA.

Provided herein are methods for sequencing genomic DNA, comprising: contacting a polynucleotide library with a plurality of genomic fragments and an additive to form a mixture, wherein the additive decreases a local concentration of the polynucleotide library or the genomic fragments in the mixture at an air-liquid interface; enriching at least one genomic fragment that binds to the polynucleotide library to generate at least one enriched target polynucleotide; and sequencing the at least one enriched target polynucleotide. Further provided herein are methods wherein the additive is oil, a nucleotide triphosphate, polyether, or urea. Further provided herein are methods wherein the additive is mineral oil. Further provided herein are methods wherein the presence of the additive decreases off-target binding. Further provided herein are methods wherein the presence of the additive decreases off-target binding by at least 10%. Further provided herein are methods wherein the presence of the additive decreases off-target binding by at least 20%. Further provided herein are methods wherein the presence of the additive decreases off-target binding by at least 30%. Further provided herein are methods wherein the off-target binding is random off-target binding. Further provided herein are methods wherein the size of the first polynucleotide library is less than 10 million bases. Further provided herein are methods wherein the size of the first polynucleotide library is less than 1 million bases. Further provided herein are methods wherein the size of the first polynucleotide library is less than 0.5 million bases. Further provided herein are methods wherein the first polynucleotide library comprises as least one exon sequence. Further provided herein are methods wherein the first polynucleotide library comprises polynucleotides encoding for at least 10 genes. Further provided herein are methods wherein the first polynucleotide library comprises polynucleotides encoding for at least 100 genes. Further provided herein are methods wherein the first polynucleotide library comprises at least one genomic fragment. Further provided herein are methods wherein the first polynucleotide library comprises RNA, DNA, cDNA, or genomic DNA. Further provided herein are methods wherein the first polynucleotide library comprises genomic DNA.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Functionalization of a Substrate Surface

A substrate was functionalized to support the attachment and synthesis of a library of polynucleotides. The substrate surface was first wet cleaned using a piranha solution comprising 90% $H_2SO_4$ and 10% $H_2O_2$ for 20 minutes. The substrate was rinsed in several beakers with DI water, held under a DI water gooseneck faucet for 5 minutes, and dried with $N_2$. The substrate was subsequently soaked in $NH_4OH$ (1:100; 3 mL:300 mL) for 5 minutes, rinsed with DI water using a handgun, soaked in three successive beakers with DI water for 1 minute each, and then rinsed again with DI water using the handgun. The substrate was then plasma cleaned by exposing the substrate surface to $O_2$. A SAMCO PC-300 instrument was used to plasma etch $O_2$ at 250 watts for 1 minute in downstream mode.

The cleaned substrate surface was actively functionalized with a solution comprising N-(3-triethoxysilylpropyl)-4-hydroxybutyramide using a YES-1224P vapor deposition oven system with the following parameters: 0.5 to 1 torr, 60 minutes, 70° C., 135° C. vaporizer. The substrate surface was resist coated using a Brewer Science 200× spin coater. SPR™ 3612 photoresist was spin coated on the substrate at 2500 rpm for 40 seconds. The substrate was pre-baked for 30 minutes at 90° C. on a Brewer hot plate. The substrate was subjected to photolithography using a Karl Suss MA6 mask aligner instrument. The substrate was exposed for 2.2 seconds and developed for 1 minute in MSF 26A. Remaining developer was rinsed with the handgun and the substrate soaked in water for 5 minutes. The substrate was baked for 30 minutes at 100° C. in the oven, followed by visual inspection for lithography defects using a Nikon L200. A descum process was used to remove residual resist using the SAMCO PC-300 instrument to 02 plasma etch at 250 watts for 1 minute.

The substrate surface was passively functionalized with a 100 μL solution of perfluorooctyltrichlorosilane mixed with 10 μL light mineral oil. The substrate was placed in a chamber, pumped for 10 minutes, and then the valve was closed to the pump and left to stand for 10 minutes. The chamber was vented to air. The substrate was resist stripped by performing two soaks for 5 minutes in 500 mL NMP at 70° C. with ultrasonication at maximum power (9 on Crest system). The substrate was then soaked for 5 minutes in 500 mL isopropanol at room temperature with ultrasonication at maximum power. The substrate was dipped in 300 mL of 200 proof ethanol and blown dry with $N_2$. The functionalized surface was activated to serve as a support for polynucleotide synthesis.

Example 2

Synthesis of a 50-Mer Sequence on a Polynucleotide Synthesis Device

A two dimensional polynucleotide synthesis device was assembled into a flowcell, which was connected to a flowcell (Applied Biosystems (ABI394 DNA Synthesizer"). The polynucleotide synthesis device was uniformly functionalized with N-(3-TRIETHOXYSILYLPROPYL)-4-HYDROXYBUTYRAMIDE (Gelest) was used to synthesize an exemplary polynucleotide of 50 bp ("50-mer polynucleotide") using polynucleotide synthesis methods described herein.

The sequence of the 50-mer was as described in SEQ ID NO.: 1. 5'AGACAATCAACCATTTGGGGTGGACAGCC TTGACCTCTAGACTTCGGCAT##TTTTTTT TTT3' (SEQ ID NO.: 1), where # denotes Thymidine-succinyl hexamide CED phosphoramidite (CLP-2244 from ChemGenes), which is a cleavable linker enabling the release of polynucleotides from the surface during deprotection.

The synthesis was done using standard DNA synthesis chemistry (coupling, capping, oxidation, and deblocking) according to the protocol in Table 3 and an ABI synthesizer.

TABLE 3

| General DNA Synthesis Process Name | Process Step | Time (seconds) |
|---|---|---|
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |

TABLE 3-continued

| General DNA Synthesis Process Name | Process Step | Time (seconds) |
|---|---|---|
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the ABI 394 synthesizer to enable faster flow. Without flow restrictor, flow rates for amidites (0.1M in ACN), Activator, (0.25M Benzoylthiotetrazole ("BTT"; 30-3070-xx from GlenResearch) in ACN), and Ox (0.02M $I_2$ in 20% pyridine, 10% water, and 70% THF) were roughly ~100 uL/second, for acetonitrile ("ACN") and capping reagents (1:1 mix of CapA and CapB, wherein CapA is acetic anhydride in THF/Pyridine and CapB is 16% 1-methylimidizole in THF), roughly ~200 uL/second, and for Deblock (3% dichloroacetic acid in toluene), roughly ~300 uL/second (compared to ~50 uL/second for all reagents with flow restrictor). The time to completely push out Oxidizer was observed, the timing for chemical flow times was adjusted accordingly and an extra ACN wash was introduced between different chemicals. After polynucleotide synthesis, the chip was deprotected in gaseous ammonia overnight at 75 psi. Five drops of water were applied to the surface to recover polynucleotides. The recovered polynucleotides were then analyzed on a BioAnalyzer small RNA chip (data not shown).

Example 3

Synthesis of a 100-Mer Sequence on a Polynucleotide Synthesis Device

The same process as described in Example 2 for the synthesis of the 50-mer sequence was used for the synthesis of a 100-mer polynucleotide ("100-mer polynucleotide"; 5' CGGGATCCTTATCGTCATCGTCGTACA-GATCCCGACCCATTTGCTGTCCACCAGTCATG CTAGCCATACCATGATGATGATGATGATGAGAACCC CGCAT##TTTTTTTTTT3', where # denotes Thymidine-succinyl hexamide CED phosphoramidite (CLP-2244 from ChemGenes); SEQ ID NO.: 2) on two different silicon chips, the first one uniformly functionalized with N-(3-TRI-ETHOXYSILYLPROPYL)-4-HYDROXYBUTYRAMIDE and the second one functionalized with 5/95 mix of 11-acetoxyundecyltriethoxysilane and n-decyltriethoxysilane, and the polynucleotides extracted from the surface were analyzed on a BioAnalyzer instrument (data not shown).

All ten samples from the two chips were further PCR amplified using a forward (5'ATGCGGGGTTCTCAT-CATC3'; SEQ ID NO. 3) and a reverse (5'CGGGATCCT-TATCGTCATCG3; SEQ ID NO. 4) primer in a 50 uL PCR mix (25 uL NEB Q5 master mix, 2.5 uL 10 uM Forward primer, 2.5 uL 10 uM Reverse primer, 1 uL polynucleotide extracted from the surface, and water up to 50 uL) using the following thermal cycling program:

98 C, 30 seconds 98 C, 10 seconds; 63C, 10 seconds; 72C, 10 seconds; repeat 12 cycles 72C, 2 minutes The PCR products were also run on a BioAnalyzer (data not shown), demonstrating sharp peaks at the 100-mer position. Next, the PCR amplified samples were cloned, and Sanger sequenced. Table 4 summarizes the results from the Sanger sequencing for samples taken from spots 1-5 from chip 1 and for samples taken from spots 6-10 from chip 2.

TABLE 4

| Spot | Error rate | Cycle efficiency |
|---|---|---|
| 1 | $^{+111}/_{763}$ bp | 99.87% |
| 2 | $^{+111}/_{824}$ bp | 99.88% |
| 3 | $^{+111}/_{780}$ bp | 99.87% |
| 4 | $^{+111}/_{429}$ bp | 99.77% |
| 5 | $1/_{1525}$ bp | 99.93% |
| 6 | $1/_{1615}$ bp | 99.94% |
| 7 | $^{+111}/_{531}$ bp | 99.81% |
| 8 | $1/_{1769}$ bp | 99.94% |
| 9 | $^{+111}/_{854}$ bp | 99.88% |
| 10 | $1/_{1451}$ bp | 99.93% |

Thus, the high quality and uniformity of the synthesized polynucleotides were repeated on two chips with different surface chemistries. Overall, 89%, corresponding to 233 out of 262 of the 100-mers that were sequenced were perfect sequences with no errors.

Finally, Table 5 summarizes error characteristics for the sequences obtained from the polynucleotides samples from spots 1-10.

TABLE 5

| | Sample ID/Spot no. | | | | | | | | | |
|---|---|---|---|---|---|---|---|---|---|---|
| | OSA_0046/1 | OSA_0047/2 | OSA_0048/3 | OSA_0049/4 | OSA_0050/5 | OSA_0051/6 | OSA_0052/7 | OSA_0053/8 | OSA_0054/9 | OSA_0055/10 |
| Total Sequences | 32 | 32 | 32 | 32 | 32 | 32 | 32 | 32 | 32 | 32 |
| Sequencing Quality | 25 of 28 | 27 of 27 | 26 of 30 | 21 of 23 | 25 of 26 | 29 of 30 | 27 of 31 | 29 of 31 | 28 of 29 | 25 of 28 |
| Oligo Quality | 23 of 25 | 25 of 27 | 22 of 26 | 18 of 21 | 24 of 25 | 25 of 29 | 22 of 27 | 28 of 29 | 26 of 28 | 20 of 25 |
| ROI Match Count | 2500 | 2698 | 2561 | 2122 | 2499 | 2666 | 2625 | 2899 | 2798 | 2348 |
| ROI Mutation | 2 | 2 | 1 | 3 | 1 | 0 | 2 | 1 | 2 | 1 |
| ROI Multi Base Deletion | 0 | 0 | 0 | 0 | 0 | 0 | 0 | 0 | 0 | 0 |
| ROI Small Insertion | 1 | 0 | 0 | 0 | 0 | 0 | 0 | 0 | 0 | 0 |
| ROI Single Base Deletion | 0 | 0 | 0 | 0 | 0 | 0 | 0 | 0 | 0 | 0 |
| Large Deletion Count | 0 | 0 | 1 | 0 | 0 | 1 | 1 | 0 | 0 | 0 |
| Mutation: G > A | 2 | 2 | 1 | 2 | 1 | 0 | 2 | 1 | 2 | 1 |
| Mutation: T > C | 0 | 0 | 0 | 1 | 0 | 0 | 0 | 0 | 0 | 0 |
| ROI Error Count | 3 | 2 | 2 | 3 | 1 | 1 | 3 | 1 | 2 | 1 |
| ROI Error Rate | Err: ~1 in 834 | Err: ~1 in 1350 | Err: ~1 in 1282 | Err: ~1 in 708 | Err: ~1 in 2500 | Err: ~1 in 2667 | Err: ~1 in 876 | Err: ~1 in 2900 | Err: ~1 in 1400 | Err: ~1 in 2349 |
| ROI Minus Primer Error Rate | MP Err: ~1 in 763 | MP Err: ~1 in 824 | MP Err: ~1 in 780 | MP Err: ~1 in 429 | MP Err: ~1 in 1525 | MP Err: ~1 in 1615 | MP Err: ~1 in 531 | MP Err: ~1 in 1769 | MP Err: ~1 in 854 | MP Err: ~1 in 1451 |

Example 4

Parallel Assembly of 29,040 Unique Polynucleotides

Figure 16:
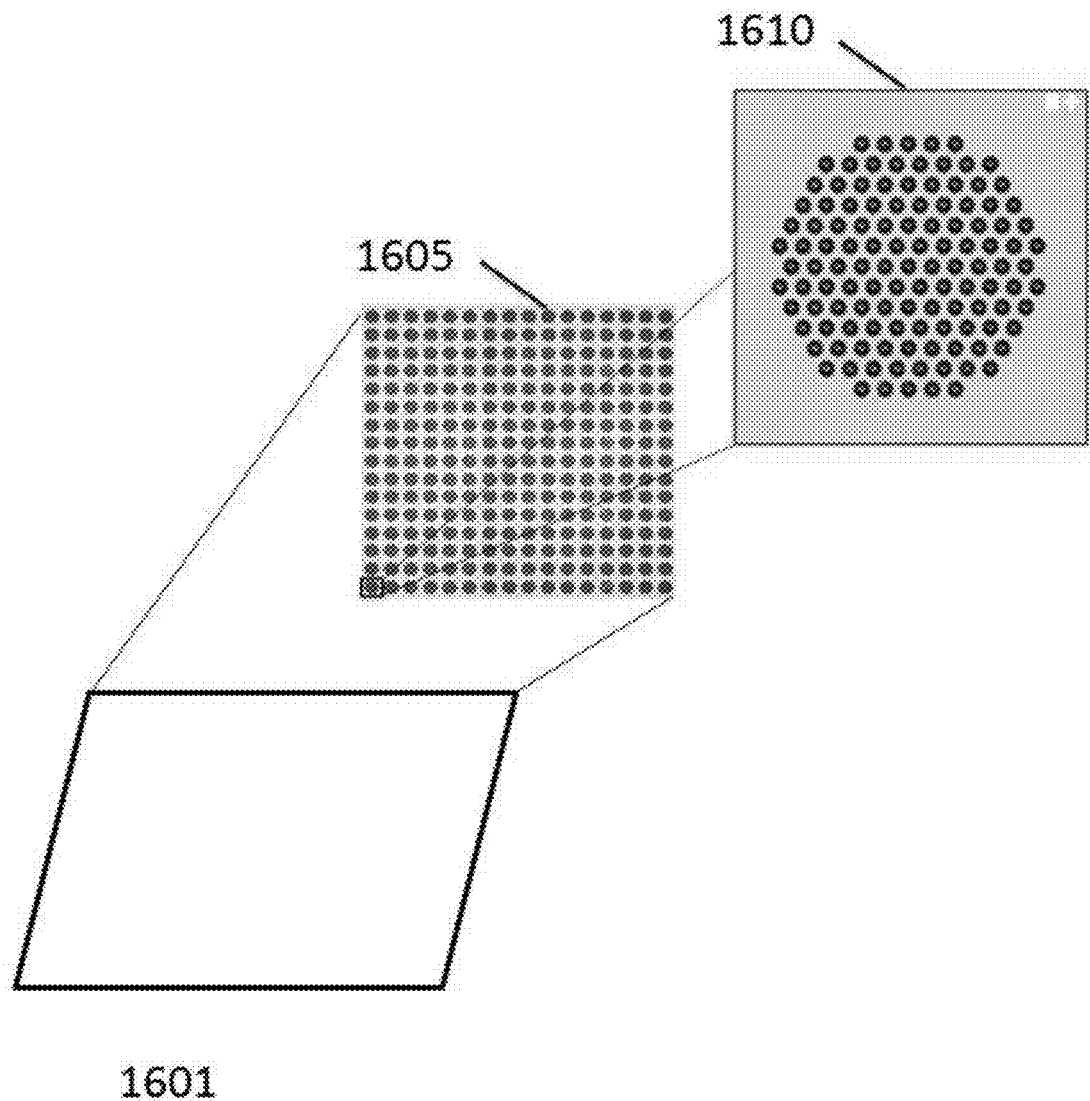
FIG. 16 is an image of a plate having 256 clusters, each cluster having 121 loci with polynucleotides extending therefrom.
Figure 17A:
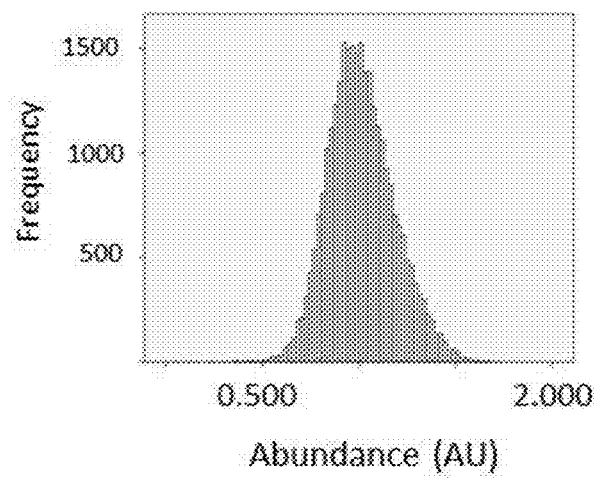
FIG. 17A is a plot of polynucleotide representation (polynucleotide frequency versus abundance, as measured absorbance) across a plate from synthesis of 29,040 unique polynucleotides from 240 clusters, each cluster having 121 polynucleotides.
Figure 17B:
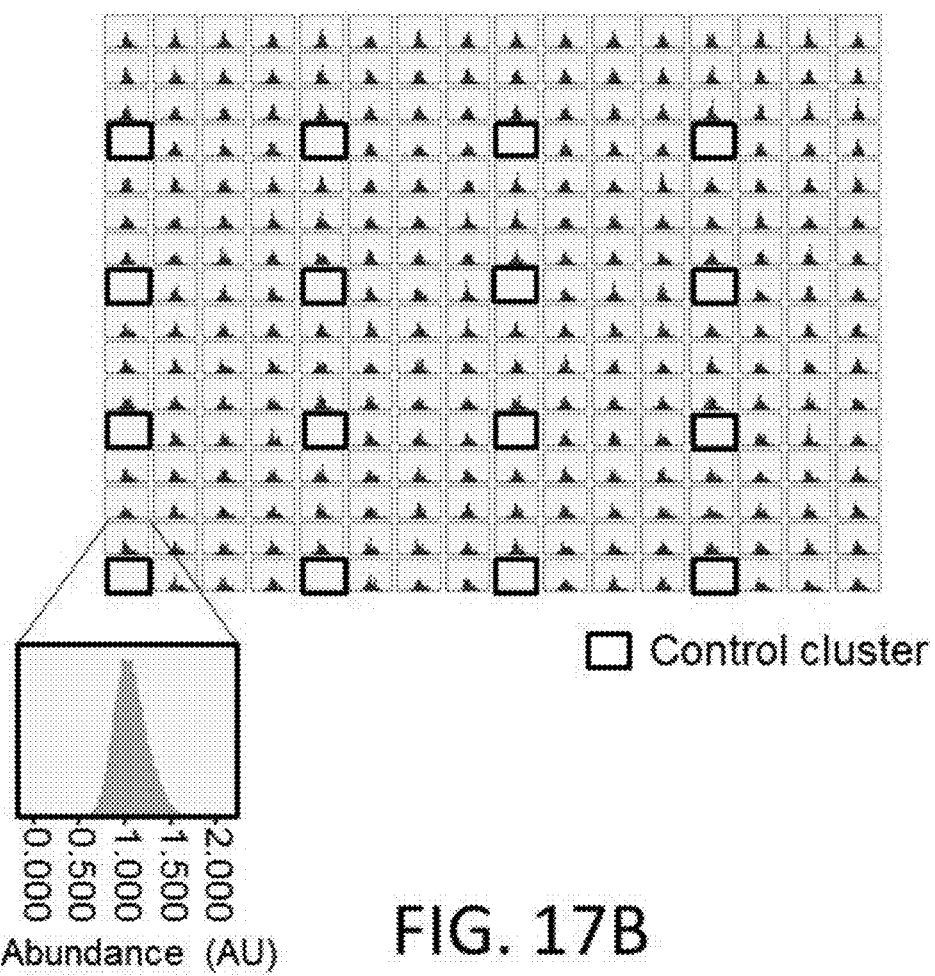
FIG. 17B is a plot of measurement of polynucleotide frequency versus abundance absorbance (as measured absorbance) across each individual cluster, with control clusters identified by a box.
Figure 18:
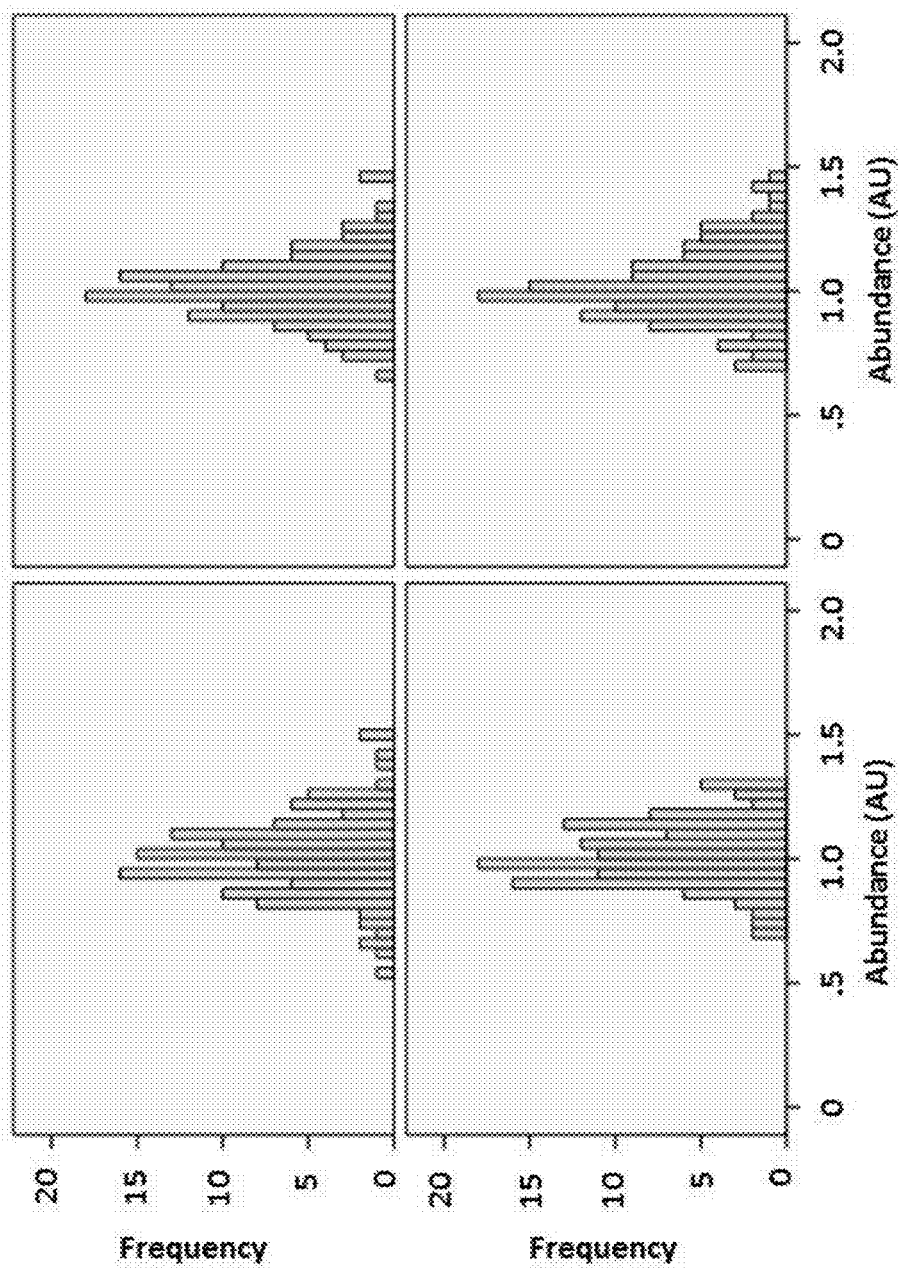
FIG. 18 is a plot of measurements of polynucleotide frequency versus abundance (as measured absorbance) across four individual clusters.

A structure comprising 256 clusters 1605 each comprising 121 loci on a flat silicon plate 1601 was manufactured as shown in FIG. 16. An expanded view of a cluster is shown in 1610 with 121 loci. Loci from 240 of the 256 clusters provided an attachment and support for the synthesis of polynucleotides having distinct sequences. Polynucleotide synthesis was performed by phosphoramidite chemistry using general methods from Example 3. Loci from 16 of the 256 clusters were control clusters. The global distribution of the 29,040 unique polynucleotides synthesized (240×121) is shown in FIG. 17A. Polynucleotide libraries were synthesized at high uniformity. 90% of sequences were present at signals within 4× of the mean, allowing for 100% representation. Distribution was measured for each cluster, as shown in FIG. 17B. The distribution of unique polynucleotides synthesized in 4 representative clusters is shown in FIG. 18. On a global level, all polynucleotides in the run were present and 99% of the polynucleotides had abundance that was within 2× of the mean indicating synthesis uniformity. This same observation was consistent on a per-cluster level.

Figure 19A:
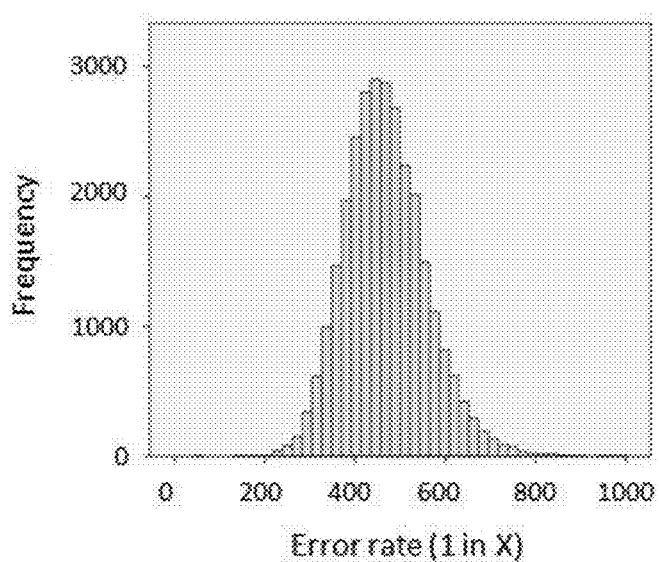
FIG. 19A is a plot of on frequency versus error rate across a plate from synthesis of 29,040 unique polynucleotides from 240 clusters, each cluster having 121 polynucleotides.
Figure 19B:
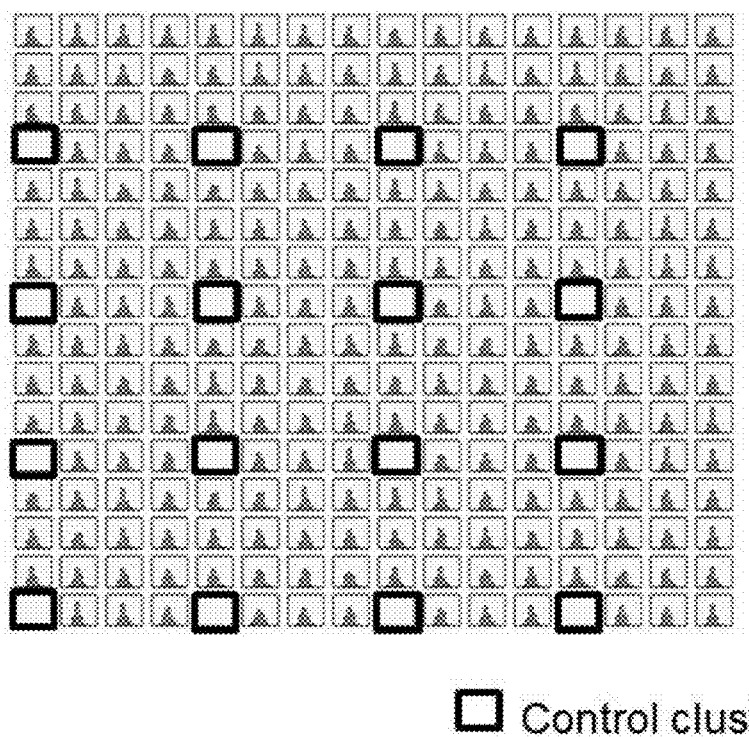
FIG. 19B is a plot of measurement of polynucleotide error rate versus frequency across each individual cluster, with control clusters identified by a box.
Figure 20:
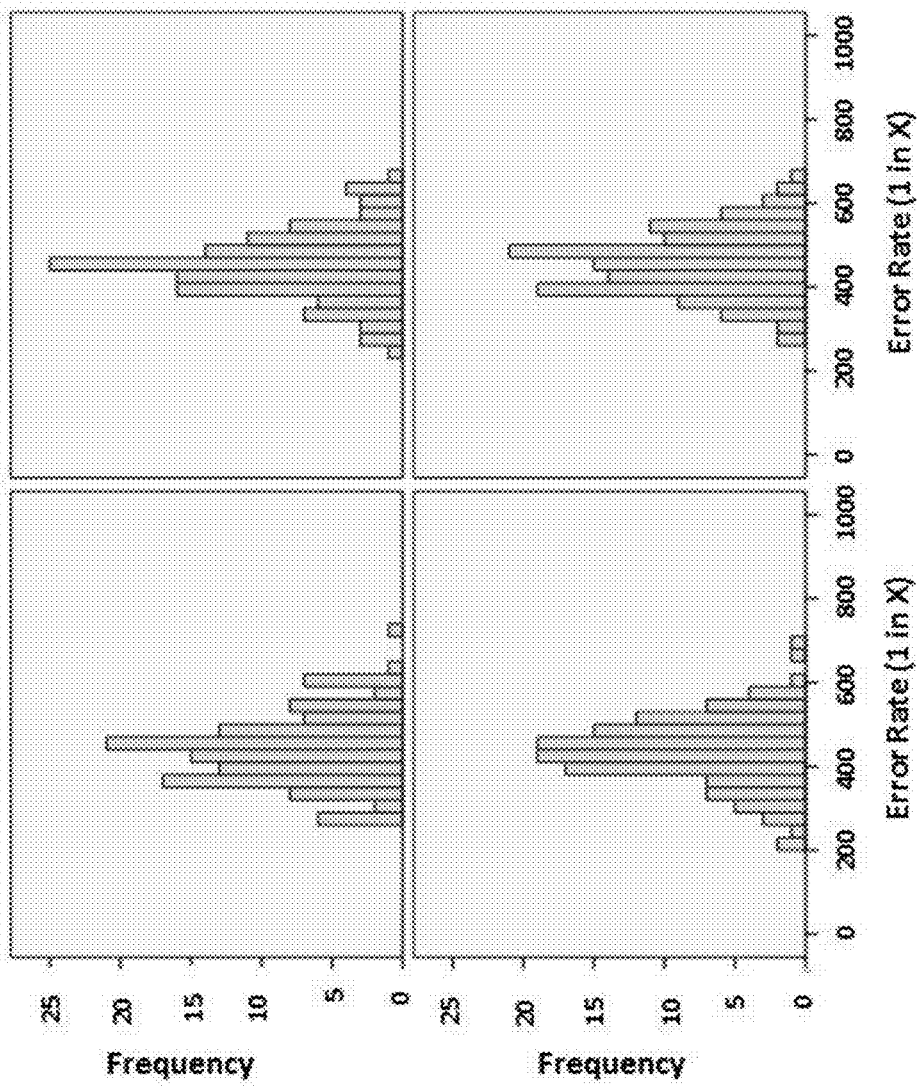
FIG. 20 is a plot of measurements of polynucleotide frequency versus error rate across four clusters.

The error rate for each polynucleotide was determined using an Illumina MiSeq gene sequencer. The error rate distribution for the 29,040 unique polynucleotides is shown in FIG. 19A and averages around 1 in 500 bases, with some error rates as low as 1 in 800 bases. Distribution was measured for each cluster, as shown in FIG. 19B. The error rate distribution for unique polynucleotides in four representative clusters is shown in FIG. 20. The library of 29,040 unique polynucleotides was synthesized in less than 20 hours.

Figure 21:
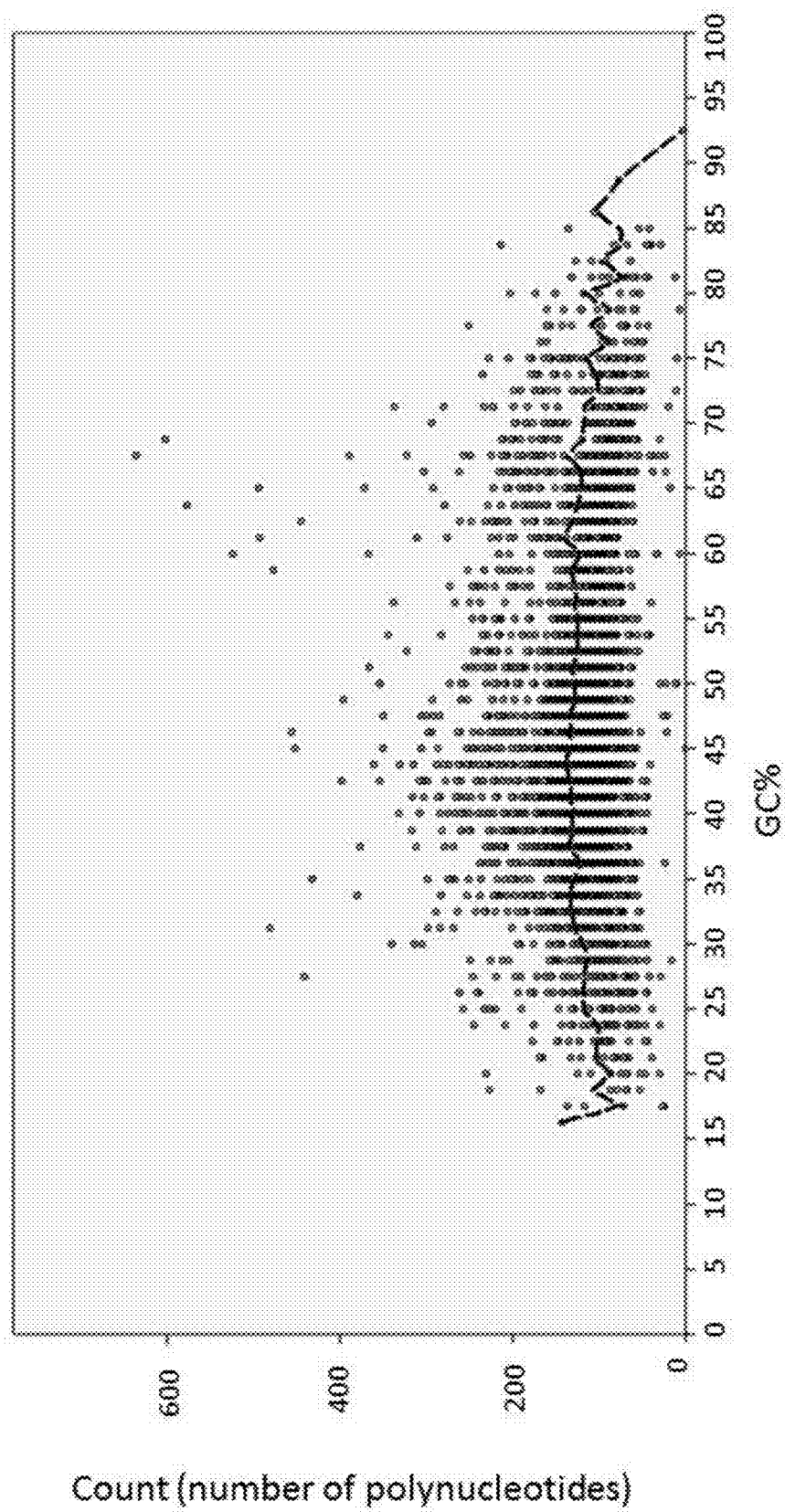
FIG. 21 is a plot of GC content as a measure of the number of polynucleotides versus percent per polynucleotide.

Analysis of GC percentage versus polynucleotide representation across all of the 29,040 unique polynucleotides showed that synthesis was uniform despite GC content, FIG. 21.

Example 5

Use of a Controlled Stoichiometry Polynucleotide Library for Exome Targeting with Next Generation Sequencing (NGS)

A first polynucleotide cDNA targeting library (probe library), comprising up to 370,000 or more non-identical polynucleotides which overlap with one or more gene exons is designed and synthesized on a structure by phosphoramidite chemistry using the general methods from Example 3. The polynucleotides are ligated to a molecular tag such as biotin using PCR (or directly during solid-phase synthesis) to form a probe for subsequent capture of the target exons of interest. The probes are hybridized to sequences in a library of genomic nucleic acids, and separated from non-binding sequences. Unbound probes are washed away, leaving the target library enriched in cDNA sequences. The enriched library is then sequenced using NGS, and reads for each expected gene are measured as a function of the cDNA probe(s) used to target the gene.

A target sequence's frequency of reads is affected by target sequence abundance, probe binding, secondary structure, or other factors which decrease representation after sequencing of the target sequence despite enrichment. Polynucleotide library stoichiometric control is performed by modifying the stoichiometry of the first polynucleotide cDNA targeting library to obtain a second polynucleotide cDNA targeting library, with increased stoichiometry for polynucleotide probe sequences that lead to fewer reads. This second cDNA targeting library is designed and synthesized on a structure by phosphoramidite chemistry using the general methods from Example 3, and used to enrich sequence exons of the target genomic DNA library as described previously.

Example 6

Genomic DNA Capture with an Exome-Targeting Polynucleotide Probe Library

A polynucleotide targeting library comprising at least 500,000 non-identical polynucleotides targeting the human exome was designed and synthesized on a structure by phosphoramidite chemistry using the general methods from Example 3, and the stoichiometry controlled using the general methods of Example 5 to generate Library 4. The polynucleotides were then labeled with biotin, and then dissolved to form an exome probe library solution. A dried indexed library pool was obtained from a genomic DNA (gDNA) sample using the general methods of Example 16.

The exome probe library solution, a hybridization solution, a blocker mix A, and a blocker mix B were mixed by pulse vortexing for 2 seconds. The hybridization solution was heated at 65° C. for 10 minutes, or until all precipitate was dissolved, and then brought to room temperature on the benchtop for 5 additional minutes. 20 μL of hybridization solution and 4 μL of the exome probe library solution were added to a thin-walled PCR 0.2 mL strip-tube and mixed gently by pipetting. The combined hybridization solution/exome probe solution was heated to 95° C. for 2 minutes in a thermal cycler with a 105° C. lid and immediately cooled on ice for at least 10 minutes. The solution was then allowed to cool to room temperature on the benchtop for 5 minutes. While the hybridization solution/exome probe library solution was cooling, water was added to 9 μl for each genomic DNA sample, and 5 μL of blocker mix A, and 2 μL of blocker mix B were added to the dried indexed library pool in the thin-walled PCR 0.2 mL strip-tube. The solution was then mixed by gentle pipetting. The pooled library/blocker tube was heated at 95° C. for 5 minutes in a thermal cycler with a 105° C. lid, then brought to room temperature on the benchtop for no more than 5 minutes before proceeding onto the next step. The hybridization mix/probe solution was mixed by pipetting and added to the entire 24 μL of the pooled library/blocker tube. The entire capture reaction well was mixed by gentle pipetting, to avoid generating bubbles. The sample tube was pulse-spun to make sure the tube was sealed tightly. The capture/hybridization reaction was heated at 70° C. for 16 hours in a PCR thermocycler, with a lid temperature of 85° C.

Binding buffer, wash Buffer 1 and wash Buffer 2 were heated at 48° C. until all precipitate was dissolved into solution. 700 μL of wash buffer 2 was aliquoted per capture and preheated to 48° C. Streptavidin binding beads and DNA purification beads were equilibrated at room temperature for at least 30 minutes. A polymerase, such as KAPA HiFi HotStart ReadyMix and amplification primers were thawed on ice. Once the reagents were thawed, they were mixed by pulse vortexing for 2 seconds. 500 μL of 80 percent ethanol per capture reaction was prepared. Streptavidin binding beads were pre-equilibrated at room temperature and vortexed until homogenized. 100 μL of streptavidin binding beads were added to a clean 1.5 mL microcentrifuge tube per capture reaction. 200 μL of binding buffer was added to each tube and each tube was mixed by pipetting until homogenized. The tube was placed on magnetic stand. Streptavidin binding beads were pelleted within 1 minute. The tube was removed and the clear supernatant was discarded, making sure not to disturb the bead pellet. The tube was removed from the magnetic stand, and the washes were repeated two additional times. After the third wash, the tube was removed and the clear supernatant was discarded. A final 200 μL of binding buffer was added, and beads were resuspended by vortexing until homogenous.

After completing the hybridization reaction, the thermal cycler lid was opened and the full volume of capture reaction was quickly transferred (36-40 μL) into the washed streptavidin binding beads. The mixture was mixed for 30 minutes at room temperature on a shaker, rocker, or rotator at a speed sufficient to keep capture reaction/streptavidin binding bead solution homogenized. The capture reaction/streptavidin binding bead solution was removed from mixer and pulse-spun to ensure all solution was at the bottom of the tube. The sample was placed on a magnetic stand, and streptavidin binding beads pelleted, leaving a clear supernatant within 1 minute. The clear supernatant was removed and discarded. The tube was removed from the magnetic stand and 200 μL of wash buffer was added at room temperature, followed by mixing by pipetting until homogenized. The tube was pulse-spun to ensure all solution was at the bottom of the tube. A thermal cycler was programmed with the following conditions (Table 6).

The temperature of the heated lid was set to 105° C.

TABLE 6

| Step | Temperature | Time | Cycle Number |
|---|---|---|---|
| 1 | 98° C. | 45 seconds | 1 |
| 2 | 98° C. | 15 seconds | 9 |
|  | 60° C. | 30 seconds |  |
|  | 72° C. | 30 seconds |  |
| 3 | 72° C. | 1 minute | 1 |
| 4 | 4° C. | HOLD |  |

Amplification primers (2.5 μL) and a polymerase, such as KAPA HiFi HotStart ReadyMix (25 μL) were added to a tube containing the water/streptavidin binding bead slurry, and the tube mixed by pipetting. The tube was then split into two reactions. The tube was pulse-spun and transferred to the thermal cycler and the cycling program in Table 6 was started. When thermal cycler program was complete, samples were removed from the block and immediately subjected to purification. DNA purification beads pre-equilibrated at room temperature were vortexed until homogenized. 90 μL (1.8×) homogenized DNA purification beads were added to the tube, and mixed well by vortexing. The tube was incubated for 5 minutes at room temperature, and placed on a magnetic stand. DNA purification beads pelleted, leaving a clear supernatant within 1 minute. The clear supernatant was discarded, and the tube was left on the magnetic stand. The DNA purification bead pellet was washed with 200 μL of freshly prepared 80 percent ethanol, incubated for 1 minute, then removed and the ethanol discarded. The wash was repeated once, for a total of two washes, while keeping the tube on the magnetic stand. All remaining ethanol was removed and discarded with a 10 μL pipette, making sure to not disturb the DNA purification bead pellet. The DNA purification bead pellet was air-dried on a magnetic stand for 5-10 minutes or until the pellet was dry. The tube was removed from the magnetic stand and 32 μL of water was added, mixed by pipetting until homogenized, and incubated at room temperature for 2 minutes. The tube was placed on a magnetic stand for 3 minutes or until beads were fully pelleted. 30 μL of clear supernatant was recovered and transferred to a clean thin-walled PCR 0.2 mL strip-tube, making sure not to disturb DNA purification bead pellet. Average fragment length was between about 375 bp to about 425 bp using a range setting of 150 bp to 1000 bp on an analysis instrument. Ideally, the final concentration values is at least about 15 ng/μL. Each capture was quantified and validated using Next Generation Sequencing (NGS).

A summary of NGS metrics is shown in Table 7, Table 8 as compared to a comparator exome capture kit (Comparator Kit D). Library 4 has probes (baits) that correspond to a higher percentage of exon targets than Comparator Kit D. This results in less sequencing to obtain comparable quality and coverage of target sequences using Library 4.

TABLE 7

| NGS Metric | Comparator Kit D | Library 4 |
|---|---|---|
| Target Territory | 38.8 Mb | 33.2 Mb |
| Bait Territory | 50.8 Mb | 36.7 Mb |
| Bait Design Efficiency | 76.5% | 90.3% |
| Capture Plex | 8-plex | 8-plex |
| PF Reads | 57.7M | 49.3M |
| Normalized Coverage | 150X | 150X |
| HS Library Size | 30.3M | 404.0M |
| Percent Duplication | 32.5% | 2.5% |
| Fold Enrichment | 43.2 | 48.6 |
| Fold 80 Base Penalty | 1.84 | 1.40 |

TABLE 8

| NGS Metric | Comparator Kit D | Library 4 |
|---|---|---|
| Percent Pass Filtered Unique Reads (PCT_PF_UQ_READS) | 67.6% | 97.5% |
| Percent Target Bases at 1X | 99.8% | 99.8% |
| Percent Target Bases at 20X | 90.3% | 99.3% |
| Percent Target Bases at 30X | 72.4% | 96.2% |

A comparison of overlapping target regions for both Kit D and Library 4 (total reads normalized to 96× coverage) is shown in Table 9. Library 4 was processed as 8 samples per hybridization, and Kit D was processed at 2 samples per hybridization. Additionally, for both libraries, single nucleotide polymorphism and in-frame deletion calls from overlapping regions were compared against high-confidence regions identified from "Genome in a Bottle" NA12878 reference data (Table 10). Library 4 performed similarly or better (higher indel precision) that Kit D in identifying SNPs and indels.

TABLE 9

| NGS Metric | Comparator Kit D | Library 4 |
|---|---|---|
| Percent Pass Filtered Reads (PCT_PF_UQ_READS) | 94.60% | 97.7% |
| Percent Selected Bases | 79% | 80% |
| Percent Target Bases at 1X | 100% | 100% |
| Percent Target Bases at 20X | 90% | 96% |
| Percent Target Bases at 30X | 71% | 77% |
| Fold Enrichment | 44.9 | 49.9 |

TABLE 9-continued

| NGS Metric | Comparator Kit D | Library 4 |
| --- | --- | --- |
| Fold 80 Base Penalty | 1.76 | 1.4 |
| HS Library Size | 122M | 267M |

TABLE 10

| | Comparator Kit D | | Library 4 | |
| --- | --- | --- | --- | --- |
| Variants | Precision | Sensitivity | Precision | Sensitivity |
| Single Nucleotide Polymorphisms (SNPs) | 98.59% | 99.23% | 99.05% | 99.27% |
| In-Frame Deletions (Indels) | 76.42% | 94.12% | 87.76% | 94.85% |
| Total | 98.14% | 99.15% | 98.85% | 99.20% |

Precision represents the ratio of true positive calls to total (true and false) positive calls. Sensitivity represents the ratio of true positive calls to total true values (true positive and false negative).

Example 7

Exome Probes with a Pain Gene Panel

Figure 3:
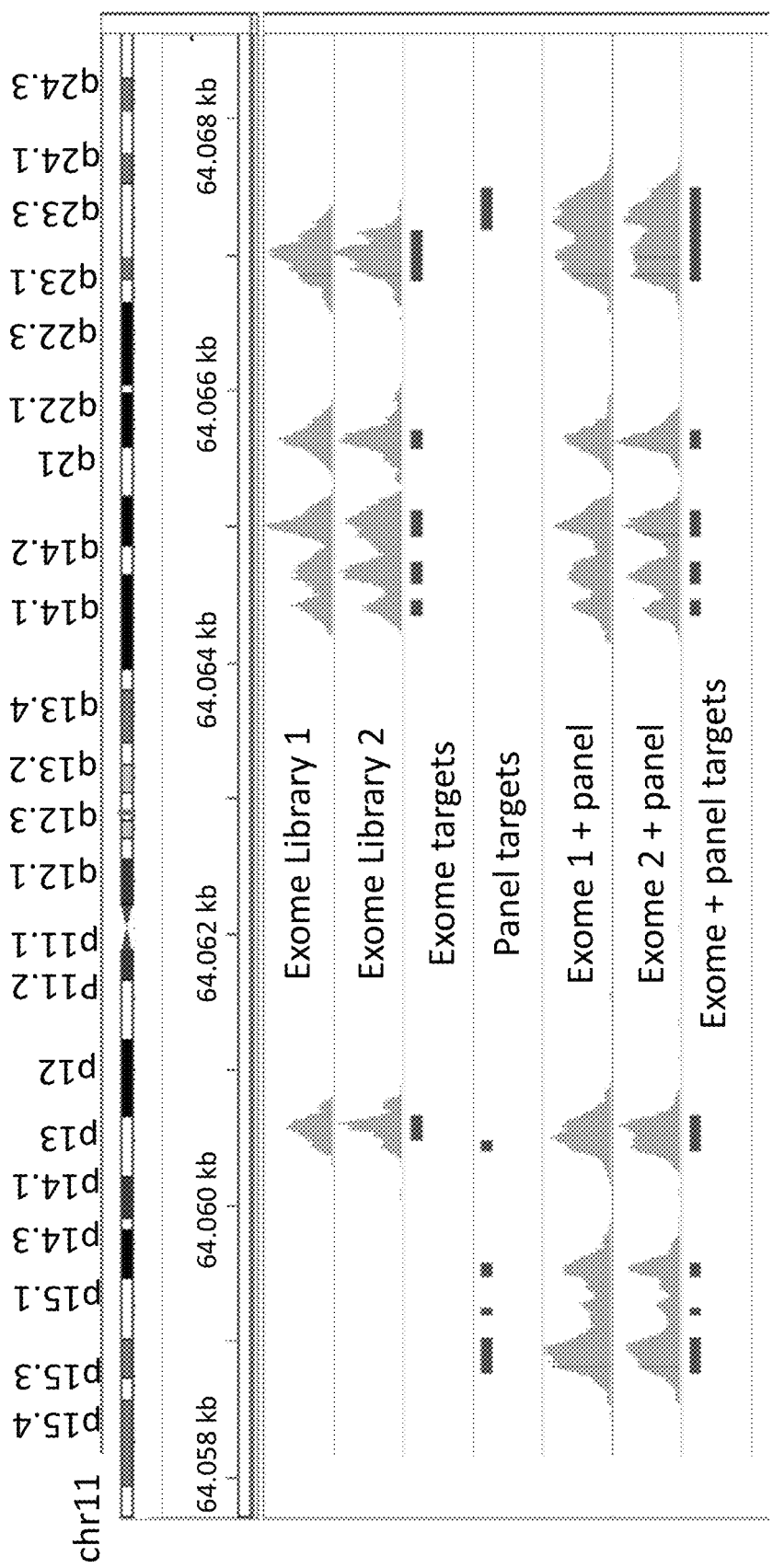
FIG. 3 depicts a plot of sequencing coverage vs. position at chromosome 11 after a genomic library is enriched with two different exome capture library, a smaller library panel targeting pain genes, or combinations of the exome and panel libraries.

Sequencing data was acquired using the general method of Example 6, with modification: different combinations of probe sets were evaluated. Two different exome probe libraries were used (Exome 1 and Exome 2) as well as a second polynucleotide probe library (panel) which targeted genes associated with pain. Both exome panels were evaluated individually, as well as with the pain gene panels mixed. This resulted in additional sequencing coverage of these genomic regions; one such exemplary region of chromosome 11 is shown in FIG. 3. This result was compared with separate analyses in which various exome panel and pain gene panels were individually evaluated, or combined for areas spanning multiple chromosomes, such as chromosome 1, 2, 6, and 22 (data not shown).

Example 8

Universal Blockers with Locked Nucleic Acids

Figure 4A:
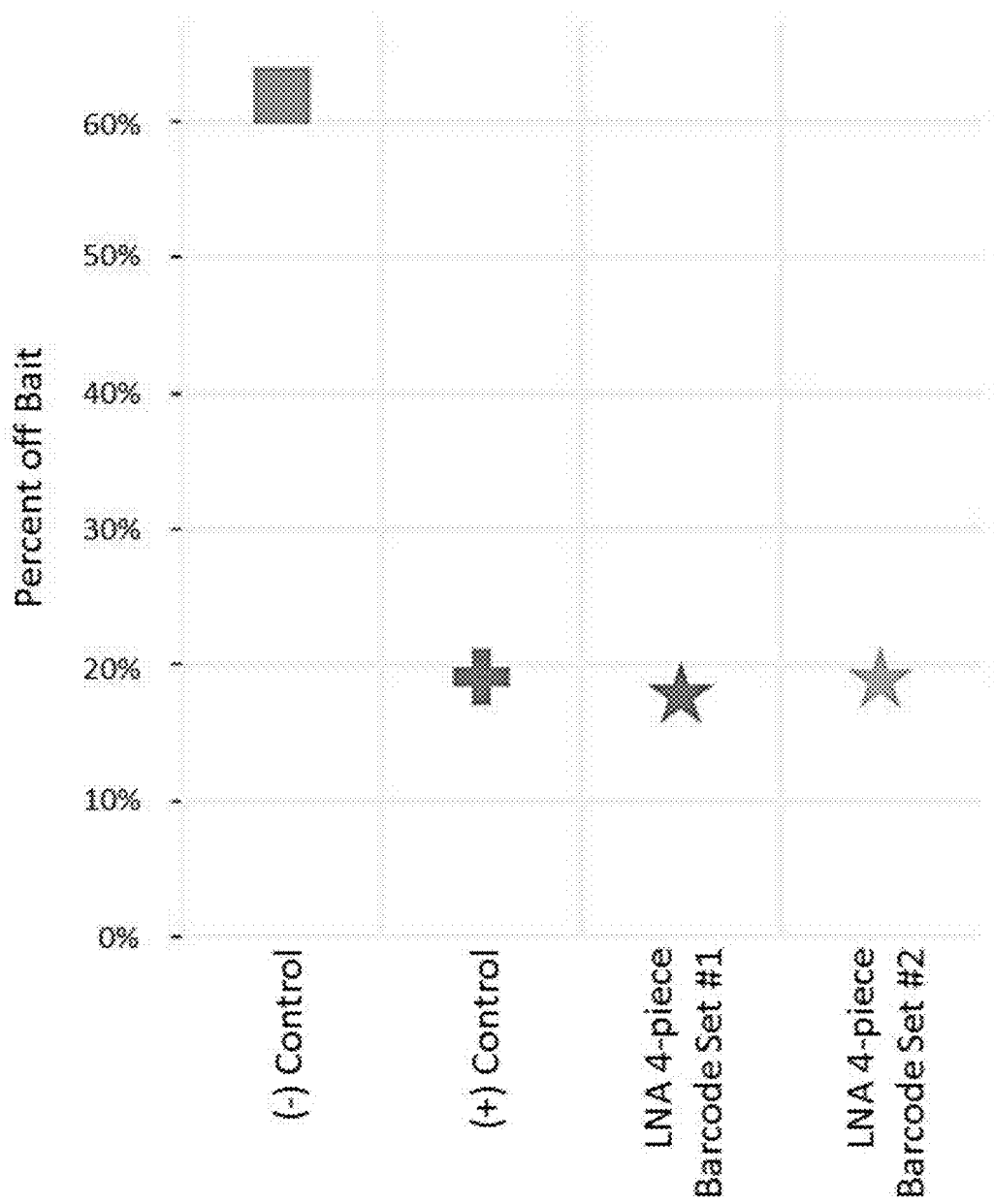
FIG. 4A depicts a plot of percent off bait vs. blocker type for an enrichment and sequencing analysis comparing types of blockers during probe hybridization. Conditions included no blockers (−control), specific blockers (+control), or two different designs of universal blockers.

Sequencing data was acquired using the general method of Example 6, with modification: four polynucleotide blockers were evaluated in separate analyses for their ability to reduce off-target binding (FIG. 4A). Universal blockers comprising LNAs performed comparably to positive control conditions with specific blockers, achieving less than 20% off bait across two different index sequences.

Example 9

Combinations of Universal Blockers with Locked Nucleic Acids

Figure 4B:
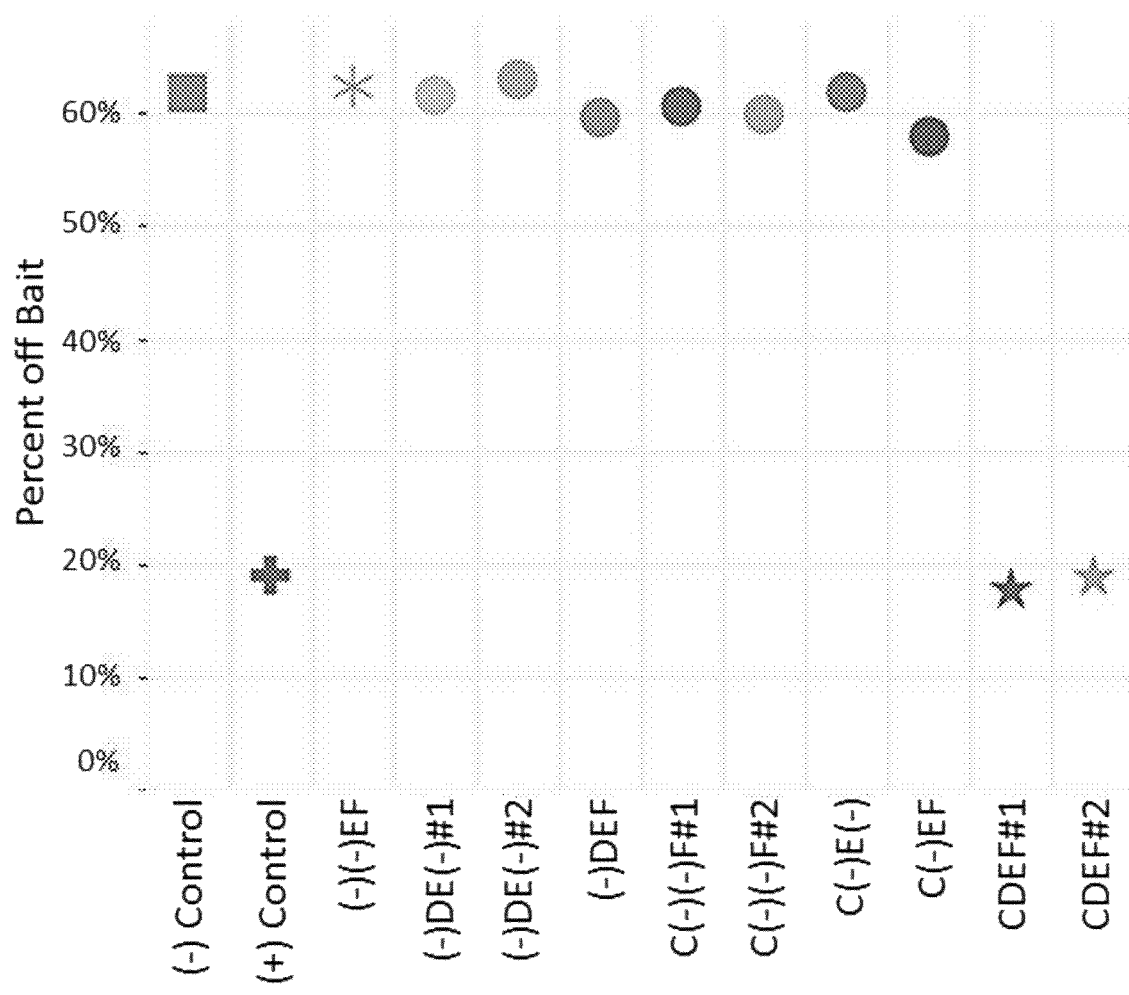
FIG. 4B depicts a plot of percent off bait vs. blocker mixtures of an enrichment and sequencing analysis comparing types of blockers during probe hybridization. Conditions included no blockers (−control), specific blockers (+control), or conditions wherein different combinations of universal blockers were independently tested.

Sequencing data was acquired using the general method of Example 6, with modification: different combinations of four polynucleotide blockers were evaluated in separate conditions for their ability to reduce off-target binding (FIG. 4B). Universal blockers comprising LNAs performed comparably to positive control conditions with specific blockers when all four blockers (C, D, E, F) were present, achieving less than 20% off bait.

Example 10

Universal Blockers with Locked Nucleic Acids

Figure 4C:
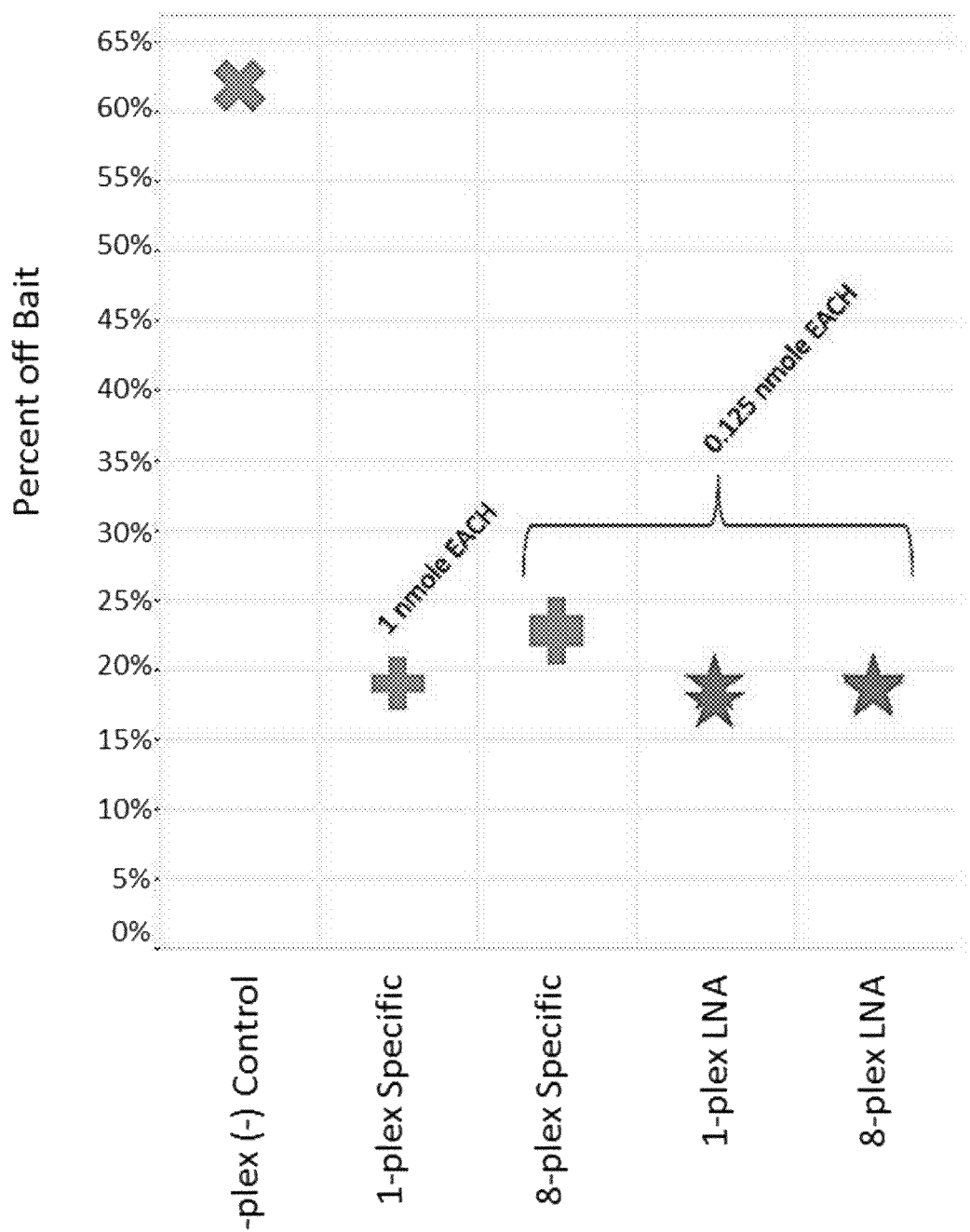
FIG. 4C depicts a plot of percent off bait vs. different designs of an enrichment and sequencing analysis comparing types of blockers during probe hybridization at different mass loadings.

Sequencing data was acquired using the general method of Example 6, with modification: four polynucleotide blockers were evaluated in separate conditions for their ability to reduce off-target binding (FIG. 4C) in conditions comprising 1 or 8 different index sequences (1- or 8-plex). Universal blockers comprising LNAs at 0.125 nmol each performed comparably to positive control conditions with 1 nmole specific blockers, achieving less than 20% off bait across both 1-plex and 8-plex conditions. Universal blockers comprising LNA performed better (less than 20% off bait) than specific blockers (more than 20% off bait) when they were each present in comparable amounts by mass (FIG. 4C).

Example 11

Titration of Universal Blockers with Locked Nucleic Acids

Figure 4D:
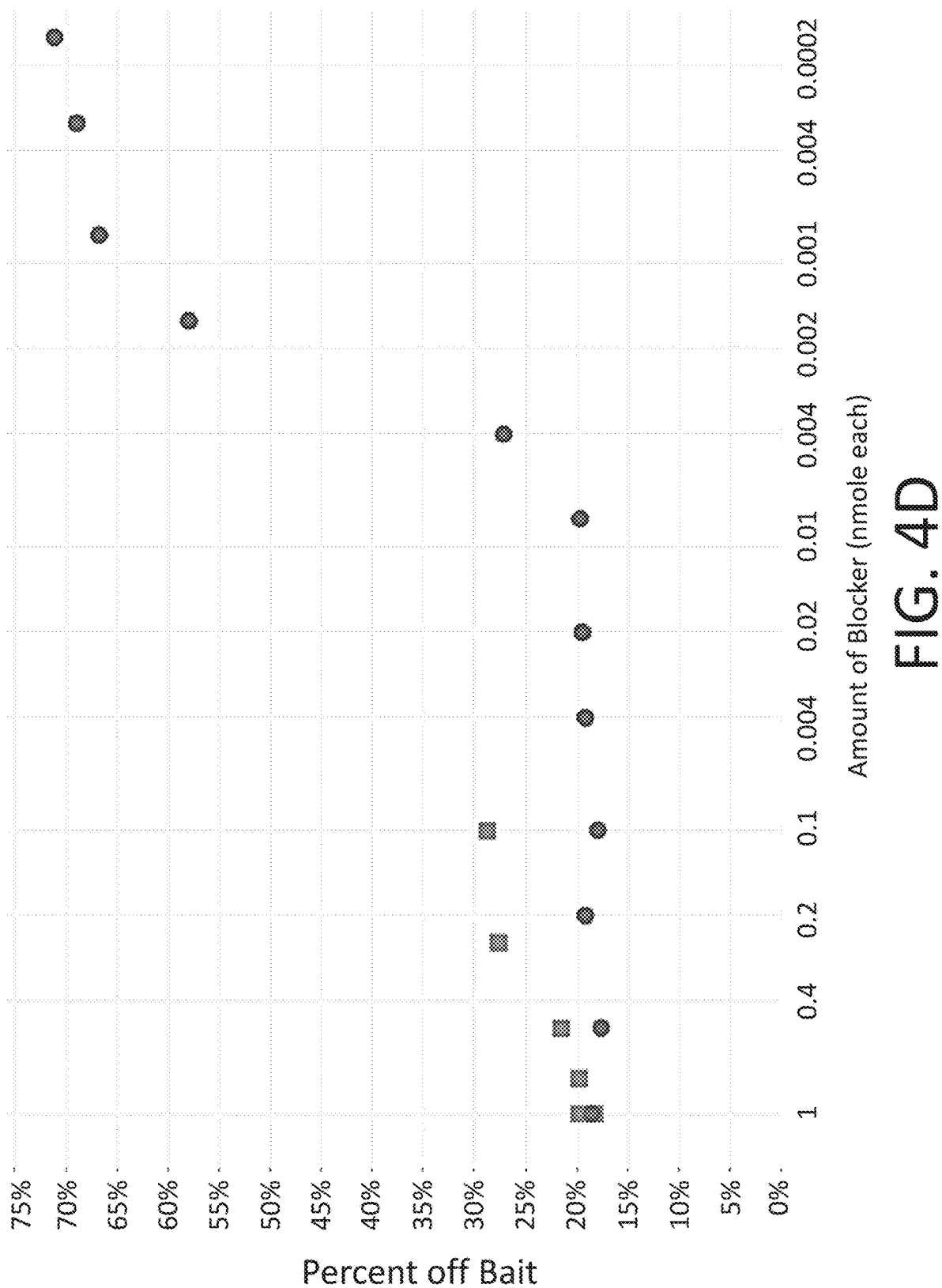
FIG. 4D depicts a plot of percent off bait vs. blocker concentration of an enrichment and sequencing analysis with universal blockers.

Sequencing data was acquired using the general method of Example 6, with modification: four polynucleotide blockers were evaluated in separate conditions for their ability to reduce off-target binding (FIG. 4D). Universal blockers comprising LNAs present in amounts less than 0.01 nmole each achieved less than 20% off bait.

Example 12

Universal Blockers with Varying Amounts of Locked Nucleic Acids

Figure 4E:
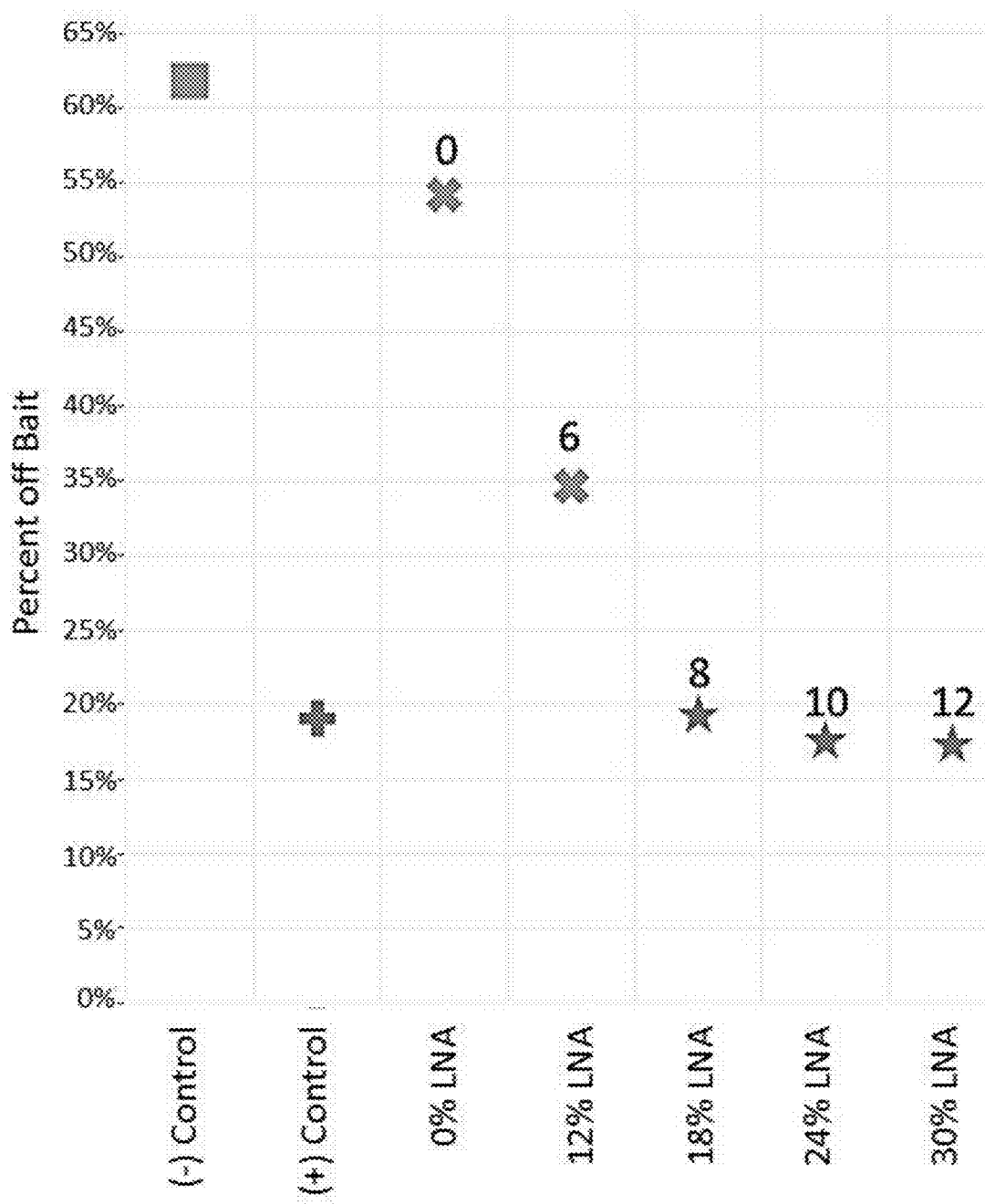
FIG. 4E depicts a plot of the percent off bait vs. universal blockers comprising various amounts of locked nucleic acids for an enrichment and sequencing analysis.

Sequencing data was acquired using the general method of Example 6, with modification: four polynucleotide blockers comprising varying amounts of LNAs were evaluated in separate conditions for their ability to reduce off-target binding (FIG. 4E). Universal blockers comprising at least 8 LNAs performed comparably to positive control conditions with specific blockers, achieving less than 20% off bait.

Example 13

Universal Blockers with Bridged Nucleic Acids

Figure 4F:
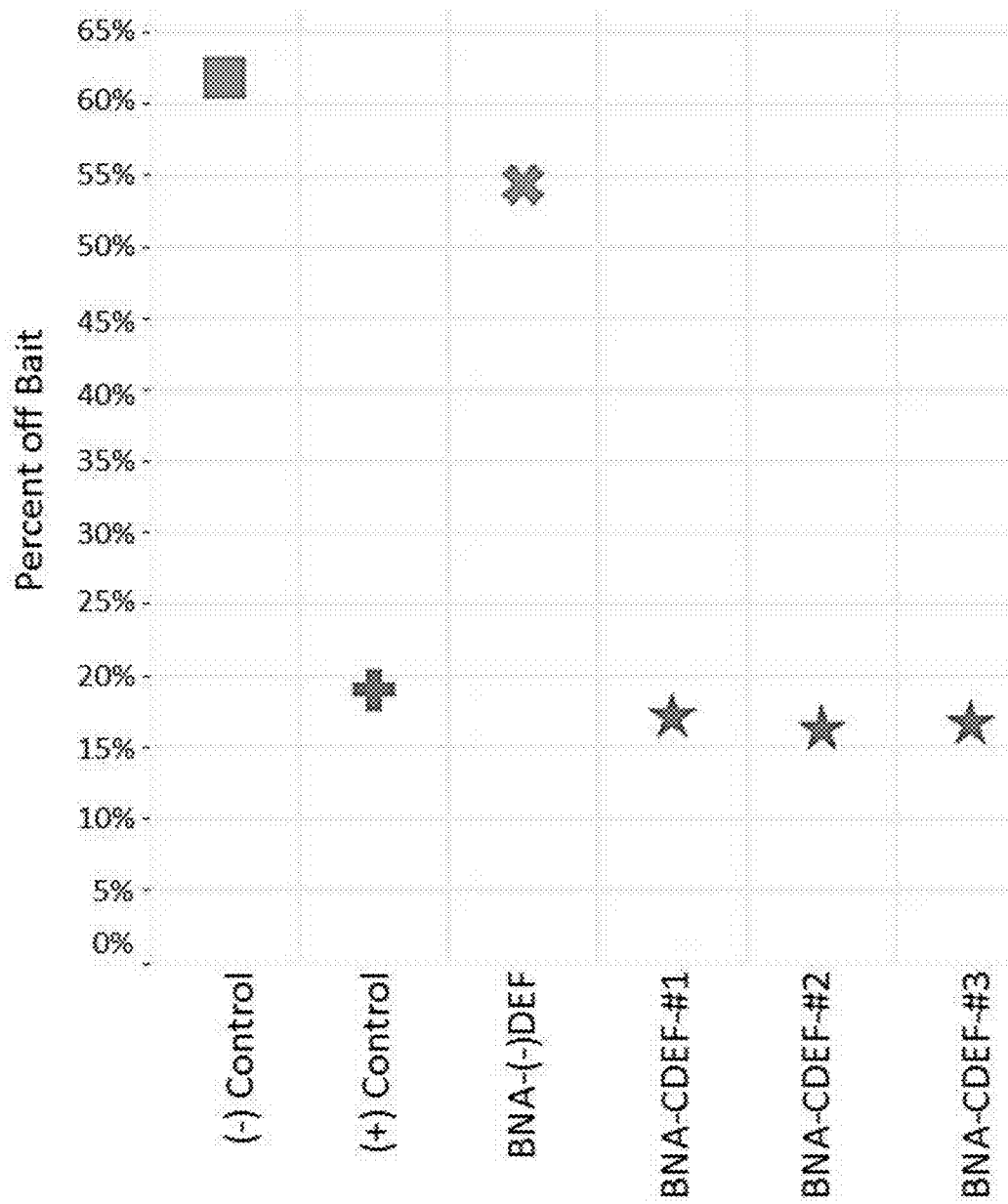
FIG. 4F depicts a plot of the percent off bait vs. universal blockers comprising various amounts of bridged nucleic acids for an enrichment and sequencing analysis.

Sequencing data was acquired using the general method of Example 6, with modification: four different polynucleotide blockers sets were evaluated in separate conditions for their ability to reduce off-target binding (FIG. 4F). Universal blockers comprising BNAs performed better than positive control conditions with specific blockers, achieving less than 27% off bait.

Example 14

Use of Partially Biotinylated Probes

Figure 5A:
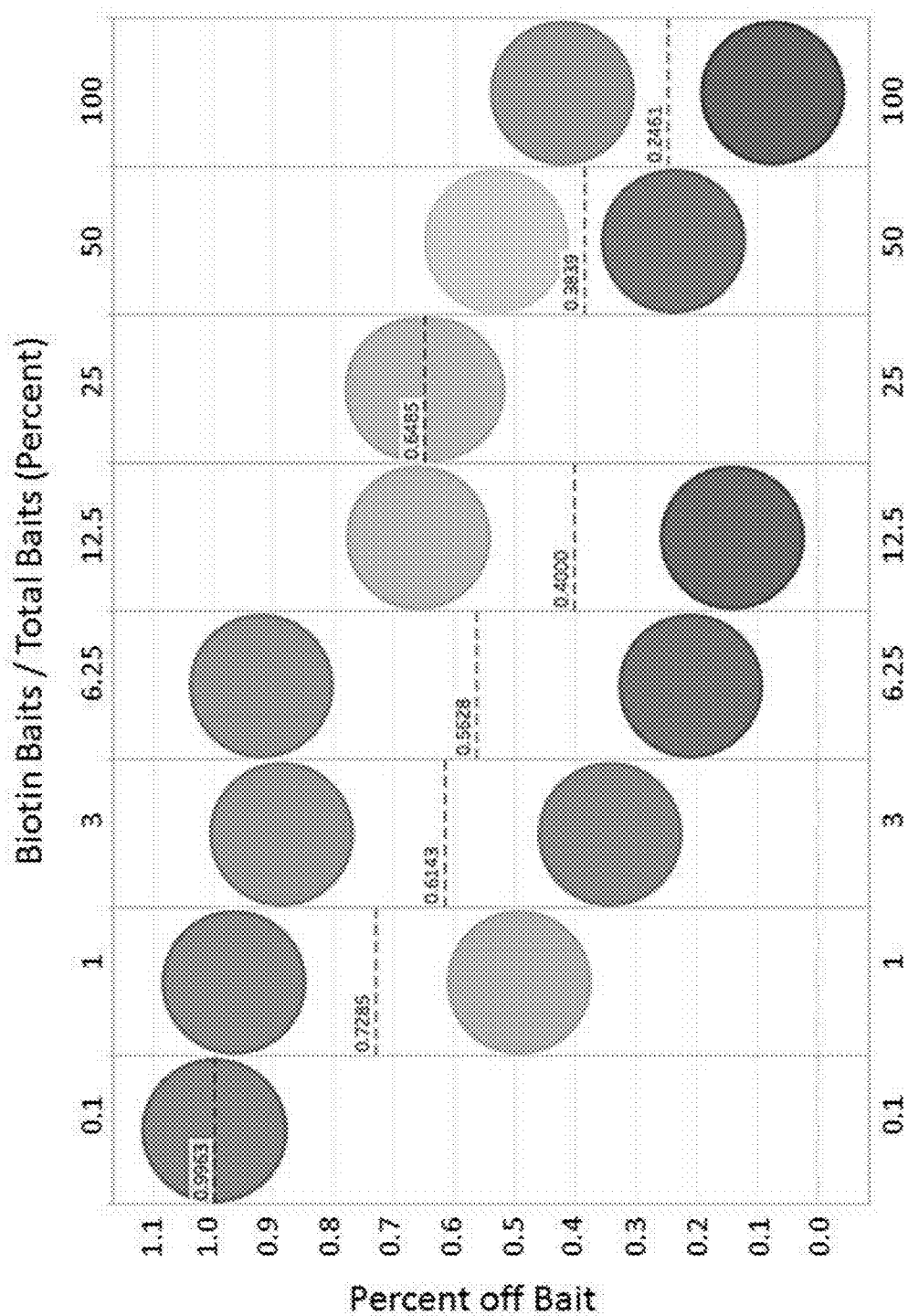
FIG. 5A depicts a plot of percent off bait vs. percent baits comprising biotin for an enrichment and sequencing analysis.
Figure 5B:
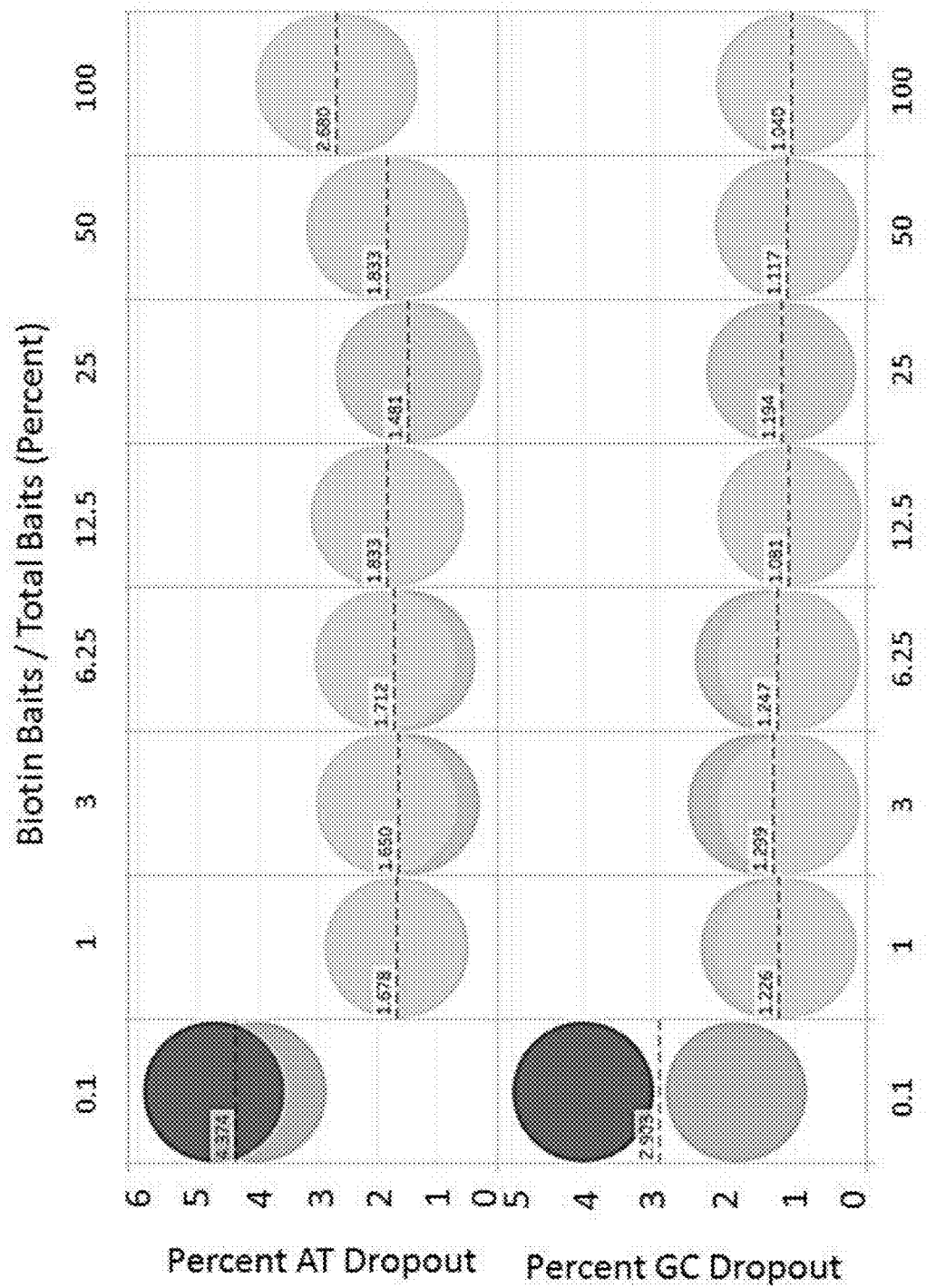
FIG. 5B depicts a plot of AT or GC dropouts vs. percent baits comprising biotin for an enrichment and sequencing analysis.

Sequencing data is acquired using the general method of Example 6, with modification: separate conditions were run varying ratios of biotinylated to non-biotinylated exome probes, and percent off bait and dropout rates were measured. Probe libraries comprising only 50% biotinylated baits achieved a percent off bait rate of less than 25% (FIG. 5A), and A/T and G/C dropout rates of less than 2% (FIG. 5B).

Example 15

Dilution Calibration

Figure 6A:
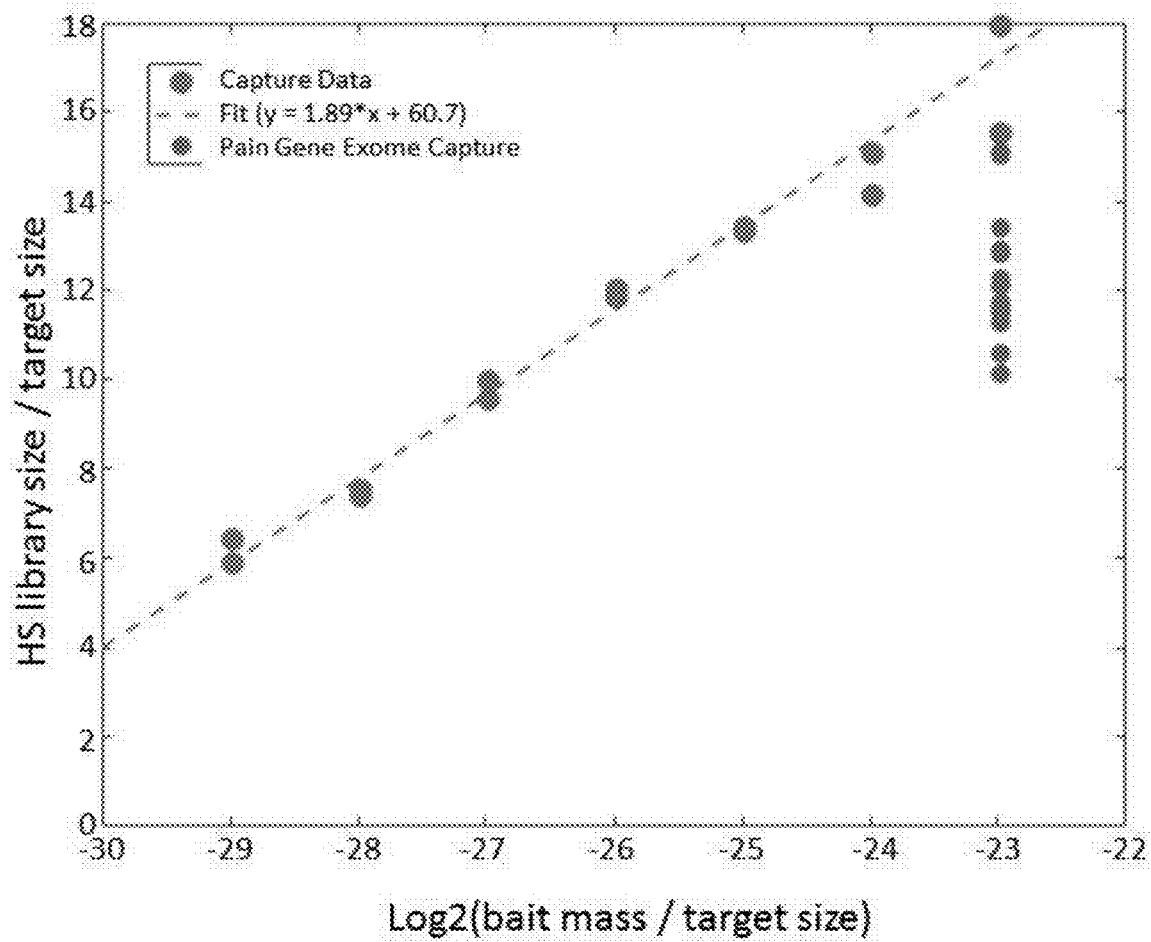
FIG. 6A depicts a plot of HS library size/target size vs. log2(bait mass/target size) for an enrichment and sequencing analysis comparing performance of an exome library and a smaller targeted pain gene exome library. The data for the exome library is fit to a linear model of dilution.
Figure 6B:
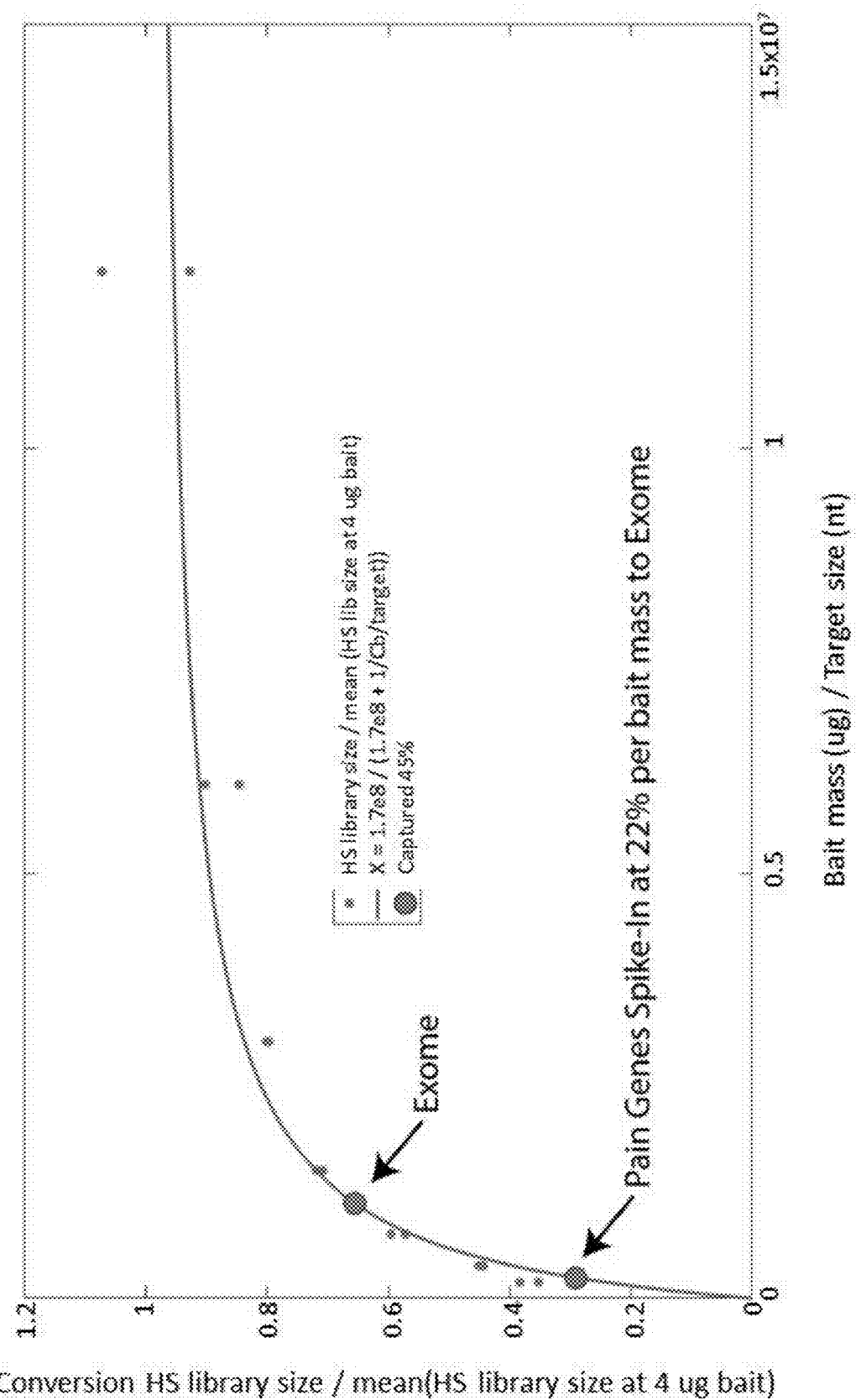
FIG. 6B depicts a plot of HS library size/target size vs. log2(bait mass/target size) for an enrichment and sequencing analysis comparing performance of an exome library and a smaller targeted pain gene exome library. The data is fit to a logarithmic model of dilution.
Figure 7:
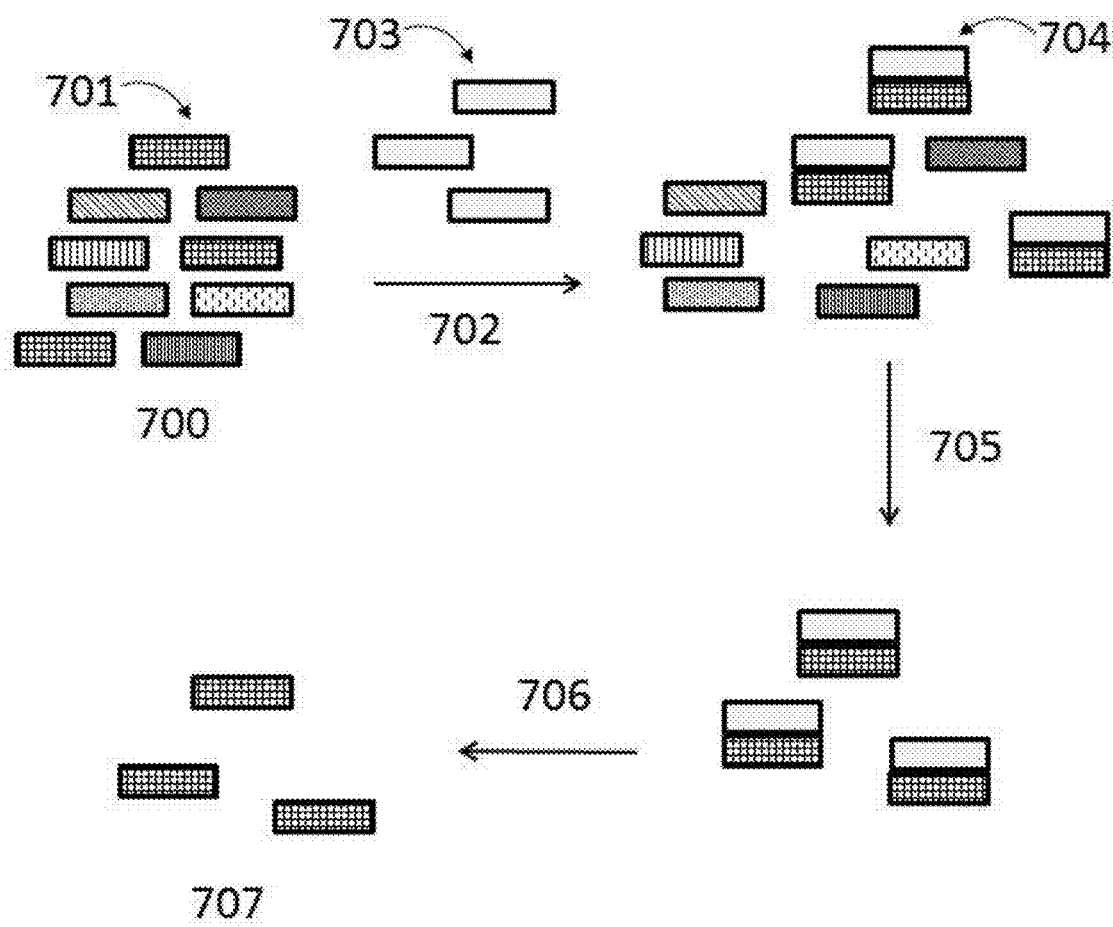
FIG. 7 depicts a schematic for enriching target polynucleotides with a target binding polynucleotide library.

Sequencing data is acquired using the general method of Example 6, with modification: separate conditions were run by varying the dilution of probes (probe mass:target size), and the HS library size:target size was analyzed. Although the exome library targets roughly followed a linear distribution, the smaller panel did not vary linearly (FIG. 6A). When the data was refit to a kinetic model, both the exome and gene panel are fit on the same curve for various dilutions (FIG. 6B). This allowed the accurate prediction of an optimal ratio of exome:gene panel probes to achieve a desired capture amount. For example, to capture 45% of the targets for both the exome and gene library, the gene panel probes were spiked in at 22% per bait mass relative to the exome library.

Example 16

Performance of a Custom Panel Library

Figure 22:
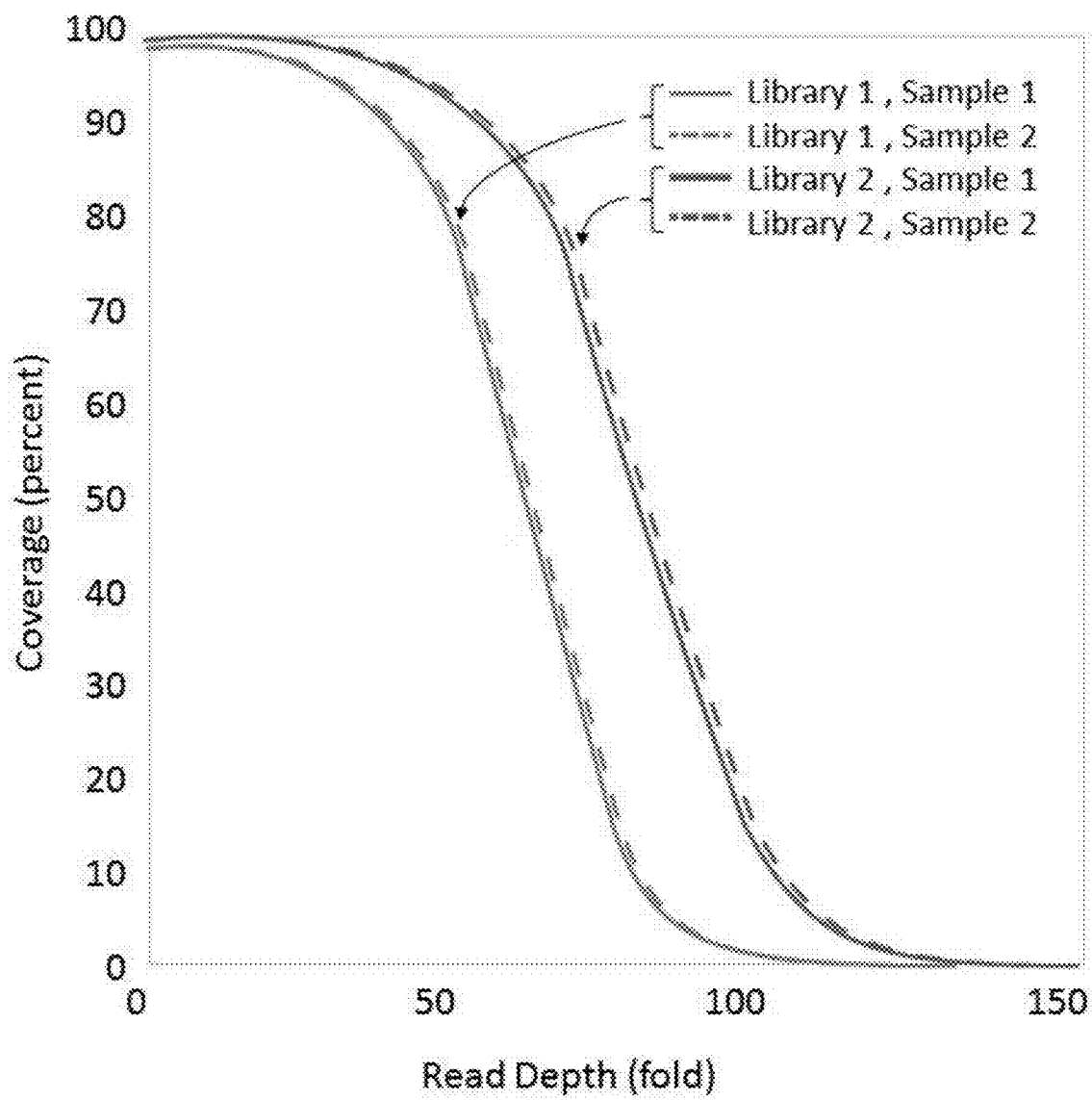
FIG. 22 is a plot of percent coverage verses read depth for an enrichment and sequencing analysis showing the performance of probe panels: Library 1 (757 kb) and Library 2 (803 kb).

Sequencing data was acquired using the general method of Example 6, with modification: two different custom probe panels Library 1 (757 kb) and Library 2 (803 kb) were used to target different areas of the genome (FIG. 22). The two panels resulted in a high percentage of on-target reads, as well as a high percentage of targets with >20% read depth (Table 10). Library 1 demonstrated an off-target rate of 9%.

TABLE 11

| Condition | HS Library Size | Fold 80 base penalty | % on-target | % targets with read depth >20% | % targets with read depth >30% |
|---|---|---|---|---|---|
| Library 1, sample 1 | 25.2 | 1.25 | 91 | 98 | 96 |
| Library 1, sample 2 | 16.9 | 1.24 | 91 | 98 | 96 |
| Library 2, sample 1 | 31.2 | 1.22 | 69 | 99 | 98 |
| Library 2, sample 2 | 24.2 | 1.22 | 70 | 99 | 98 |

Example 17

Evaluation of Probe Performance and Tuning

A subset of polynucleotide probes is selectively removed from the capture library of Example 6, and the capture/sequencing method is repeated on the same sample using the general method of Example 6. Outcome metrics such as on-bait coverage, off-target, and fold 80 base penalty are measured. The process is iterated with different probe subsets, and the sequencing results correlated. The best performing probe subsets are then combined and evaluated in a similar manner.

Example 18

Exome Probes with Additional SNP Panel

A subset of polynucleotide probes (panel) is selectively added to the capture library of Example 6, and the capture/sequencing method is repeated on the same sample using the general method of Example 6. The subset of polynucleotides targets areas of the genome comprising single nucleotide polymorphisms (SNPs). The panel allows for the identity of bases at each of the SNPs to be determined by increasing the read depth at these sites, including sites which are heterozygous.

Example 19

Exome Probes with an Intron Panel

Sequencing data is acquired using the general method of Example 6, with modification: a second polynucleotide probe library which targets introns is mixed with the exome library. This results in additional sequencing coverage of these genomic regions. Data not shown.

Example 20

Universal Blockers with Bridged Nucleic Acids (8-Plex)

Sequencing data is acquired using the general method of Example 6, with modification: adapter-tagged genomic fragments comprising 8 different barcode sequences are used, and four different polynucleotide blockers are evaluated for their ability to reduce off-target binding.

Example 21

Exome Probes with a Custom Panel

Sequencing data is acquired using the general method of Example 6, with modification: different combinations of probe sets are evaluated. Two different exome probe libraries are used (Exome 1 and Exome 2) as well as either Library 1 or Library 2 which target additional regions of the genome. Both exome panels are evaluated individually, as well as with Library 1 or Library 2 panels mixed in with each. Sequencing metrics are obtained and evaluated for both the exome, as well as areas targeted by Library 1 or Library 2.

Example 22

Universal Blockers with Improved On-Target Performance

Figure 23A:
FIG. 23A is a schematic of universal blockers.
Figure 23B:
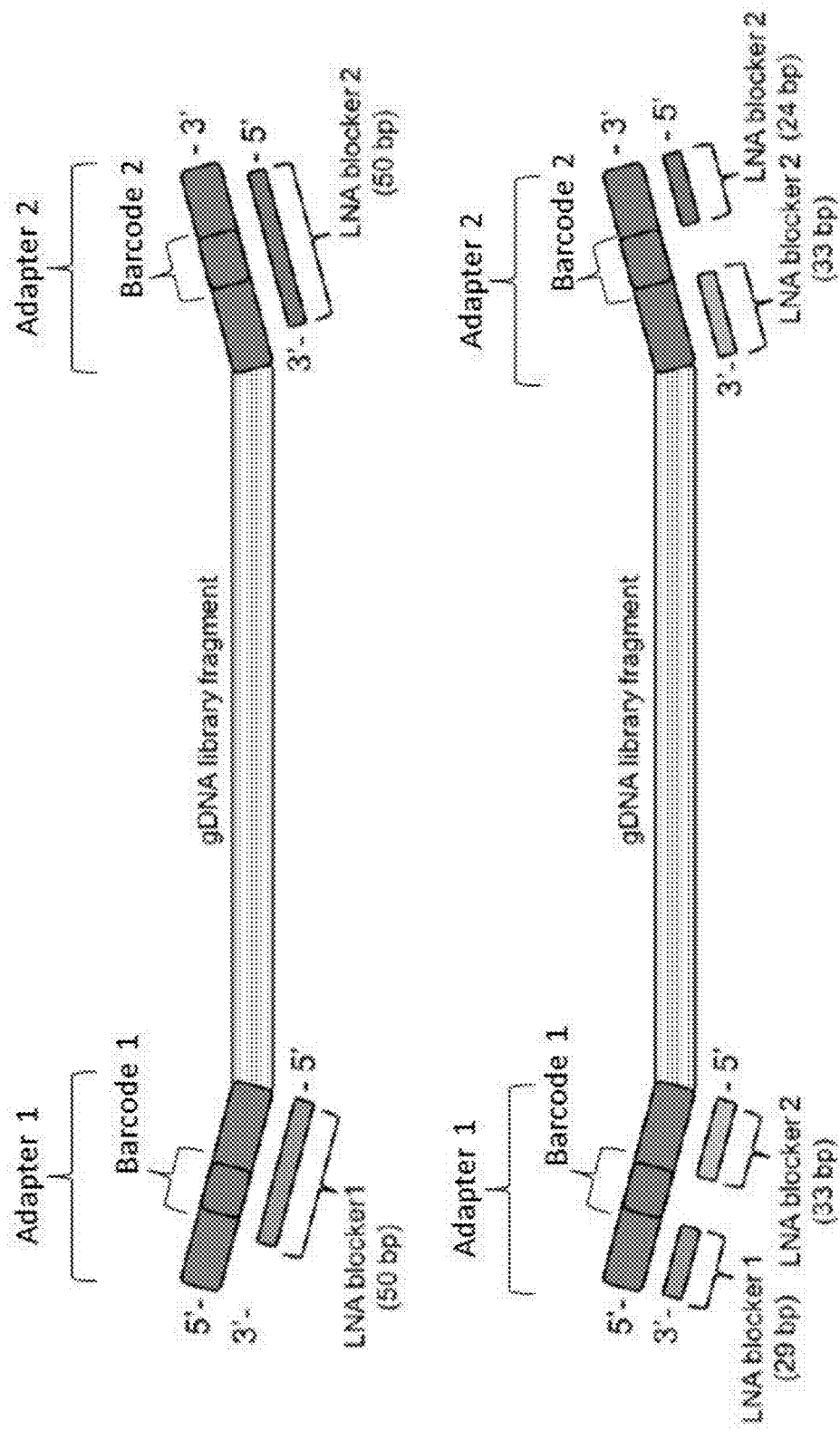
FIG. 23B is a schematic of LNA blocker designs.
Figure 24:
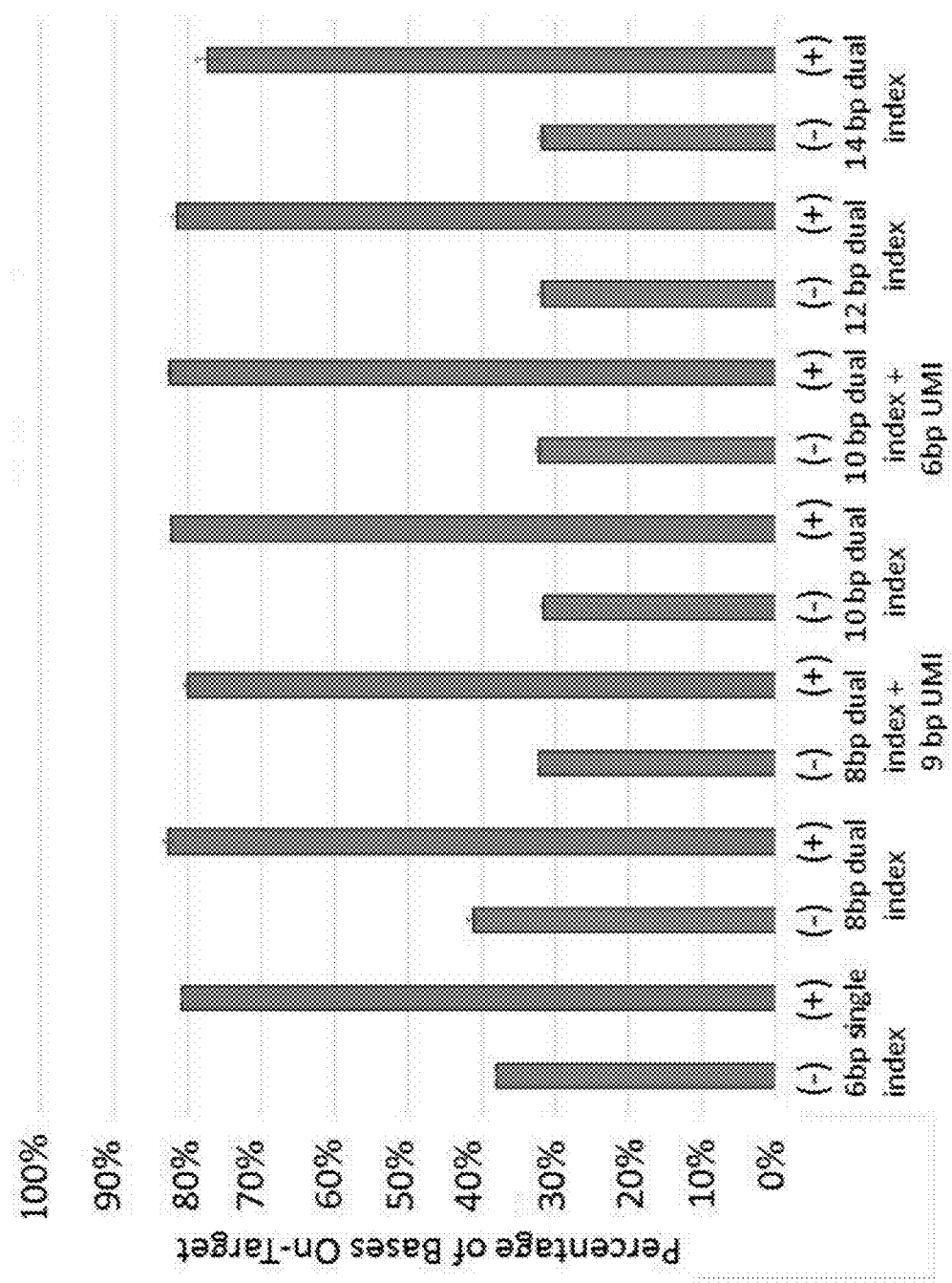
FIG. 24 is a graph of on-target performance across for various index designs.
Figure 25:
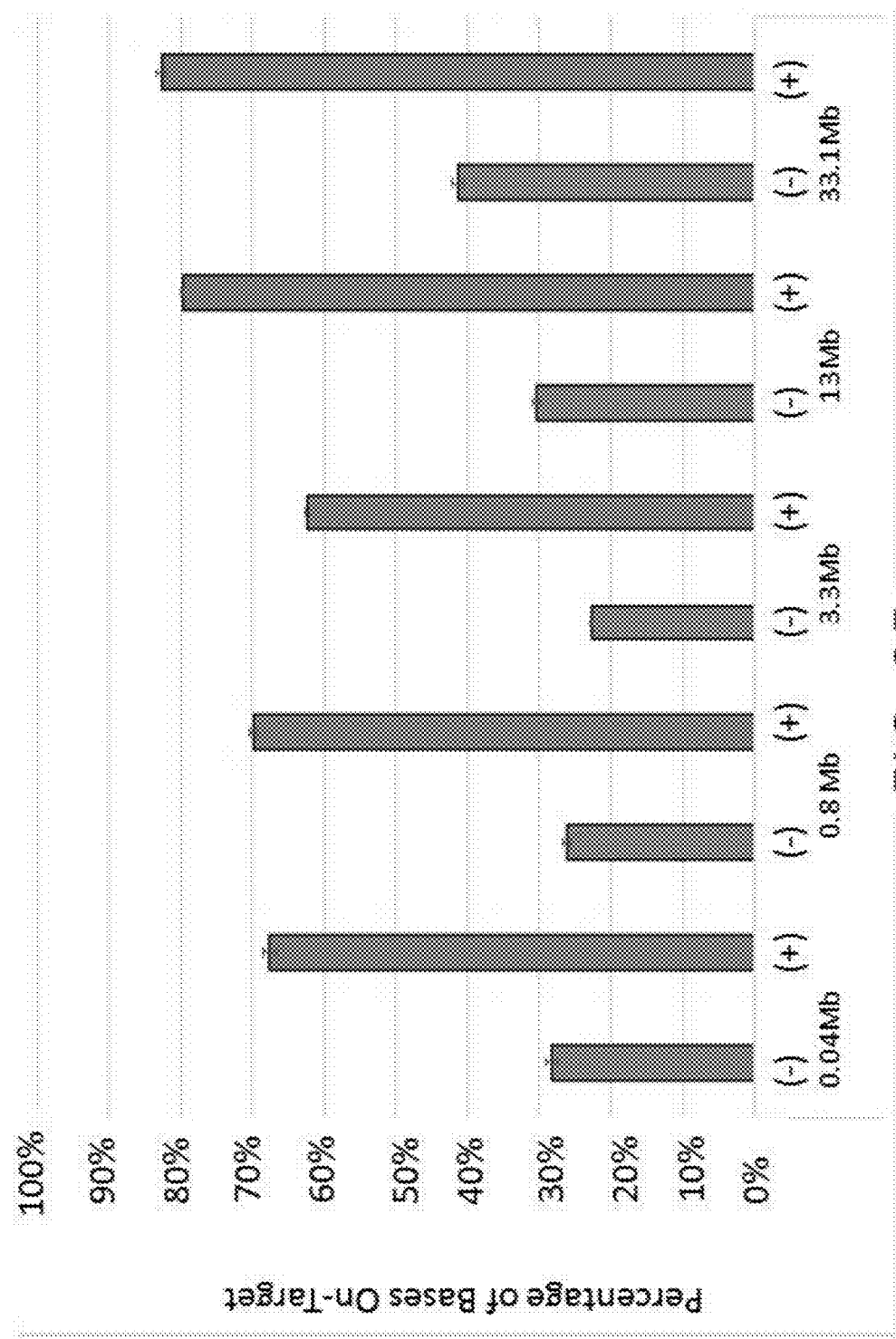
FIG. 25 is a graph of on-target performance across for various panel sizes.

Universal blockers were used with adapter-tagged genomic fragments. See as an example FIG. 23A. Individual libraries were generated from a single genomic source (NA12878; Coriell) and compatible adapters. Each prepared library was then captured either in the absence or presence of universal blockers. Following sequencing, reads were downsampled to 150× of targeted bases and evaluated using Picard metric tools with a MapQuality filter=20. Error bars denote one standard deviation; N≥2. As seen in FIG. 24, there was improved on-target performance across a wide range of index designs. Cot DNA was present in all samples. As seen in FIG. 25, there was improved on-target performance across a range of panel sizes using the universal blockers.

Example 23

Custom Panel Designs Across a Range of Panel Sizes and Target Regions

Sequencing data was acquired using the general method of Example 6. Details of the library are seen in Table 12.

Figure 26A:
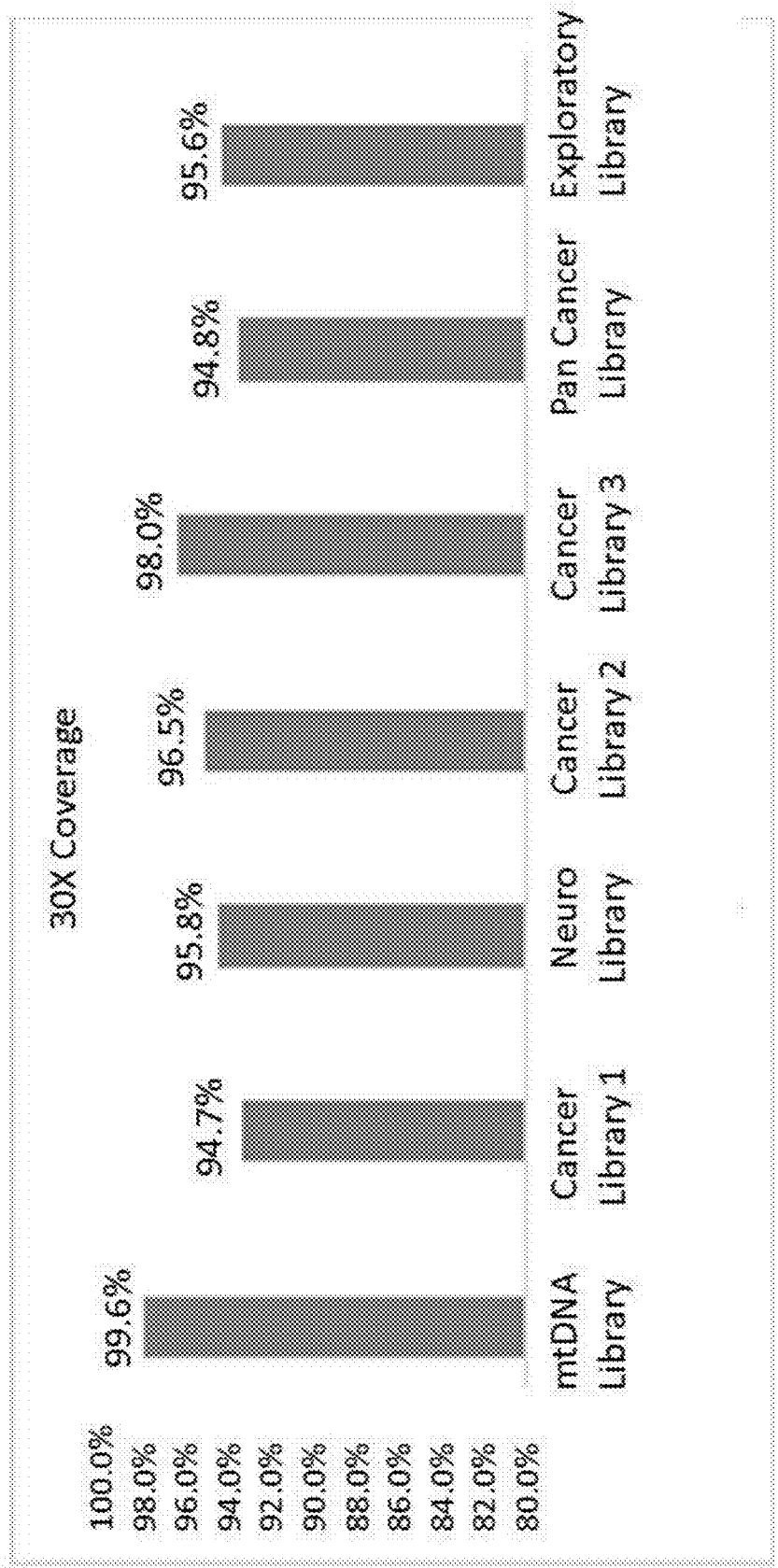
FIG. 26A is a graph of percentage of reads in each custom panel achieving 30× coverage.
Figure 26B:
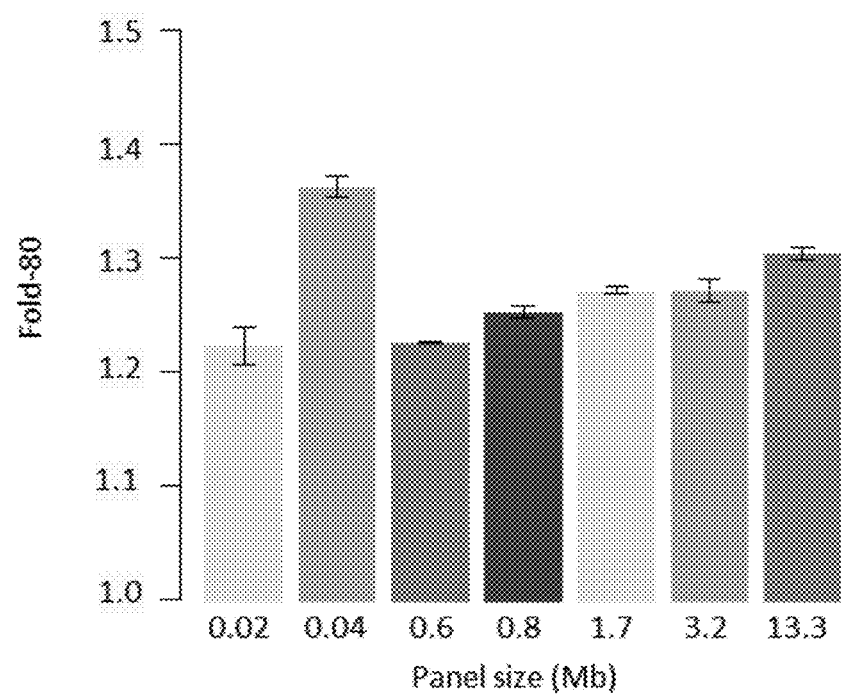
FIG. 26B is a graph of uniformity (fold-80) of each custom panel.

Briefly, hybrid capture was performed using several target enrichment panels designed herein using 500 ng of gDNA (NA12878; Coriell) per single-plex pool following manufacturer's recommendations. Sequencing was performed with a NextSeq 500/550 High Output v2 kit to generate 2×76 paired end reads. Data was downsampled to 150× of target size and analyzed using Picard Metrics with a mapping quality of 20; N=2. The panels resulted in a high percentage of on-target reads, as well improved uniformity and low duplication rate (Table 12). FIG. 26A shows percentage of reads in each panel achieving 30× coverage and FIG. 26B shows uniformity (fold-80).

TABLE 12

| Panel Description | | | | Performance (Picard Metrics) | | |
| --- | --- | --- | --- | --- | --- | --- |
| Name | Target Size (Mb) | Probes | Genes | Uniformity (Fold-80) | On-Target Rate | Duplication Rate |
| mtDNA Library | 0.017 | 139 | 37 | 1.22 | 82% | 0.8% |
| Cancer Library | 0.037 | 384 | 50 | 1.36 | 68% | 1.9% |
| Neurodegenerative Library | 0.6 | 6,024 | 118 | 1.23 | 61% | 1.0% |
| Cancer Library 2 | 0.81 | 7,446 | 127 | 1.25 | 70% | 2.2% |
| Cancer Library 3 | 1.69 | 19,661 | 522 | 1.27 | 78% | 1.4% |
| Pan-Cancer Library | 3.4 | 31,002 | 578 | 1.27 | 62% | 1.9% |
| Exploratory Cancer Library | 13.2 | 135,937 | 5,442 | 1.30 | 80% | 3.0% |

Example 24

Custom Panel Performance During Multiplex Target Enrichment

Figure 27A:
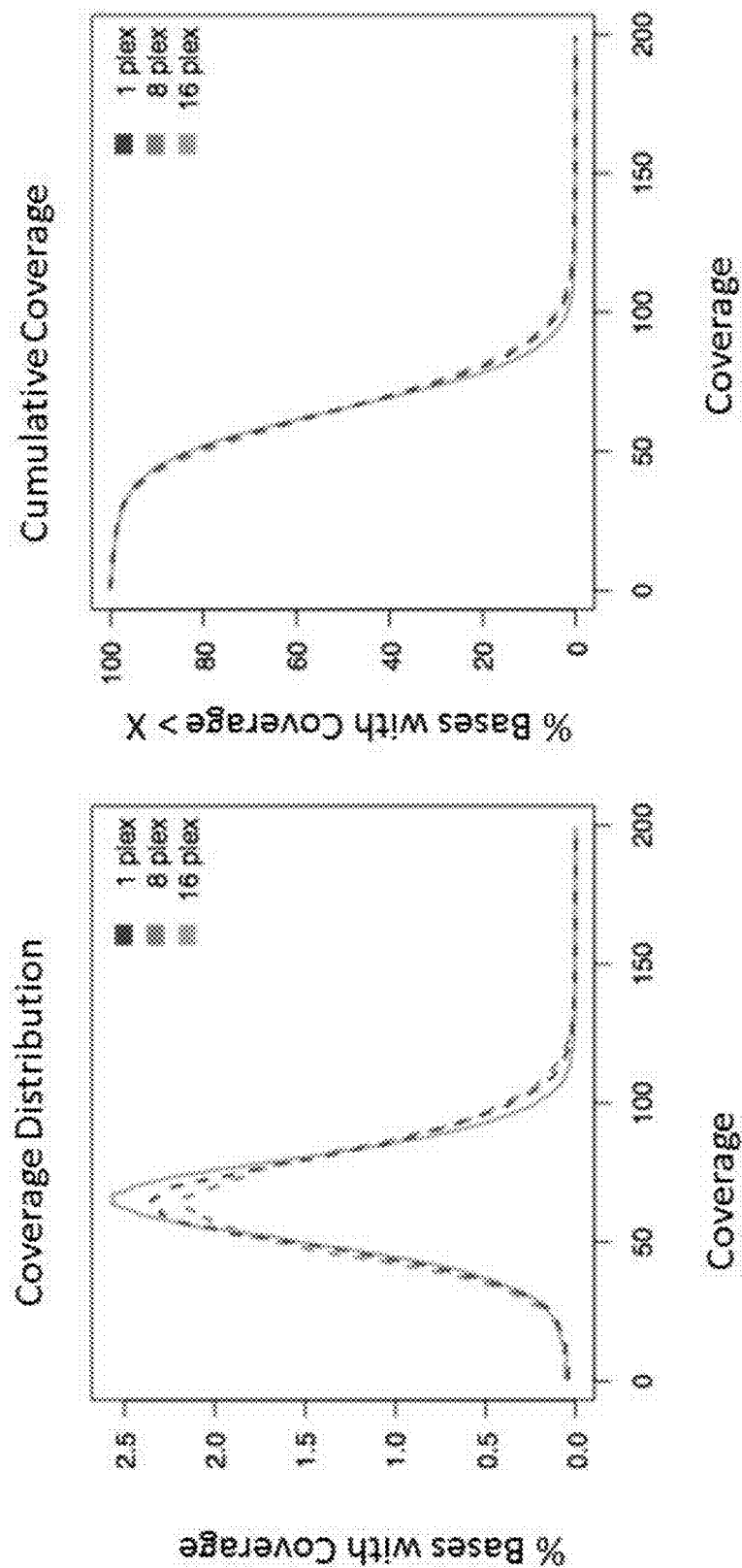
FIG. 27A shows performance data using 810 kb panel.

Sequencing data was acquired using the general method of Example 6. Data from multiplex target enrichment is seen in Table 13 below and FIG. 27A. FIG. 27A shows coverage distribution and cumulative coverage with the x-axis for both charts of FIG. 27A is coverage, and the y-axis for the left chart is % bases with coverage, and for the right chart is bases with % bases with coverage>X. All data were subsampled to 150× coverage. MapQuality filter=20. Sequencing was performed on an Illumina® NextSeq® instrument using 2×76 reads. The data show high uniformity for all levels of multiplexing, high on-target rates that do not vary with higher levels of multiplexing, and low duplication rates across all levels of multiplexing.

TABLE 13

| | Performance (Picard Metrics) | | |
| --- | --- | --- | --- |
| Multiplexing | Uniformity (Fold-80) | On-Target Rate | Duplication Rate |
| Singleplex | 1.25 | 70% | 1.8% |
| 8-Plex | 1.27 | 69% | 2.2% |
| 16-Plex | 1.30 | 69% | 2.7% |

Figure 27B:
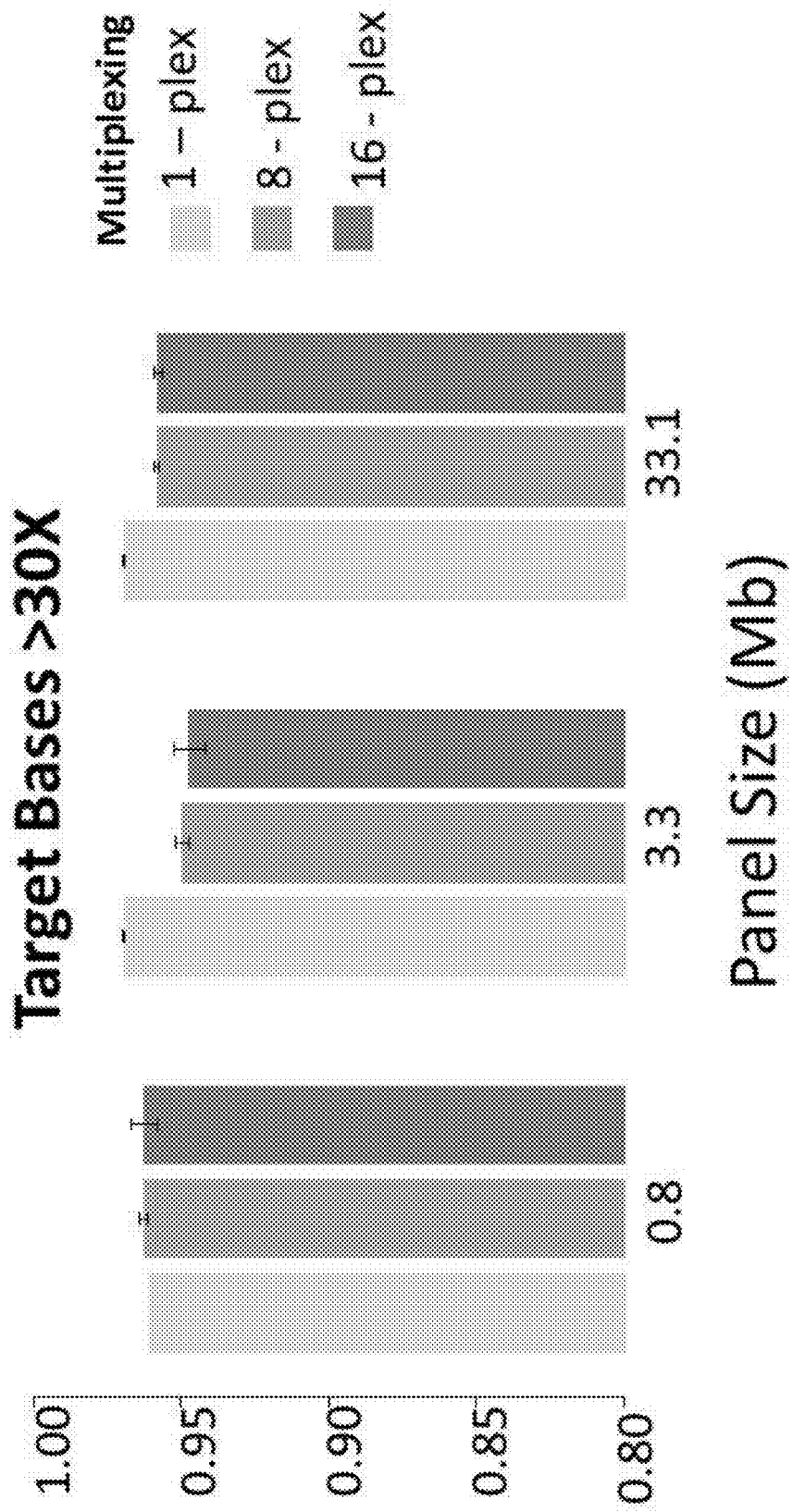
FIG. 27B shows multiplexing performance for three panels at 1-, 8-, or 16-plex.

Probes were designed to maximize the capture of unique molecules and minimize sequencing duplicates to delivery high multiplex performance. High capture performance was determined on three panels of 800 kb, 3.3 Mb and a fixed Exome of 33.1 Mb. Consistent capture coverage at 30× is observed across all samples and multiplexing conditions (FIG. 27B). The magnitude of duplicate rate increase was minimal. For an 800 kb panel duplication rate increased from 1.8% to 2.7% between 1-plex and 16-plex captures, respectively, and similar observations were made with larger panels. The impact to performance was confirmed with consistent 30× coverage.

Figure 27C:
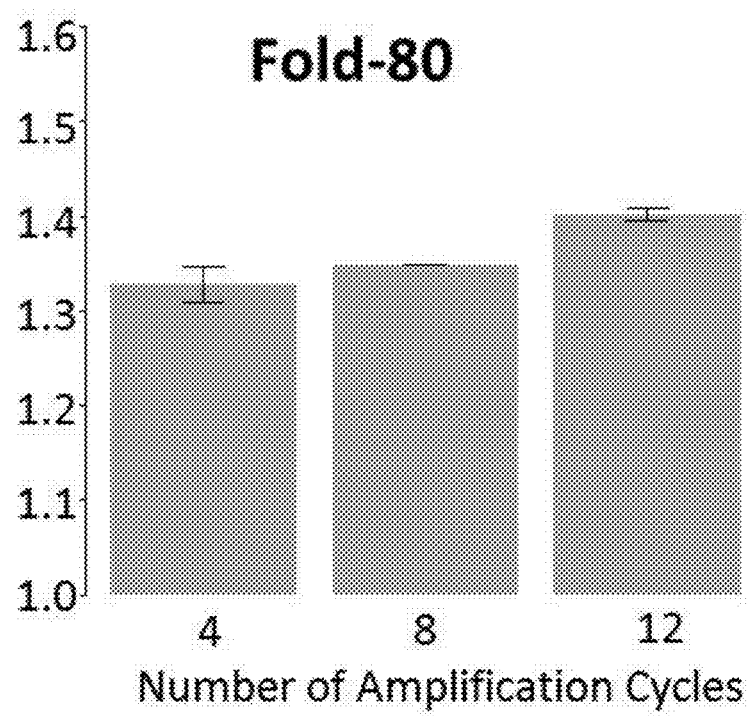
FIG. 27C shows effects of PCR cycles on uniformity.

Probes were also designed to support multiplexing without increasing sample mass. Hybrid capture was performed using an exome target enrichment panel described herein (33.1 Mb) using 500 ng of library (NA12878; Coriell) as a single-plex capture following manufacturer's recommendations. N=2. FIG. 27C shows effect on number of PCR cycles on uniformity.

Figure 27D:
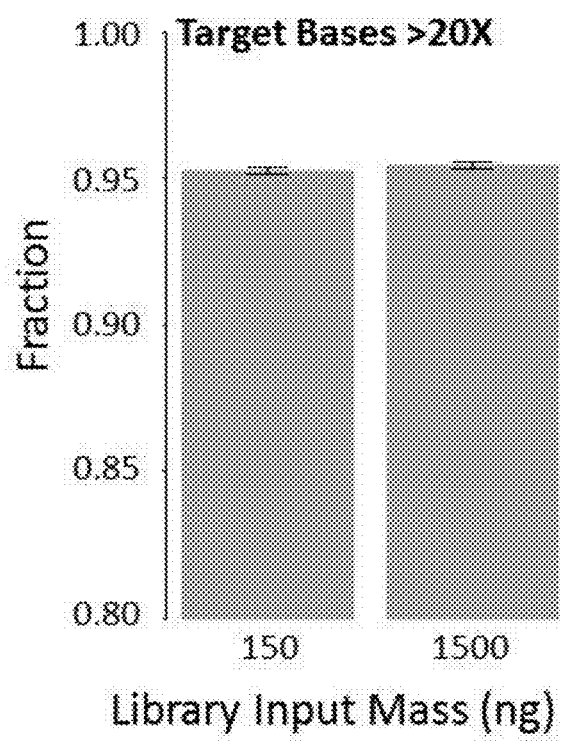
FIG. 27D shows effects of library input mass on capture.

Hybrid capture was performed using an exome target enrichment panel described herein (33.1 Mb) using 150 ng (18.75 ng per library) or 1500 ng (187.5 ng per library) of library (NA12878; Coriell) per 8-plex pool following manufacturer's recommendations. Data was down-sampled to 100× of target size; N=2. Consistent 30× coverage clearly demonstrates the capacity of this system to multiplex with reduced mass input without degradation to performance (FIG. 27D).

Example 25

Custom Panel Reproducibility

Figure 28A:
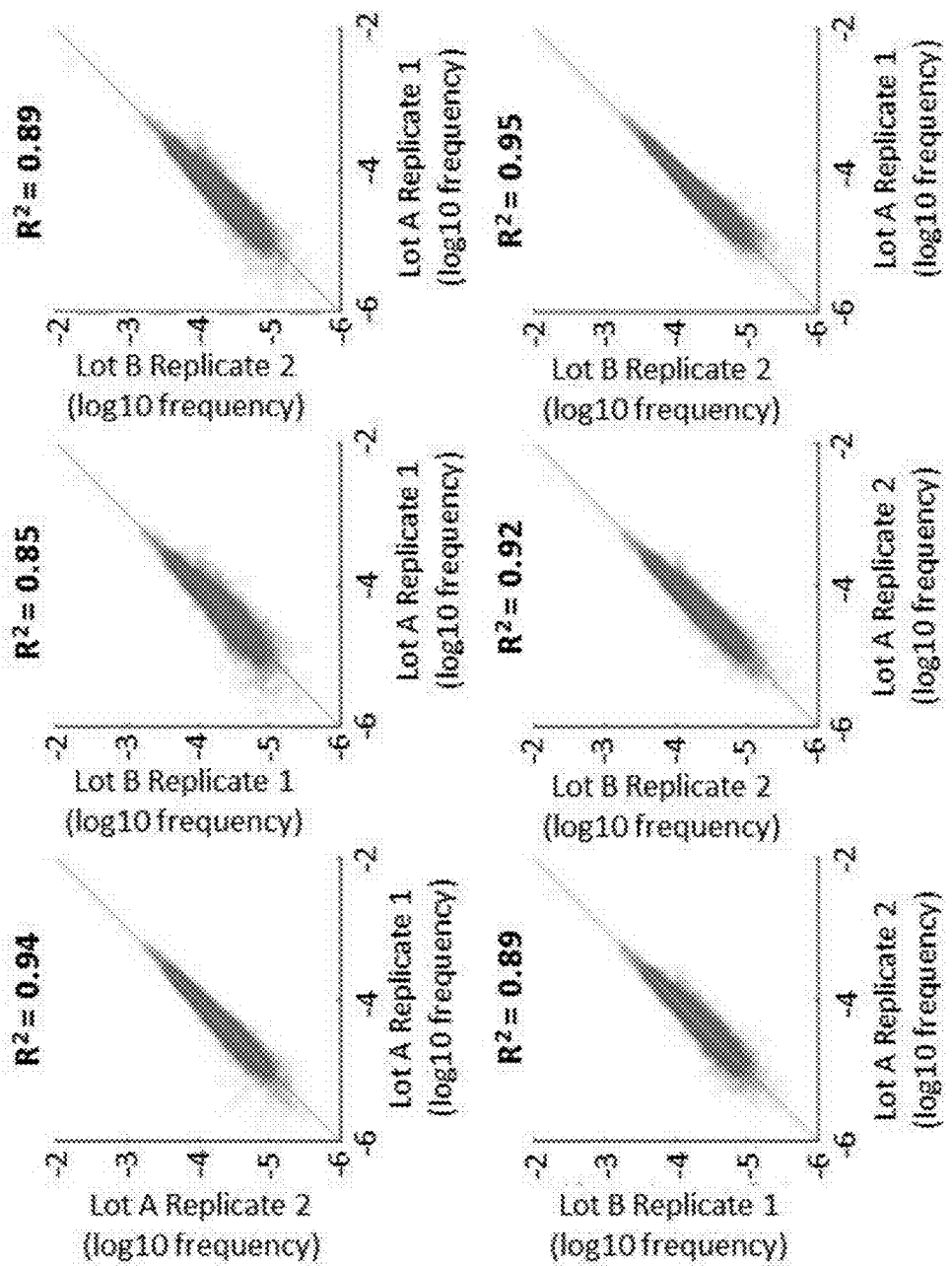
FIGS. 28A-28I show reproducibility between custom panels.
Figure 28B:
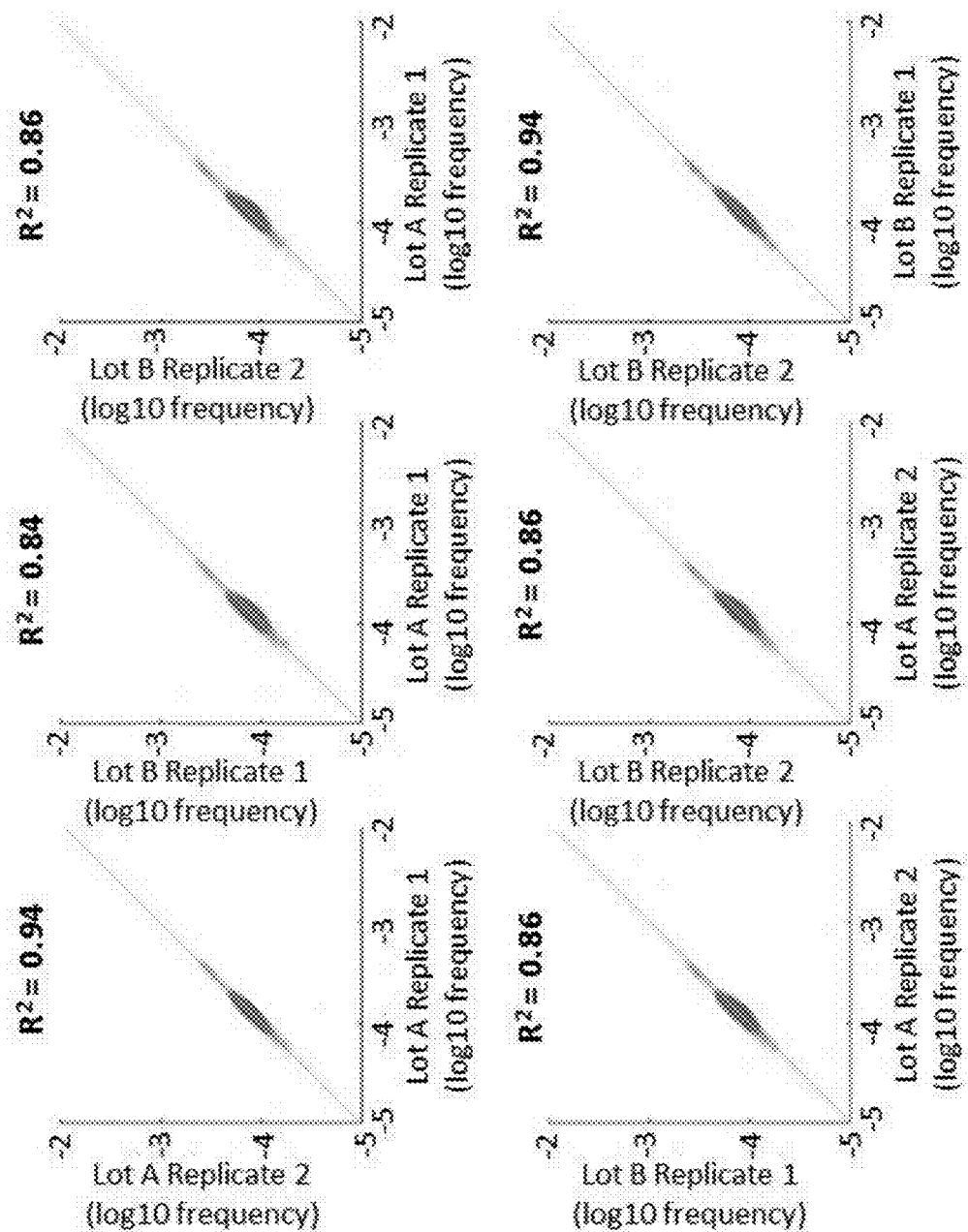

Sequencing data was acquired using the general method of Example 6 to assess the reproducibility of custom panels from lot to lot. As seen in FIGS. 28A-28I, the custom panels demonstrate a low lot-to-lot variation. Lots A and B were independent lots produced using two synthesis runs. Each dot represents probe abundance (FIG. 28A) or probe coverage following NGS target enrichment at 1500× coverage (FIG. 28B). FIG. 28A shows consistent quality of 800 kb panels as assessed by NGS.

Figures 28C, 28D:
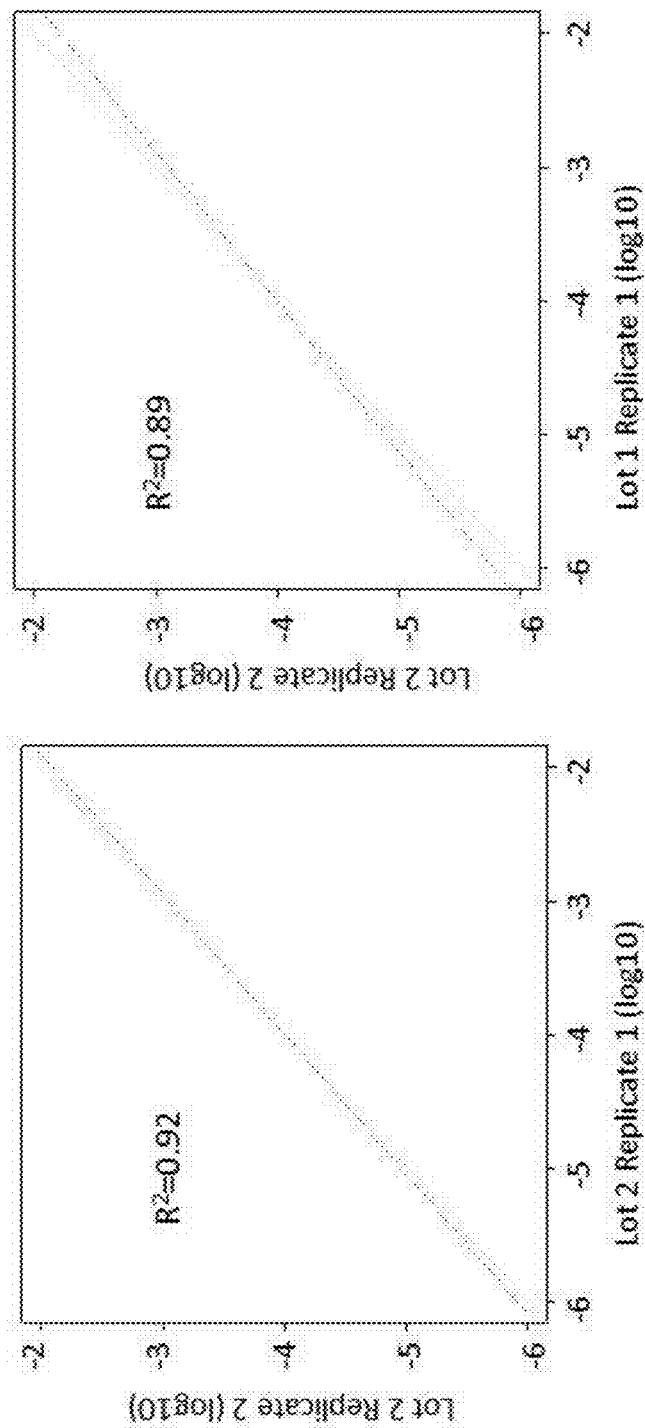

A panel containing roughly 7,400 probes (800 kb) was re-synthesized ~1 month apart (Lot1 and Lot2), with two amplification replicates in each Lot (Replicate 1 and 2). FIG. 28C shows reproducibility of probe representation within same synthesis and different amplifications. FIG. 28D shows reproducibility of probe representation between syntheses.

Figure 28E:
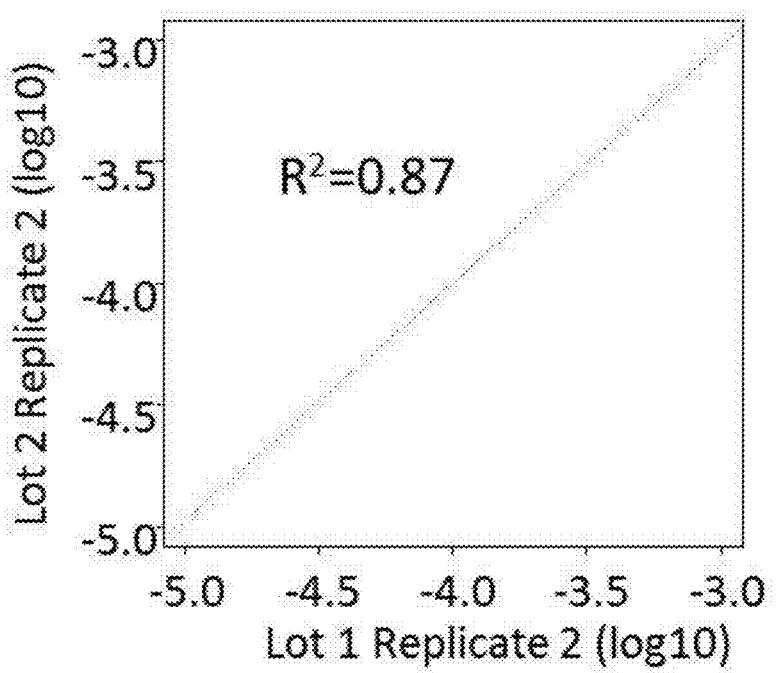
Figures 28F, 28G:
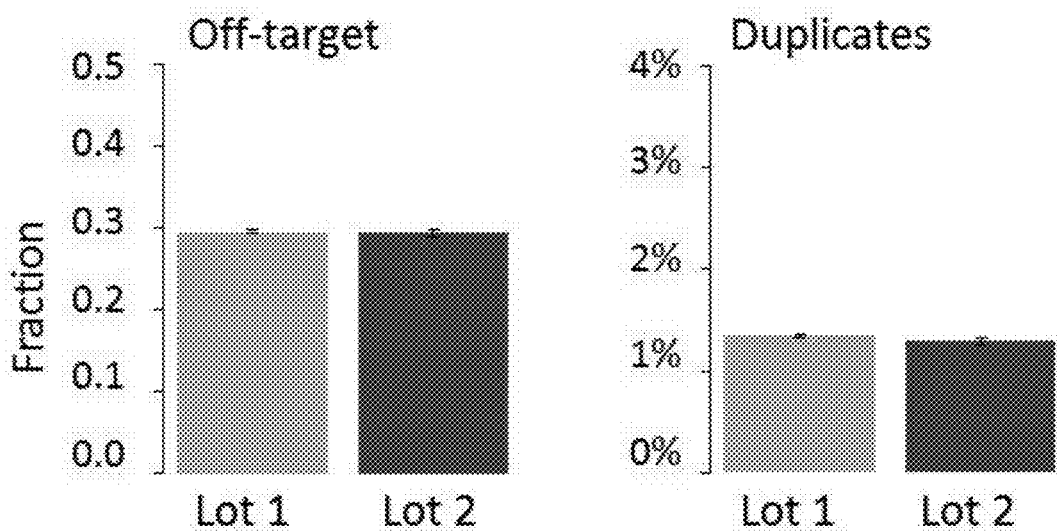
Figure 28H:
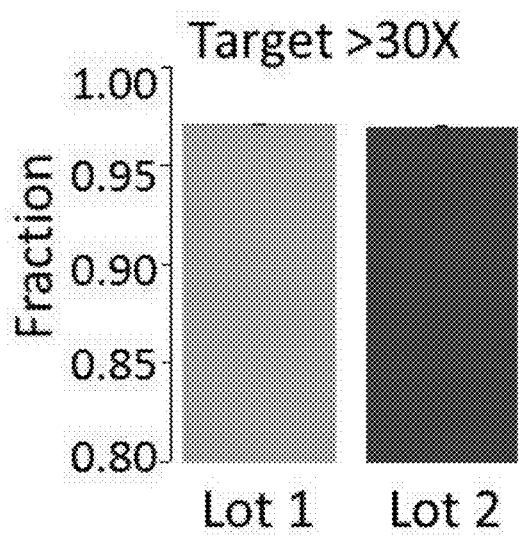
Figure 28I:
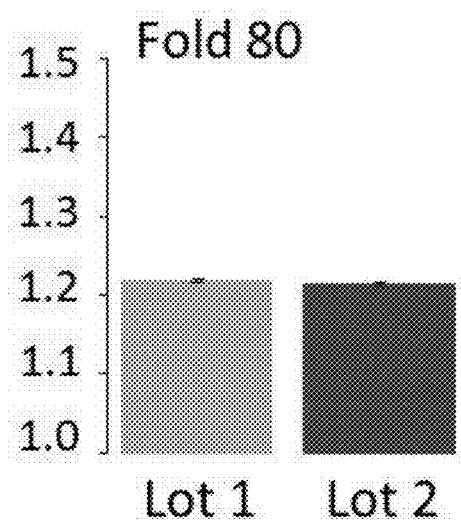

FIGS. 28E-28I show data that was downsampled to 150× of target size and analyzed using Picard Metrics with a mapping quality of 20; N=2. FIG. 28E show lot to lot reproducibility capture per probe. FIGS. 28F-28I show reproducibility of probe target enrichment performance between syntheses.

Example 26

Flexible and Modular Custom Panels

Content can be added to or enhanced. See FIG. 29A. Adding content to the panel increases the number of targets covered. Enhancing content to the panel refers to the coverage of specific regions.

3 Mb of additional target regions was added derived from the RefSeq database. The production of this panel increased coverage and did not decrease performance. Coverage improved to >99% of the RefSeq, CCDS, and GENCODE databases. Further, the custom panel displayed high uniformity and on-tamet rate, as well as a low duplicate rate (all results based on 150× sequencing).

The database coverage as seen in Table 14 was increased using the custom panels as described herein. The data compared the overlap between panel content to the protein-coding regions in the databases annotated on the primary human genome assembly (alternative chromosomes were excluded) as of May 2018 (UCSC genome browser). A1, A2, and I-1 are commercially available comparator panels from different vendors. Comparisons were performed using the BEDtools suite and genome version indicated in parentheses. The addition of 3 Mb of content improved the coverage of RefSeq and GENCODE databases to >99%.

TABLE 14

| | Database Coverage | | |
| --- | --- | --- | --- |
| | RefSeq (35.9 Mb) | CCDS21 (33.2 Mb) | GENCODE v28 (34.8 Mb) |
| Panel 1 | 92.3% | 99.5% | 95.1% |
| Panel 1 + Added Content | 99.2% | 99.5% | 99.1% |
| A-1 (hg19)* | 88.3% | 91.9% | 90.8% |
| A-2 (hg38)* | 91.0% | 94.6% | 94.0% |
| I-1 (hg19) | 94.1% | 98.3% | 95.7% |

Figure 29B:
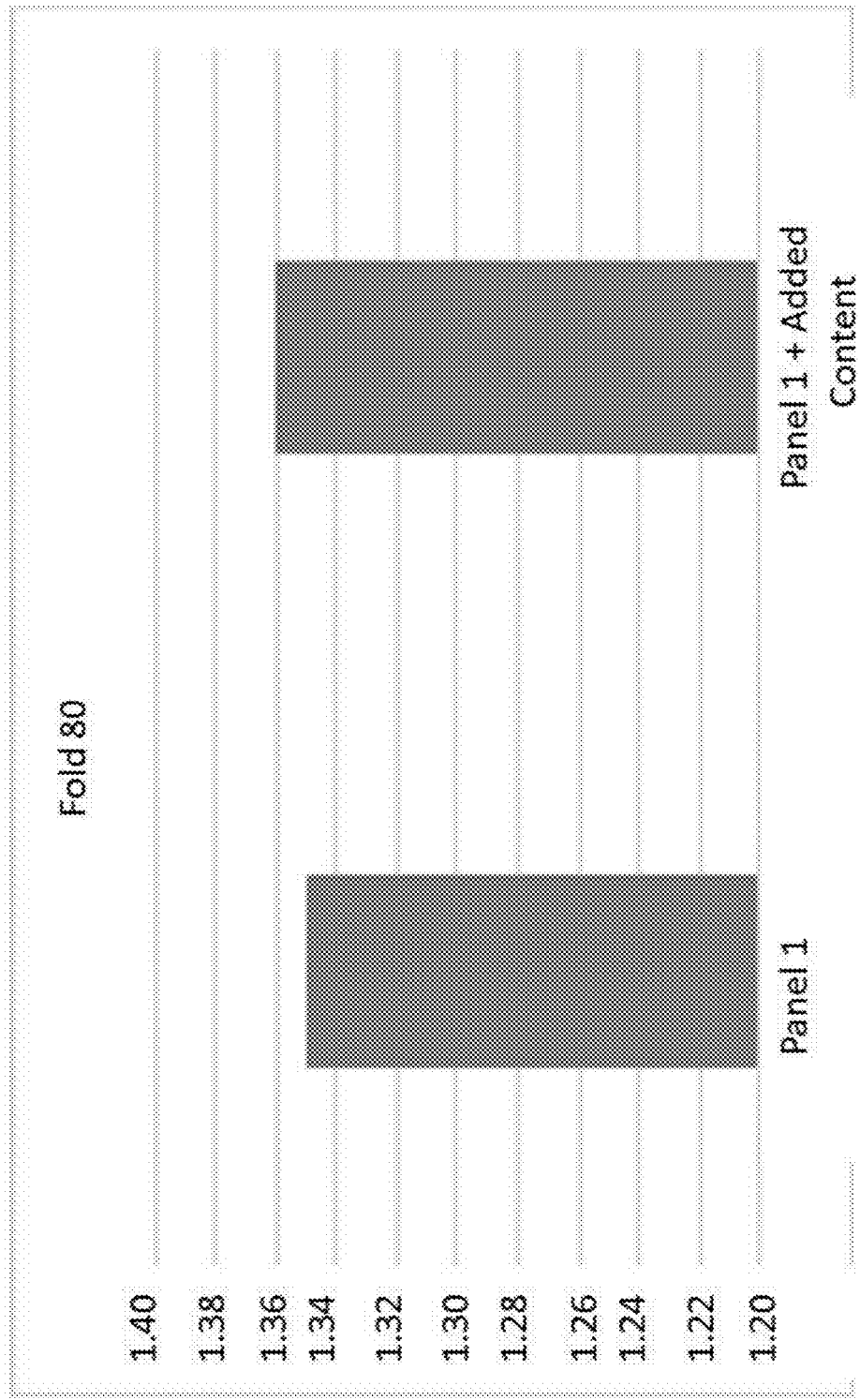
FIG. 29B is a graph of uniformity (fold-80) comparing a panel with and without added content.
Figure 29C:
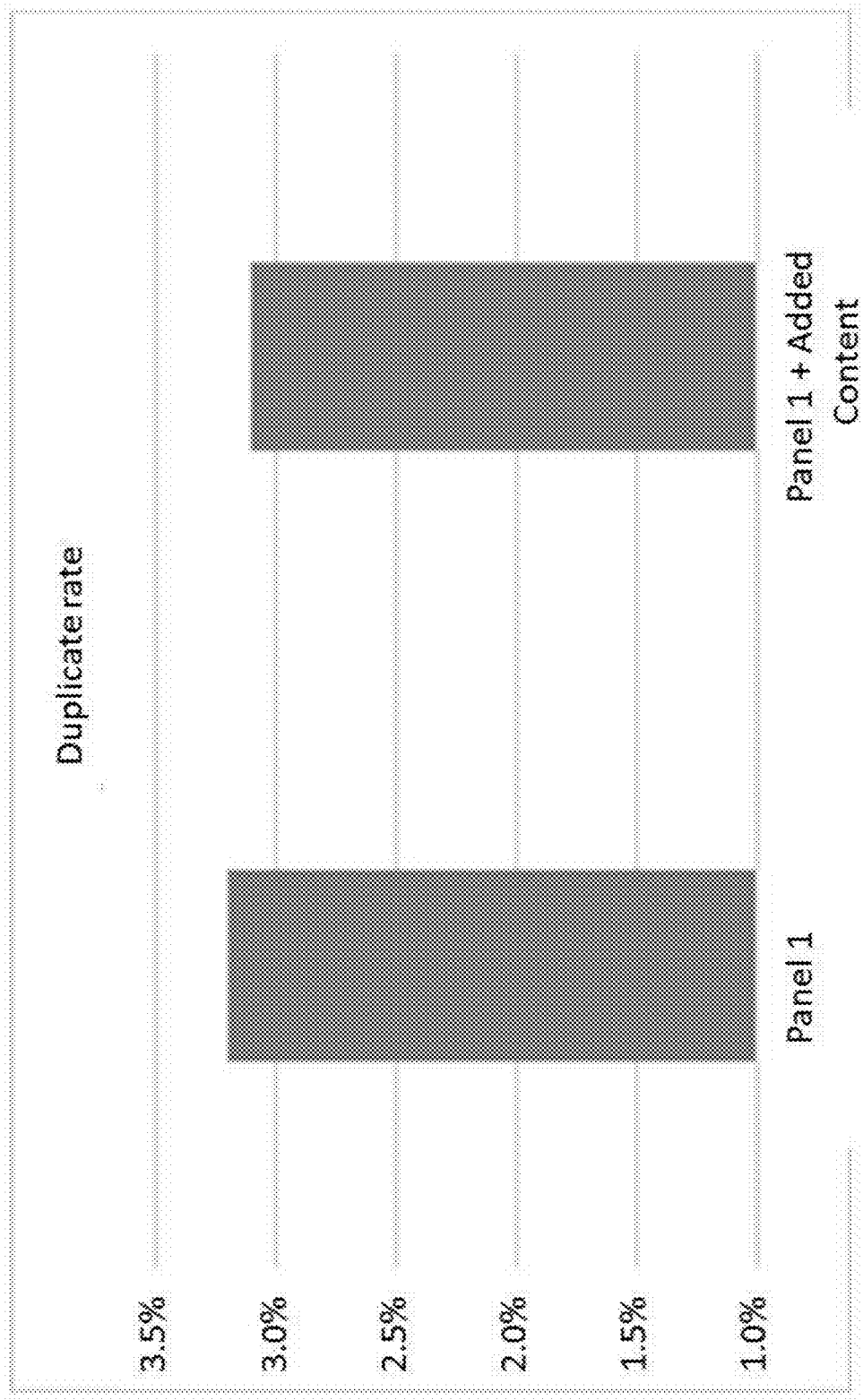
FIG. 29C is a graph of duplicate rate comparing a panel with and without added content.
Figure 29D:
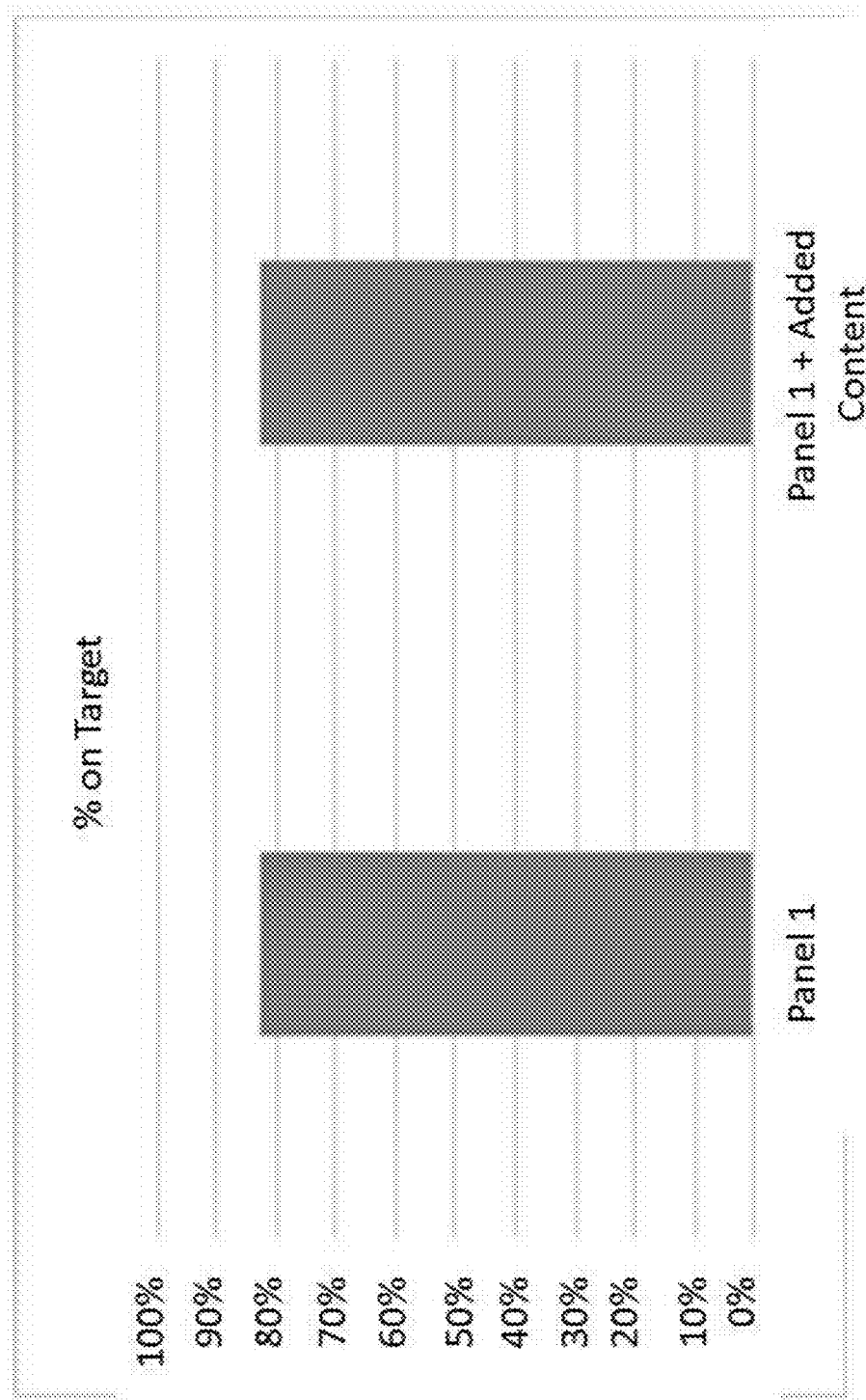
FIG. 29D is a graph of percent on rate comparing a panel with and without added content.
Figure 29E:
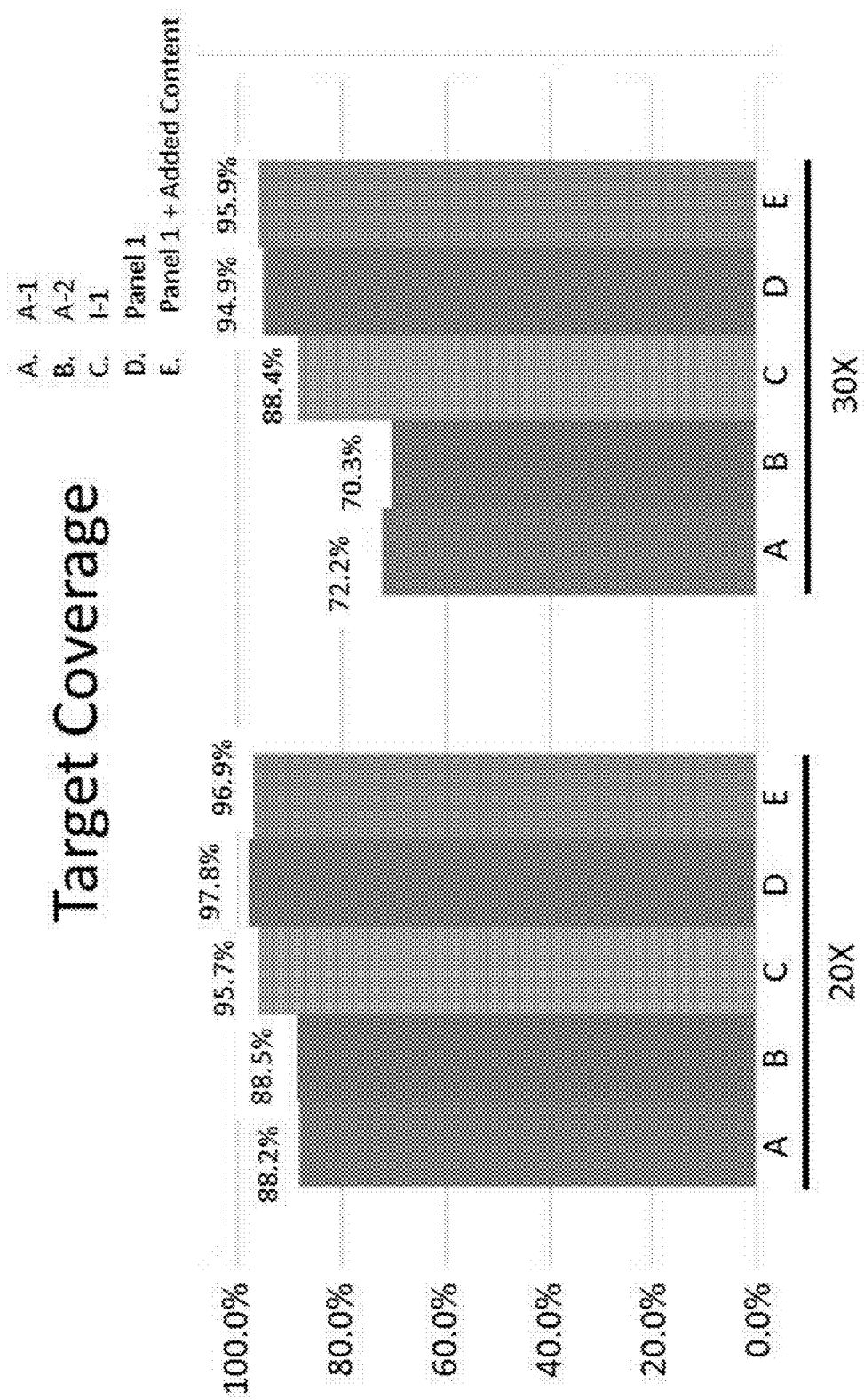
FIG. 29E is a graph of percent target coverage comparing a panel with and without added content, and comparator enrichment kits.
Figure 29F:
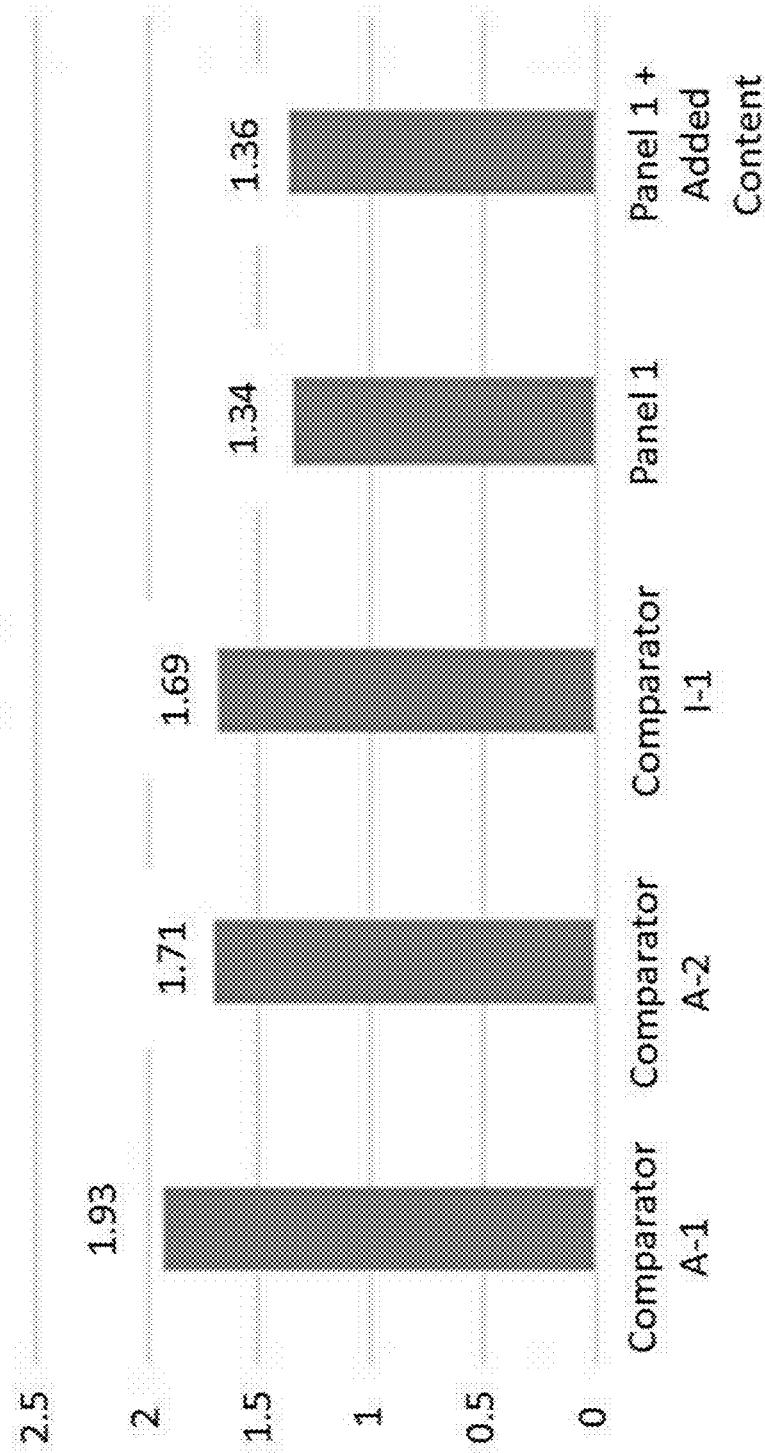
FIG. 29F is a graph of 80-fold base penalty comparing a panel with and without added content, and comparator enrichment kits.

FIGS. 29B-29D show data from Panel 1 and Panel 1+Added Content on Fold (FIG. 29B), duplicate rate (FIG. 29C), and percent on target (FIG. 29D). FIG. 29E and FIG. 29F show comparative data for target coverage (FIG. 29E) and fold-80 base penalty (FIG. 29F).

Example 27

Effect of 30,000 Probes on Capture

Figure 30A:
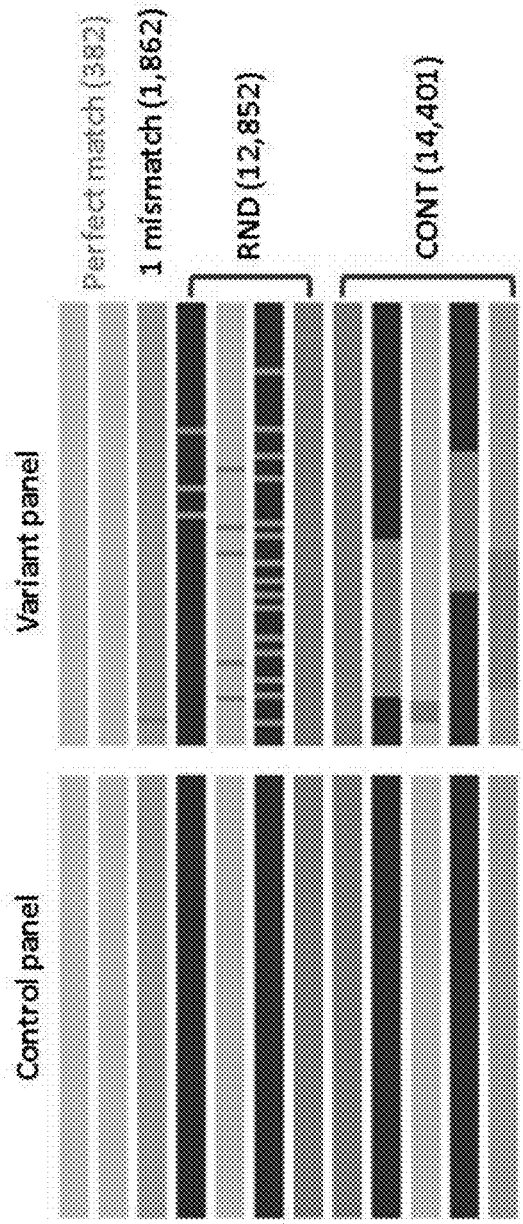
FIG. 30A shows a design of control and variant panels.

The effect of mismatches on capture was determined for optimizing probe design. To examine the effects of number and distribution of mismatches on capture efficiency, two panels, Control and Variant were designed and synthesized. Each panel (Variant and Control) contained 28,794 probes. The Control panel contained probes selected from the human exome panel designed and synthesized using methods as described herein that perfectly match the human genome reference. The Variant panel contained the same probes but with 1-50 mismatches distributed at random, or as one continuous stretch (FIG. 30A). In the control panel, the probes were designed to be complementary to their targets. In the variant panel 1-50 mismatches (yellow) were introduced either randomly along the probe (RND) or all together in a single continuous stretch (CONT). Also, 382 control probes without mismatches were added to both panels for normalization (in grey), thus the Control and Variant pools contained a total of 29,176 probes.

Figure 30B:
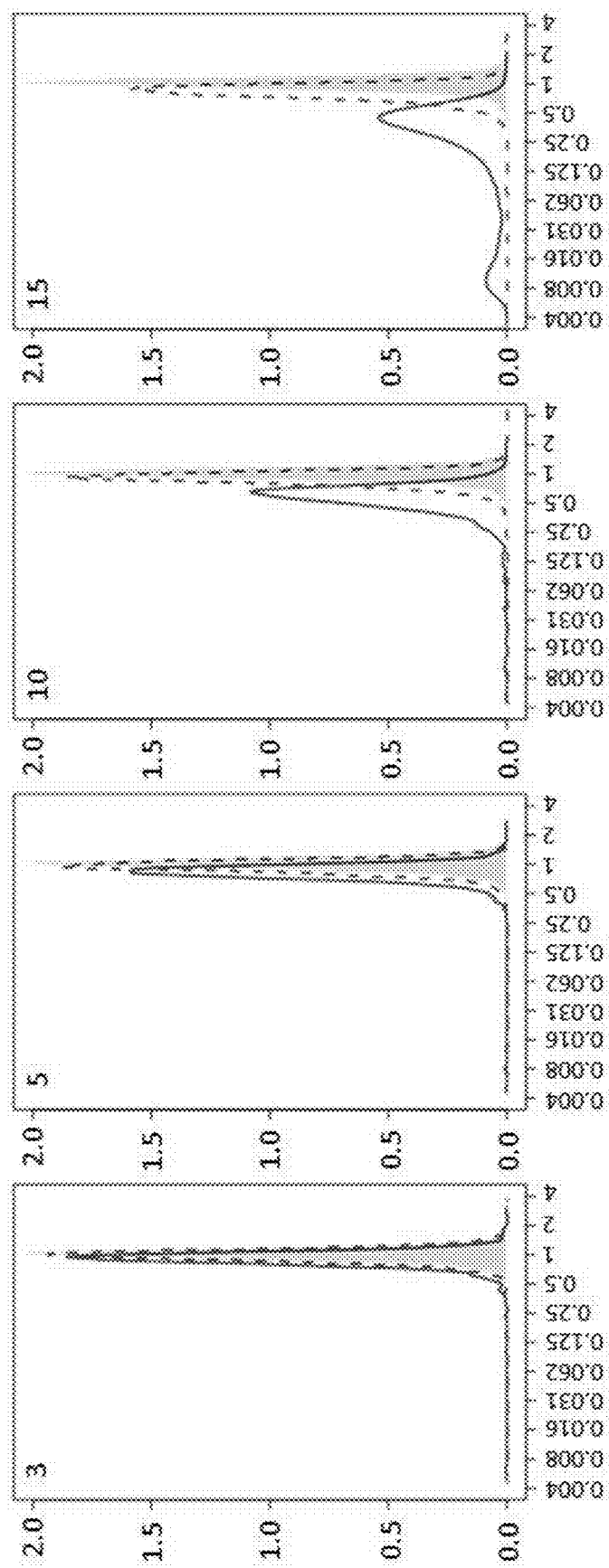
FIGS. 30B-30C show distribution of mismatches on probe performance. Distribution of relative capture efficiency for probes with a single mismatch (gray) and probes with multiple mismatches (green lines; the number of mismatches is indicated in the left top corner) is shown. Solid line depicts the distribution for probes with randomly distributed mismatches (RND), and the dotted line indicates the distribution for probes with continuous mismatches (CONT).
Figure 30C:
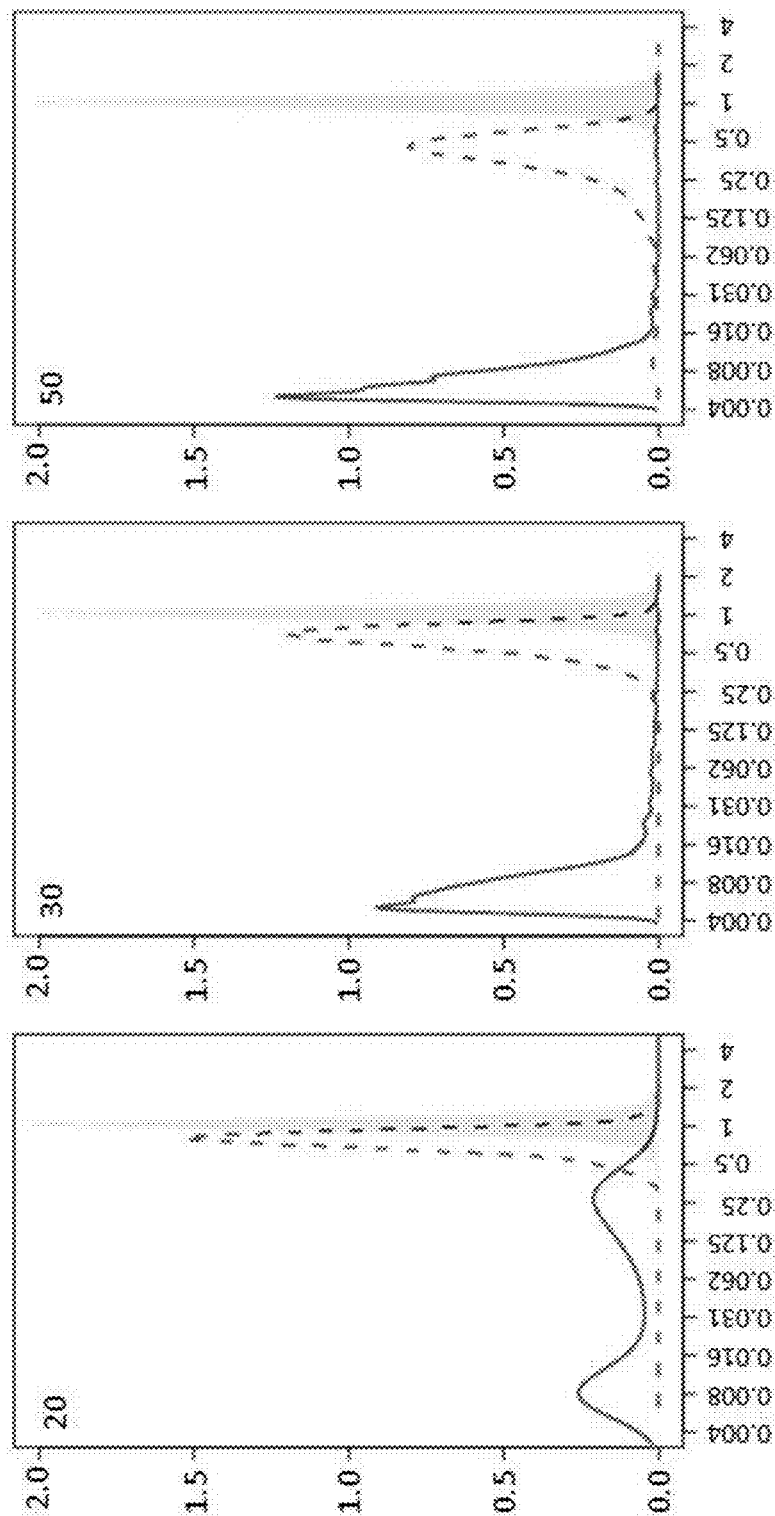

FIGS. 30B-30C shows probes with varying numbers of mismatches on capture efficiency. Distribution of relative capture efficiency for probes with a single mismatch (gray) and probes with multiple mismatches (green lines; the number of mismatches is indicated in the left top corner) is shown. Solid line depicts the distribution for probes with randomly distributed mismatches (RND), and the dotted line indicates the distribution for probes with continuous mismatches (CONT). Probes with 50 mismatches arranged in one continuous stretch capture as well as probes with 10-15 mismatches distributed randomly, while probes with 50 mismatches distributed randomly were completely ineffective.

Figure 30D:
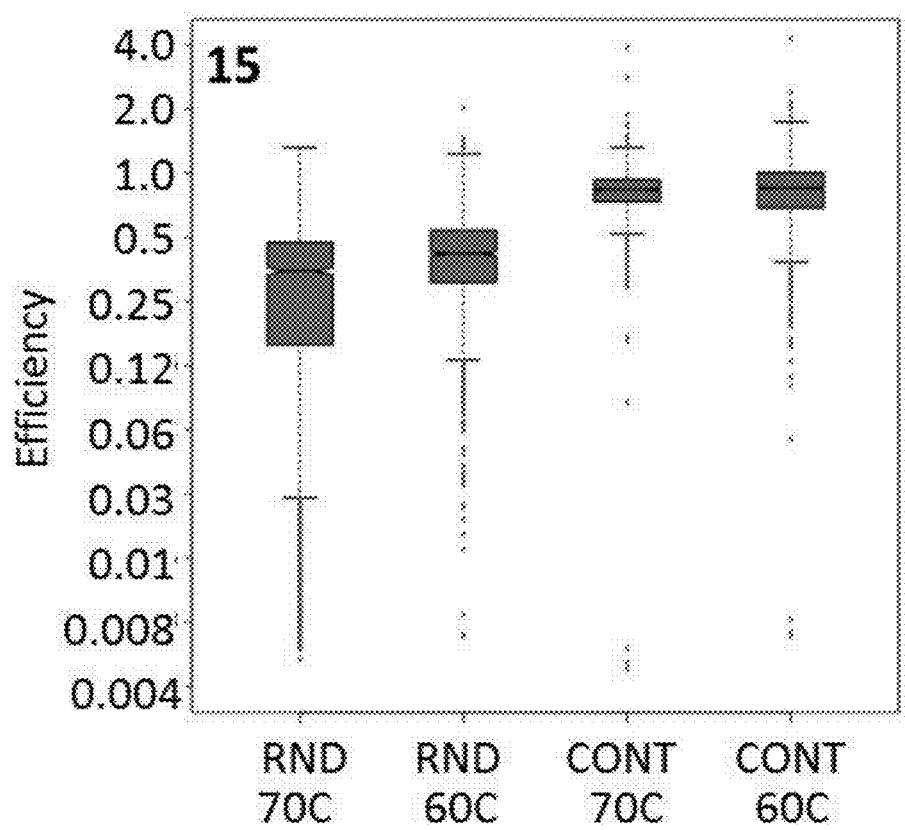
FIG. 30D shows effect of temperature on capture efficiency.

Other factors such as GC, length of perfect match and hybridization temperature can modulate capture efficiency in the presence of mismatches. FIG. 30D shows the effect on temperature on capture efficiency in the presence of mismatches.

Figures 30E, 30F:
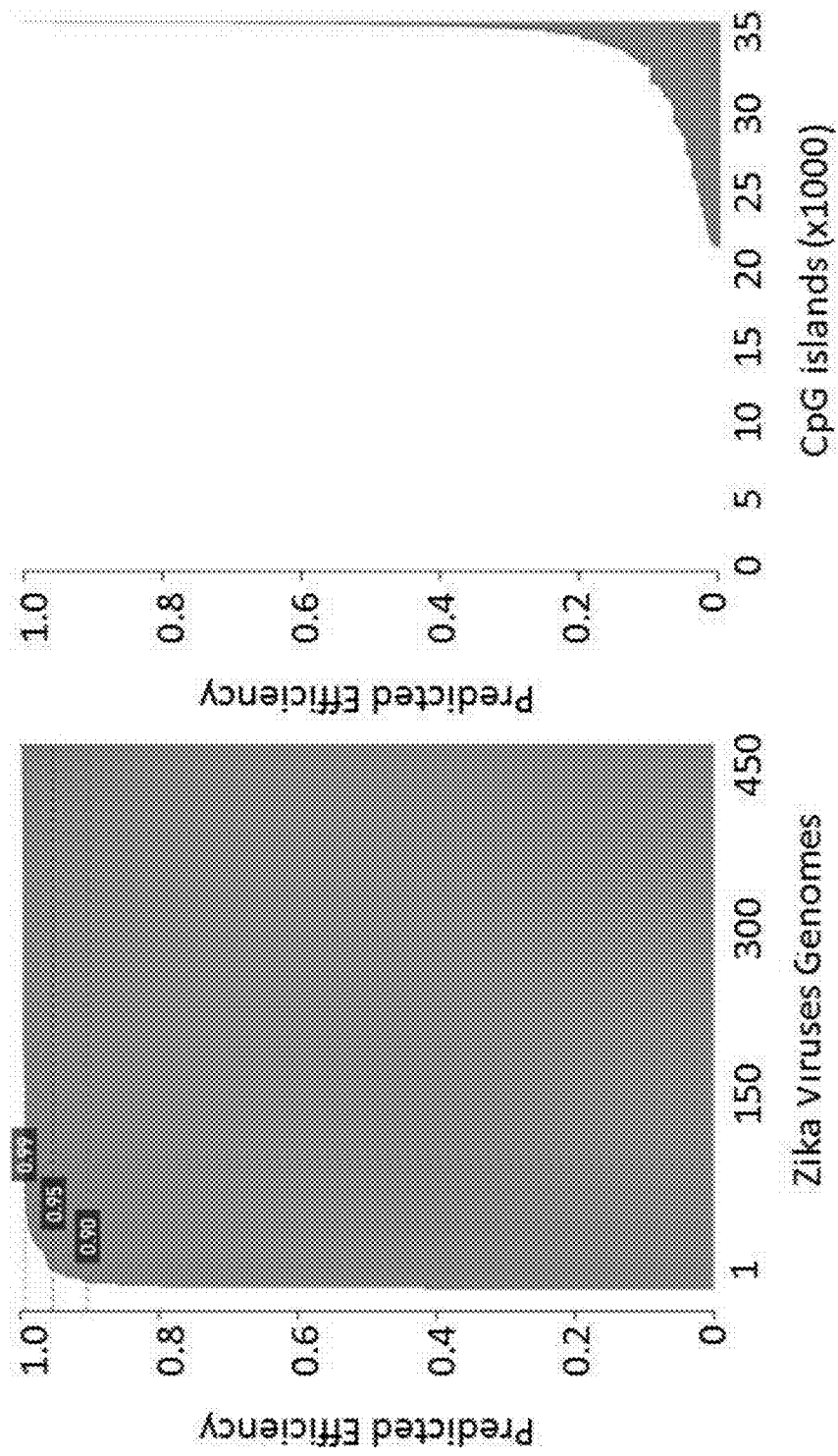
FIGS. 30E-30F shows efficiency prediction for the design of 450 whole genome Zika isolates from human samples (FIG. 30E) and all CpG islands in the human genome (FIG. 30F).

FIGS. 30E-30F show metagenomic and bisulfide capture efficiency prediction for the design of 450 whole genome Zika isolates from human samples (FIG. 30E) and all CpG islands in the human genome (FIG. 30F). CpG islands were downloaded from the UCSC annotation track for human genome hg38 and designed using design methods as described herein.

Example 28

Probe Specificity for Downstream Applications

Figure 31A:
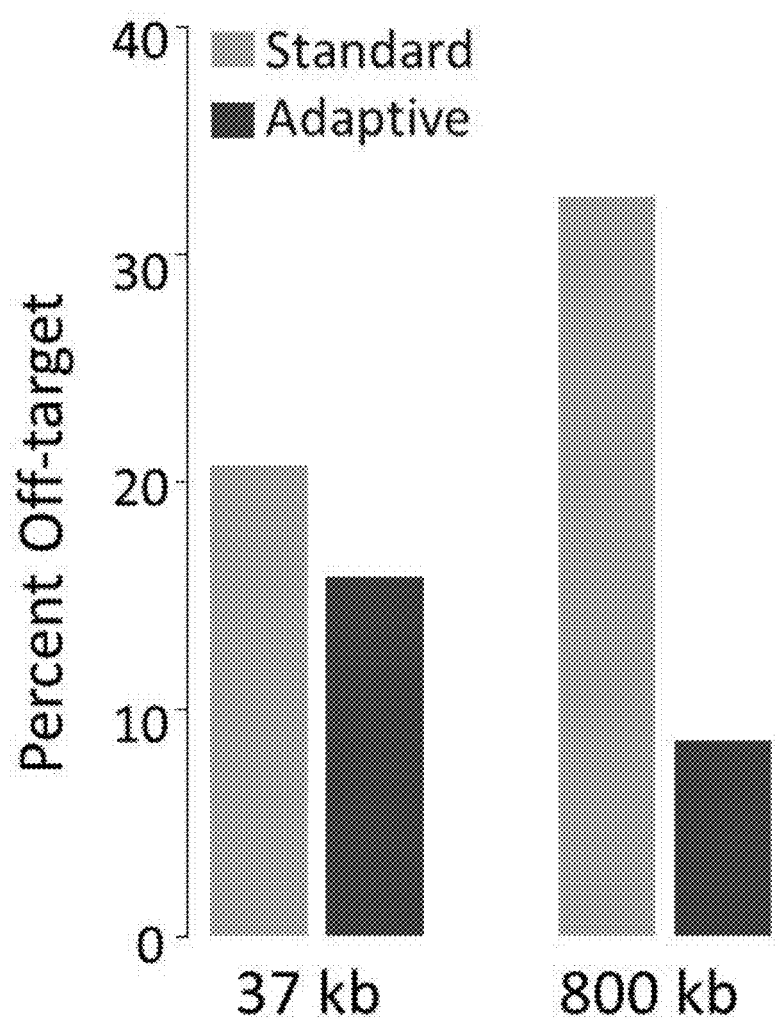
FIGS. 31A-31C show graphs of standard vs. adaptive probe designs.
Figure 31B:
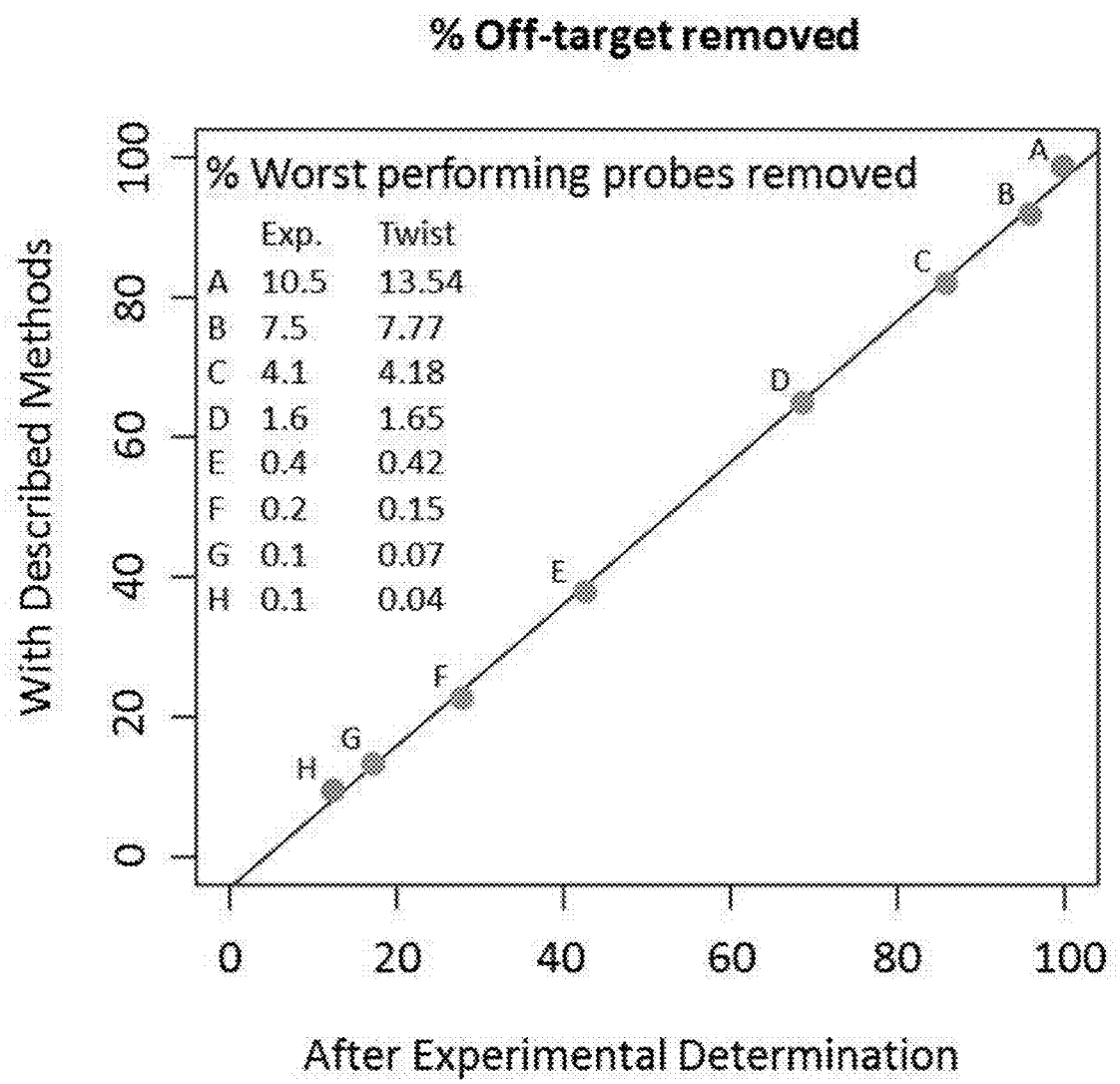
Figure 31C:
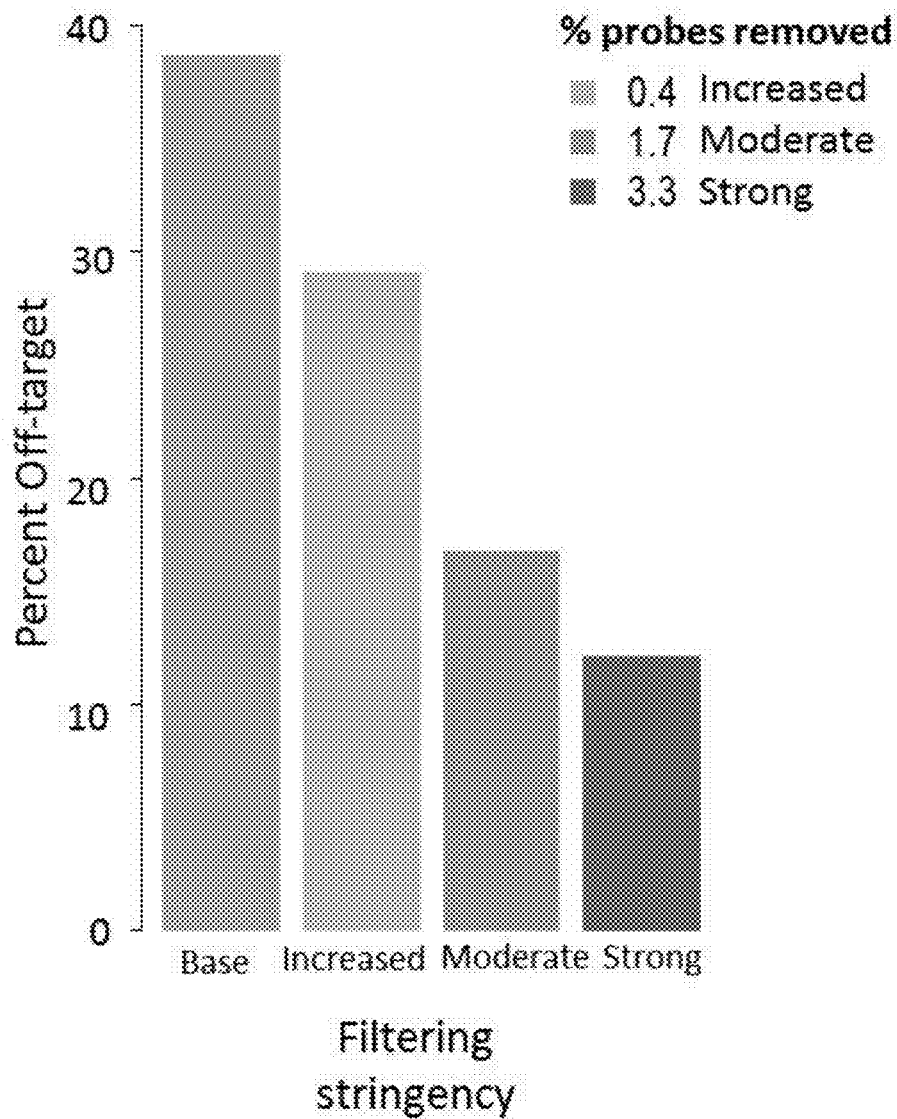

Adaptive designs where experimental results from a first pass design were used to determine sequences that should be removed. FIG. 31A shows improvements after a single pass adaptive design for moderate and aggressive off target reduction in panels with challenging target regions (respectively 37 Kb and 800 Kb, 3 probes and ~4% of probes removed). FIG. 31B shows the level off target predicted by our model compared to that measured by experimentation (axes) and the fraction out of the total number of baits required in each case to achieve it. FIG. 31C shows results for a custom design against a particularly hard set of target regions, various levels of stringency, and the effectiveness of bait removal based on methods described herein.

Example 29

RefSeq Design

A RefSeq panel design was designed in hg38 and included the union of CCDS21, RefSeq all coding sequence, and GENCODE v28 basic coding sequences. The size of RefSeq alone (Exome) was 3.5 Mb and the combined Core Exome+ RefSeq (Exome+RefSeq) was 36.5 Mb. Experiments were run using 50 ng of gDNA (NA12878) as 1-plex and 8-plex run in triplicate, and evaluated at 150× sequencing with 76 bp reads. The target file was 36.5 Mb.

Figure 32A:
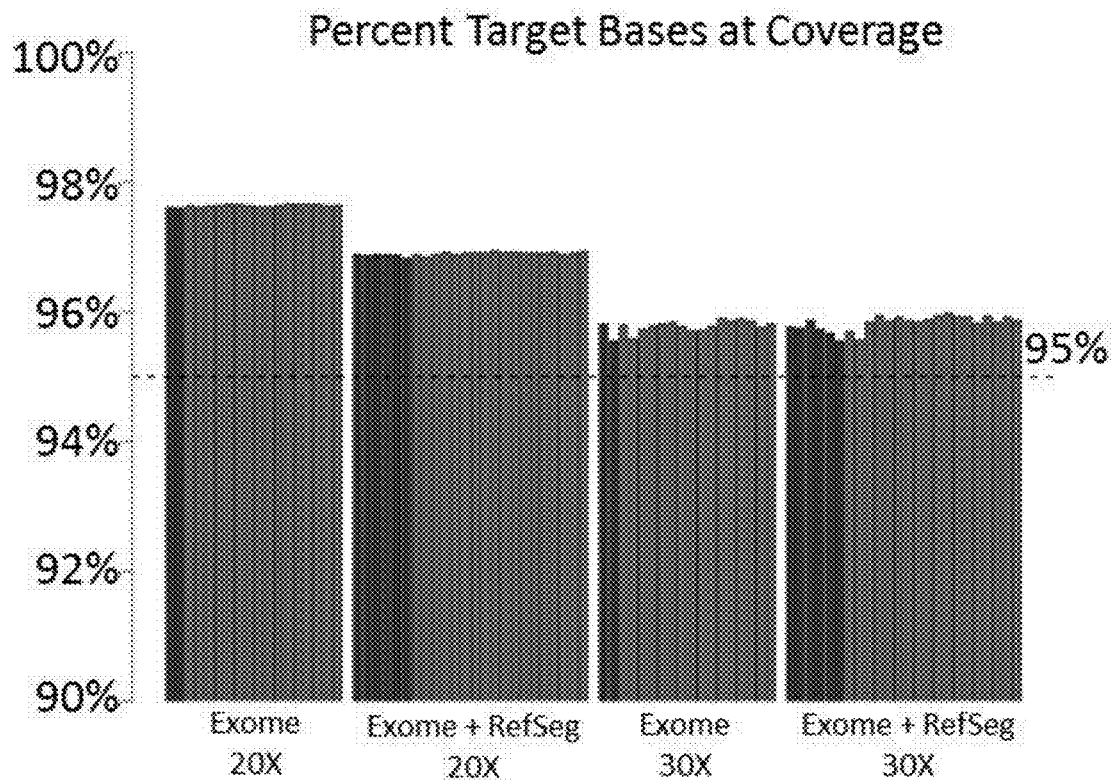
FIG. 32A shows a graph of depth coverage as percent target bases at coverage of the exome panel alone or with the RefSeq panel added.
Figure 32B:
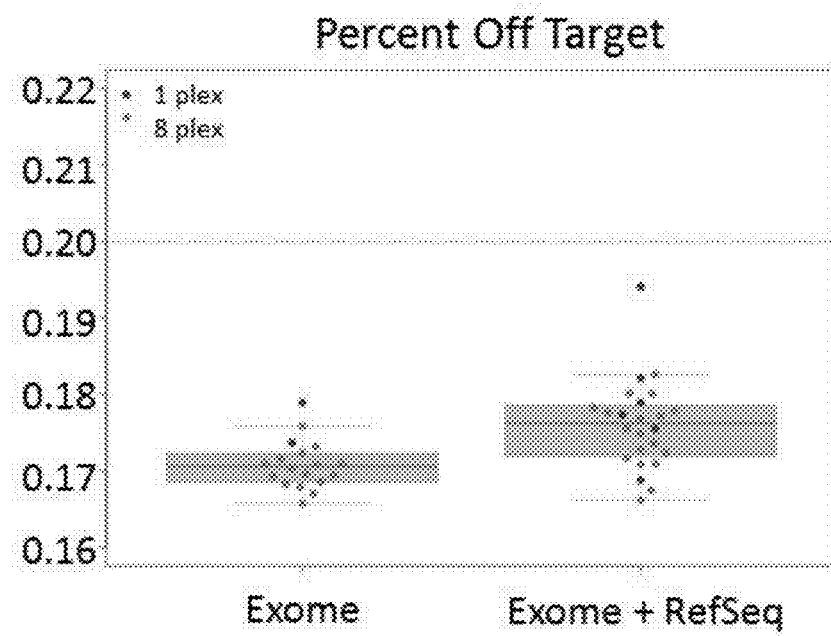
FIGS. 32B-32F depict graphs of various enrichment/capture sequencing metrics for a standard exome panel vs. the exome panel combined with the RefSeq panel in both singleplex and 8-plex experiments.
Figure 32C:
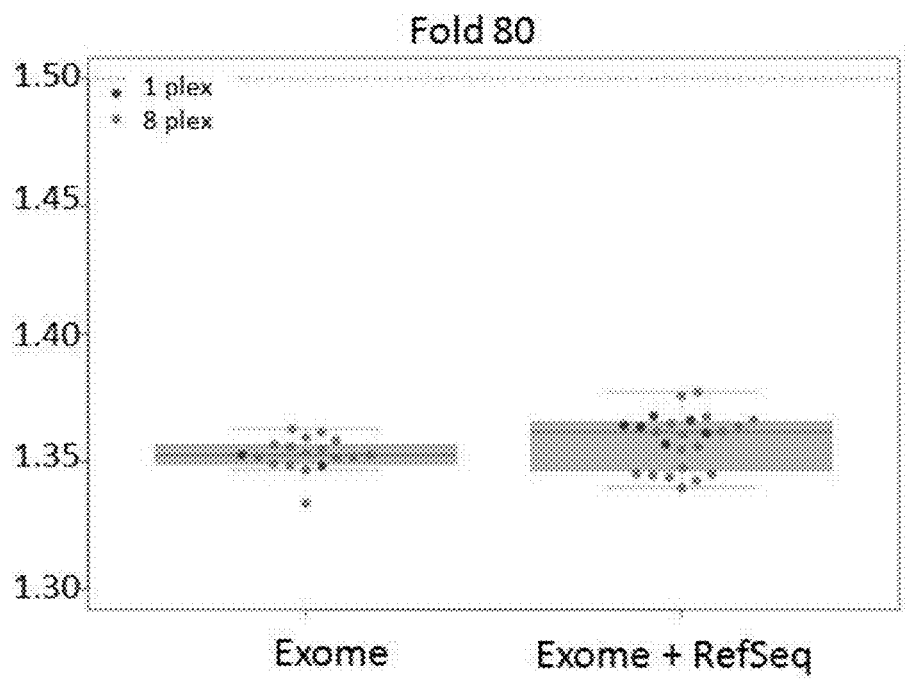
Figure 32D:
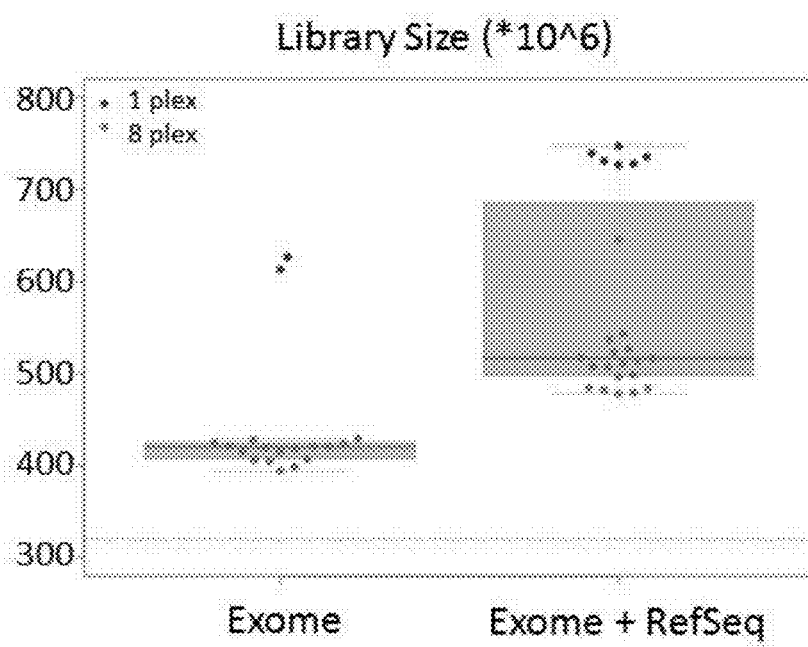
Figure 32E:
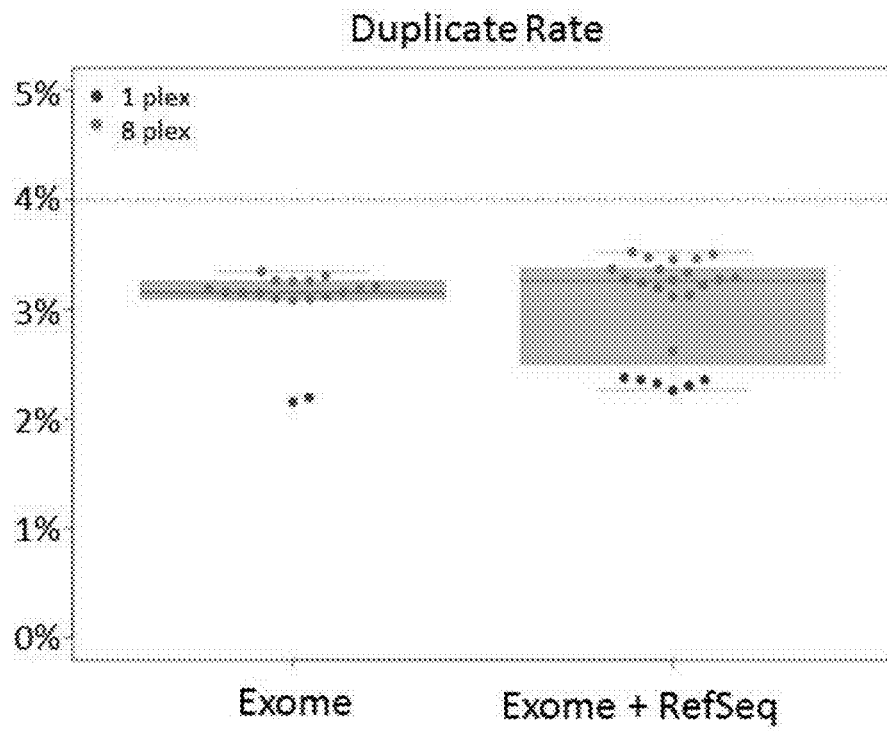
Figure 32F:
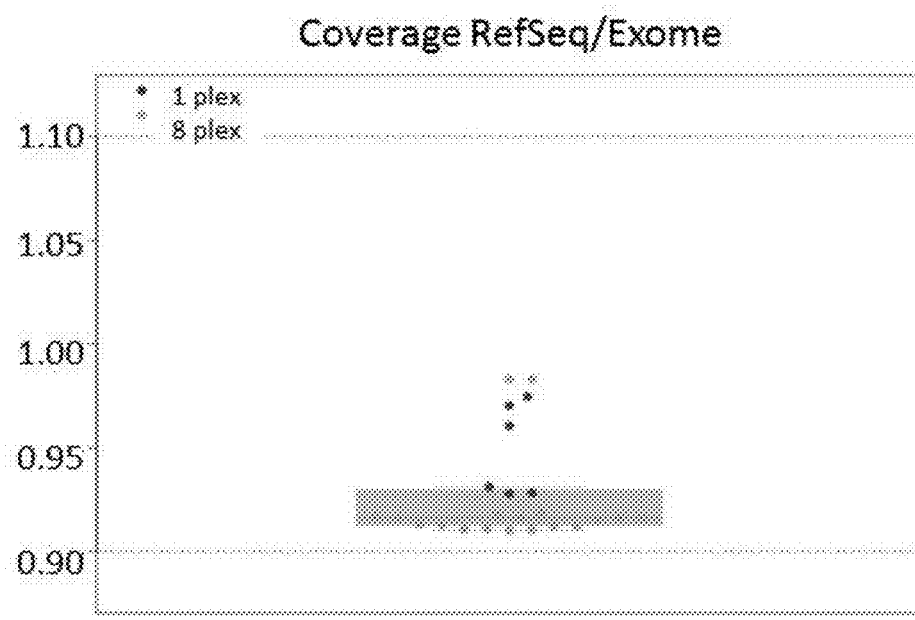

The RefSeq panel design was assessed for depth of coverage, specificity, uniformity, library complexity, duplicate rate, and coverage rate. FIG. 32A shows depth of coverage. More than 95% of target bases at 20× were observed. More than 90% of target bases at 30× were observed. FIG. 32B shows specificity of the RefSeq panel. The percent off target was less than 0.2. FIG. 32C shows uniformity of the RefSeq panel. The fold 80 was less than 1.5. FIG. 32D shows the complexity of the library. The library size was greater than 320 million. FIG. 32E shows the duplicate rate of the RefSeq panel. The duplicate rate was less than 4%. FIG. 32F shows the coverage ratio of the RefSeq panel. The coverage ratio was between 0.9 and 1.1. As seen in FIG. 32F, the coverage ratio was less than 1.1.

Example 30

Genomic DNA Capture with an Exome-Targeting Polynucleotide Probe Library, Using Various Additives in the Binding Buffer Sequencing data is acquired using the general method of Example 6, with modification: various binding buffers comprising different additives were used in separate sequencing runs, and a 0.8 Mb custom probe panel library was used instead of the 36.7 Mb probe library. The results of the sequencing analysis are found in FIG. 33C. Addition of mineral oil to the binding buffer led to a significant decrease in the percent off target rates. Addition of 5% PEG to the binding buffer also led to a decrease in off target rates relative to the control run (water added).

Example 31

Figure 34A:
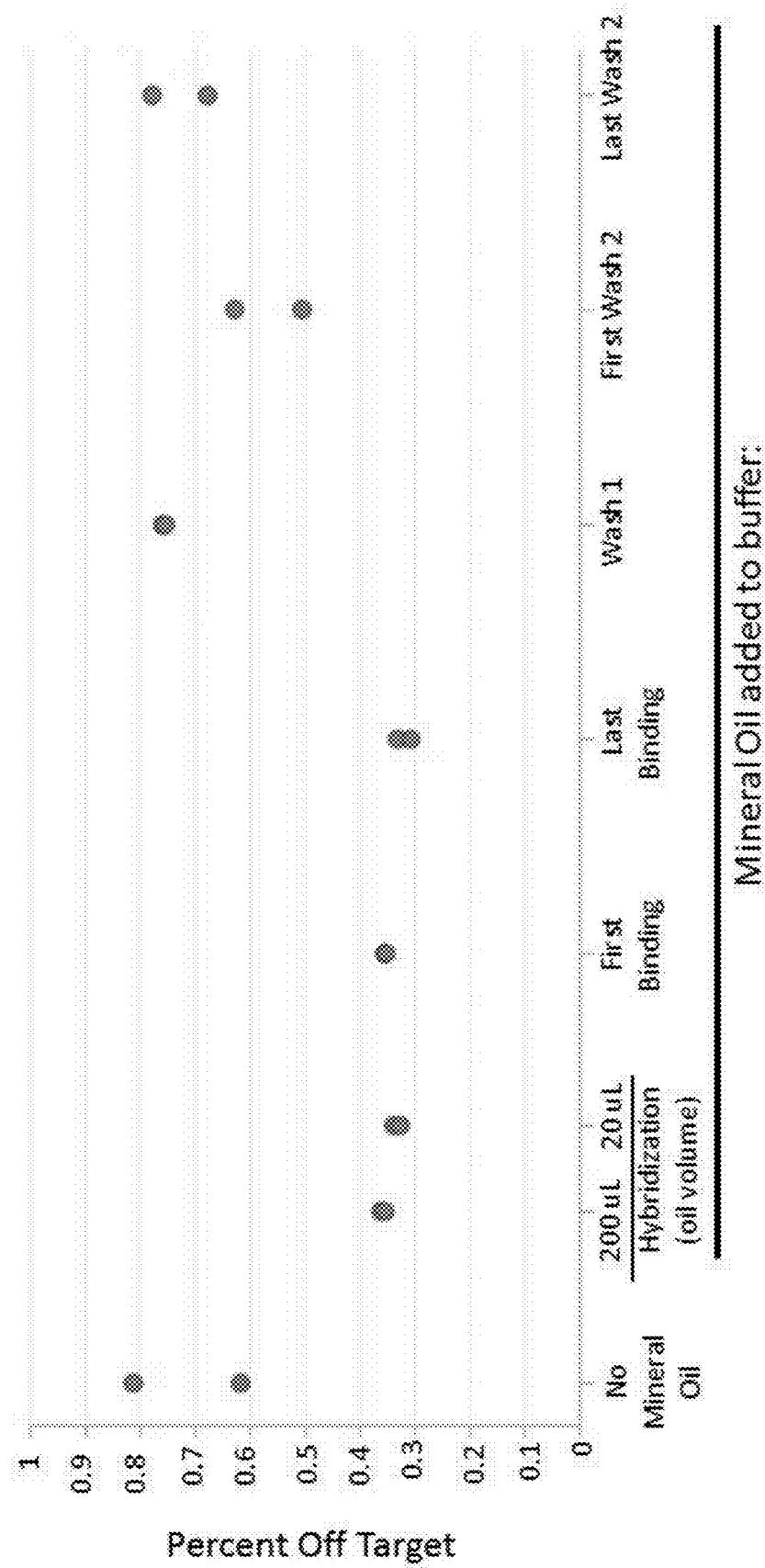
FIG. 34A depicts a plot of the percent off target vs. various buffers comprising different additives for an enrichment and sequencing analysis.

Genomic DNA Capture with an Exome-Targeting Polynucleotide Probe Library, Using Mineral Oil in Buffers Sequencing data is acquired using the general method of Example 6, with modification: various buffers comprising mineral oil were used in separate sequencing runs, the number of washes was varied, and a 0.8 Mb custom probe panel library was used instead of the 36.7 Mb probe library. Conditions were run in duplicate. The results of the sequencing analysis for off target rates are found in FIG. 34A. Addition of mineral oil to wash buffer 1, first wash with wash buffer 2, or last wash with wash buffer 2 gave off-target rates that were comparable to no mineral oil conditions. Addition of mineral oil to hybridization buffer, first binding buffer, or last binding buffer led to a significant decrease in the percent off target rates.

Example 32

Figure 34B:
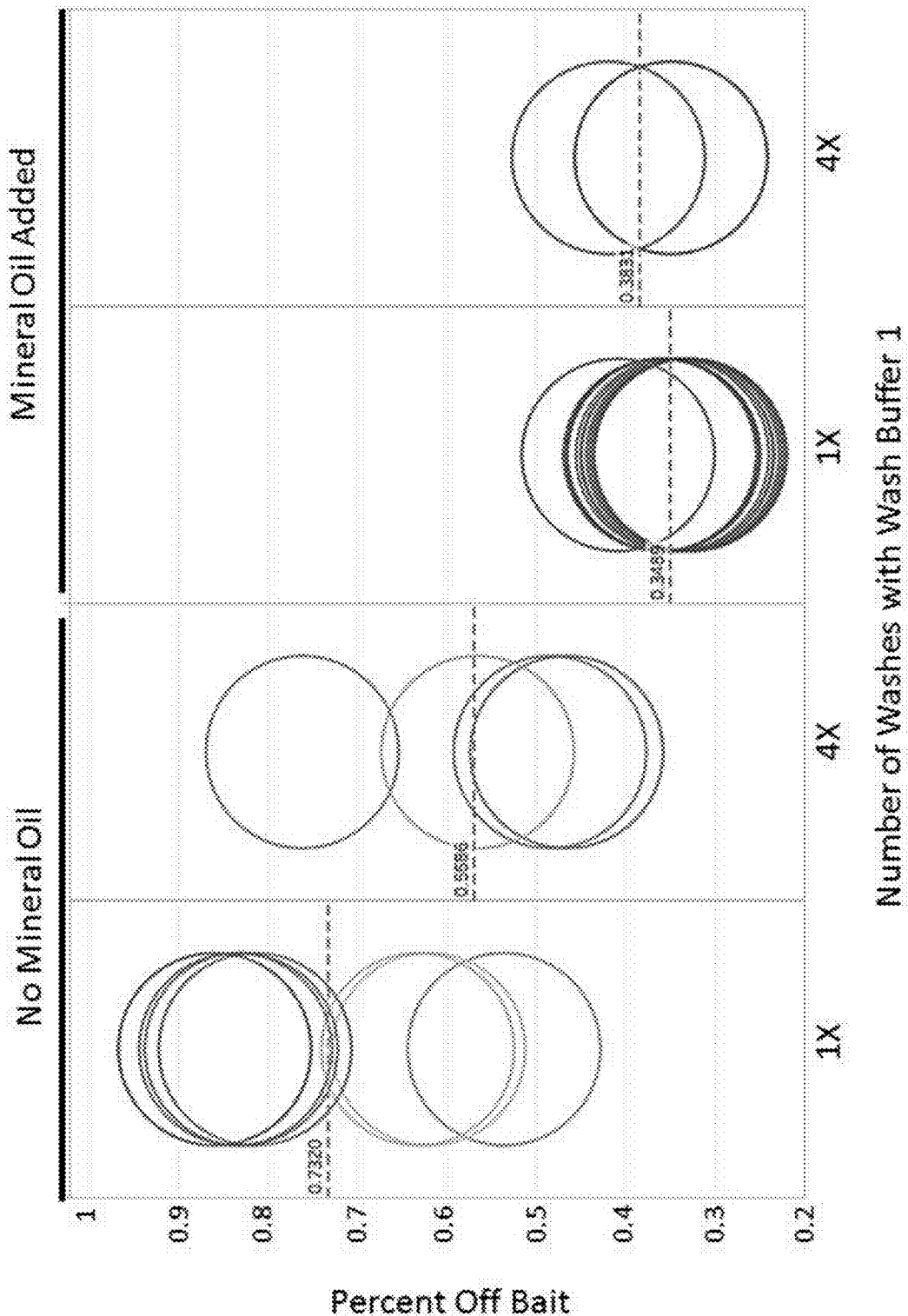
FIG. 34B depicts a plot of the percent off bait vs. number of washes and the presence of mineral oil for an enrichment and sequencing analysis.
Figure 34C:
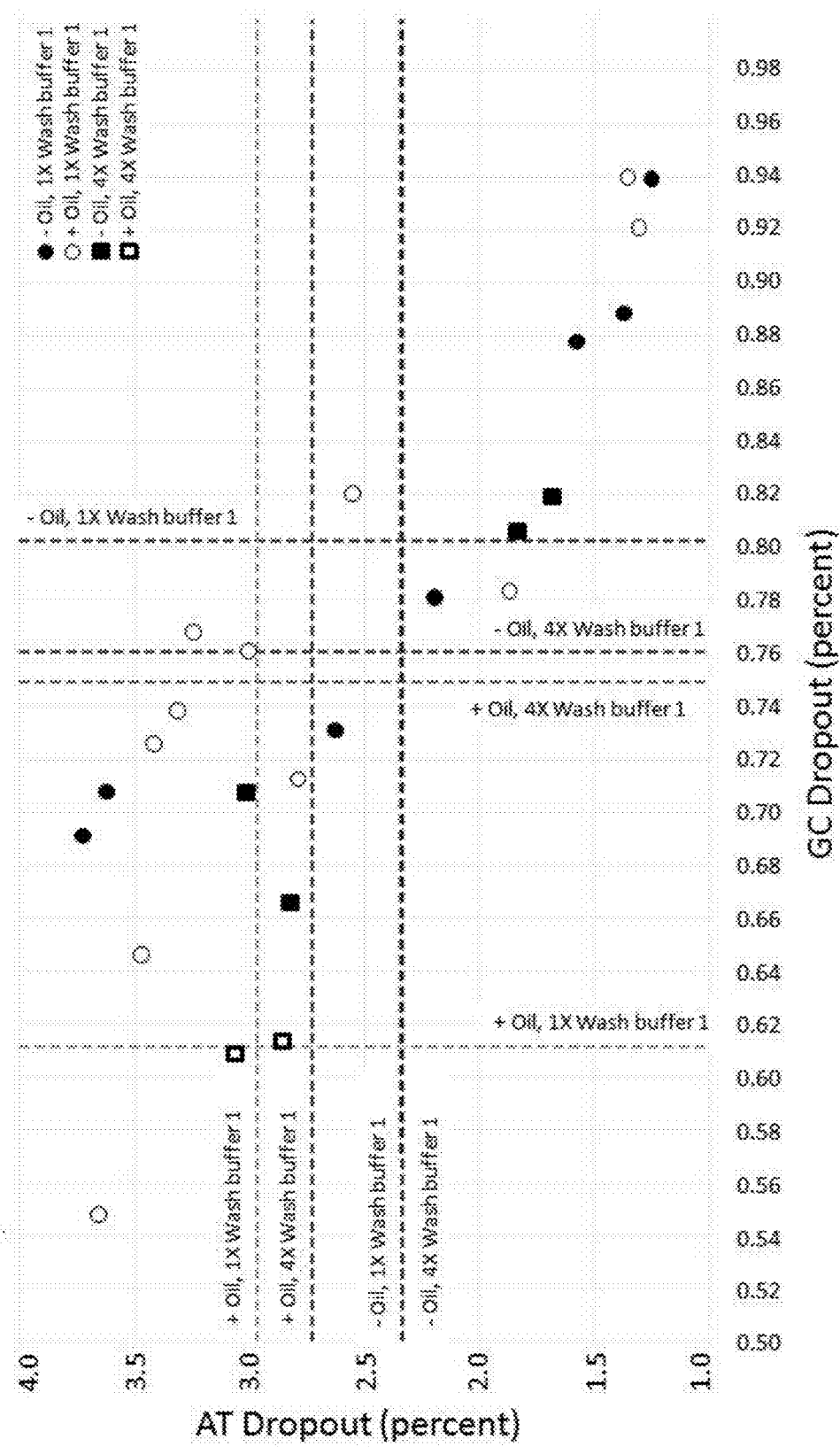
FIG. 34C depicts a plot of AT dropout vs. GC dropout for conditions comprising different wash numbers and the presence or absence of mineral oil for an enrichment and sequencing analysis.
Figure 34D:
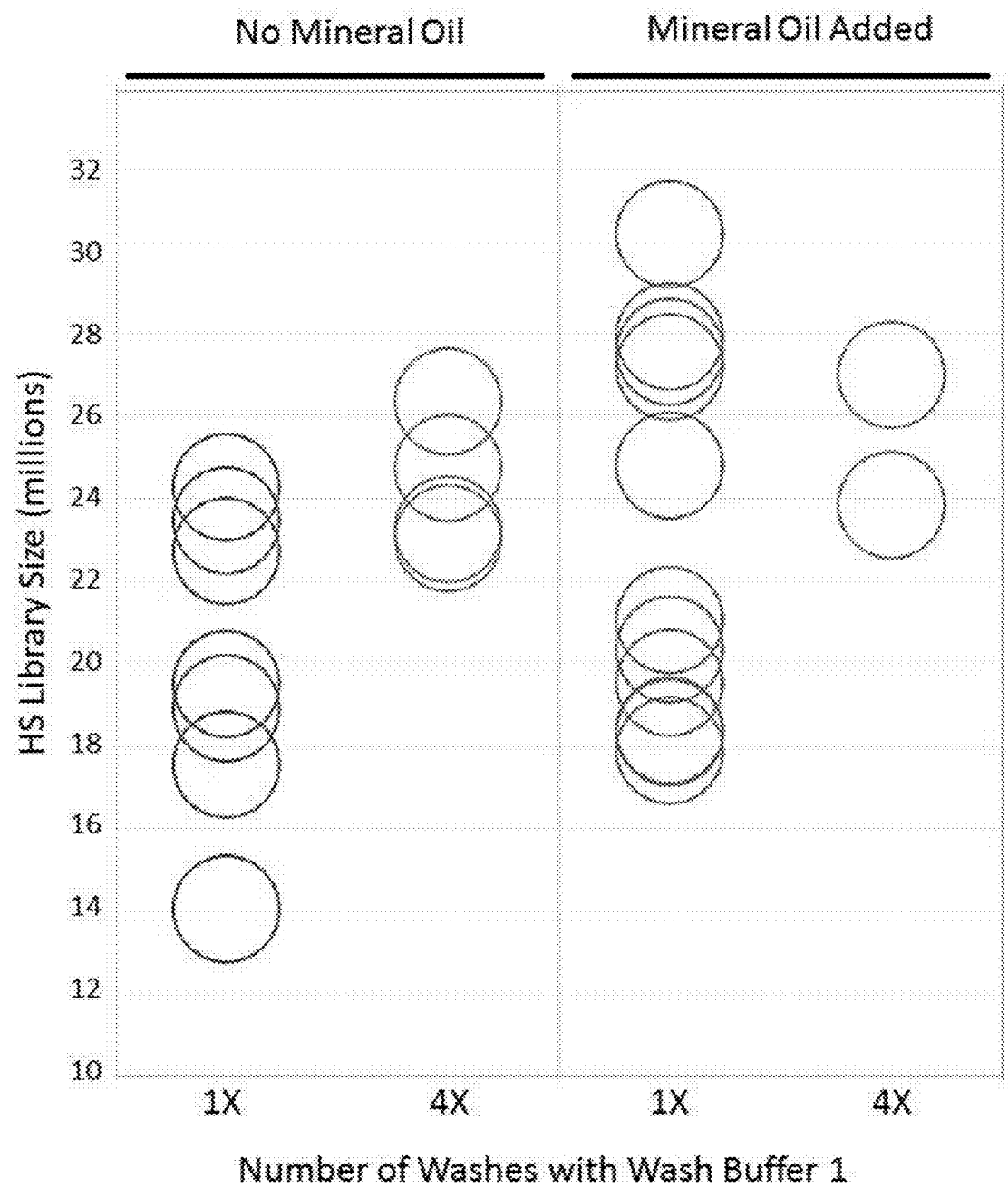
FIG. 34D depicts a plot of HS library size for conditions comprising different numbers of washes with wash buffer 1 and the presence or absence of mineral oil for an enrichment and sequencing analysis.
Figure 34E:
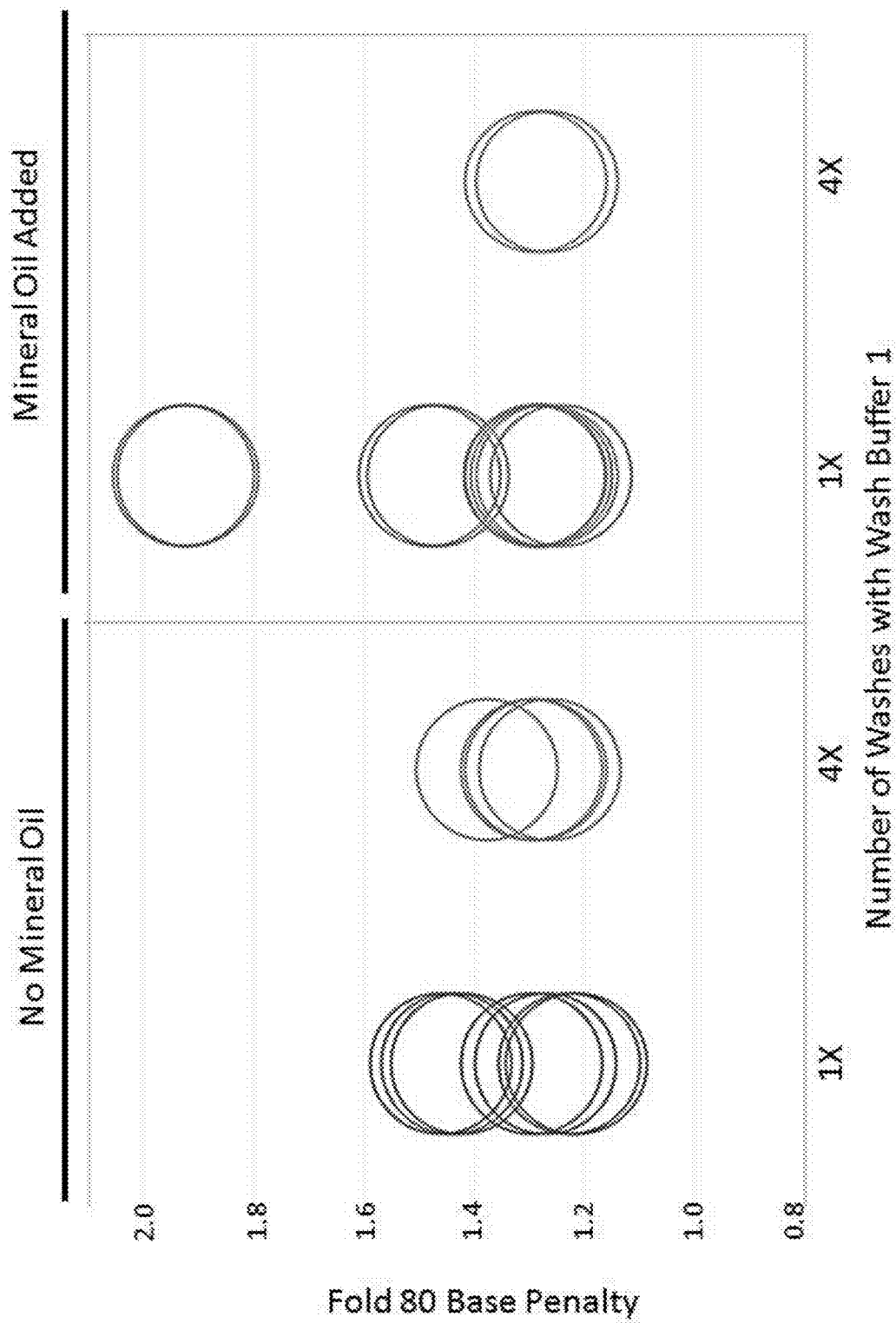
FIG. 34E depicts a plot of 80 fold base penalty for conditions comprising different numbers of washes with wash buffer 1 and the presence or absence of mineral oil for an enrichment and sequencing analysis.

Genomic DNA Capture with an Exome-Targeting Polynucleotide Probe Library, Using Mineral Oil and Washes Sequencing data is acquired using the general method of Example 6, with modification: hybridization and binding buffers comprising mineral oil were used in, the number of washes was varied, and a 0.8 Mb custom probe panel library was used instead of the 36.7 Mb probe library. Conditions were run in 2-7 replicates. The results of the sequencing analysis are found in FIG. 34B-34E. Four washes with wash buffer 1 generally led to a decrease in percent off bait (4 washes: 38.31% vs. 1 wash: 56.86%, without mineral oil), unless mineral oil was used (1 wash: 34.89% vs. 4 washes: 38.31% FIG. 34B); mineral oil in conjunction with a single wash with wash buffer 1 led to an average off bait percentage of 34.89%. Addition of mineral oil in general lowered GC dropout rates (FIG. 34C, intersections of dashed lines indicate average values). Additional washes led to less run to run variance in HS library size and fold 80 base penalty, independent of mineral oil addition (FIG. 34D and FIG. 34E).

Example 33

Figure 35A:
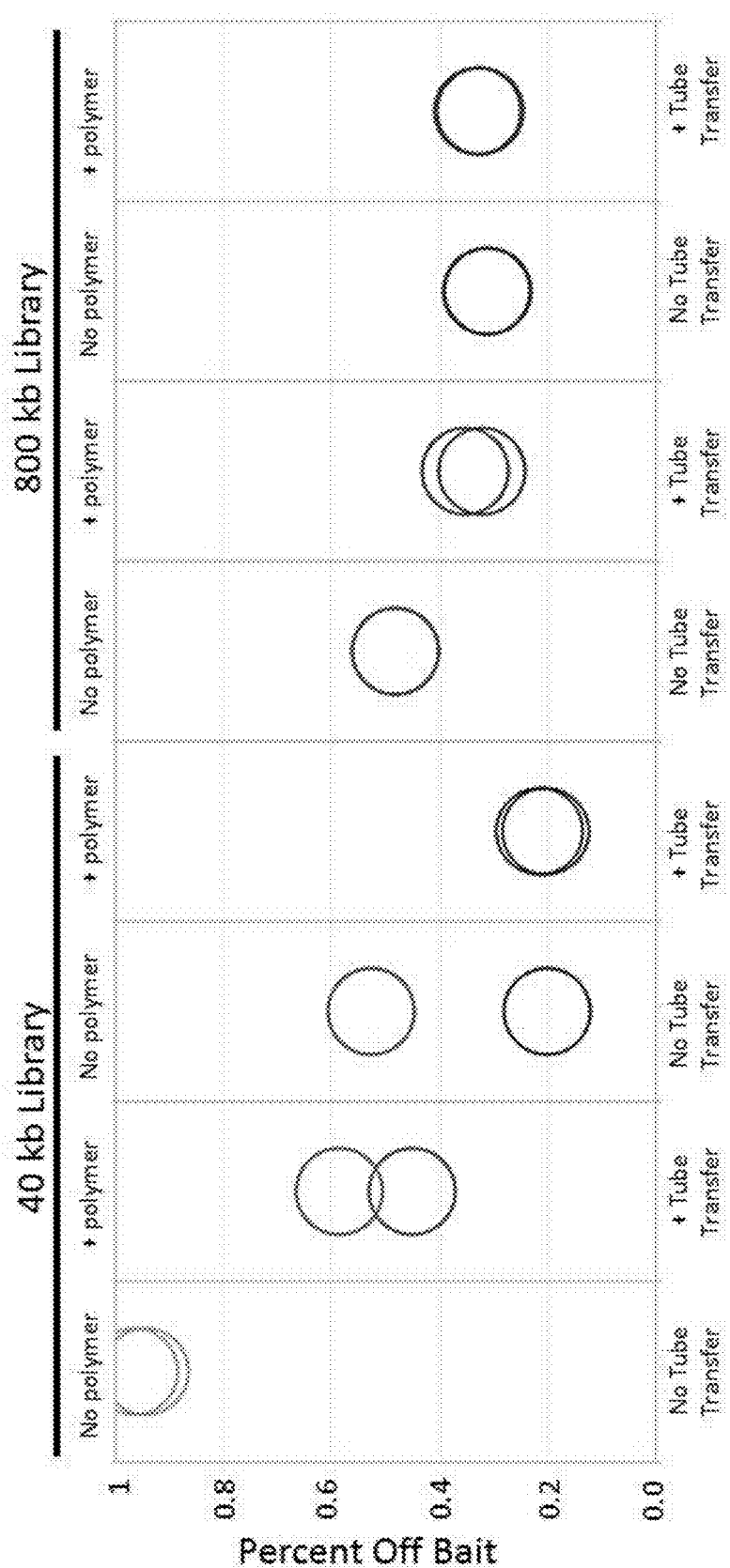
FIG. 35A depicts a plot of the percent off bait vs. tube transfer and the presence of Polymer A for an enrichment and sequencing analysis.
Figure 35B:
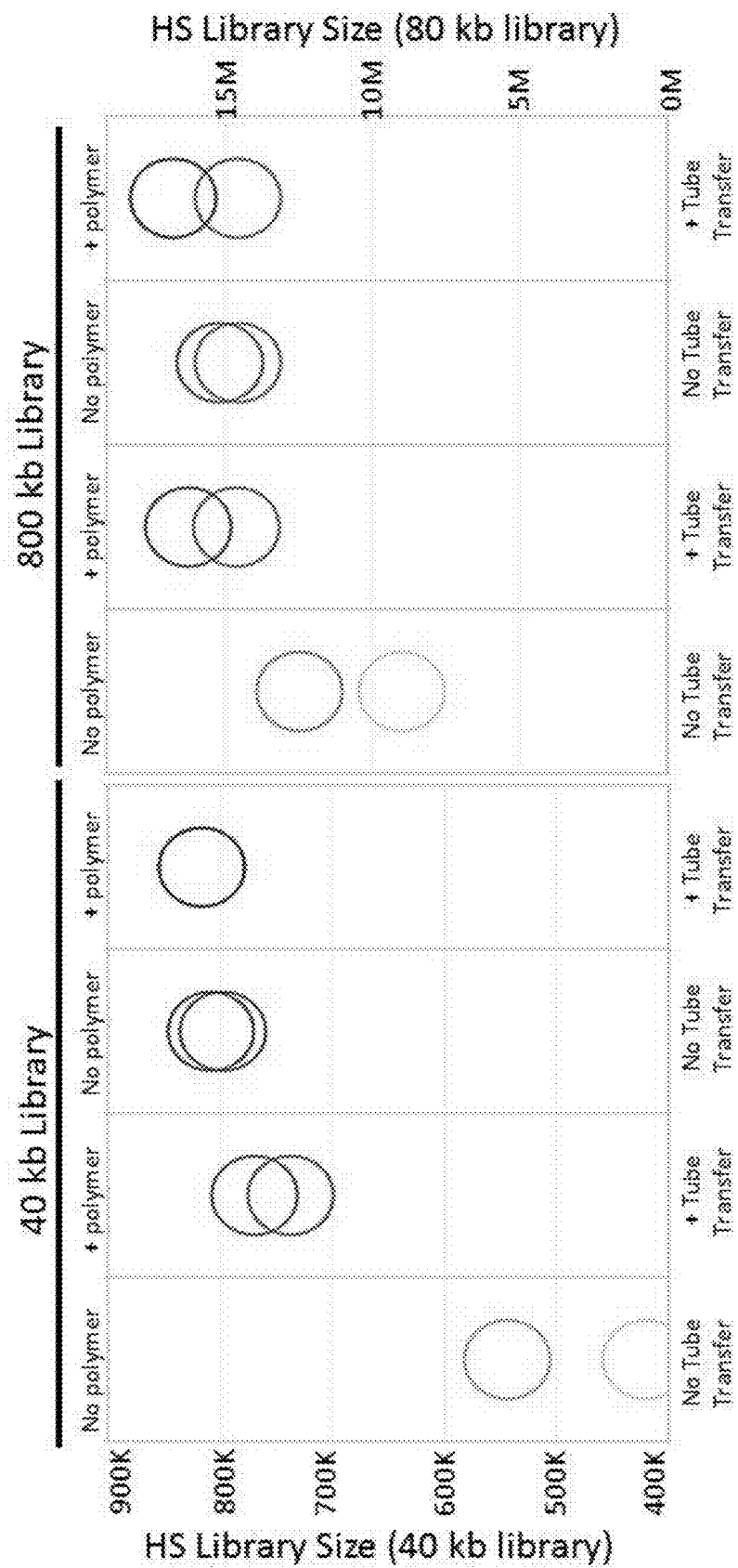
FIG. 35B depicts a plot of HS library size vs. tube transfer and the presence of Polymer A for an enrichment and sequencing analysis.

Genomic DNA Capture with an Exome-Targeting Polynucleotide Probe Library, Using a Liquid Polymer and Tube Transfers Sequencing data is acquired using the general method of Example 6, with modification: hybridization and binding buffers comprising a liquid polymer (Polymer A) additive were used in, a tube transfer was optionally performed during washes, and 800 kb and 40 kb custom probe panel libraries were used in independent runs instead of the 36.7 Mb probe library. Polymer A is a high molecular weight liquid polymer, that has a vapor pressure of <1 mm Hg, and a water solubility of <100 ppb. Conditions were generally run in duplicate. Transferring tubes between washes and/or use of liquid polymer generally led to a decrease in percent off bait (FIG. 35A), as well as an increase in HS Library size for both 40 kb and 800 kb libraries (FIG. 35B). Other variables such as fold 80 base penalty and GC dropouts were relatively unaffected, although use of either tube changes, liquid polymer additive, or a combination of both resulted in fewer AT dropouts (data not shown).

Example 34

Figure 36:
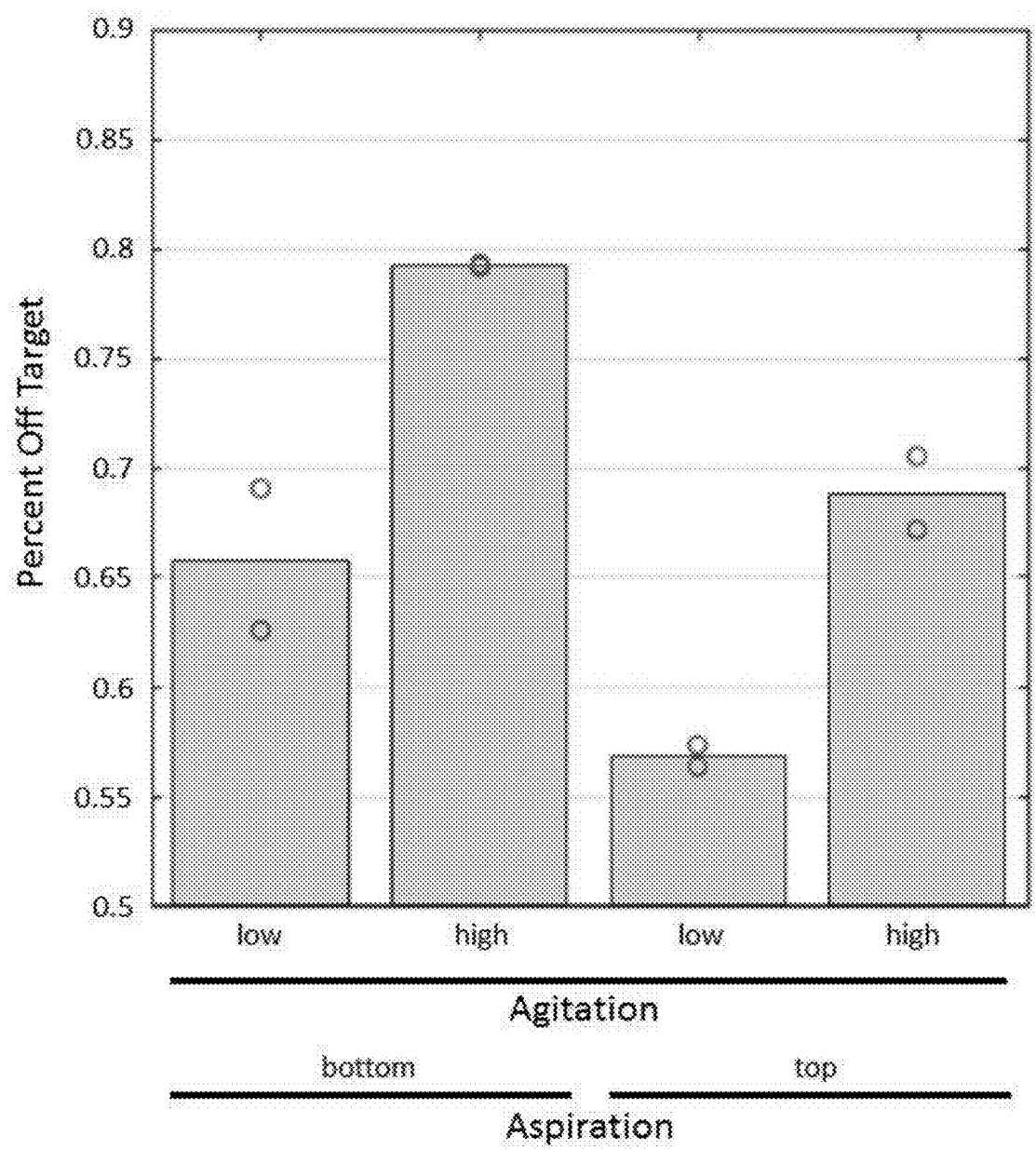
FIG. 36 depicts a plot of percent off target for conditions comprising different levels of agitation and methods of aspiration for an enrichment and sequencing analysis.
Figure 37A:
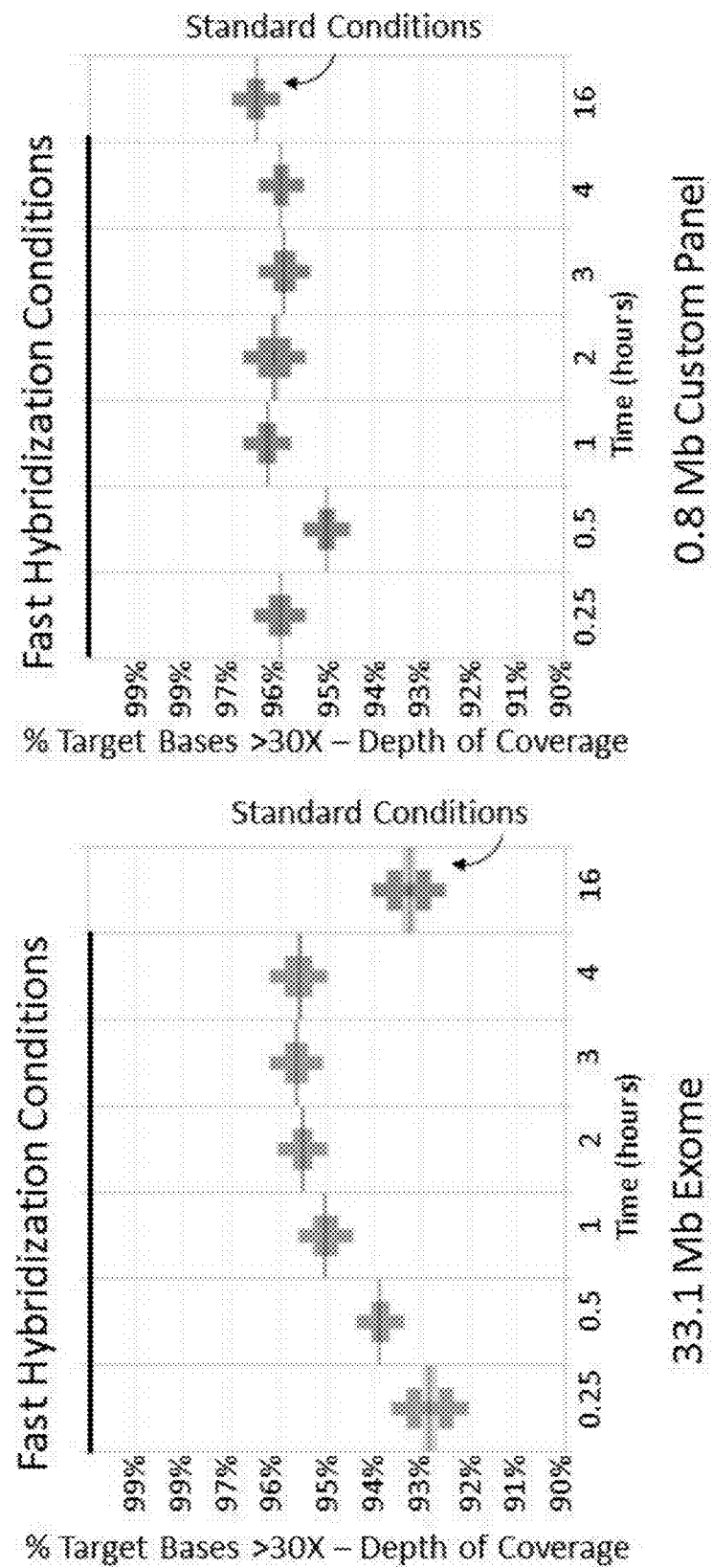
FIG. 37A is a plot of depth of coverage achieved (% target bases at 30×) vs. various hybridization times using either standard or fast hybridization buffers.
Figure 37B:
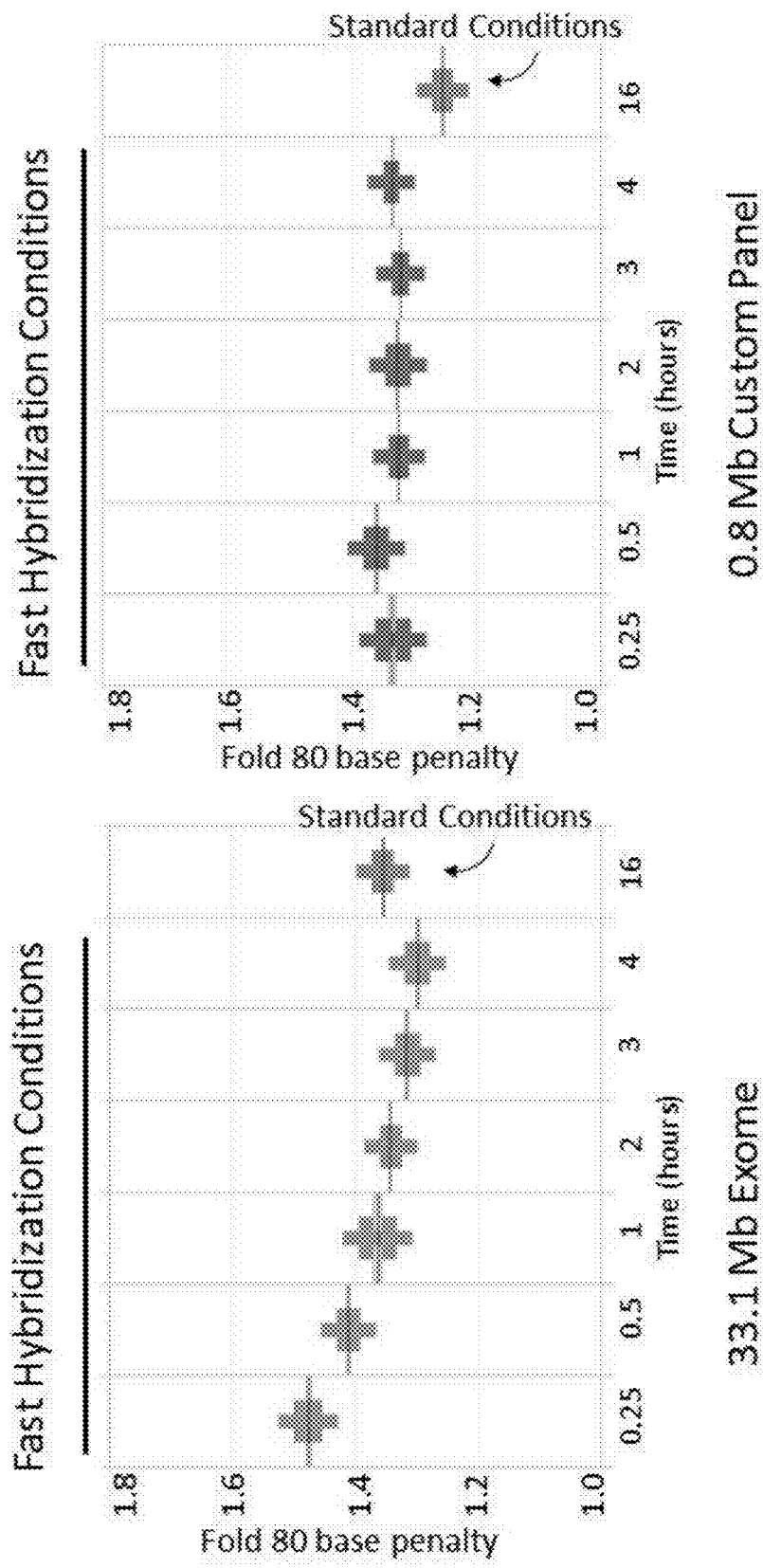
FIG. 37B is a plot of fold 80 base penalty vs. various hybridization times using either standard or fast hybridization buffers.
Figure 37C:
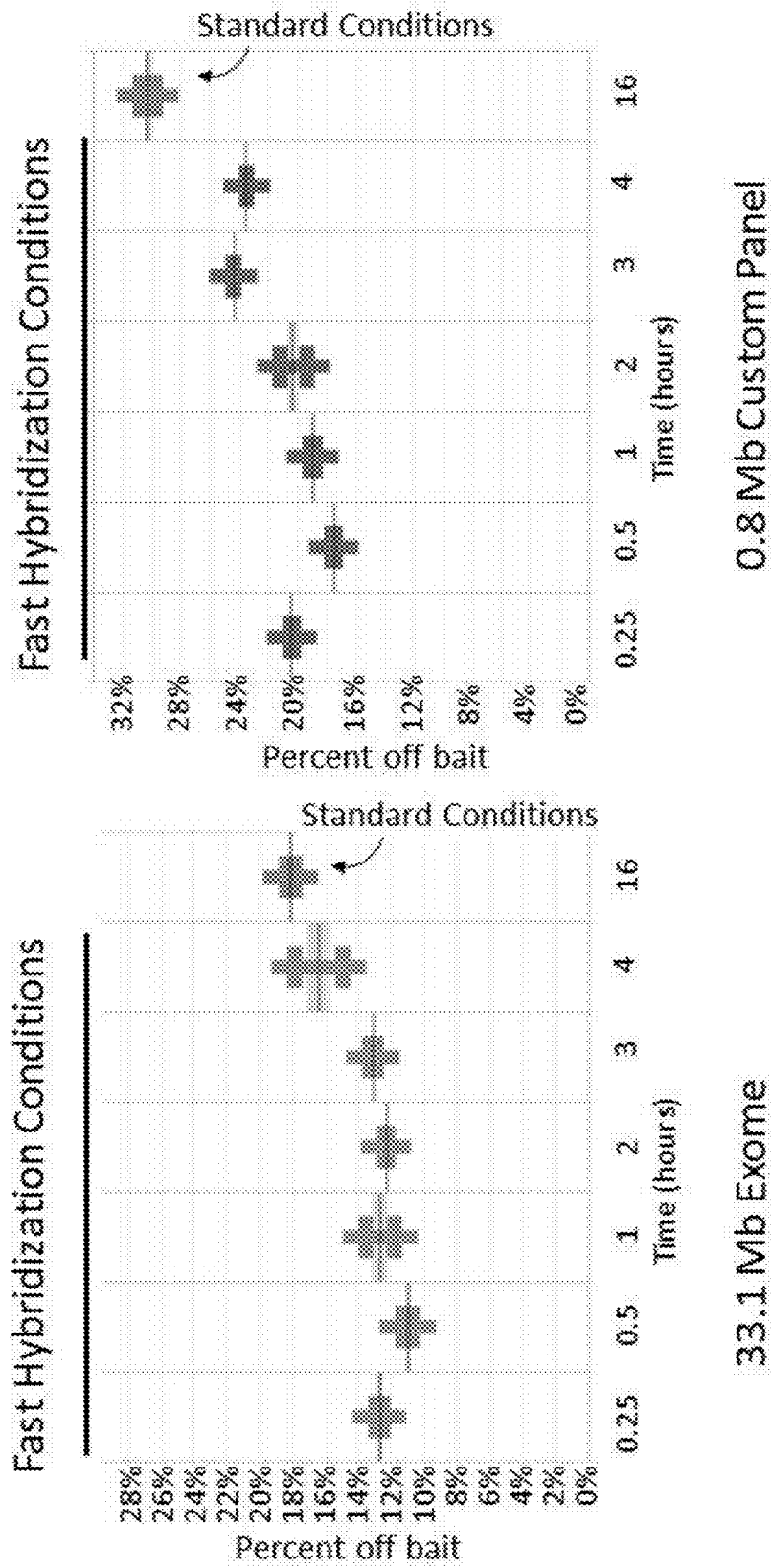
FIG. 37C is a plot of percent off bait vs. various hybridization times using either standard or fast hybridization buffers.
Figure 37D:
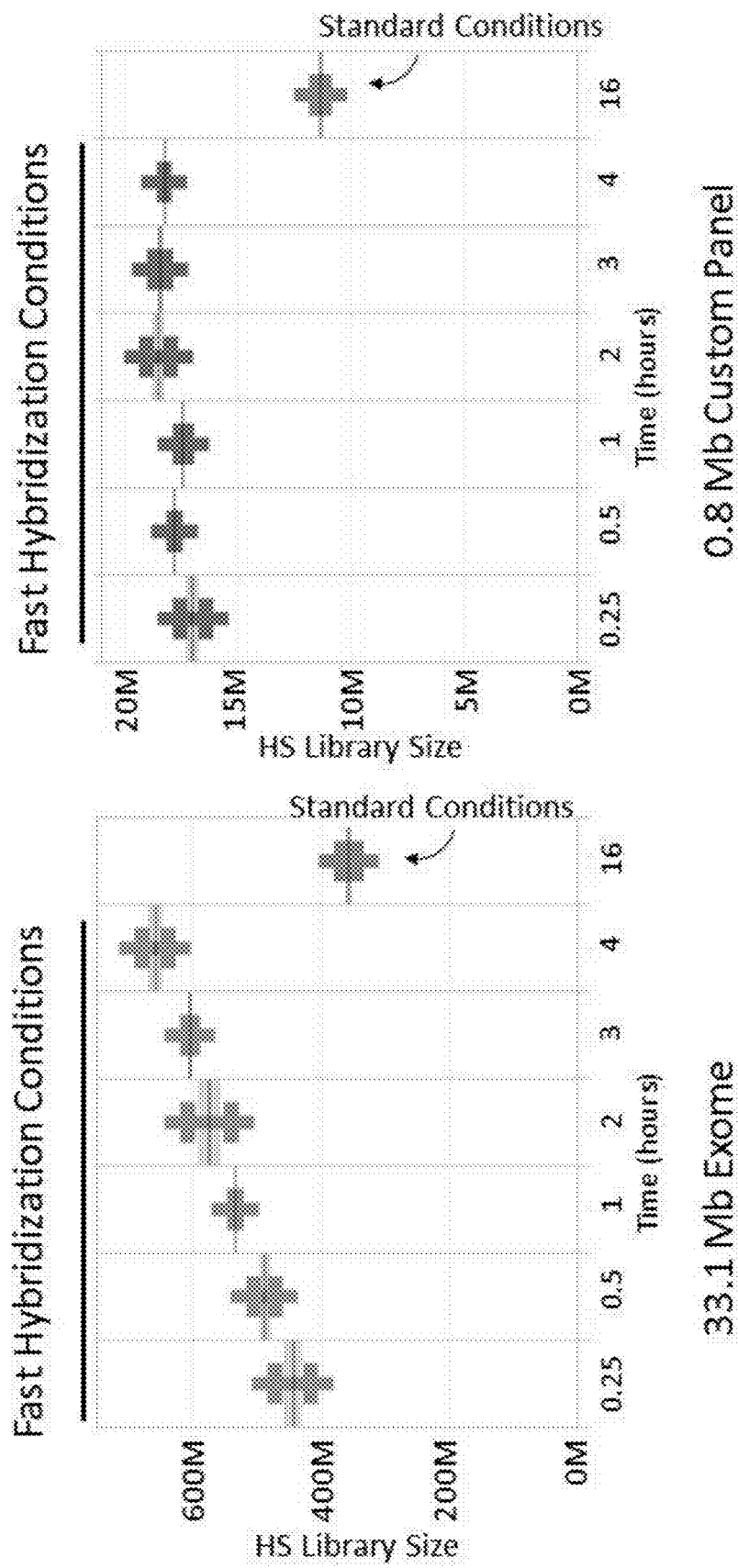
FIG. 37D is a plot of HS library size vs. various hybridization times using either standard or fast hybridization buffers.
Figure 37E:
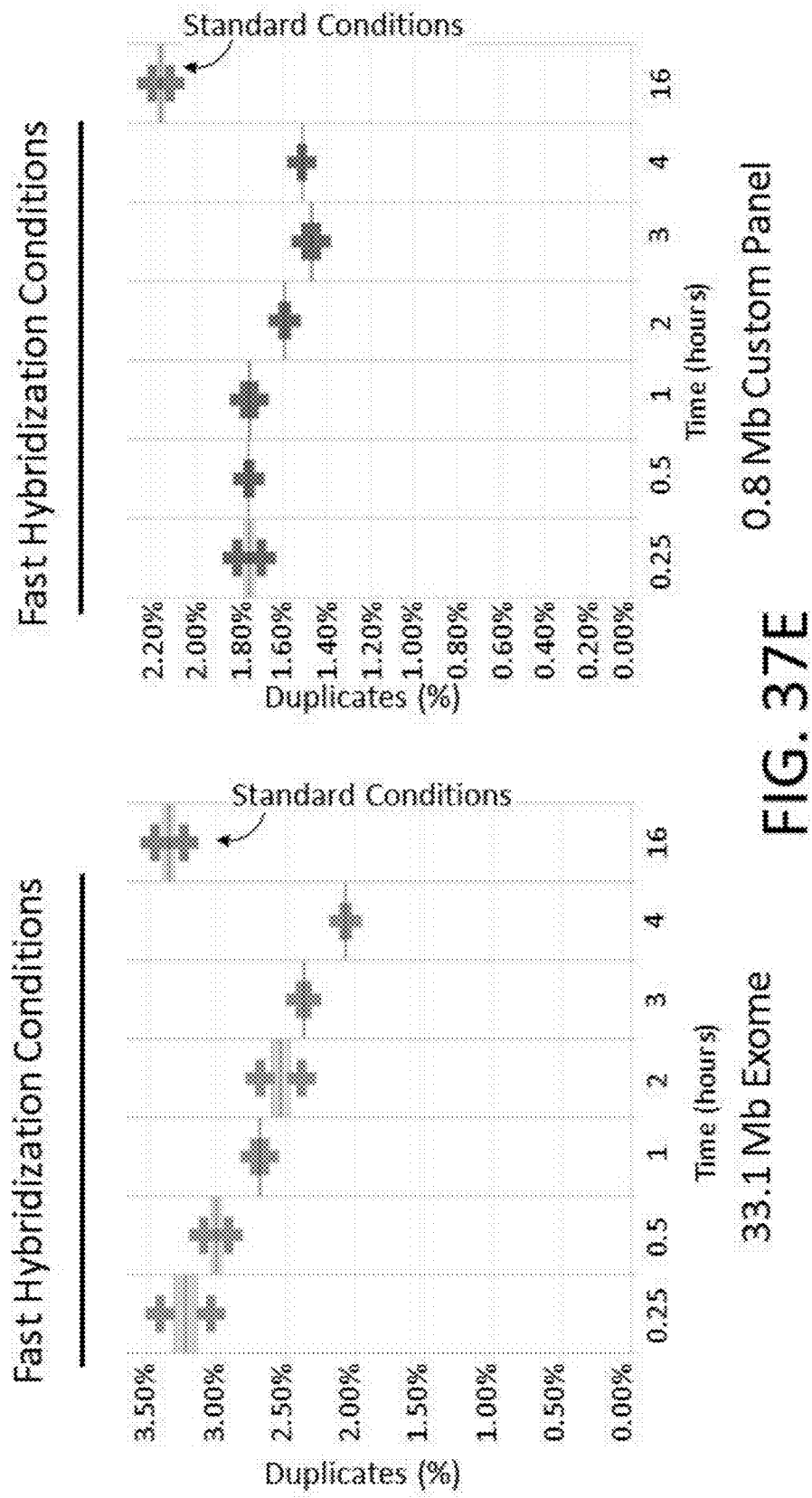
FIG. 37E is a plot of percent duplicates vs. various hybridization times using either standard or fast hybridization buffers.

Genomic DNA Capture with an Exome-Targeting Polynucleotide Probe Library, Using Agitation and Controlled Aspiration Sequencing data is acquired using the general method of Example 6, with modification: different levels of agitation/mixing and aspiration methods were used in separate sequencing runs, and a 0.8 Mb custom probe panel library was used instead of the 36.7 Mb probe library. High agitation comprised a short vortexing of the hybridization and binding buffer during mixing, while low agitation comprised flicking the tube during mixing. Top aspirate comprised collecting only liquid near the air-water interface, and slowly lowering a pipette tip as the liquid level dropped. Higher levels of agitation increased the off target rates relative to low levels of agitation (FIG. 36). The lowest off target rates were achieved with a combination of low agitation and aspirating from the top of the tube.

Example 35

Fast Hybridization Buffers

Sequencing data is acquired using the general method of Example 6, with modification: genomic DNA (NA12878, Cornell) is hybridized and captured using either the a 33.1 Mb exome probe library or an 800 kb targeted library. Two different workflows are compared (FIG. 38). A standard buffer or "fast" hybridization buffer is used during hybridization of two different probe libraries (exome probes or an 800 kb custom panel) to the nucleic acid sample, and the capture/hybridization reaction is heated to 50-75° C. for various periods of time (15 minutes to 8 hours) in a PCR thermocycler, with a lid temperature of 80-95° C. Following sequencing, Picard HS Metric tools (Pct Target Bases 30×) with default values are used for sequence analysis. Data are downsampled to 150×raw coverage of targeted bases for evaluation. Use of fast hybridization buffers results in a workflow that is completed in 5-9 hours.

Example 36

Fast Hybridization Buffers with Liquid Polymer

Figure 39A:
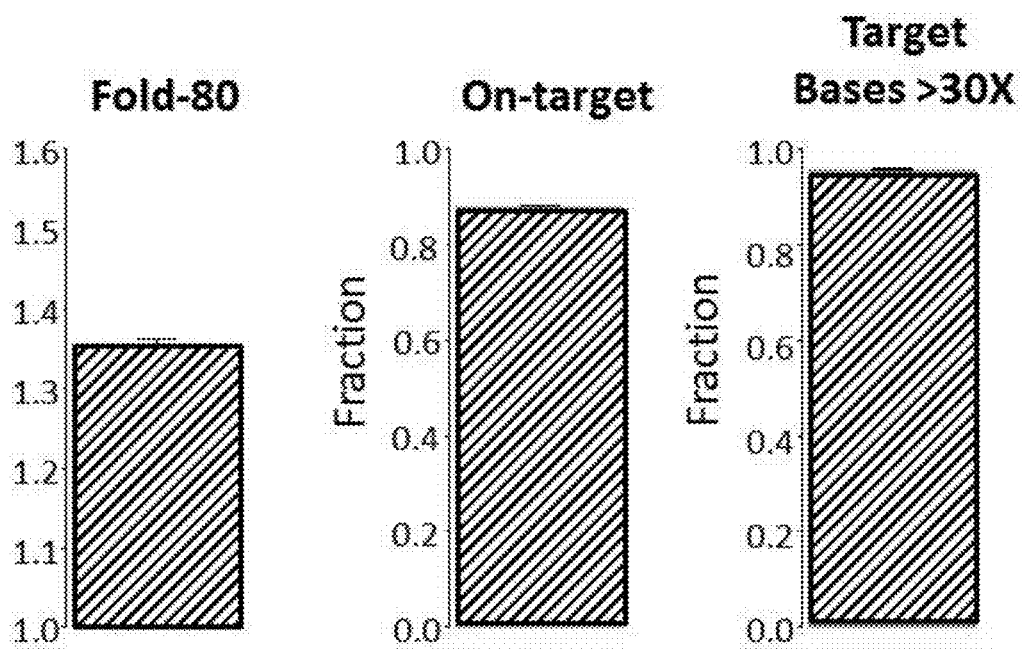
FIG. 39A is a series of plots for Fold-80 base penalty, On-target rate, and target bases with greater than 30× coverage obtained using a fast hybridization buffer with a 33.1 Mb exome enrichment probe library.
Figure 39B:
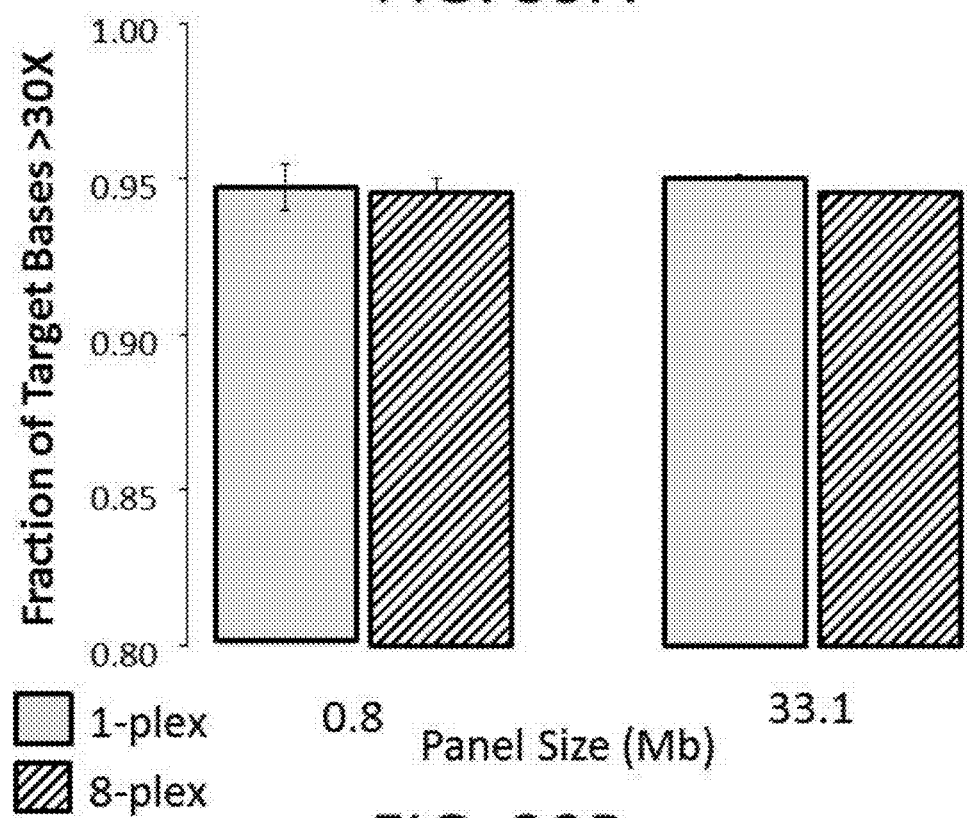
FIG. 39B is a plot of the fraction of target bases with greater than 30× coverage for 1 plex, and 8-plex experiments using either a 33.1 Mb exome probe panel or a 0.8 Mb custom cancer panel.
Figure 39C:
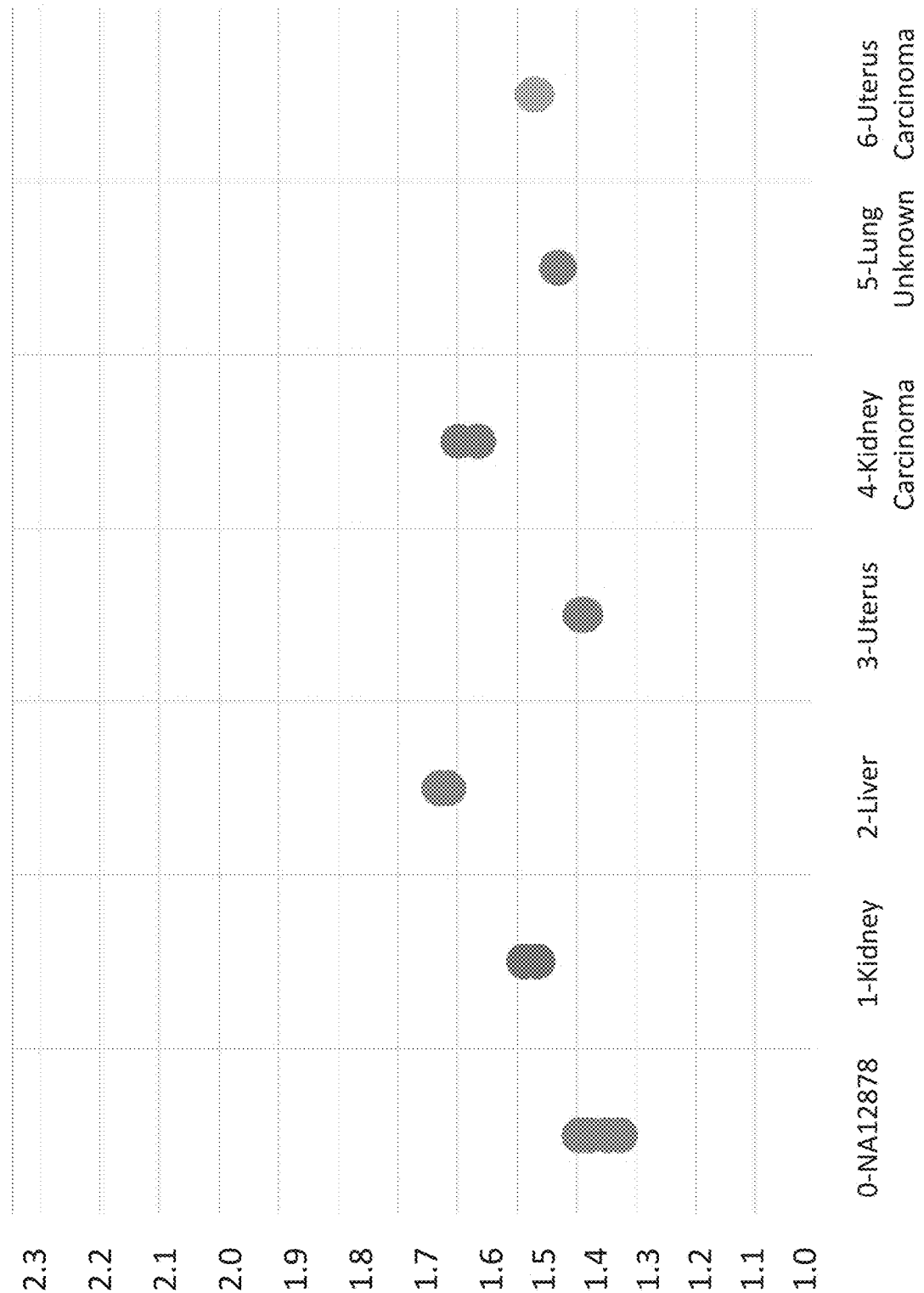
FIG. 39C is a plot of 80 fold base penalties vs. various FFPE samples.
Figure 39D:
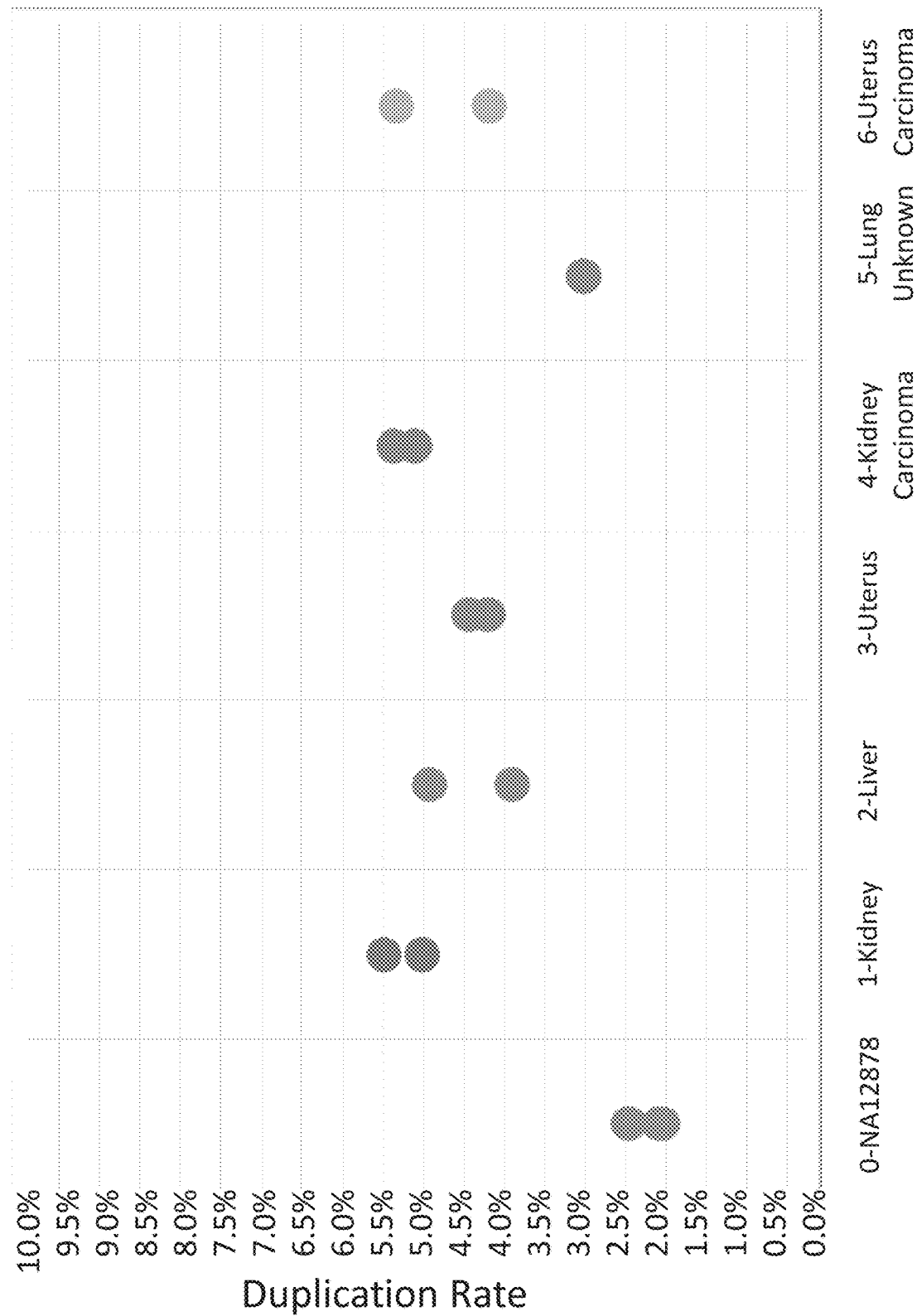
FIG. 39D is a plot of duplicate rate percentage vs. various FFPE samples.
Figure 39F:
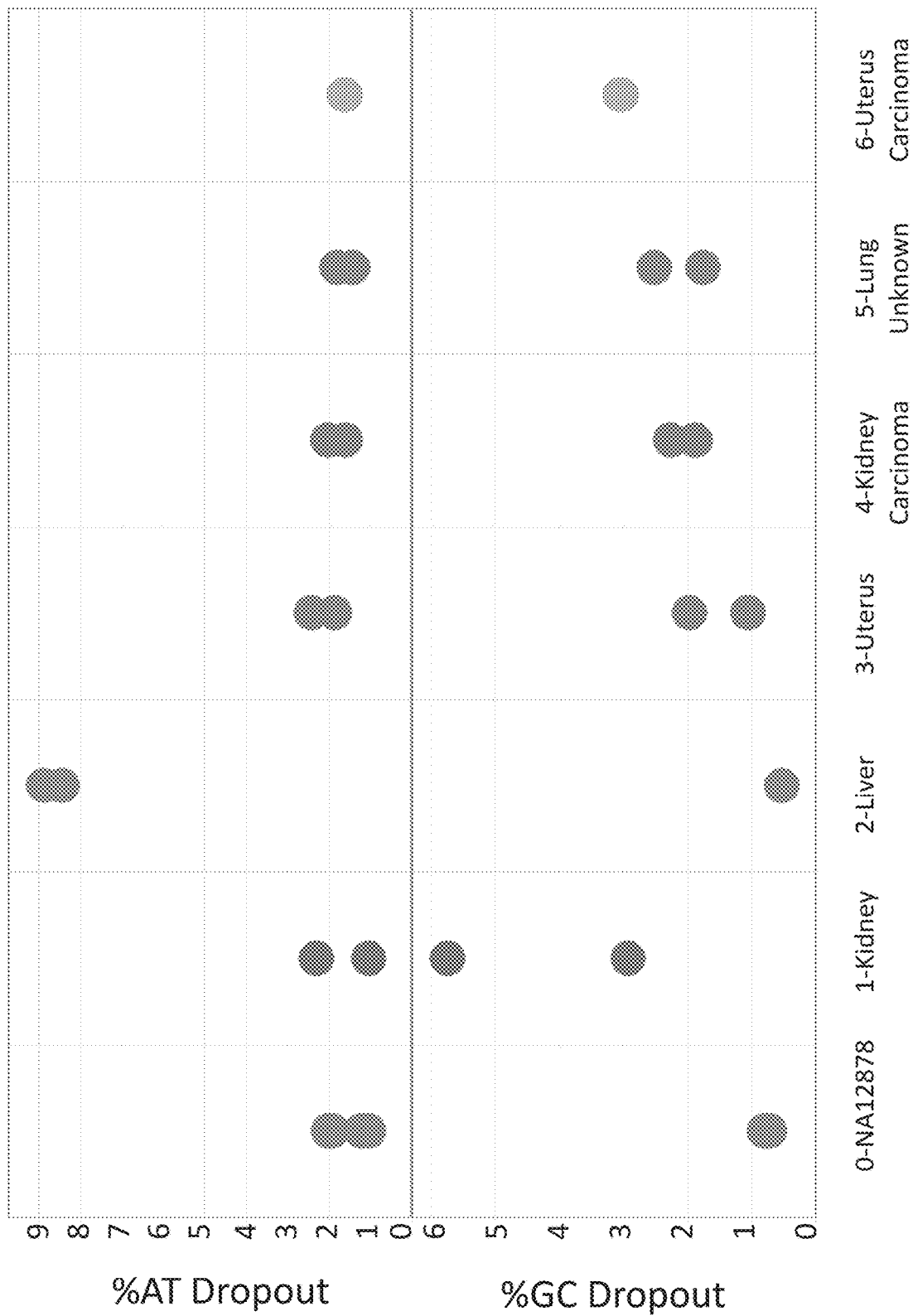
FIG. 39F is a plot of AT and GC dropout rates vs. various FFPE samples.
Figure 39G:
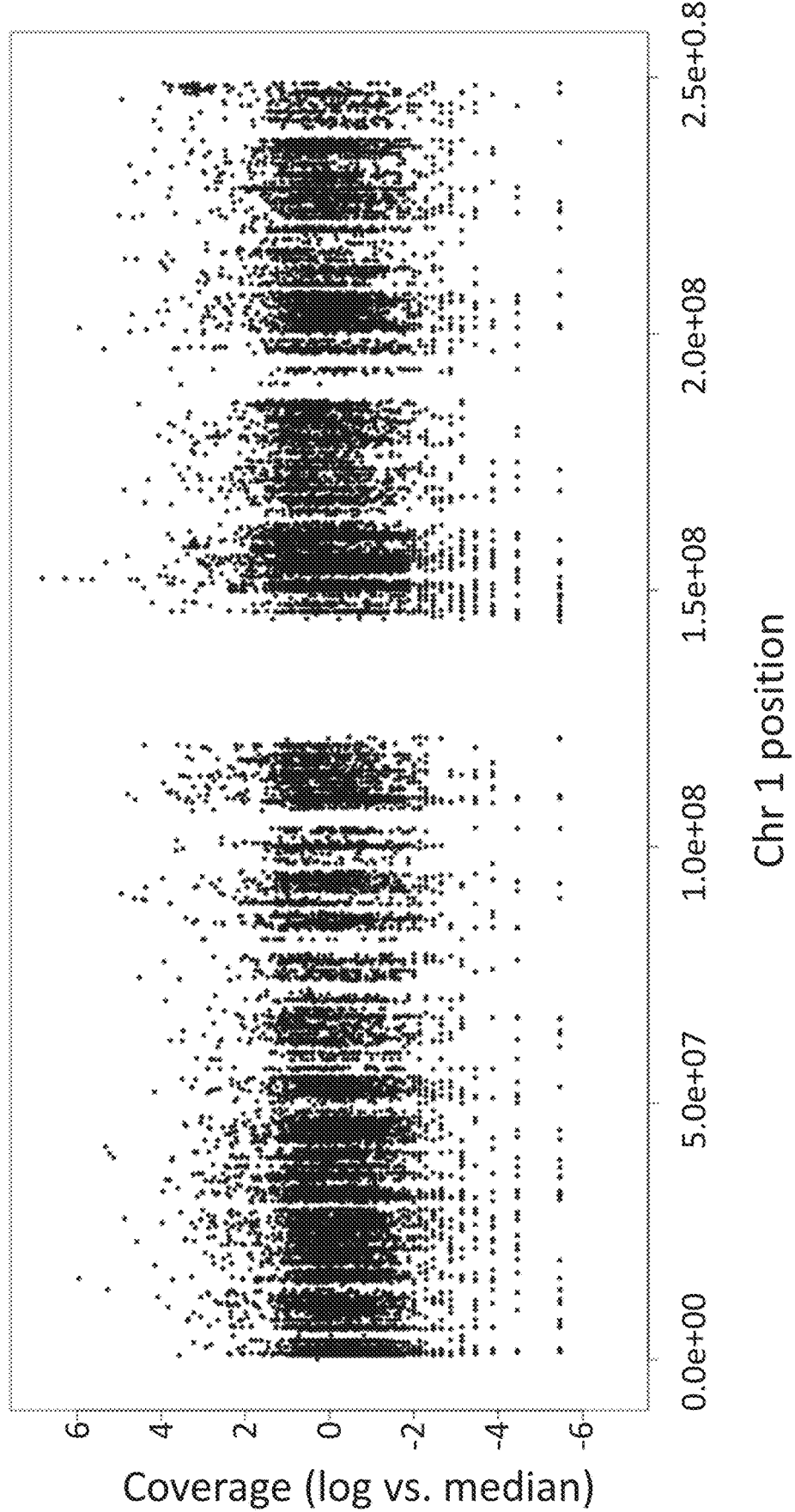
FIG. 39G is a plot of coverage (log vs. median) vs. position on chromosome 1 for an FFPE sample.

Sequencing data was acquired using the general method of Examples 6 and 10, with modification: genomic DNA (NA12878, Cornell) was hybridized and captured using either a 33.1 Mb exome probe library or an 800 kb targeted library. A "fast" hybridization buffer was used with liquid polymer during hybridization of two different probe libraries (exome probes or an 800 kb custom panel) to the nucleic acid sample, and the capture/hybridization reaction was heated at 65° C. for various periods of time in a PCR thermocycler, with a lid temperature of 85° C. Following sequencing, Picard HS Metric tools (Pct Target Bases 30×) with default values were used for sequence analysis. Data were downsampled to 150× raw coverage of targeted bases for evaluation. For either panels a 15-min hybridization in Fast Hybridization Solution produced an equivalent performance to the 16-hr standard hybridization, and increasing hybridization times improved performance over the standard protocol using conventional hybridization buffers (FIG. 37A-37E). Overall, fast hybridization conditions led to low 80 fold base penalty, high on target rate, and >90% of target bass sequenced at greater than 30×. (FIG. 39A, 39B) The protocol also performed similarly in a multiplex experiment (FIG. 39B).

Example 37

Capture of Genomic DNA from an FFPE Sample

Sequencing data was acquired using the general method of Example 8, with modification: six different formalin-fixed paraffin-embedded (FFPE) samples covering four different tissues were used as samples. Genomic DNA samples from FFPE samples were sheared mechanically with Covaris AFA equipment with compatible oneTUBE AFA vessels. The instrument settings were adjusted for gDNA fragmentation to target a size distribution with a mode of 200-250 bp. Following end repair, A-tailing, and ligation of adapters, indexed libraries were subjected to capture in multiplexed reactions (8 libraries; 187.5 ng each; 1500 ng total) with a 33.1 Mb target region exome capture prove set in 16-hour hybridization reactions. Samples were sequenced on a NextSeq system (Illumina) with a NextSeq 500/550 High Output v2 kit to generate 2×76 paired-end reads and downsampled to 150× of targeted bases for evaluation. Picard HS metrics tools with a mapping quality of 20 were utilized for sequence analysis. Average values presented with N≥3 for all observations. Positive controls were sheared with AFA but not subject to FFPE extraction (Table 15). Sequencing metrics for the FFPE samples are shown in FIGS. 39C-39G.

strip-tube or 96-well plate. 4 uL comprising the exome capture probe panel, optionally 4 uL of a second panel, 8 uL of universal blockers, and 5 uL of blocker solution/buffer were added, the mixture pulse-spun, and the mixture evaporated using low or no heat.

Step 2. A 96-well thermal cycler was programmed with the following conditions and the heated lid set to 85° C., as shown in Table 16.

TABLE 16

| Step | Temperature | Time |
|---|---|---|
| 1 | 95° C. | HOLD |
| 2 | 95° C. | 5 minutes |
| 3 | Hybridization temperature (e.g., 60° C.) | HOLD |

The dried hybridization reactions were each resuspended in 20 µl fast hybridization buffer, and mixed by flicking. The tubes were pulse spun to minimize bubbles. 30 µl of liquid polymer was then added to the top of the hybridization reaction, and the tube pulse-spun. Tubes were transferred to the preheated thermal cycler and moved to Step 2 of the thermocycler program (incubate at 95° C. for 5 minutes). The tubes were then incubated at 60° C. for a time of 15 minutes to 4 hours in a thermal cycler with the lid at 85° C. 450 µl wash buffer 1 was heated the desired temperature (e.g., 70° C., or other temperature depending on desired sequencing metrics) and 700 µl wash buffer 2 was heated to 48° C. Streptavidin Binding Beads were equilibrated to room temperature for at least 30 minutes and then vortexed until mixed. 100 µl Streptavidin Binding Beads were added

TABLE 15

Sequencing results using mechanical shearing of FFPE samples.

| | Metric | | | | |
|---|---|---|---|---|---|
| | Q-ratio | | Fold-80 base penalty | 30 × depth of coverage | Percent On-Target | Percent duplication rate |
| | | | | Variable | | |
| | Q129/Q41 | Q305/Q41 | FOLD_ 80_BASE_ PENALTY | PCT_TARGET BASES_30X | 1- (PCT_OFF_ BAIT) | PCT_EXC_ DUPE |
| High-Quality gDNA (positive control; NA12878) | — | — | 1.31 | 93.3% | 83.4% | 3.1% |
| Uterus | 1.24 | 0.34 | 1.43 | 93.9% | 83.6% | 5.7% |
| Uterus Carcinoma | 0.99 | 0.19 | 1.4 | 94.9% | 84.2% | 7.2% |
| Lung | 0.78 | 0.12 | 1.55 | 92.1% | 83.7% | 5.8% |
| Liver | 0.91 | 0.09 | 1.69 | 88.4% | 84.0% | 10.6% |
| Kidney | 0.62 | 0.06 | 1.69 | 89.7% | 84.9% | 8.9% |

Example 38

Fast Hybridization Buffers with Variable Wash Buffer 1 Temperature

Sequencing data was acquired using the general method of Examples 6 and 10, with modification: the temperature of wash buffer 1 was varied to modify sequencing results, and the protocol was carried out as described below.

Step 1. Eight samples, each approximately 187.5 ng (1500 ng total) were transferred to a 0.2-ml thin-walled PCR to a 1.5-ml microcentrifuge tube. One tube was prepared for each hybridization reaction. 200 µl fast binding buffer was added to the tubes and mixed by pipetting. The tubes were placed on a magnetic stand for 1 minute, then removed and the clear supernatant discarded, without disturbing the bead pellet. The tube was then removed from the magnetic stand. The pellet was washed two more times for a total of three washes with the fast binding buffer. After removing the clear supernatant from the third wash, a final 200 µl fast binding buffer was added and the beads resuspended by vortexing until homogenized. The tubes of the hybridization reaction were mixed with the Streptavidin Binding Beads for 30 minutes at room temperature on a shaker, rocker, or rotator at a speed sufficient to keep the solution mixed.

Step 3. Tubes containing the hybridization reaction with Streptavidin Binding Beads were removed from the mixer and pulse-spun to ensure solution was at the bottom of the tubes, and the tubes were placed on a magnetic stand for 1 minute. The clear supernatant including the liquid polymer was removed and discarded with disturbing the pellet. The tubes were removed from the magnetic stand and 200 µl preheated fast wash buffer 1 was added, then mixed by pipetting. The tubes were incubated for 5 minutes at 70° C., and placed on a magnetic stand for 1 minute. The clear supernatant was removed and discarded without disturbing the bead pellet. The tubes were then removed from the magnetic stand and an additional 200 µl of preheated fast wash buffer 1 was added, followed by mixing and incubation 5 minutes at 70° C. The tubes were pulse-spun to ensure solution was at the bottom of the tubes. After the hybridization is complete, the thermal cycler lid was opened and the volume of each hybridization reaction including liquid polymer quickly transferred into a corresponding tube of washed Streptavidin Binding Beads, then mixed. The entire volume (~200 µl) was transferred into a new 1.5-ml microcentrifuge tube, one per hybridization reaction. The tubes were placed on a magnetic stand for 1 minute, followed by removal and discard of the clear supernatant. The tubes were removed from the magnetic stand and 200 µl of 48° C. wash buffer 2 was added, mixed by pipetting, and then pulse-spun to ensure the solution was at the bottom of the tubes. The tuber were then incubated for 5 minutes at 48° C., placed on a magnetic stand for 1 minute, and the clear supernatant removed and discarded with disturbing the pellet. The wash step was repeated two more times, for a total of three washes. After the final wash, a 10 µl pipette was used to remove traces of supernatant. Without allowing the pellet to dry, the tubes were removed from the magnetic stand and 45 µl of water added, mixed, and then incubated on ice (hereafter referred to as the Streptavidin Binding Bead slurry).

Step 4. A thermal cycler was programmed with the following conditions in Table 17, and the heated lid set to 105° C. 22.5 µl of the Streptavidin Binding Bead slurry was transferred to a 0.2-ml thin-walled PCR strip-tubes and kept on ice until ready for use in the next step. A PCR mixture was prepared by adding a PCR polymerase mastermix and adapter-specific primers to the tubes containing the Streptavidin Binding Bead slurry and mixed by pipetting. The tubes were pulse-spun, and transferred to the thermal cycler and start the cycling program.

TABLE 17

Thermocycler program for PCR library amplification.

| | Step | Temperature | Time | Number of Cycles |
|---|---|---|---|---|
| 1 | Initialization | 98 C. | 45 seconds | 1 |
| 2 | Denaturation | 98 C. | 15 seconds | Varies |
| | Annealing | 60 C. | 30 seconds | |
| | Extension | 72 C. | 30 seconds | |
| 3 | Final Extension | 72 C. | 1 minute | 1 |
| 4 | Final Hold | 4 C. | HOLD | — |

| Custom Panel Size | Number of Cycles |
|---|---|
| >100 Mb | 5 |
| 50-100 Mb | 7 |

TABLE 17-continued

Thermocycler program for PCR library amplification.

| 10-500 Mb | 8 |
| 1-10 Mb | 9 |
| 500-1,000 kb | 11 |
| 100-500 kb | 13 |
| 50-100 kb | 14 |
| <50 kb | 15 |

50 µl (1.0×) homogenized DNA Purification Beads were added to the tubes, mixed by vortexing, and incubated for 5 minutes at room temperature. The tubes were then placed on a magnetic plate for 1 minute. The clear supernatant was removed from the tubes. The DNA Purification Bead pellet was washed with 200 µl freshly prepared 80% ethanol for 1 minute, then the ethanol was removed and discarded. This wash was repeated once, for a total of two washes, while keeping the tube on the magnetic plate. A 10 µl pipet was used to remove residual ethanol, making sure to not disturb the bead pellet. The bead pellet was air-dried on a magnetic plate for 5-10 minutes or until the bead pellet was dry. The tubes were removed from the magnetic plate and 32 µl water was added. The resulting solution was mixed by pipetting until homogenized and incubated at room temperature for 2 minutes. The tubes were then placed on a magnetic plate and let stand for 3 minutes or until the beads fully pelleted. 30 µl of the clear supernatant containing the enriched library was transferred to a clean thin-walled PCR 0.2-ml strip-tube.

Figure 40:
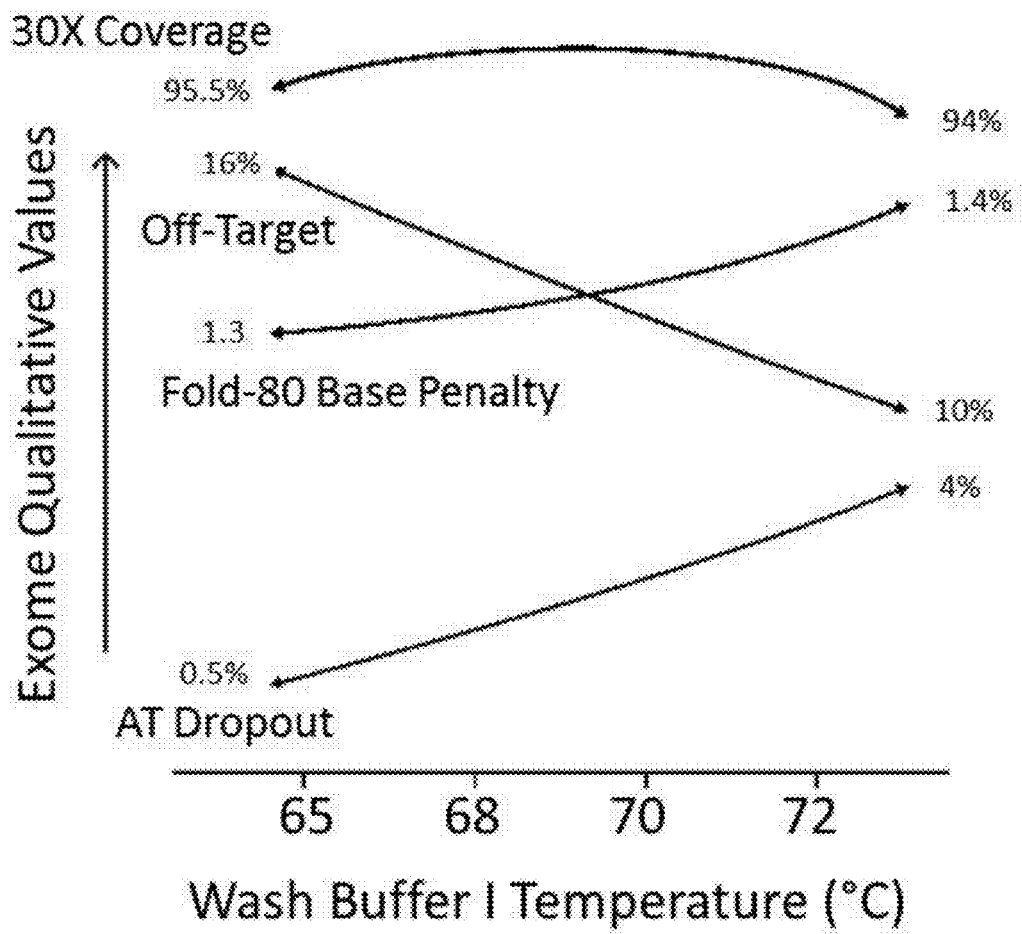
FIG. 40 is a plot of exome qualitative values vs. wash buffer 1 temperature for an experiment utilizing the fast hybridization buffer.

Step 5. Each enriched library was validated and quantified for size and quality using an appropriate assay, such as the Agilent BioAnalyzer High Sensitivity DNA Kit and a Thermo Fisher scientific Qubit dsDNA High Sensitivity Quantitation Assay. Samples were then loaded onto an Illumina sequencing instrument for analysis. Sampling was conducted at 150× (theoretical read depth), and mapping quality was >20. The effects on various NGS sequencing metrics for various fast hybridization wash buffer 1 temperatures are shown in FIG. 40.

Example 39

Blockers Targeting Strands of the Adapter

Figure 41:
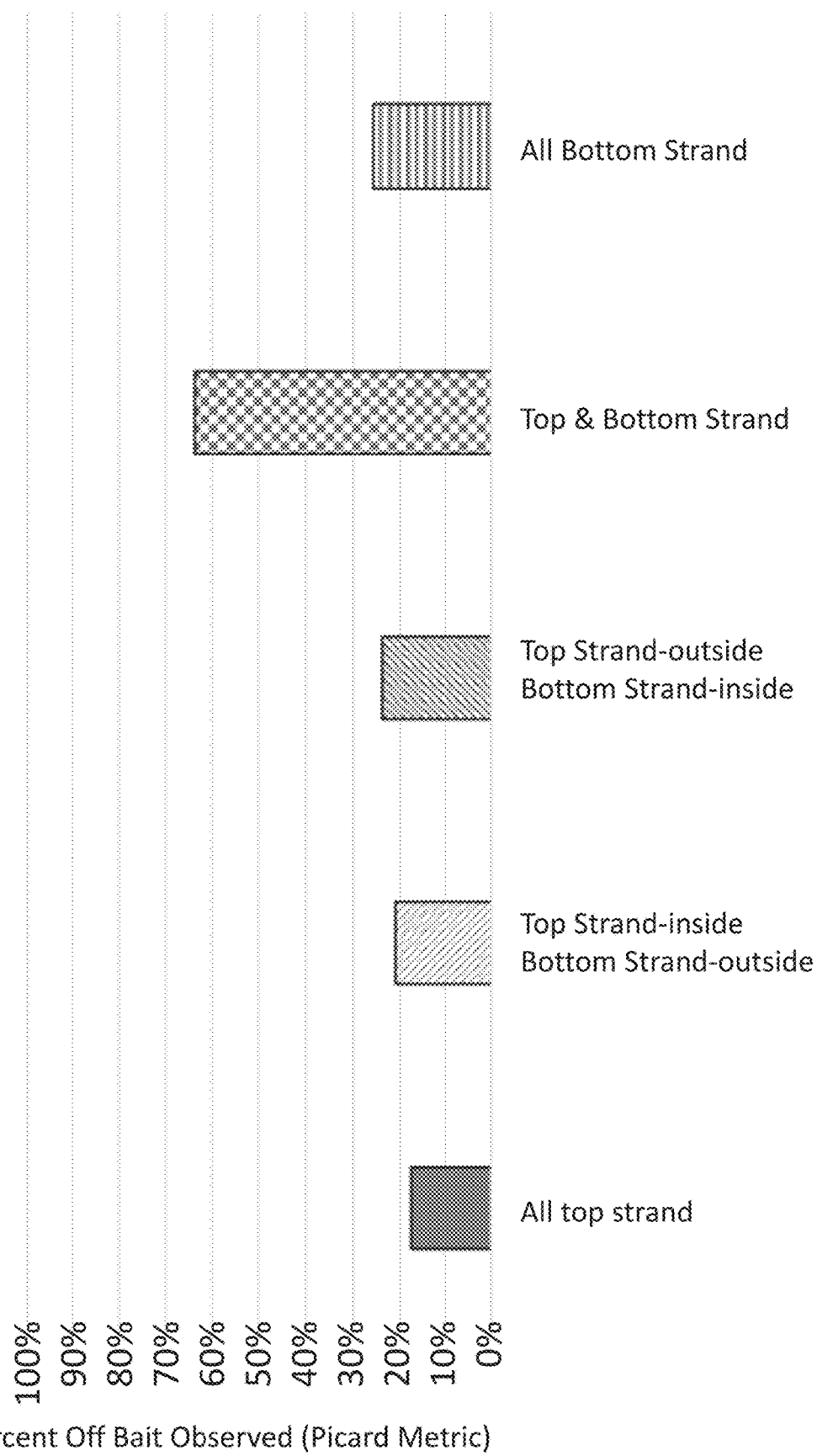
FIG. 41 is a plot of percent off bait for various blocker designs which target top or bottom strands of the adapters.
Figure 42A:
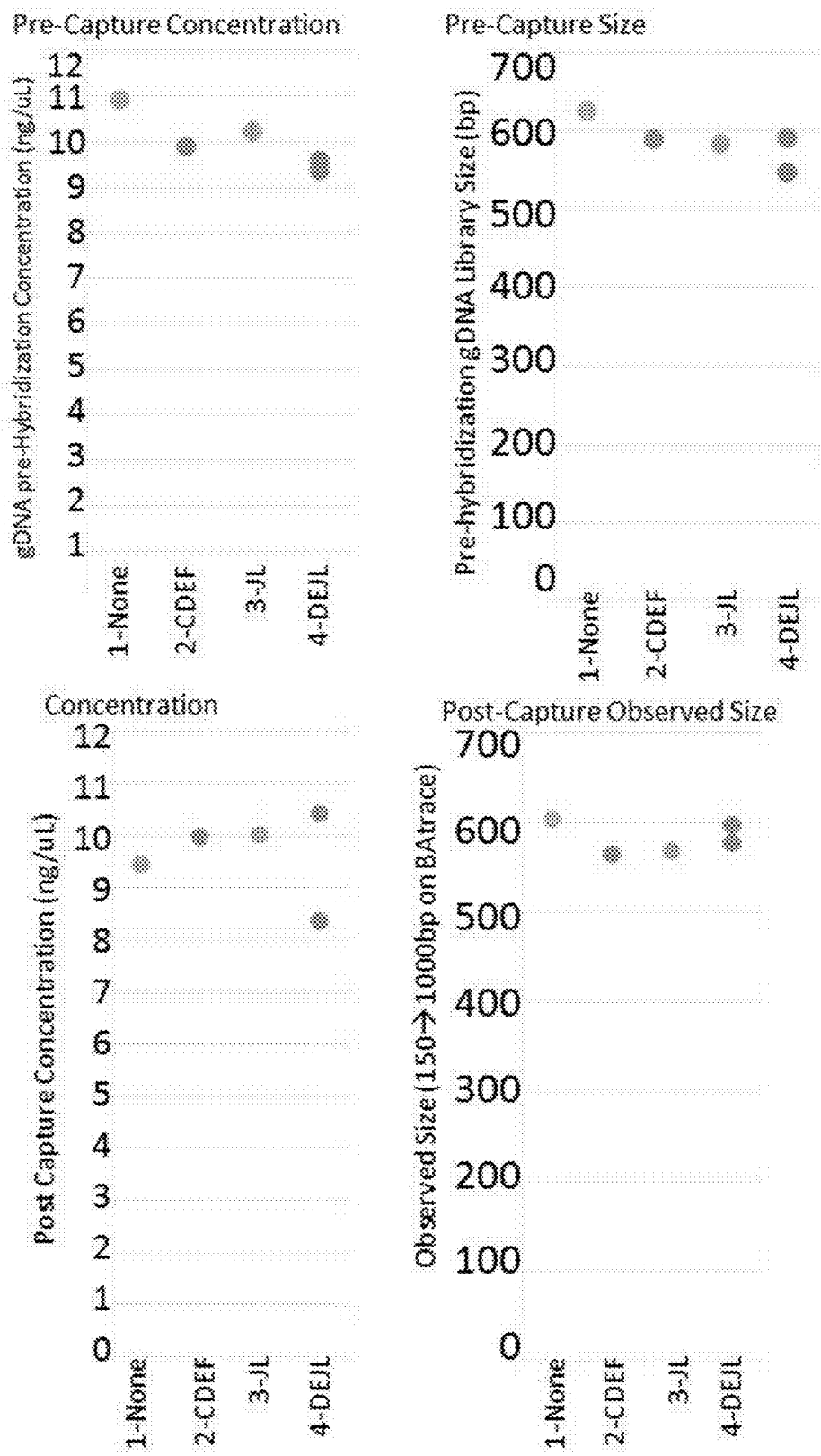
FIG. 42A are plots of pre-hybridization concentration, pre-capture size, post-capture concentration, and observed size for a library generated using a tagmentation method and various configurations of universal blockers.
Figure 42B:
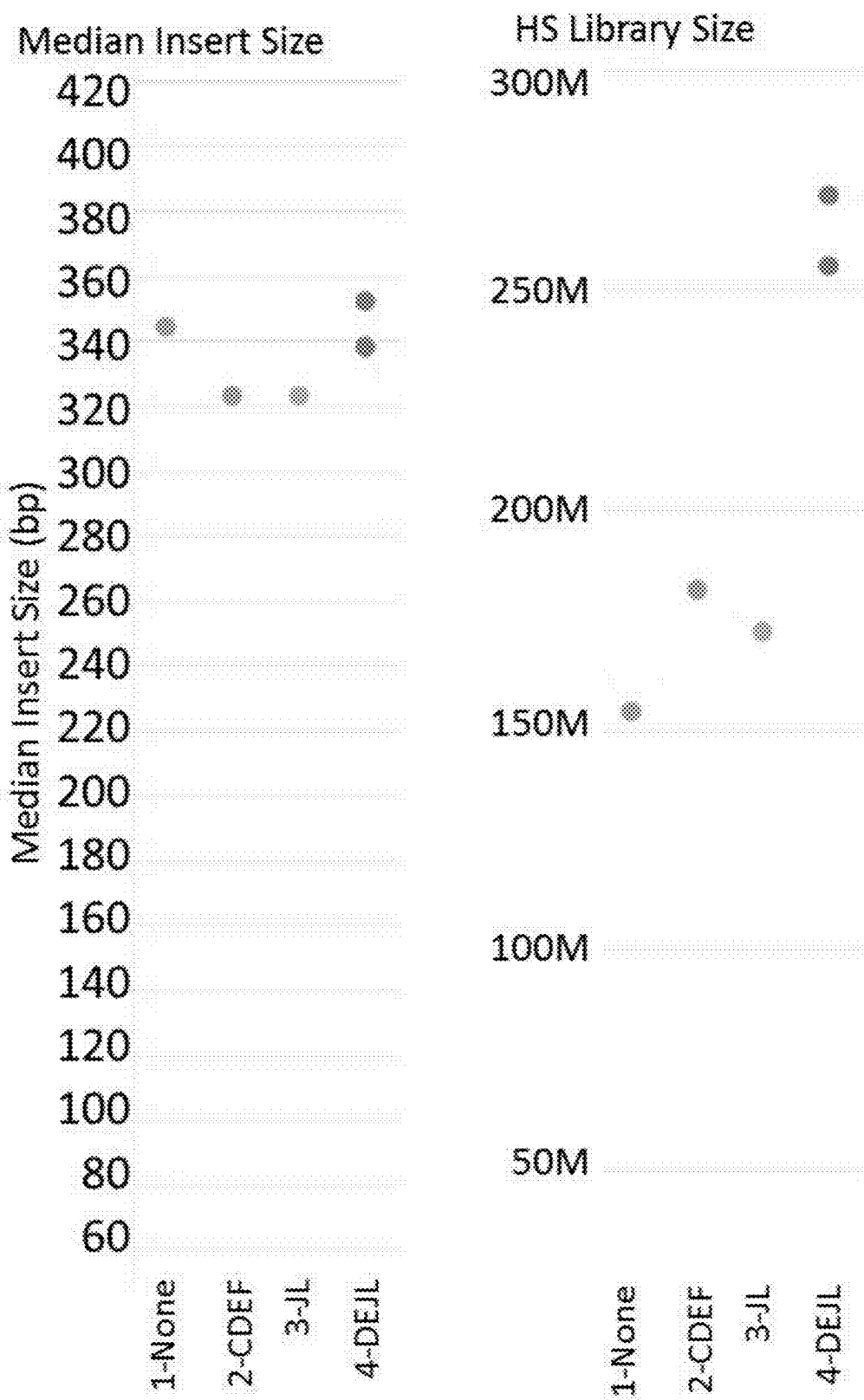
FIG. 42B are plots of median insert size and HS library size for a library generated using a tagmentation method and various configurations of universal blockers.
Figure 42C:
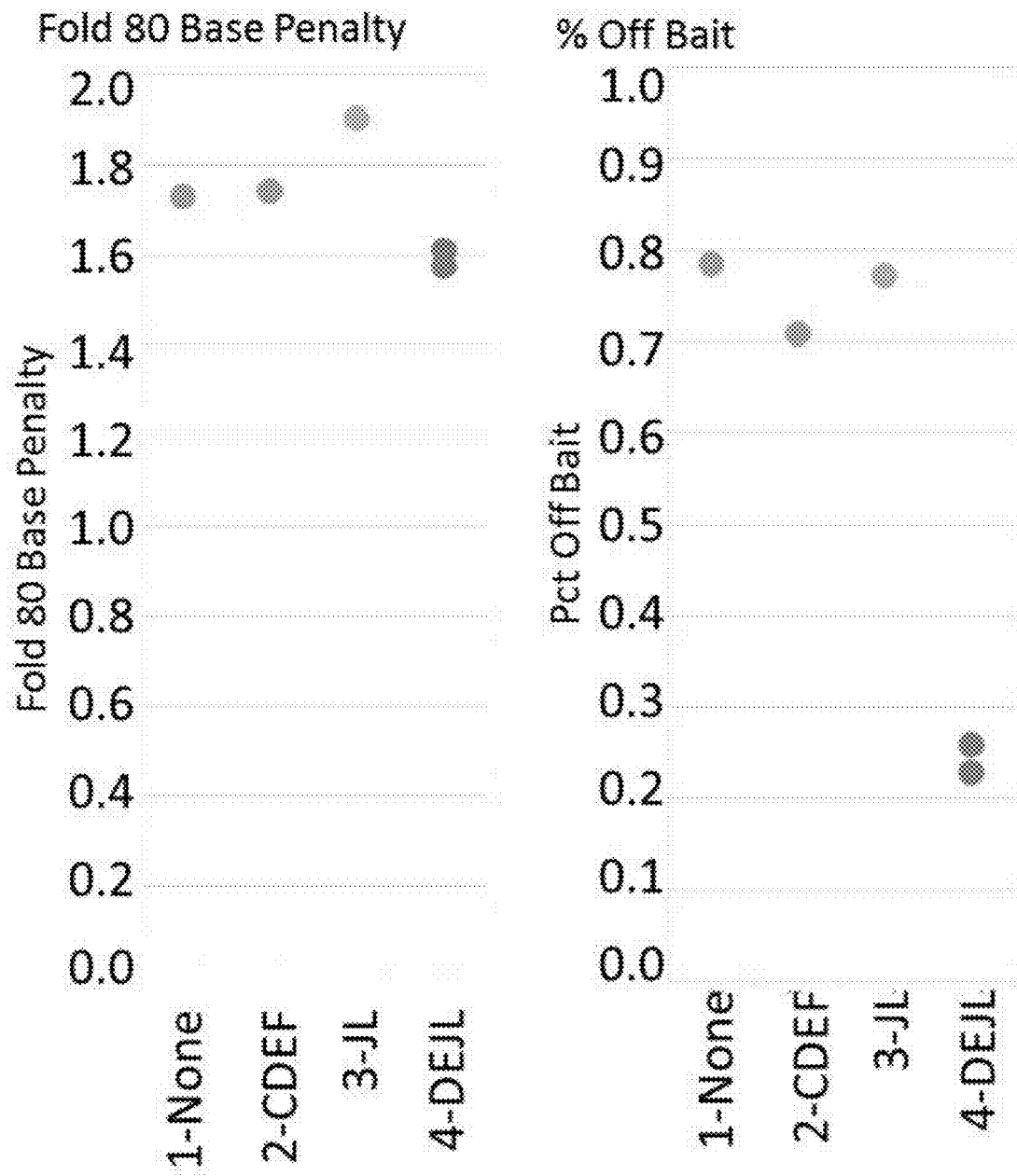
FIG. 42C are plots of sequencing metrics including Fold 80 base penalty and percent off bait for a library generated using a tagmentation method and various configurations of universal blockers.
Figure 42D:
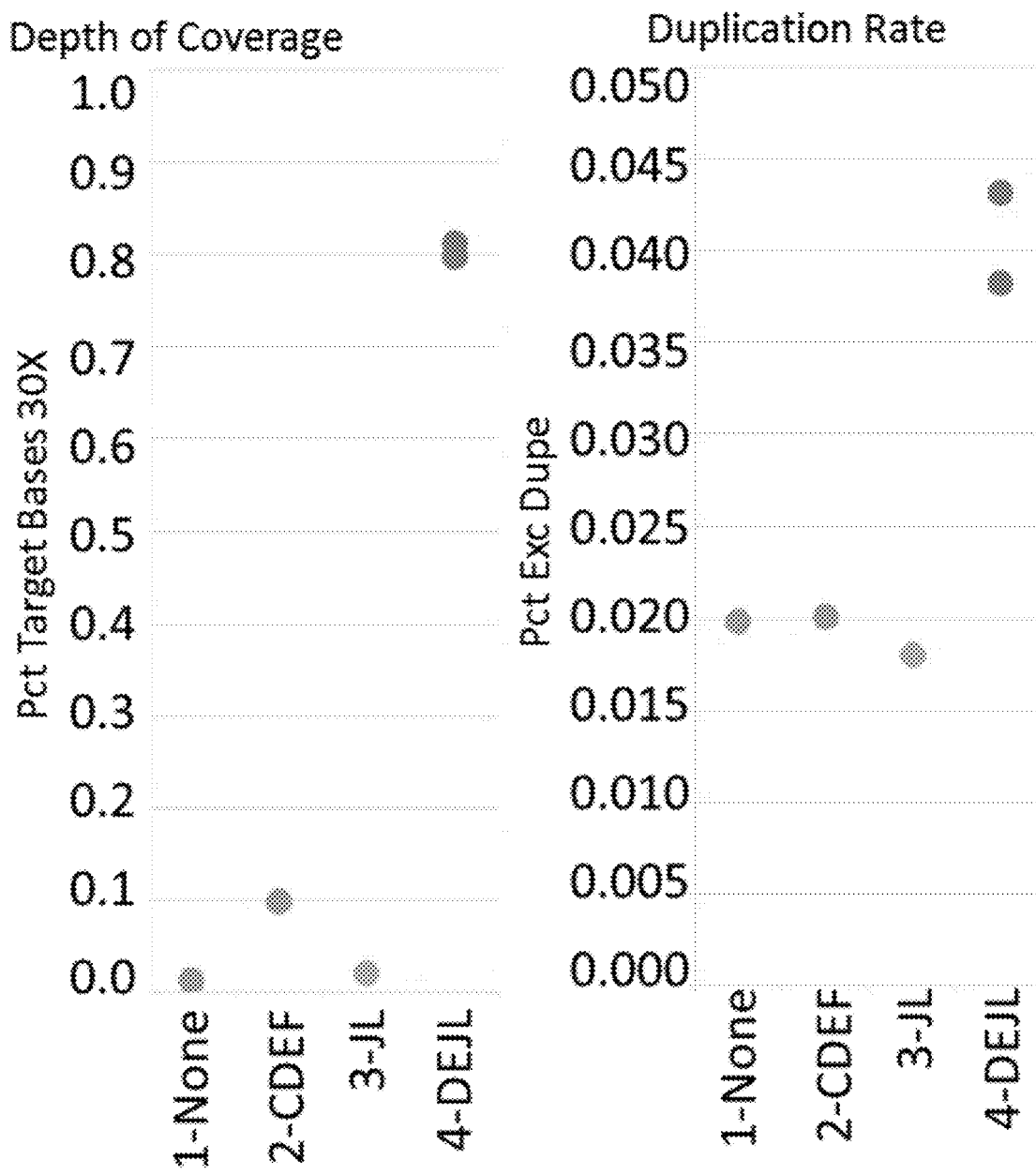
FIG. 42D are plots of sequencing metrics including percent target bases with at least 30× coverage, and duplication rate for a library generated using a tagmentation method and various configurations of universal blockers.
Figure 42E:
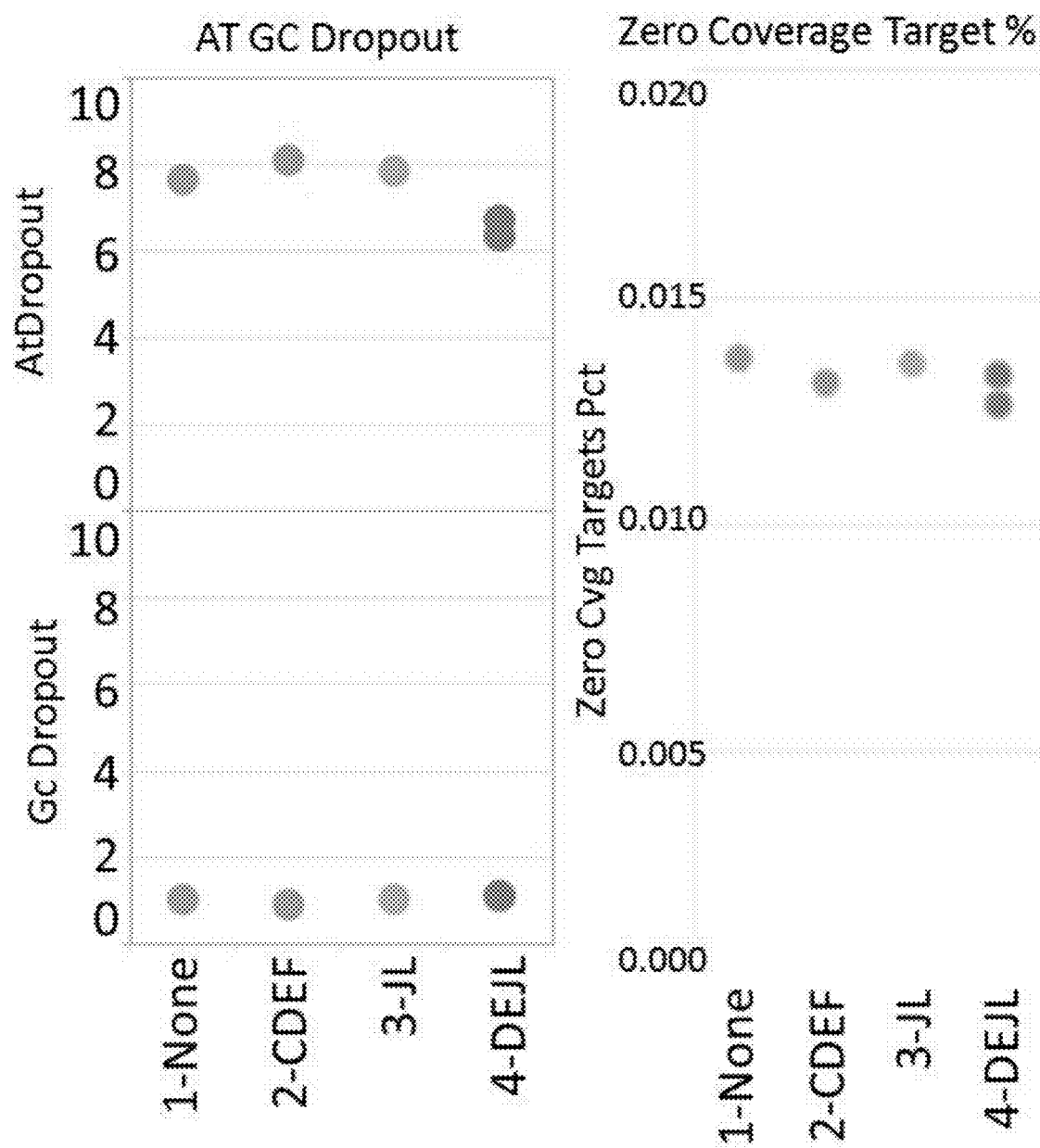
FIG. 42E are plots of sequencing metrics including AT and GC dropout rates and zero coverage target percentage for a library generated using a tagmentation method and various configurations of universal blockers.

The general procedures of Example 8 were executed with modification: additional blockers were added that target the top strand, bottom strand, or both strands of the adapter sequence. The results are shown in Table 18. "Outside" refers to the portion of the adapter between the terminus and the barcode. "Inside" refers to the portion of the adapter between the barcode and genomic insert. The percent off bait is shown in FIG. 41.

TABLE 18

Strand-specific blockers

| Blockers used during hybridization (to target strands of the adapter) | Percent off-bait observed post-sequencing of target enriched genomic material |
|---|---|
| Standard four blockers targeting the top strand | 17.4% |
| Two "outside" blockers targeting the top strand and two "inside" blockers targeting the bottom strand | 20.7% |
| Two "inside" blockers targeting the top strand and two "outside" blockers targeting the bottom strand | 23.6% |

TABLE 18-continued

Strand-specific blockers

| Blockers used during hybridization (to target strands of the adapter) | Percent off-bait observed post-sequencing of target enriched genomic material |
|---|---|
| Four blockers targeting the top strand and four blockers targeting the bottom strand | 64.1% |
| Four blockers targeting the bottom strand | 25.7% |

Example 40

Blockers with Tagmentation-Based Library Generation

Following the general procedures of Example 8, a genomic library was treated with an engineered transposon to fragment the DNA and tag the fragments with an adapter sequencing in a single step to generate fragments of approximately 300 bases in length. The resulting library of fragments were then amplified with a limited PCR-cycle procedure using primers that add additional adapter sequences to both ends of the DNA fragments. Prior to sequencing, the adapter-ligated genomic library was enriched using an exome panel in the presence of either four universal blockers designed specifically for the tagmentation adapters (DEJL-1 or DEJL-2); four non-tagmentation universal blockers (CDEF), two universal blockers targeting the adapter region adjacent to the genomic insert (JL), or a control experiment without blockers (NB). Blockers targeting the tagmentation adapters comprised 11-13 locked nucleic acids (32-45% of the bases), a Tm of 84-90 degrees C., and a length of 29-34 bases. The addition of blockers led to significant decreases in off-bait capture. Off-bait percentage was approximately 25%, AT dropout was approximately 7%, percent 30× base coverage was approximately 30%, and fold 80 base penalty was 1.6. The results after sequencing for various NGS metrics are shown in 42A-42E and FIG. 43. Without being bound by theory, gDNA library size Example 41

Location of Modified Bases in Blockers

The general procedures of Example 8 were followed with modification: three of four universal blockers were held constant, and the fourth blocker designed was manipulated by changing the location of the positions comprising locked nucleic acids. All blocker designs maintained an overall $T_m$ of at least 82 degrees C., regardless of locked nucleic acid placement. All designs tested gave comparable results that were independent of locked nucleic acid placement, provided the overall $T_m$ was at least 82 degrees C. (data not shown).

Example 42

Blockers and Alternative Adapter Designs

The general procedures of Example 8 are followed with modification: Y-adapters are replaced with "bubble" adapters or "clamp" adapters. After capture using blockers, sequencing metrics such as percent bases at 30×, off-bait percentage, AT/GC dropout, 80 fold base penalty, and on-target percent are measured.

Example 43

Multiplex Fast Hybridization Buffers with Liquid Polymer

Sequencing data is acquired using the general method of Example 38, with modification: samples from 16 different sources are individually, uniquely barcoded by sample and processed using the fast hybridization buffer protocol. Sequencing metrics for the 16 samples are comparable to experiments using only a single sample.

Example 44

Multiplex Fast Hybridization Buffers with Liquid Polymer

Sequencing data is acquired using the general method of Example 38 with modification: samples from 96 different sources are individually, uniquely barcoded by sample and processed using the fast hybridization buffer protocol. Sequencing metrics for the 96 samples are comparable to experiments using only a single sample.

Example 45

Fast Hybridization Buffers with Tagmentation Blockers

Sequencing data is acquired using the general method of Example 38 with modification: the library was prepared using the tagmentation procedure of Example 40.

Example 46

Fast Hybridization Buffers with Blockers and Alternative Adapter Designs

Sequencing data is acquired using the general method of Example 38 with modification: the Y-adapters are replaced with "bubble" adapters or "clamp" adapters. After capture using blockers with the fast hybridization buffer, sequencing metrics such as percent bases at 30×, off-bait percentage, AT/GC dropout, 80 fold base penalty, and on-target percent are measured.

Example 47

Melting Curve Analysis for Universal Blockers

Figure 44:
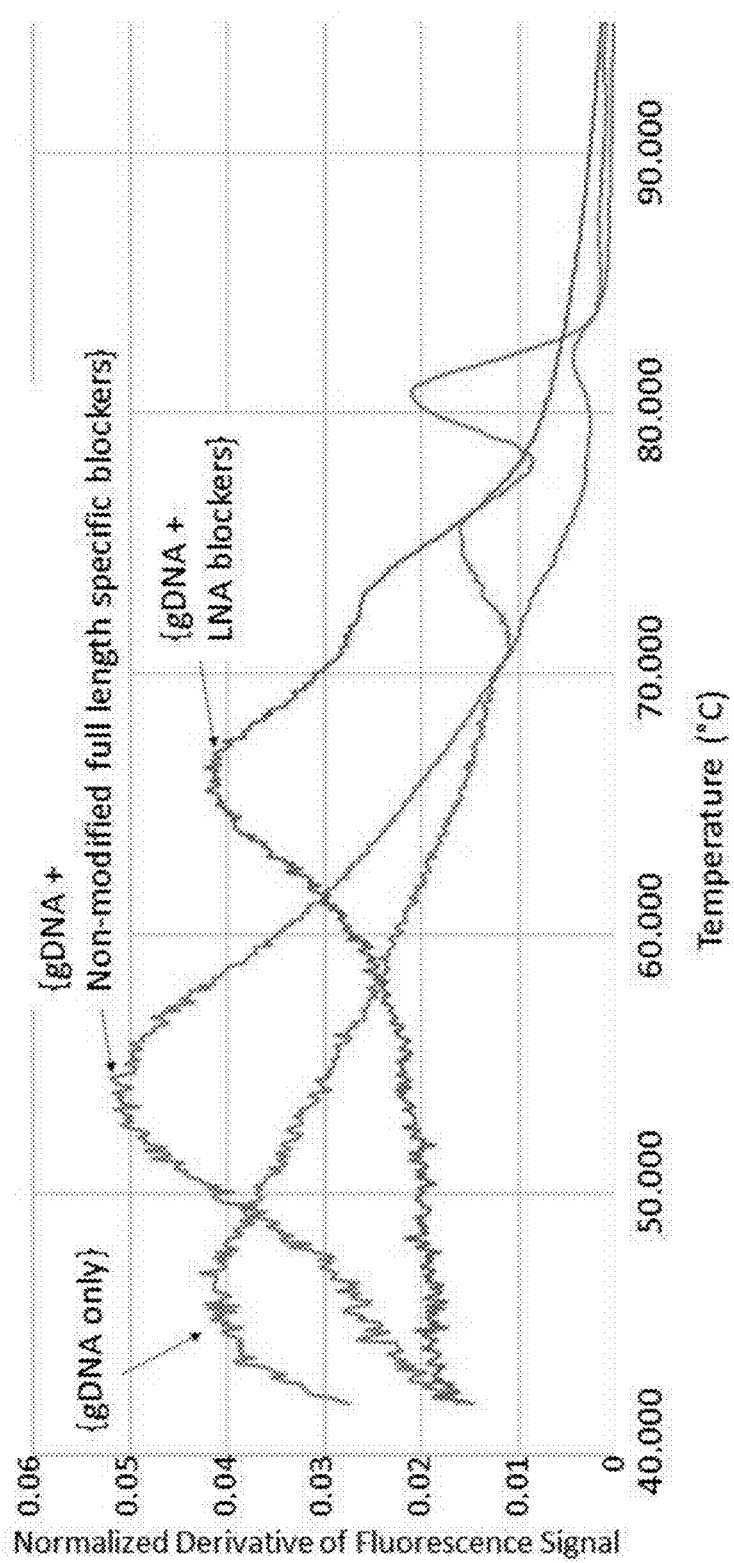
FIG. 44 is a plot of melt curves in the presence or absence of blockers.

An experiment was conducted to empirically measure $T_m$ between universal blockers and adapter-ligated genomic DNA (gDNA). gDNA libraries with adapters at 27 ng/μl, non-modified full length specific blockers at 1 nmol/μl total, and LNA-containing blockers at 0.5 nmol/μl total were used. Appropriate components were mixed with 10 μM SYTO9 and 50 nM ROX fluorescence dyes, denatured at 95° C., and heated from 40° to 95° C. over 16 hours, holding at each 0.1° for 1 minute and 44 seconds. During the heat curve, fluorescence was recorded in a qPCR system and graphed as a normalized derivative. (FIG. 44). {gDNA} provided a maximum value at ~45° C., {gDNA+non-modified full length specific blockers} provided a maximum value at ~55° C., and {gDNA+LNA blockers} provided a maximum value at ~65° C. in this experiment.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An aqueous composition for polynucleotide hybridization comprising:
   at least one solvent, wherein the at least one solvent comprises dimethyl sulfoxide (DMSO) at 10-30% (v/v);
   at least one surfactant; and
   at least one thickening agent.

2. The composition of claim 1, wherein the at least one solvent further comprises DMF, DMAc, or HEMPA.

3. The composition of claim 1, wherein the at least one solvent further comprises acetone, methyl ethyl ketone, THF, or diethyl ether.

4. The composition of claim 1, wherein the at least one surfactant comprises SDS, CTAB, tergitol, or sodium lauryl sulfate.

5. The composition of claim 1, wherein the at least one surfactant comprises a trialkylammonium salt.

6. The composition of claim 1, wherein the at least one thickening agent comprises cellulose, or starch.

7. The composition of claim 1, wherein the at least one thickening agent comprises dextran sulfate, hydroxymethylcellulose, hydroxyethylcellulose, polyethylene glycol, or ficoll.

8. The composition of claim 1, wherein the at least one thickening agent is 10-40% (w/v).

9. The composition of claim 1, wherein the at least one surfactant is 0.001-0.1% (w/v).

10. The composition of claim 4, wherein the at least one surfactant is 0.001-0.1% (w/v).

11. The composition of claim 5, wherein the at least one surfactant is 0.001-0.1% (w/v).

12. The composition of claim 6, wherein the at least one thickening agent is 10-40% (w/v).

13. The composition of claim 7, wherein the at least one thickening agent is 10-40% (w/v).

14. The composition of claim 1, wherein a hybridization temperature of the composition is at least 50° C.

15. The composition of claim 1, wherein a hybridization temperature of the composition is at least 65° C.

16. The composition of claim 1, wherein the aqueous composition comprises a plurality of polynucleotides.

17. The composition of claim 16, wherein the plurality of polynucleotides are in solution.

* * * * *

SEQUENCE LISTING

```
<160> NUMBER OF SEQ ID NOS: 5

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(52)
<223> OTHER INFORMATION: Thymidine-succinyl hexamide CED phosphoramidite

<400> SEQUENCE: 1
agacaatcaa ccatttgggg tggacagcct tgacctctag acttcggcat tttttttttt    60
tt                                                                    62

<210> SEQ ID NO 2
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (101)..(102)
<223> OTHER INFORMATION: Thymidine-succinyl hexamide CED phosphoramidite

<400> SEQUENCE: 2
cgggatcctt atcgtcatcg tcgtacagat cccgacccat ttgctgtcca ccagtcatgc    60
tagccatacc atgatgatga tgatgatgag aaccccgcat tttttttttt tt           112

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgcggggtt ctcatcatc                                                  19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgggatcctt atcgtcatcg                                                 20

<210> SEQ ID NO 5
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atagctacct                                                          10
```